United States Patent [19]

Tomczuk et al.

[11] Patent Number: 4,914,109

[45] Date of Patent: Apr. 3, 1990

[54] METHOD OF TREATING ANIMALS USING FUSED IMIDAZOHETEROCYCLIC COMPOUNDS

[75] Inventors: Bruce E. Tomczuk; Deborah S. Sutherland, both of Richmond, Va.

[73] Assignee: A. H. Robins Company, Incorporated, Richmond, Va.

[21] Appl. No.: 384,618

[22] Filed: Jul. 25, 1989

Related U.S. Application Data

[62] Division of Ser. No. 215,170, Jul. 5, 1988, which is a division of Ser. No. 871,772, Jun. 9, 1986, Pat. No. 4,772,600.

[51] Int. Cl.⁴ .............................................. A61K 31/44
[52] U.S. Cl. ..................................................... 514/303
[58] Field of Search ........................................ 514/303

[56] References Cited

U.S. PATENT DOCUMENTS 4,421,755 12/1983 Benedikter et al. ................ 514/303

*Primary Examiner*—Robert W. Ramsuer

[57] ABSTRACT

Imidazoheterocyclic compounds having the formula:

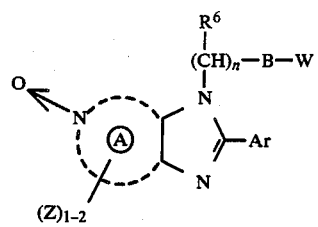

wherein the A ring is pyridine in any of its four positions; B is carbonyl, thioxomethyl or hydroxymethylene; Z is hydrogen, halogen, loweralkyl, hydroxy, loweralkoxy, diloweralkylamino or nitro; Ar is phenyl, pyrido, thienyl or furanyl; and W forms a wide combination of groups with B, including acids, esters, alcohols, amides and ketones. The compounds have CNS activity in a method for treating a living animal body as muscle relaxants, anticonvulsants and antianxiety agents.

1 Claim, No Drawings

METHOD OF TREATING ANIMALS USING FUSED IMIDAZOHETEROCYCLIC COMPOUNDS

This is a division, of application Ser. No. 215,170, filed July 5, 1988, which is a division of application Ser. No. 871,772 filed June 9, 1986, now U.S. Pat. No. 4,772,600 issued Sept. 20, 1988.

BACKGROUND OF THE INVENTION

1. Field of Invention.

The present invention relates to novel fused imidazoheterocyclics which have one substituted imidazo nitrogen and an aryl substitution on the carbon atom between the two imidazo nitrogens, a novel process therefor and novel intermediates in the preparation thereof. The imidazoheterocyclic compounds have CNS activity.

2. Information Disclosure Statement.

The preparation of 2-aryl-substituted imidazo [4,5-b]pyridines has been described by Garmaise, D. L. and Komlossy, J. in J. ORG. CHEM. 29(1) 3403–5 (1964). Unlike the present invention, the compounds have no substitution on the imidazo nitrogen.

Preparation of imidazopyridines having alkylaminoalkyl substitution on one imidazo nitrogen and benzyl substitution on the carbon between the two imidazo nitrogens (position 2) has been described in U.S. Pat. No. 2,987,518. The compounds of the present invention do not have alkylaminoalkyl substitution on an imidazo nitrogen.

2-Phenyl-imidazopyridines have been disclosed in U.S. Pat. Nos. 4,327,100, 4,353,909 and 3,985,891 as cardiotonics and blood pressure altering drugs. In U.S. Pat. No. 3,985,891, one compound is substituted in the 3-position by methyl. The compounds of the present invention are substituted in the 3-position by other radicals.

Benzimidazoles substituted on nitrogen by, for example, N,N-diethylacetamide, and in the two position by an ethoxybenzyl radical, are disclosed in Chemical Abstracts Vol. 66, 65425g.

Benzimidazoles substituted on nitrogen by carboxylic acid ethyl ester and in the two position by a 2-pyridinyl radical are disclosed in J. Med. Chem. 1980, 23(7), 734-8 as having anti-inflammatory activity.

(2-Phenyl-1 benzimidazolyl)propionic acid having growth-stimulating activity in the cotton plant is disclosed in Chemical Abstracts 100, 81244r (1984).

Imidazo[4,5-b]pyridines substituted in the 2-position by

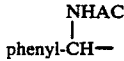

have been disclosed in Monatsh. Chem. (1975) 106(5), pp 1059–69 (C.A. 84, 59315u) as having no significant biological activity as compared to 2-(α-hydroxybenzyl)benzimidazole.

N,N-6-Trimethyl-2-(4-methylphenyl)imidazo[1,2a]pyridine-3-acetamide has been disclosed in NAUNYN-SCHMIEDBERG's ARCH. PHARMACOL (1985), Vol 330, pp 248-251. In contrast to the compounds of the present invention, the compound has a nitrogen shared by both the imidazo moiety and the pyridine moiety and the acetamide radical is on a carbon of the imidazo moiety rather than on an imidazo nitrogen.

OBJECTS AND SUMMARY OF THE INVENTION

The novel imidazoheterocyclic compounds of the present invention have the formula:

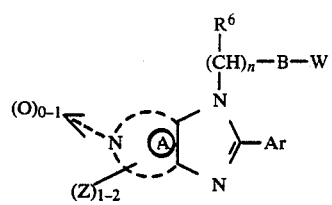

Formula I wherein;

A represents a heterocyclic ring having two of its carbon atoms held mutually with the imidazo moiety, selected from the group consisting of pyridine in any of its four positions wherein nitrogen is unshared by the imidazo moiety and substituted by one or two Z radicals on a carbon not shared by the imidazo moiety selected from the group consisting of hydrogen, halogen, loweralkyl, hydroxy, loweralkoxy, diloweralkylamino or nitro;

n is 1 to 3;

$R^6$ is hydrogen or loweralkyl;

Ar is selected from:

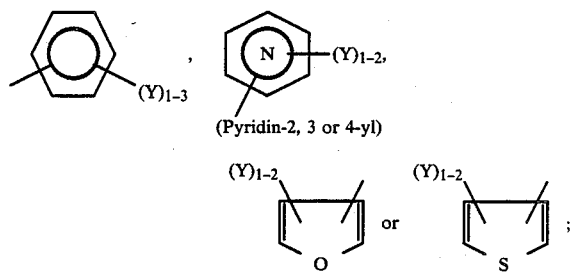

(Pyridin-2, 3 or 4-yl)

B is selected from carbonyl, i.e.

thioxomethyl, i.e.

or hydroxymethylene, i.e.

W is selected from:
hydrogen, loweralkyl, $(Y)_{1-3}$-phenyl, $(Y)_{1-3}$-phenylloweralkyl, —OR$^1$, —OM, —O(CH$_2$)$_p$—OH, —NR$^2$(CH$_2$)$_p$COOR$^1$, —NR$^2$(CH$_2$)$_p$OR$^1$, —NR$^2$(CH$_2$)$_p$COOM, —NR$^2$[(CH$_2$)$_p$NHC(O)R$^1$], —NR$^2$(CH$_2$)$_p$Q, —NR$^2$(CH$_2$)$_p$Ar$^1$ wherein Ar$^1$ is selected from the same group as Ar, —NR$^3$R$^4$, or —NR²(CH₂)ₚNR³R⁴, wherein R¹ and R² are selected from: Hydrogen, loweralkyl, (Y)₁₋₃-phenyl, or (Y)₁₋₃-phenyl-loweralkyl, R³ and R⁴ are selected from:
hydrogen,
loweralkyl,
loweralkenyl,
cycloalkyl,
cycloalkyl-loweralkyl,
(Y)₁₋₃-phenyl, (Y)₁₋₃-phenyl-loweralkyl, (Y)₁₋₂-pyridin-2, 3 or 4-yl, or R³ and R⁴ when taken together with the adjacent nitrogen atom may form a heterocyclic amino radical selected from:
azetidin-1-yl,
piperidin-1-yl,
loweralkyl-piperidin-1-yl,
morpholin-4-yl,
4-R⁵-piperazin-1-yl,
thiazolidin-3-yl,
with the proviso that when B is hydroxymethylene, W is always limited to hydrogen, loweralkyl, (Y)₁₋₃-phenyl or (Y)₁₋₃-phenyl-loweralkyl wherein Y is as defined below and a further proviso that when B is thioxomethyl, W is other than (Y)₁₋₃-phenyl, (Y)₁₋₃-phenyl-loweralkyl, loweralkyl, —OR¹, —OM, —O(CH₂)ₚOR¹, or hydrogen;

p is 0–3;

R⁵ is selected from loweralkyl,

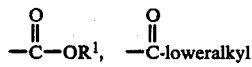

or (Y)₁₋₃-phenyl;

Q is selected from:

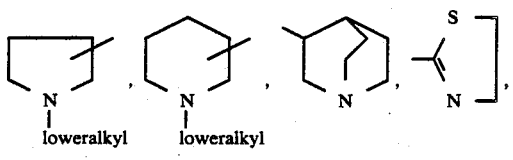

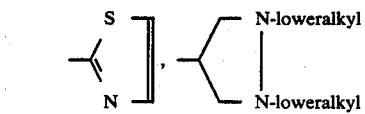

wherein all of the above Y is selected from hydrogen, halo, loweralkoxy, loweralkyl, trifluoromethyl, cyano, nitro or diloweralkylamino;

M is a pharmaceutically acceptable metal; the optical isomers, the oxides represented by >0, and the pharmaceutically acceptable acid addition salts including hydrates and quaternary salts thereof.

The 3H-imidazo[4,5-b]pyridine derivatives encompassed by Formula I have the formula:

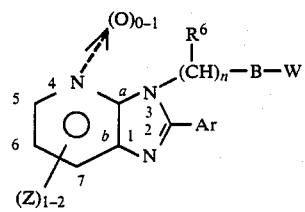

Iw

The 1H-imidazo[4,5-b]pyridine derivatives encompassed by Formula I have the formula:

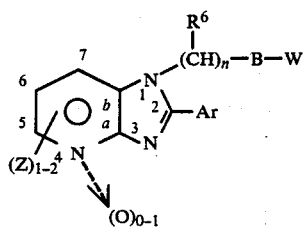

Ix

The 3H-imidazo[4,5-c] pyridine derivatives encompassed by Formula I have the formula:

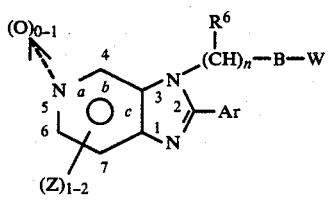

Iy

The 1H-imidazo[4,5-c]pyridine derivatives encompassed by Formula I have the formula:

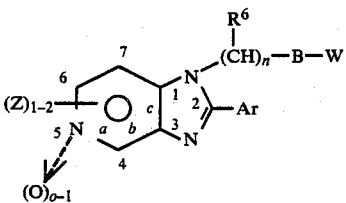

Iz

In the further definitions of symbols in the formulas hereof and where they appear elsewhere throughout this specification and the claims, the terms have the following significance.

The term "loweralkyl" as used herein, unless otherwise specified, includes straight and branched chain radicals of up to eight carbons inclusive and is exemplified by such groups as methyl, ethyl, propyl, isopropyl, butyl, sec. butyl, tert. butyl, amyl, isoamyl, hexyl, heptyl and octyl radicals and the like. The term "loweralkoxy" has the formula -O-loweralkyl.

The term "cycloalkyl" as used herein includes primarily cyclic alkyl radicals containing 3–9 carbon atoms inclusive and includes such groups as cyclopropyl, cyclobutyl, cyclopentyl, cyclohexyl, methylcyclohexyl, cycloheptyl and the like.

The terms "halo" or "halogen" when referred to herein include fluorine, chlorine, bromine and iodine unless otherwise stated.

"Pharmaceutically acceptable salts" include acid addition salts, hydrates, alcoholates and quaternary salts of the compounds of Formula I, which are physiologically compatible in warm-blooded animals. The acid addition salts may be formed by either strong or weak acids. Representative of strong acids are hydrochloric, sulfuric, and phosphoric acids. Representative of weak acids are fumaric, maleic, succinic, oxalic, citric, tartaric, hexamic and the like.

Suitable quaternary salts include the loweralkyl halides and loweralkyl sulfates.

Formulas Iw, Ix, Iy, and Iz illustrate what is meant by the term, "a pyridine ring in any of its four positions."

By the term "sulfurizing" is meant any agent or mixture of agents which will convert an amide to a thioamide such as phosphorus pentasulfide or phosphorus pentasulfide plus alkali-metal sulfide.

The compounds of Formula I are useful in the pharmaceutical method of this invention because of their pharmacological action on the central nervous system. This method employs the compounds of Formula I to treat a living animal body including humans for muscle tension and spasticity (i.e., to relax muscles), anxiety and convulsions. Compounds of Formula I wherein B-W forms an acid radical, i.e., —COOH or —COOM, generally have weak CNS activity; however, these compounds are also chemical intermediates in the preparation of other more active compounds.

The procedure for testing compounds for muscle relaxant activity is the Morphine-Induced-Straub-Tail-In-Mice Test. The procedure for indicating anti-anxiety response of the compounds is the Vogel Conflict Test based on shock-suppressed drinking behavior of rats and reaction to subcutaneous administration of metrazole in mice. The procedure for testing compounds for their anticonvulsant activity is based on evaluation of protective activity against seizures caused by electrical or chemical challenge. All of these evaluation techniques are described in greater detail under Pharmacological Test Procedures hereinbelow.

It is therefore an object of the present invention to provide certain novel imidazoheterocyclic compounds as described hereinabove and as defined by Formula I, which have CNS activity and a process for the preparation thereof.

Another object is to provide certain novel derivatives of diaminopyridines as intermediates in the preparation of the imidazoheterocyclic compounds.

Other objects are to provide methods of treatment for epilepsy, anxiety and spastic muscles.

Additional objects and advantages of the present invention will be apparent to one skilled in the art and others will become apparent from the following description of the best mode of carrying out the present invention and from the appended claims.

A schematic preparation of compounds of Formula I is given in Chart I.

CHART I

Preparation of Imidazo Compounds
(x and y are alternately carbon or nitrogen)

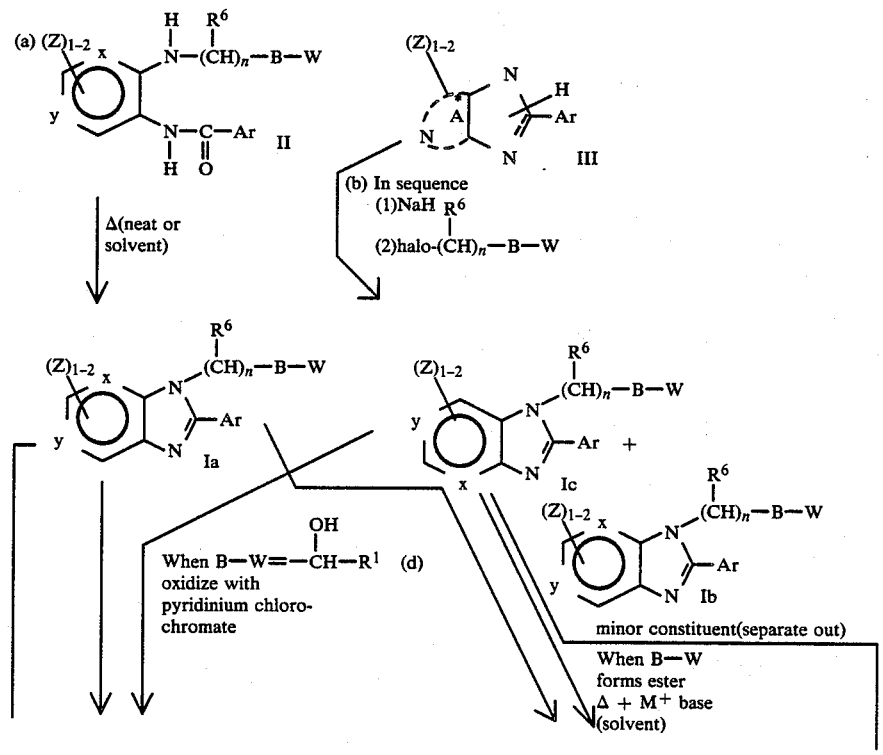

-continued

CHART I

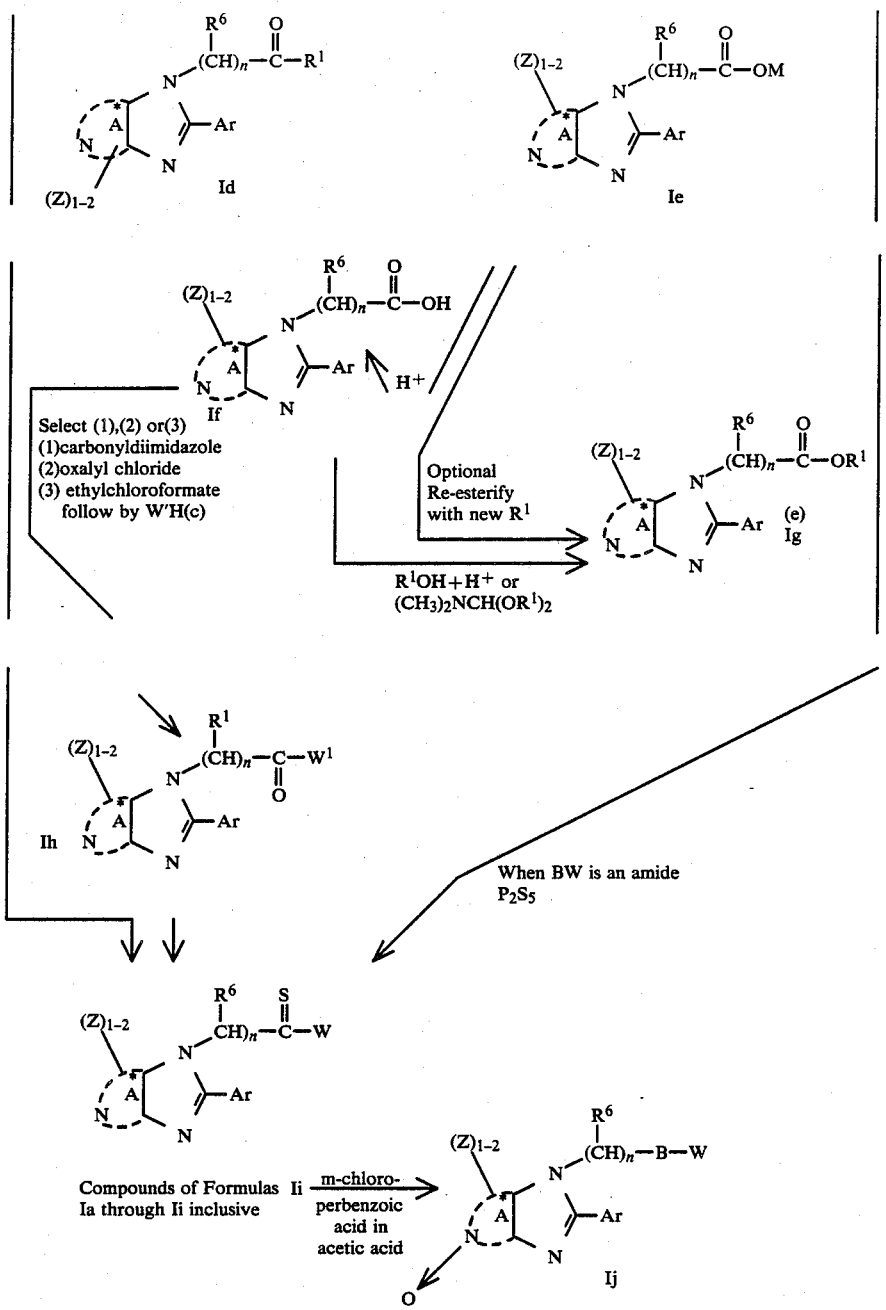

Footnotes to Chart I (a) B is —C(O)— or —CHOH—. When B is —C(O)—, W is any radical capable of forming an amide with B given under the definition of W in Formula I including preferably, —NH$_2$ or W is —OR$^1$ wherein R$^1$ is as defined under Formula I except hydrogen. When B is —CHOH—, W is limited to R$^1$.

(b) B is —C(O)— or —CHOH—. When B is $-\overset{\overset{O}{\|}}{C}-$, W is R$^1$ or —OR$^1$ wherein R$^1$ is as defined under Formula I including hydrogen**, or any radical capable of forming an amide with B given under the definition of W in Formula I, including —NH$_2$. When B is —CHOH, W is limited to R$^1$.

(c) W$^1$ is any amine radical under the definition of W in Formula I, including —NH$_2$.

(d) R$^1$ is loweralkyl, phenyl or phenyl-loweralkyl wherein phenyl may be substituted.

(e) Ig or If compounds may be reduced to compounds: wherein BW is —CH$_2$OH, e.g., -continued
CHART I

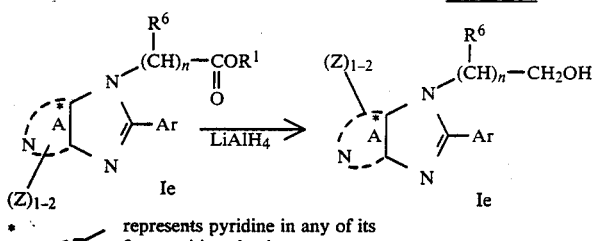

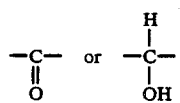 represents pyridine in any of its four positions having one or two Z radicals substituted on a carbon not shared by the imidazo moiety.

**As an aldehyde in the form of dilower alkyl acetal.

The free base of acid addition salts of Formula I compounds may be regenerated by commonly recognized procedures of partitioning between dilute aqueous base and a suitable solvent, separating the free base in the solvent layer, drying and evaporating the solvent.

The following process Steps 1-a, 1-b, and 2-6 each illustrate preparation of various compounds within the definition of Formula I, some of which preparations depend on the stepwise progression. Step 1-b of the process represents a novel method of obtaining a predominant isomer from a tautomeric starting material.

Step 1-a, heating a compound of the formula

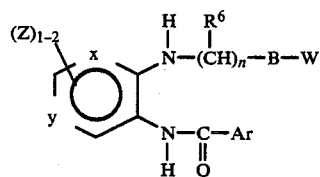

wherein
x and y are alternately either carbon or nitrogen;
Ar, n, Z and $R^6$ are as defined under Formula I;
B is selected from

and when B is

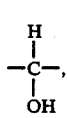

W is any radical capable of forming an amide with B or an —$OR^1$ group as defined under Formula I, except wherein $R^1$ is H, and when B is

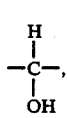

W is limited to $R^1$; without solvent (neat) or in a suitable solvent such as ethylene glycol to give a compound of the formula:

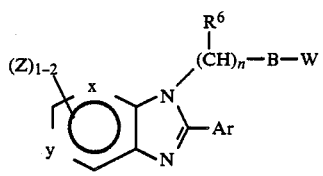

wherein x, y, B, W, Ar, Z, $R^6$ and n have the starting values, compounds of Formula Ia being encompassed by Formula I;

or Step 1-b, reacting a compound of the formula

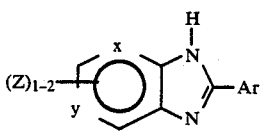

wherein x and y are alternately either carbon or nitrogen, and Ar and Z are as defined under Formula I in sequence with the following agents (a) and (b):

(a) base, e.g. sodium hydride or potassium carbonate in a suitable solvent such as dimethylformamide; and (b) a compound having the formula

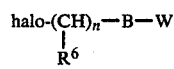

wherein B is selected from

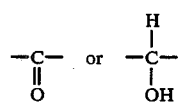

and W, $R^6$ and n are as defined under Formula I to give a compound of the formula

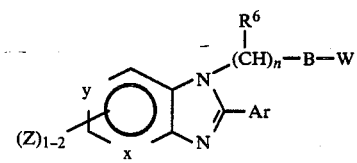

wherein x and y are alternately carbon or nitrogen and W, $R^6$, Z and n are as defined under Formula I, compounds of Formula $I_c$ being encompassed by Formula I;

Step 2, oxidizing a compound prepared in Steps 1-a or 1-b selected from those having the formula

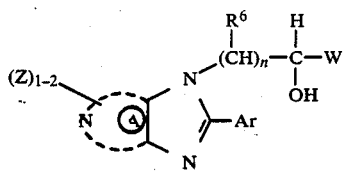

wherein A is a pyridine ring in any of its 4 positions; Ar, Z, n and $R^6$ are as defined above and W is loweralkyl, phenyl or phenylloweralkyl, i.e. $R^1$ except hydrogen, with pyridinium chlorochromate to give a compound having the formula:

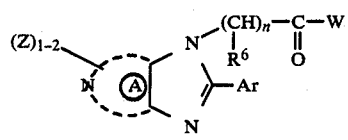

wherein A, Ar, Z, $R^6$, n and W have the starting values in this step, compounds of Formula Id being encompassed by Formula I;

Step 3, reacting a compound obtained in steps 1-a, or 1-b selected from those having the formula

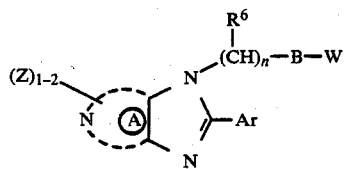

wherein A is a pyridine in any of its 4 positions; B is

and W forms an ester with B consistent with the above definition of W, or a similarly prepared compound wherein W is any feasible esterifying radical;

Ar, Z, $R^6$ and n are as defined above with an alkali-metal base in the presence of water in a suitable solvent such as ethylene glycol (de-esterifying) to give a compound of the formula:

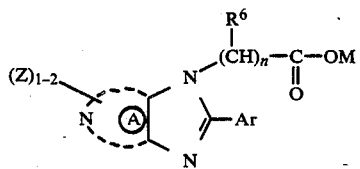

wherein A, Ar, Z, $R^6$ and n are the same as in the starting compound in this step, and M is an alkali-metal, Formula Ie being encompassed by Formula I and thereafter neutralizing the compound of Formula Ie with an acid to obtain a compound having the formula

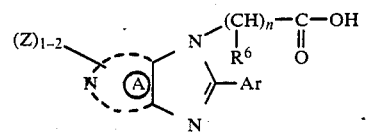

wherein A, Ar, Z, $R^6$ and n are unchanged;

Step 4, reacting and acid compound prepared in Step 3 with one of the following (a), (b), or (c):

(a) 1,1'-carbonyldiimidazole,
(b) oxalyl chloride,
(c) ethyl chloroformate, followed by reacting an amine having the formula:

W'H wherein W' is selected from
—$NR^2(CH_2)_pCOOR^1$,
—$NR^2(CH_2)_pOR^1$,
—$NR^2(CH_2)_pCOOM$,
—$NR^28(CH_2)_pNHC(O)R^1$],
—$NR_2(CH_2)_pQ$,
—$NR^2(CH_2)_p$—$Ar^1$,
—$NR^3R^4$, or
—$NR^2(CH_2)_pNR^3R^4$, and wherein R, $R^2$, $R^3$, $R^4$, Q, $Ar^1$, p and M are as defined under Formula I above to give a compound having the formula:

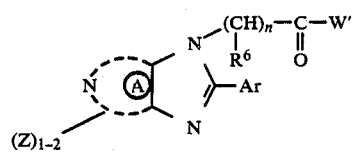

wherein A is a pyridine ring in any of its four positions; Ar, n, Z and $R^6$ are as defined above and W' has the same value as in the starting W'H compound, compounds of Formula Ih being encompassed by Formula I;

Step 5, sulfurizing an amide prepared in Steps 1-a, I-b, or 4 wherein B is

and B-W forms an amide to give a thioamide of the formula:

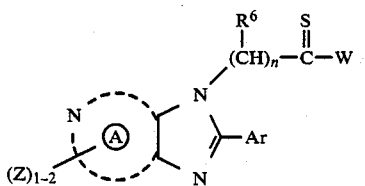

wherein A is a pyridine in any of its four positions;

Ar, Z, $R^6$ and n are as defined above, and W may have any of the amine values as defined under Formula I, compounds of Formula $I_i$ being encompassed by Formula I;

Step 6, oxidizing any of the compounds prepared in Steps 1-5 with m-chloroperbenzoic acid in a anhydrous medium such as glacial acetic acid to obtain an oxide compound having the formula

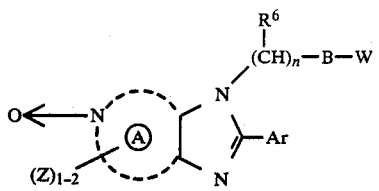 Ij wherein A, Ar, $R^6$, Z, n, B and W have the values given under Formula I above, compounds of Formula $I_j$ being encompassed by Formula I.

In reference to the process steps summarized above as they apply to the preparation of compounds of Formula I, the following description is applicable.

In step 1-a, starting compounds of Formula II (see Chart I) wherein B is

W is $OR^1$ (except $R^1$ is never hydrogen), or W is $NH_2$ or any amino radical given under the definition of Formula I and when B is

W is limited to $R^1$ wherein phenyl may be substituted are heated to cyclize to the imidazoheterocyclic compound. Heating (and consequently the cyclization) may be done with or without solvent, the temperature range encompassed thereby for all the conditions being approximately 100°-240° C. Water is given off during cyclization and usual methods for dehydration and collecting water may be incorporated if desired. When the cyclization is conducted without solvent (i.e. neat) temperatures of about 180°-240° C. may be employed to bring about cyclization in about 5-30 minutes time. When a refluxing solvent such as toluene is used, the water is advantageously collected in a Dean-Stark apparatus and the solvent is returned to the reaction vessel. In the instance at the boiling point of toluene of about 110° C., the cyclization is slower and may require as long as 24 hr. Strong acid catalysts including toluene sulfonic acid are advantageously added to the solvent to shorten the cyclization time. Ethylene glycol may also be used as solvent at higher temperatures to aid in cyclization. In this instance the water tends to be absorbed by the ethylene glycol and does not have to be driven off. If certain cyclizations, ethylene glycol may be the preferred solvent, since the mix can be used directly in Step 3 without separating the product. Thus, from the foregoing description, it may be seen that the temperature used will depend on whether the reaction is conducted neat or with solvent and the type of solvent employed. The extent of reaction may be determined by employing TLC using a low boiling solvent such as methylene chloride on silica base and using Mass Spectrometer readings of the molecular weight.

In step 1-b, 2-aryl-imidazopyridine compounds in which one of the imidazo nitrogens carries a hydrogen radical is added slowly to a slurry of sodium hydride or a suitable base such as anhydrous potassium carbonate in a suitable carrier, preferably dimethylformamide, and the mixture is heated at about 60°-90° C. for 1-2 hr. The

compound is added and the mixture is stirred at ambient temperature for a period of time, usually 12-24 hr. Water is added to decompose any unreacted sodium hydride and the product is isolated by conventional crystallizing procedures, utilizing, if necessary, evaporation of solvent, additional solvents and charcoal or converting to acid addition salts. The [4,5-b] and [4,5-c]-1H isomers are generally the predominant isomers formed in this step. The isomers may be separated by crystallizing out the major component first.

In Step 2, an imidazopyridine having a secondary or tertiary alkanol side chain is oxidized by contacting it with excess pyridinium chlorochromate in a suitable carrier such as methylene chloride at about room temperature until oxidation is complete. The product is isolated by decanting the solution, evaporation and recrystallizing from a suitable solvent such as isopropyl alcohol.

In Step 3, imidazopyridines having a side chain terminated by an ester moiety on the imidazo nitrogen are hydrolyzed by heating with water and alkali-metal base in a suitable solvent such as ethylene glycol or an alkanol such as ethanol to give a solution of alkali-metal acid salt of the resulting acid. The acid salt may be neutralized with any suitable acid to give the free acid which may be separated by precipitation.

In Step 4, the imidazopyridine obtained in Step 3 bearing a side chain terminated by a carboxy radical on one of the imidazo nitrogens is reacted with one of 3 reagents: 1,1'-carbonyldiimidazole, oxalyl chloride, or ethyl chloroformate, followed by the desired amine. When the reagent is 1,1'-carbonyldiimidazole, reaction with the acid is carried out in a suitable carrier, preferably tetrahydrofuran, at about room temperature with a stream of nitrogen gas bubbling through the mixture, usually in about 2-4 hr times. The nitrogen sweeps out carbon dioxide. The amine, W'H, is added and stirring is continued at room temperature, usually for several hours. The resulting amide is isolated by evaporation and redissolving the residue in an appropriate solvent such as methylene chloride followed by common crystallization methods as the free base or an acid addition salt. When oxalyl chloride is the reagent used, it and the carboxylic acid derivative are mixed in a suitable solvent, preferably dimethylformamide, at about 5°-30° C. and the mixture is heated at about 50°-70° C. for 3-5 hr and then added to a cold solution of the W'H amine in dimethylformamide and triethylamine. The product amide is also isolated by usual techniques as the free base or acid addition salt. When ethyl chloroformate is the reagent (see Example 29), it and acid derivative are reacted in a suitable solvent, preferably methylene chloride usually in about 1-3 hr time at room temperature. The W'H amine in solvent is added slowly and the mixture is allowed to stir several hours at ambient temperature. The product amide is separated by conventional means such as evaporation, partitioning between dilute acid and solvent such as diethyl ether followed by column chromatography, if necessary.

In Step 5, a compound prepared in Steps 1-a, 1-b, or 4 wherein B-W forms an amide function is optionally converted to a thioamide by sulfurizing, preferably with phosphorus pentasulfide. Acetonitrile is a suitable and preferred carrier during sulfurization. Product thioamides are isolated by conventional methods which may include chromatography (see Example 53).

In Step 6, the imidazopyridine compounds prepared in Steps 1-5 may be reacted with m-chloroperbenzoic acid, preferably in glacial acetic acid at a temperature of about 40°–70° C. for several hours (see Examples 120 and 121) to produce imidazopyrido-nitrogen oxides. The reaction mixture is diluted with water to precipitate organic acid residue of the spent m-chloroperbenzoic acid and any peroxides are destroyed, preferably with a sulfite reagent. Product oxides are separated and purified by usual methods.

Starting compounds of Formula II:

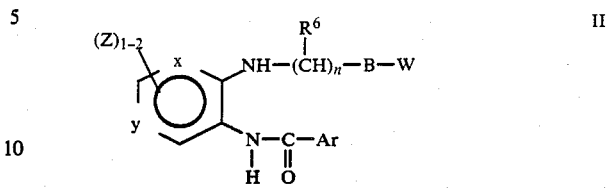

wherein x and y are alternately either carbon or nitrogen, Z, Ar, $R^6$ and n are as defined under Formula I and B and W are as defined in footnote (a) of Chart I are prepared by reactions illustrated by equations A, B and C in Chart II.

CHART II
Preparation of Starting Formula II Compounds (A)

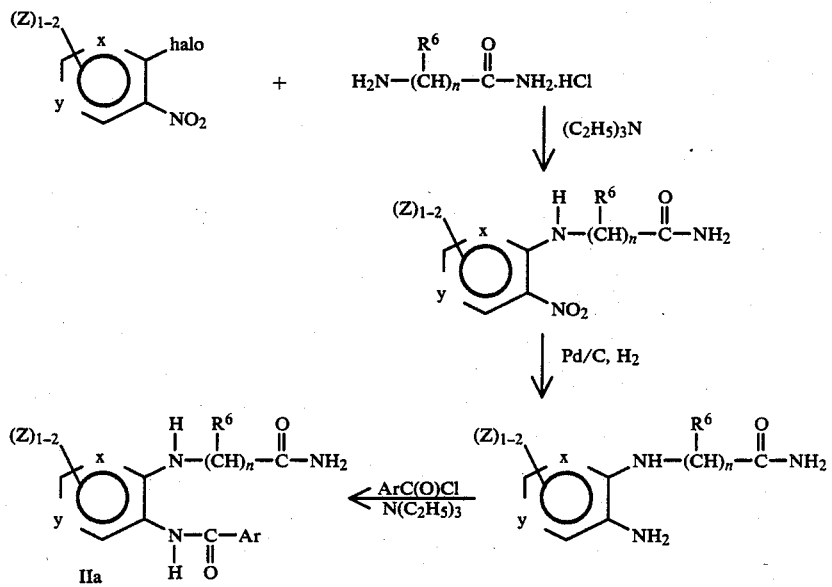

(B)

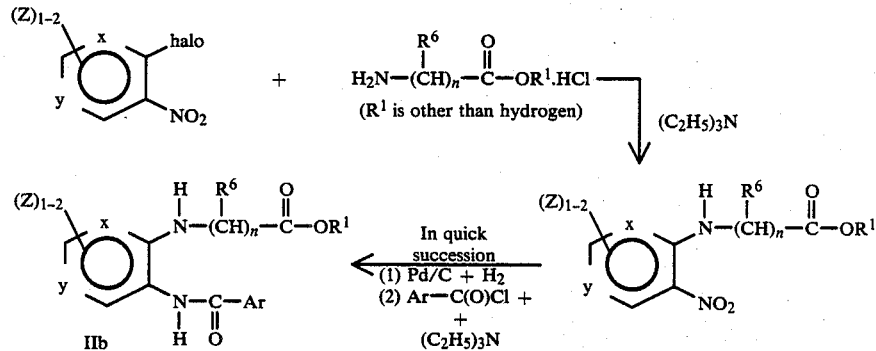

-continued
CHART II
Preparation of Starting Formula II Compounds (C)

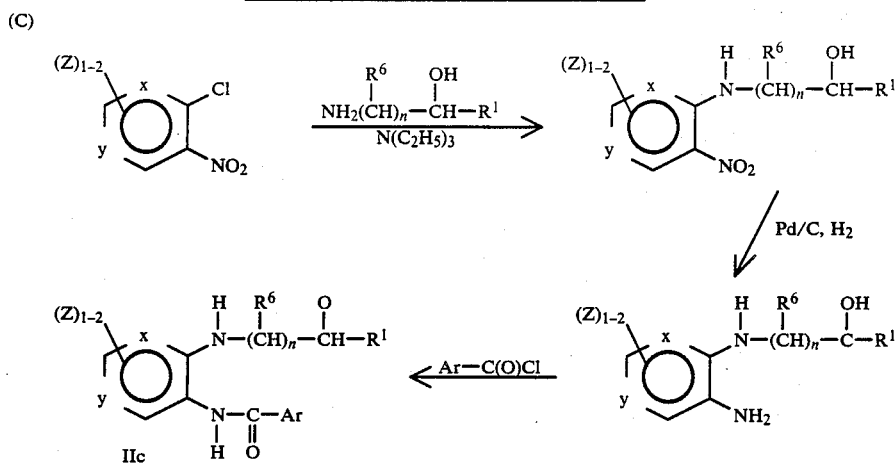

Compounds of Formulas IIa, IIb, and IIc are encompassed by Formula II.

Procedure (B) above in Chart II represents a novel process for the preparation of compounds of Formula IIb. Early attempts to prepare IIb compounds stepwise by this route gave cyclized intermediates after the reduction step. The discovery that addition of ArC(O)Cl immediately after reduction or cooling during the reduction and/or acylation steps prevents the cyclization is the basis of novelty of this novel process. The method B) has application for any compound wherein $R^1$ is an esterifying radical of any kind, such compounds being usable to prepare compounds of Formula I as the end product independent of what the esterifying radical is.

Starting compounds of Formula III:

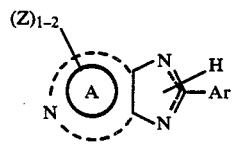

III wherein A, Z and Ar are as defined under Formula I are prepared by reactions represented by the equation in Chart III.

CHART III
Preparation of Starting III Compounds

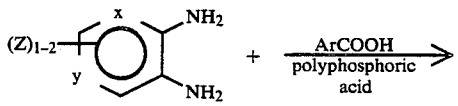

-continued
CHART III
Preparation of Starting III Compounds

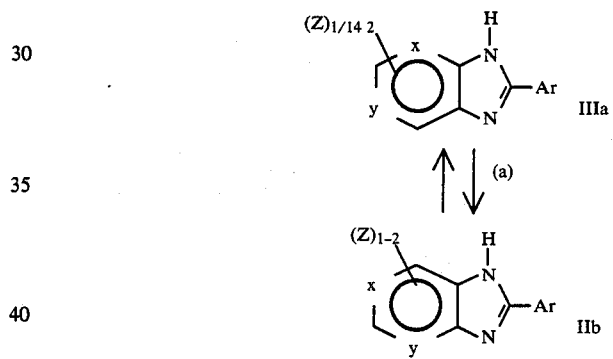

Footnote Chart III
(a) Compounds of IIIa and IIIb in equilibrium are equivalent to II.

The following preparations and examples serve to illustrate methods of preparing the compounds. The scope of the invention is not limited by the preparations and examples; however, structures of the compounds of the examples are given for reference in Table 1.

PREPARATION 1

N-(3-Nitro-2-pyridinyl)glycine ethyl ester

A solution of 2-chloro-3-nitropyridine (50 g, 0.315 mole), glycine ethyl ester hydrochloride (220 g, 1.58 mole), and triethylamine, (155 g, 1.53 mole) in 1 liter of absolute ethanol was stirred and heated to reflux overnight. The reaction mixture was evaporated to a solid mass, which was partitioned between water and ethyl acetate. The aqueous layer was separated and extracted with ethyl acetate (3×). The combined ethyl acetate layer was evaporated to an oil, which was dried by azeotropic distillation with benzene. The residue was purified by silica gel chromatography (8 cm×27 cm column) by elution with 5% methanol/95% benzene. The appropriate fractions totaled 59.2 g of the title product, m.p. 38°-9° C.

Analysis: Calculated for $C_9H_{11}N_3O_4$: C, 48.00; H, 4.92; N, 18.66. Found: C, 48.01; H, 4.94; N, 18.55.

PREPARATION 2

N-[3-(Benzoylamino)-2-pyridinyl]glycine ethyl ester

A solution of N-(3-nitro-2-pyridinyl)glycine ethyl ester (1.0 g, 0.0044 mole) in 140 ml of tetrahydrofuran was hydrogenated over 5% palladium on carbon (0.2 g) at room temperature for 4 hr. The reaction mixture was dried over magnesium sulfate and filtered through a Celite pad. To this stirred solution was added triethylamine (0.6 g, 0.0059 mole) and benzoyl chloride (0.62 g, 0.0044 mole). The reaction mixture was allowed to stir at room temperature overnight. The triethylamine hydrochloride was filtered off and the filtrate was evaporated to dryness. The residue was taken up in ether-methylene chloride solution. Sodium sulfate was added to adsorb an immiscible dark oil. The filtrate was evaporated to dryness to give a residue which was recrystallized from ether. The precipitate was collected, washed with a solution of 75% hexanes/25% ether, and dried at room temperature under high vacuum to yield 1.1 g, of title compound, m.p. 115°–16° C.

Analysis: Calculated for $C_{16}H_{17}N_3O_3$: C, 64.20; H, 5.72; N, 14.04. Found: C, 64.05; H, 5.77; N, 14.00.

PREPARATION 3

2-[(3-Nitro-2-pyridinyl)amino]acetamide

A mixture of 2-chloro-3-nitropyridine (1.0 g, 0.0063 mole), glycinamide hydrochloride (3.11 g, 0.028 mole), triethylamine (3.1 g, 0.031 mole) in 35 ml of acetonitrile was heated at reflux for 16½ hrs. The yellow precipitate was filtered off. The precipitate was slurried and filtered successively with water, absolute alcohol and acetone. The yellow solid was dried under high vacuum at room temperature to give 0.9 g (73.2%), of title compound, m.p. 250°–51° C. with decomposition.

Analysis: Calculated for $C_9H_8N_4O_3$: C, 42.86; H, 4.11; N, 28.56. Found: C, 42.84; H, 4.08; N, 28.43.

PREPARATION 4

N-[2-[[(Aminocarbonyl)methyl]amino]-3-pyridinyl]-benzamide

A mixture of 2-[(3-nitro-2-pyridinyl)amino]acetamide (2.0 g, 0.01 mole) in 160 ml of tetrahydrofuran was hydrogenated over 5% palladium on carbon (0.3 g) at ~55° C. overnight. The reaction mixture was diluted with hot acetonitrile and dried over magnesium sulfate. The mixture was filtered through a Celite pad.

To the stirred filtrate under nitrogen atmosphere was added triethylamine (1.21 g, 0.012 mole) and benzoyl chloride (1.41 g, 0.01 mole). The reaction mixture was allowed to stir at ambient temperature overnight. The reaction mixture was evaporated to a solid residue. The solid was washed with methylene chloride, filtered and the filter cake washed with methylene chloride. The solid was added to water and broken up well with a glass rod, and the solid was again collected by filtration. The solid was dried under high vacuum at room temperature overnight to give 0.7 g (26%) of title compound, m.p. 194°–95° C. with decomposition.

Analysis: Calculated for $C_{14}H_{14}N_4O_2$: C, 62.21; H, 5.22; N, 20.73. Found: C, 61.87; H, 5.17; N, 20.50.

PREPARATION 5

2-[(3-Amino-2-pyridinyl)amino]acetamide

A mixture of 2-[(3-nitro-2-pyridinyl)amino]acetamide (19.6 g, 0.1 mole) in 160 ml of ethyl acetate was hydrogenated over 5% palladium on carbon (2.0 g) at ~55° C. overnight. The reaction mixture was warmed with acetonitrile and filtered through a Celite pad. The pad was washed with hot acetonitrile and the filtrate was evaporated to a solid. A 1.2-g sample of this solid was recrystallized from methanol-acetonitrile to give a light yellow solid, which was dried under high vacuum at room temperature to give 0.4 g, of title compound, m.p. 153°–55° C. with decomposition.

Analysis: Calculated for $C_7H_{10}N_4O$: C, 50.59; H, 6.06; N, 33.71. Found: C, 50.62; H, 6.09; N, 33.40.

PREPARATION 6

N-[3-[(2-Pyridinylcarbonyl)amino]1-2-pyridinyl]glycine ethyl ester

A solution of N-(3-nitro-2-pyridinyl)glycine ethyl ester (2.25 g, 0.01 mole) was hydrogenated over 5% palladium on carbon (0.3 g) at room temperature for 4 hours. The reaction mixture was dried over magnesium sulfate and the mixture was filtered through a Celite pad. The filtrate was added at room temperature over ¾ hour to the imidazolide, which was prepared by adding 1,1'-carbonyldiimidazole (1.69 g, 0.01 mole) in portions to a solution of picolinic acid (1.23 g, 0.01 mole) in 100 ml of tetrahydrofuran while stirring at room temperature for 4 hours. The reaction mixture was filtered and the filtrate was evaporated to a solid. The solid was dissolved in tetrahydrofuran and diluted with ether. The supernatant liquid was decanted from the dark oil which had formed and was evaporated. The residue was dissolved in boiling water, and the solution was filtered, and allowed to crystallize with seeding to give 0.68 g, of title compound, mp 95°–6° C.

Analysis: Calculated for $C_{15}H_{16}N_4O_4$: C, 59.99; H, 5.37; N, 18.66. Found: C, 59.97; H, 5.35; N, 18.58.

PREPARATION 7

N-[2-[(2-Amino-2-oxoethyl)amino]-3-pyridinyl]-2-pyridinecarboxamide

While bubbling nitrogen through a solution of picolinic acid (1.23 g, 0.01 mole) in 100 ml of tetrahydrofuran, solid 1,1'-carbonyldiimidazole (1.62 g, 0.01 mole) was added in portions. The reaction mixture was allowed to stir at room temperature for 5 hours. Then, a solution of 2-[(3-amino-2-pyridinyl)amino]acetamide (1.66 g, 0.01 mole) in acetonitrile was added in portions to the imidazolide solution and the reaction mixture was allowed to stir at room temperature overnight. The solvents were evaporated. The residue completely solidified upon standing. The solid was washed with methylene chloride and the solid was filtered off. The solid was recrystallized from ethyl acetate to give several crops of crystals, which were combined and recrystallized from ethyl acetate to give 0.52 g of title compound, mp 188°–90° C. with decomposition.

Analysis: Calculated for $C_{13}H_{13}N_5O_2$: C, 57.26; H, 4.83; N, 25.81. Found: C, 57.41; H, 4.76; N, 25.66.

PREPARATION 8

N-[3-[[(4-Chloro-2-pyridinyl)carbonyl]amino]-2-pyridinyl] glycine ethyl ester A mixture of 4-chloro picolinic acid (7.38 g, 0.06 mole) and thionyl chloride (29 ml) in 50 ml of benzene was heated at reflux for 3 to 4 hrs, then evaporated to remove solvent and excess thionyl chloride. The residue was azeotroped with benzene (2×). The crude liquid was used without purification.

Meanwhile, N-(3-nitro-2-pyridinyl)glycine ethyl ester (11.25 g, 0.05 mole) dissolved in 160 ml of tetrahydrofuran was hydrogenated at room temperature over 5% palladium on carbon for 1 hr. The reaction mixture was dried over sodium sulfate and filtered through a Celite pad.

The crude 4-chloro picolinoyl chloride and triethylamine (5.55 g, 0.055 mole) were added dropwise simultaneously to the above stirred filtrate of N-(3-amino-2-pyridinyl)glycine ethyl ester at room temperature and allowed to stir overnight.

The reaction mixture was filtered. The tetrahydrofuran filtrate was treated with 50 g of Florisil ®, filtered, and the filtrate evaporated to dryness. A 4 g sample of the dark oil was dissolved in 500 ml of hexane and seeded to initiate crystallization. The hexane was decanted and the solid residue was dissolved in methylene chloride and hexane, and the solution was treated with Florisil ®, and evaporated to an oil, which was crystallized from hexane. The solid was filtered off and dried under high vacuum at room temperature to give 0.9 g of title compound, mp 78°-80° C.

Analysis: Calculated for $C_{15}H_{15}N_4O_3Cl$: C, 53.82; H, 4.52; N, 16.74. Found: C, 53.81; H, 4.51; N, 16.90.

PREPARATION 9

N-[3-[(4-Methoxybenzoyl)amino]-2-pyridinyl]glycine ethyl ester

A solution of N-(3-nitro-2-pyridinyl)glycine ethyl ester (64.4 g, 0.286 mole) in 900 ml of tetrahydrofuran was hydrogenated in a 2-liter Parr bottle over 5% palladium on carbon (6.5 g) at room temperature for 1 hr. The reaction mixture was dried over magnesium sulfate and filtered through a Celite pad. A 235-ml portion of the filtrate was used in this reaction.

Under nitrogen atmosphere, p-anisoyl chloride (9.72 g, 0.057 mole) and triethylamine (6.33 g, 0.063 mole) were added dropwise simultaneously to the above-stirred filtrate at room temperature. The reaction mixture was allowed to stir overnight. The reaction mixture was filtered and the filtrate was treated with Florisil ® (30 g), and evaporated to a solid.

The solid (~½ sample) was dissolved in tetrahydrofuran and diluted with water. The tetrahydrofuran was boiled off and a light green solid was collected. The solid was dissolved in tetrahydrofuran, and the solution was decolorized with charcoal, and filtered through a Celite pad. The tetrahydrofuran solution was diluted with petroleum ether to produce a crystalline crop. The solid was filtered off, washed with petroleum ether, and dried under high vacuum at room temperature to give 2.8 g of title compound, mp 130°-31° C.

Analysis: Calculated for $C_{17}H_{19}N_3O_4$: C, 62.00; H, 5.81; N, 12.76. Found: C, 62.14; H, 5.89; N, 12.61.

PREPARATION 10

N-[3-[(2-Chlorobenzoyl)amino]-2-pyridinyl]glycine ethyl ester

A solution of N-(3-nitro-2-pyridinyl)glycine ethyl ester (64.4 g, 0.286 mole) in 900 ml of tetrahydrofuran was hydrogenated in a 2-liter Parr bottle over 5% palladium on carbon (6.5 g) at room temperature for 1 hr. The reaction mixture was dried over magnesium sulfate and filtered through a Celite pad. A 235-ml portion of the filtrate was used in this reaction.

Under nitrogen atmosphere, o-chlorobenzoyl chloride (9.97 g, 0.057 mole) and triethylamine (6.33 g, 0.063 mole) were added dropwise simultaneously to the above-stirred filtrate at room temperature. The reaction mixture was allowed to stir overnight, filtered, and the filtrate was treated with Florisil ® (30 g), and evaporated to a solid. A 2-g portion was recrystallized from tetrahydrofuran/petroleum ether. The solid was collected, washed with 3:1 petroleum ether/tetrahydrofuran, and dried under high vacuum at room temperature to give 1.45 g of title compound, mp 111°-12° C.

Analysis: Calculated for $C_{16}H_{16}N_3O_3Cl$: C, 57.58; H, 4.83; N, 12.59. Found: C, 57.62; H, 4.86; N, 12.67.

PREPARATION 11

N-[3-[(2-Methoxybenzoyl)amino]-2-pyridinyl]glycine ethyl ester

A solution of N-(3-nitro-2-pyridinyl)glycine ethyl ester (64.4 g, 0.286 mole) in 900 ml of tetrahydrofuran was hydrogenated in a 2-liter Parr bottle over 5% palladium on carbon (6.5 g) at room temperature for 1 hour. The reaction mixture was dried over magnesium sulfate and filtered through a Celite pad. A 235-ml portion of the filtrate was used in this reaction. Under nitrogen atmosphere, o-anisoyl chloride (9.72 g, 0.057 mole) and triethylamine (6.33 g, 0.063 mole) were added dropwise simultaneously to the above-stirred filtrate at room temperature. The reaction mixture was allowed to stir overnight. The reaction mixture was filtered, and the filtrate was treated with Florisil ® (30 g), and evaporated to a solid. The solid was recrystallized from hot tetrahydrofuran (minimum). The solid was filtered off, washed with cold tetrahydrofuran, and dried under high vacuum at room temperature to give 5.7 g of title compound, mp 111°-12° C.

Analysis: Calculated for $C_{17}H_{19}N_3O_4$: C, 62.00; H, 5.81; N, 12.76. Found: C, 62.00; H, 5.81; N, 12.85.

PREPARATION 12

N-[3-[(3-Chlorobenzoyl)amino]-2-pyridinyl]glycine ethyl ester

A solution of N-(3-nitro-2-pyridinyl)glycine ethyl ester (64.4 g, 0.286 mole) in 900 ml of tetrahydrofuran was hydrogenated in a 2-liter Parr bottle over 5% palladium on carbon (6.5 g) at room temperature for 1 hr. The reaction mixture was dried over magnesium sulfate and filtered through a Celite pad. A 235-ml portion of the filtrate was used in this reaction.

Under nitrogen atmosphere, m-chlorobenzoyl chloride (9.97 g, 0.057 mole) and triethylamine (6.33 g, 0.063 mole) were added dropwise simultaneously to the above-stirred filtrate at room temperature. The reaction mixture was allowed to stir overnight, filtered, and the filtrate was treated with Florisil ® (30 g), and evaporated to a solid. A 2-g portion was recrystallized from tetrahydrofuran/petroleum ether. The solid was collected, washed with 3:1 petroleum ether/tetrahydrofuran, and dried under high vacuum at room temperature to give 1.4 g of title compound, mp 143°-44° C.

Analysis: Calculated for $C_{16}H_{16}N_3O_3Cl$: C, 57;58; H, 4.83; N, 12.59. Found: C, 57.57; H, 4.83; N, 12.60.

PREPARATION 13

N-[3-[(4-Chlorobenzoyl)amino]-2-pyridinyl]glycine ethyl ester

A solution of N-(3-nitro-2-pyridinyl)glycine ethyl ester (64.4 g, 0.286 mole) in 900 ml of tetrahydrofuran was hydrogenated in a 2-liter Parr bottle over 5% palladium on carbon (6.5 g) at room temperature for 1 hour.

The reaction mixture was dried over magnesium sulfate and filtered through a Celite pad. A 235-ml portion of the filtrate was used in this reaction.

Under nitrogen atmosphere, p-chlorobenzoyl chloride (9.97 g, 0.057 mole) and triethylamine (6.33 g, 0.063 mole) were added dropwise simultaneously to the above stirred filtrate at room temperature. The reaction mixture was allowed to stir overnight. The reaction mixture was filtered, and the filtrate was treated with Florisil® (30 g), and evaporated to a solid. The solid was recrystallized from tetrahydrofuran-water. The product was collected, washed with water, and dried under high vacuum first at 50° C. overnight, then at 65° C. overnight to give 16.5 g of title compound, mp 133°–4° C.

Analysis: Calculated for $C_{16}H_{16}N_3O_3Cl$: C, 57.58; H, 4.83; N, 12.59. Found: C, 57.35; H, 4.80; N, 12.44.

PREPARATION 14

N-[2-[(2-Amino-2-oxoethyl)amino]-3-pyridinyl]-4-chlorobenzamide hydrate [2:1].

A mixture of 2-[(3-nitro-2-pyridinyl)amino]acetamide (26.0 g, 0.133 mole) in 200 ml of ethyl acetate was hydrogenated over 5% palladium on carbon (3.0 g) at 55°–60° C. for 2 hr. The reaction mixture was diluted with hot methanol and filtered through a Celite pad. The pad was washed several times with hot methanol until the filtrate was clear and colorless. The filtrate was evaporated and dried by azeotropic evaporation of benzene (3×). The solid residue was placed under high vacuum overnight at room temperature.

To a stirred mixture of the above solid in 1 liter of acetone was added dropwise simultaneously p-chlorobenzoyl chloride (23.28 g, 0.133 mole) and triethylamine (14.75 g, 0.146 mole). The reaction mixture was allowed to stir overnight at room temperature. The precipitate was filtered off, washed with acetone, and allowed to dry under ambient conditions. The solid was dissolved in hot methanol, filtered, and the filtrate was concentrated to produce a crystalline crop. The solid was filtered, washed with cold methanol and water, then dried under high vacuum at room temperature over the weekend. The sample was redried under high vacuum at 60° C. overnight to give 18.36 g of title compound, mp 194°–5° C. with decomposition.

Analysis: Calculated for $C_{14}H_{13}N_4O_2Cl.\frac{1}{2}\,H_2O$: C, 53.60; H, 4.50; N, 17.86. Found: C, 53.89; H, 4.59; N, 17.75.

PREPARATION 15

N-[2-[(2-Amino-2-oxoethyl)amino]-3-pyridinyl]-2-chlorobenzamide hydrochloride [1:1]

A mixture of 2-[(3-nitro-2-pyridinyl)amino]acetamide (26.0 g, 0.133 mole) in 200 ml of ethyl acetate was hydrogenated over 5% palladium on carbon (3.0 g) at 55°–60° C. for 2 hr. The reaction mixture was diluted with hot methanol and filtered through a Celite pad. The pad was washed several times with hot methanol until the filtrate was clear and colorless. The filtrate was evaporated and dried by azeotropic evaporation of benzene (3×). The solid residue was placed under high vacuum overnight at room temperature.

To a stirred mixture of the above solid in 1 liter of acetone was added dropwise simultaneously o-chlorobenzoyl chloride, (23.28 g, 0.133 mole) and triethylamine (14.75 g, 0.146 mole). The reaction mixture was allowed to stir overnight at room temperature. The reaction mixture was filtered and the filter cake washed with acetone and discarded. The filtrate and wash were evaporated to a foamy solid, which was dried under high vacuum at room temperature. A 5-g sample was dissolved in methanol and the solution was acidified with methanolic hydrogen chloride to slowly produce a crystalline solid. The solid was filtered, washed with cold methanol, and dried under high vacuum at room temperature over 3 days to give 4.33 g of title compound, mp 198°–200° C. with decomposition.

Analysis: Calculated for $C_{14}H_{13}N_4O_2Cl.HCl$: C, 49.28; H, 4.14; N, 16.42. Found: C, 48.94; H, 4.34; N, 16.22.

PREPARATION 16

N-[3-[(3-Fluorobenzoyl)amino]-2-pyridinyl]glycine ethyl ester

Under a nitrogen atmosphere, 3-fluorobenzoyl chloride (12.9 g, 0.0816 mole) was added dropwise to a stirred and chilled (10°–15° C.) mixture of N-(3-amino-2-pyridinyl)glycine ethyl ester (0.0816 mole) [freshly prepared by the hydrogenation of a solution of N-(3-nitro-2-pyridinyl)glycine ethyl ester in tetrahydrofuran over 5% palladium on carbon at room temperature], triethylamine (8.3 g, 0.0816 mole), anhydrous tetrahydrofuran (200 ml), and powdered molecular sieves. The reaction mixture was stirred at room temperature for 1 hour and was filtered. The filtrate was concentrated in vacuo and the residual solid triturated in isopropyl ether-isopropyl alcohol, giving 24.2 g (94%). Recrystallization of a 2.0-g sample gave 1.72 g of a white powder, mp 134°–135° C.

Analysis: Calculated for $C_{16}H_{16}N_3O_3F$: C, 60.56; H, 5.08; N, 13.24. Found: C, 60.45; H, 5.07; N, 13.20.

PREPARATION 17

3-[(3-Nitro-2-pyridinyl)amino]propanoic acid ethyl ester hydrochloride [1:1]

The mixture of 2-chloro-3-nitropyridine (25.8 g, 0.16 mole), β-alanine ethyl ester hydrochloride (50 g, 0.33 mole), triethylamine (49.4 g, 0.49 mole), and 300 ml of absolute ethanol was warmed at 50°–55° C. for 4 hr with mechanical stirring. The reaction mixture was evaporated and the residue was partitioned between water and methylene chloride. The water layer was separated and extracted with methylene chloride (2×). The combined methylene chloride extracts were washed with water (2×) and dried over anhydrous sodium sulfate. The filtrate was evaporated to an orange oil (39.2 g). A 2-g sample of the oil was dissolved in acetonitrile acidified with ethereal hydrogen chloride (excess), and scratched to initiate crystallization. The yellow solid was filtered off, washed with ether, and dried under high vacuum at room temperature overnight to give 1.62 g of the title compound, mp 137°–40° C. (sealed tube).

Analysis: Calculated for $C_{10}H_{13}N_3O_4.HCl$: C, 43.57; H, 5.12; N, 15.24. Found: C, 43.53; H, 5.14; N, 15.27.

PREPARATION 18

3-[(3-Nitro-2-pyridinyl)amino]propanoic acid ethyl ester

A mixture of 2-chloro-3-nitropyridine (68.6 g, 0.434 mole), β-alanine ethyl ester hydrochloride (100 g, 0.651 mole), triethylamine (103.7 g, 1.03 mole) and 95% ethanol (675 ml) was refluxed for 5 hr and then stirred at room temperature overnight. The solvent was evaporated at reduced pressure and the residue was triturated in ethyl acetate (700 ml). The solid was filtered and washed with ethyl acetate. The filtrate was washed three times with water, dried over anhydrous sodium sulfate, filtered and evaporated at reduced pressure to give 113.4 g of an oil. The oil was eluted through a silica gel column (400 g) with ethyl acetate. The eluent was evaporated at reduced pressure to give 106.2 g of an oil (100% yield). A small portion of the oil was crystallized from petroleum ether to give 0.7 g of yellow solid of the title compound, mp. 32.5°–33.5° C.

Analysis: Calculated for $C_{10}H_{13}N_3O_4$: C, 50.21; H, 5.48; N, 17.56. Found: C, 50.22; H, 5.49; N, 17.65.

PREPARATION 19

N-[3-[(4-Bromobenzoyl)amino]-2-pyridinyl]glycine ethyl ester

To a stirred and chilled (10°–20° C.) solution of N-(3-amino-2-pyridinyl)glycine ethyl ester (14.7 g, 0.075 mole) [freshly prepared by the hydrogenation of a solution of N-(3-nitro-2-pyridinyl) glycine ethyl ester in tetrahydrofuran over 5% palladium on carbon at room temperature], triethylamine 8.1 g, 0.080 mole), and tetrahydrofuran (150 ml) was added (rapid drop) 4-bromobenzoyl chloride (6.9 g, 0.077 mole), followed by 100 ml of methylene chloride. The reaction mixture was stirred at room temperature for 2 hr and was filtered. The filtrate was concentrated in vacuo and the residue combined with the filter cake. The combined mixture was twice suspended in water and filtered. The filter cake was recrystallized from ethanol, giving 22.7 g of crystals (80%). Recrystallization of a 1.6-g samples from ethanol gave 1.5 g of white flocculent solid, mp 153°–154° C.

Analysis: Calculated for $C_{16}H_{16}N_3O_3Br$: C, 50.81; H, 4.26; N, 11.11. Found: C, 50.47; H, 4.27; N, 11.09.

PREPARATION 20

3-[[3-[(4-Chlorobenzoyl)amino]-2-pyridinyl]amino]-propanoic acid ethyl ester A solution of the free base of 3-[(3-nitro-2-pyridinyl)-amino]propanoic acid ethyl ester monohydrochloride, (73.2 g, 0.31 mole) in 900 ml of tetrahydrofuran was hydrogenated over 5% palladium on carbon (7.3 g) at room temperature for 1 hr. The reaction mixture was dried over magnesium sulfate, filtered, and the filtrate was divided into 3 equal volumes.

To this stirred filtate (⅓ volume, 0.102 mole) was added simultaneously triethylamine (11.33 g, 0.11 mole) and p-chlorobenzoyl chloride (17.85 g, 0.102 mole). The reaction mixture was allowed to stir at room temperature overnight and filtered to remove triethylamine hydrochloride. The filtrate was treated with Florisil ® (50 g), then filtered. The filtrate was treated with charcoal (6 g) overnight, filtered through Celite, and evaporated to a solid. A 3-g sample was dissolved in tetrahydrofuran (minimum) and diluted with petroleum ether (bp 50°–110° C.) until crystallization was initiated. The solid was collected and recrystallized twice from tetrahydrofuran/petroleum ether to give a light tan solid which was dried under high vacuum at 55°–60° C. to give 1.6 g of title compound, mp 124°–25° C.

Analysis: Calculated for $C_{17}H_{18}N_3O_3Cl$: C, 58.71; H, 5.22; N, 12.08. Found: C, 58.63; H, 5.24; N, 12.00.

PREPARATION 21

3-[[3-[(3-Chlorobenzoyl)amino]-2-pyridinyl]amino]-propanoic acid ethyl ester A solution of 3-[(3-nitro-2-pyridinyl)amino]-propanoic acid ethyl ester (73.2 g, 0.31 mole) in 900 ml of tetrahydrofuran was hydrogenated over 5% palladium on carbon (7.3 g) at room temperature for 1 hr. The reaction mixture was dried over magnesium sulfate, filtered, and the filtrate was divided into 3 equal volumes.

To this stirred filtrate (⅓ volume, 0.102 mole) was added simultaneously triethylamine (11.33 g, 0.11 mole) and m-chlorobenzoyl chloride (17.85 g, 0.102 mole). The reaction mixture was allowed to stir at room temperature overnight. The reaction mixture was filtered to remove triethylamine hydrochloride. The filtrate was treated with Florisil ® (50 g), then refiltered. The filtrate was treated with charcoal (6 g) overnight, filtered through Celite, and evaporated to dryness. A portion of the solid residue (~3–4 g) was treated with ~50 ml of tetrahydrofuran, filtered, and the filtrate was diluted with petroleum ether (bp 50°–110° C.) until crystallization was inititated. The solid was collected and dried under high vacuum at 55° C. overnight. The solid was recrystallized using tetrahydrofuran-water (with methanol to eliminate phasing) with filtering to remove insoluble dark oil. The crystalline solid was collected, washed with water, and dried under high vacuum (50°–55° C.) overnight to give 0.55 g of title compound, mp 111°–12° C.

Analysis: Calculated for $C_{17}H_{18}N_3O_3Cl$: C, 58.71; H, 5.22; N, 12.08. Found: C, 58.64; H, 5.26; N, 12.07.

PREPARATION 22

3-[[3-[(2-Chlorobenzoyl)amino]-2-pyridinyl]amino]-propanoic acid ethyl ester A mixture of 3-[(3-nitro-2-pyridinyl)amino]propanoic acid ethyl ester (73.2 g, 0.306 mole) in 900 ml of tetrahydrofuran was hydrogenated over 5% palladium on carbon (7.3 g) at room temperature for 1 hour. The reaction mixture was dried over magnesium sulfate and filtered. The filtrate was divided into 3 equal parts.

To the above stirred filtrate (⅓ volume, 0.102 mole) was added dropwise simultaneously o-chlorobenzoyl chloride (17.85 g, 0.102 mole) and triethylamine (11.33 g, 0.11 mole). The reaction mixture was allowed to stir overnight at room temperature. The reaction mixture was filtered to remove triethylamine hydrochloride. The filtrate was treated with Florisil ® (50 g), filtered, and evaporated to dryness. The dark residue was dissolved in ethanol, diluted with water, and refrigerated overnight with seed crystals. The dark crystalline precipitate was filtered off and dried under high vacuum at room temperature overnight. A ~9 g sample was heated to boiling in ~600 ml of water and the mixture was filtered hot through a Celite pad to remove an insoluble dark oil. The crystalline precipitate, which formed upon cooling, was filtered off and dried under high vacuum at room temperature overnight (~1.6 g). The solid was recrystallized from methanol-water. The crystalline precipitate was filtered and dried under high vacuum at 50° C. overnight to give 0.95 g of title compound, mp 90°–92° C.

Analysis: Calculated for $C_{17}H_{18}N_3O_3Cl$: C, 58.71; H, 5.22; N, 12.08. Found: C, 58.80; H, 5.20; N, 12.05.

PREPARATION 23

N-[2-[(2-Amino-2-oxoethyl)amino]-3-pyridinyl]-3-chlorobenzamide

A mixture of 2-[(3-nitro-2-pyridinyl)amino]acetamide (26.0 g. 0.133 mole) in 200 ml of ethyl acetate was hydrogenated over 5% palladium on carbon (3.0 g) at 55°–60° C. for 2 hours. The reaction mixture was diluted with hot methanol and filtered through Celite. The Celite pad was washed with hot methanol until the filtrate was colorless. The filtrate was evaporated to dryness and azeotropically dried with benzene. The solid was dried under high vacuum overnight.

To a stirred mixture of the above solid in 1 liter of acetone was added dropwise simultaneously m-chlorobenzoyl chloride (23.28 g, 0.133 mole) and triethylamine (14.75 g, 0.146 mole). The reaction mixture was allowed to stir overnight. The precipitate was filtered off and the filter cake was washed with acetone. The filter cake was dried under high vacuum overnight. The solid was dissolved in methanol (~25 g in 1.4 liter) and filtered. The clear filtrate was concentrated to ~700 ml to produce a crystalline precipitate; which was filtered, washed with cold methanol and water, and dried under high vacuum at 50° C. overnight to give 11.6 g of title compound, mp 210°–11° C.

Analysis: Calculated for $C_{14}H_{13}N_4O_2Cl$: C, 55.18; H, 4.30; N, 18.38. Found: C, 55.15; H, 4.33; N, 18.77.

Two additional concentrations gave 18.6 g additional crystals for a total yield of 30.2 g of product.

PREPARATION 24

N-[3-[[3-(Trifluoromethyl)benzoyl]amino]-2-pyridinyl]glycine ethyl ester

Under a nitrogen atmosphere, 3-trifluoromethylbenzoyl chloride (15.2 g, 0.073 mole) and triethylamine (7.4 g, 0.073 mole) were added dropwise and simultaneously to a stirred and chilled (10°–15° C.) solution of freshly prepared N-[(3-amino)-2-pyridinyl]glycine ethyl ester (0.070 mole), obtained by 5% palladium on carbon hydrogenation of N-(3-nitro-2-pyridinyl)glycine ethyl ester at room temperature, in dry tetrahydrofuran (200 ml). The reaction mixture was stirred overnight at room temperature and filtered. The filtrate was concentrated in vacuo and the residue dissolved in ethyl acetate (150 ml). The ethyl acetate solution was extracted with saturated sodium bicarbonate (3×50 ml), water (2×50 ml), dried over anhydrous sodium sulfate and concentrated to give a crude yield of 25.5 g (99%). A 3.5-g portion was recrystallized from tetrahydrofuran-isopropyl ether to give 2.7 g of off-white needles, mp 129°–130° C.

Analysis: Calculated for $C_{17}H_{16}N_3O_3F_3$: C, 55.59; H, 4.39; N, 11.44. Found: C, 55.61; H, 4.41; N, 11.42.

PREPARATION 25

N-[3-[(3-Bromobenzoyl)amino]-2-pyridinyl]glycine

Under a nitrogen atmosphere, 3-bromobenzoyl chloride (0.10 mole) (freshly prepared) and triethylamine (10.1 g, 0.010 mole) were added dropwise and simultaneously to a stirred and chilled (10°–15° C.) solution of freshly prepared N-[(3-amino)-2-pyridinyl]glycine ethyl ester (0.07 mole), obtained by 5% palladium on carbon hydrogenation of N-(3-nitro-2-pyridinyl) glycine ethyl ester at room temperature, in dry tetrahydrofuran (200 ml). The reaction mixture was stirred overnight at room temperature and then was filtered. The filtrate was concentrated and the residue dissolved in ethyl acetate (150 ml) and washed with saturated sodium bicarbonate (3×50 ml), water (2×50 ml), saturated sodium chloride brine (30 ml), dried over anhydrous sodium sulfate, and concentrated. The residue was recrystallized from isopropyl alcohol-isopropyl ether giving 22 g (83%) of crystals. A 1.7-g portion was recrystallized from isopropyl alcohol/isopropyl ether to give 1.2 g of white solid, mp 139°–140° C.

Analysis: Calculated for $C_{16}H_{16}N_3O_3Br$: C, 50.81; H, 4.26; N, 11.11. Found: C, 50.76; H, 4.28; N, 11.02.

PREPARATION 26

N-[3-[(2-Pyridinylcarbonyl)amino]-2-pyridinyl]glycine ethyl ester

Under a nitrogen atmosphere, triethylamine (0.30 mole) and a solution of freshly prepared acid chloride of 2-pyridine carboxylic acid (0.150 mole), obtained by heating at reflux 2-pyridine carboxic acid and excess thionyl chloride in benzene and then azeotropic distillation with benzene, in dry tetrahydrofuran (50 ml) were added simultaneously (dropwise) to a stirred and chilled (10°–20° C.) solution of freshly prepared N-(3-amino-2-pyridinyl)glycine ethyl ester prepared by reducing N-(3-nitro-2-pyridinyl)glycine ethyl ester (0.106 mole) in 200 ml of dry tetrahydrofuran. The reaction mixture was stirred overnight at room temperature and was filtered. The filtrate was concentrated in vacuo and dissolved in ethyl acetate (250 ml). The solution was washed with saturated sodium bicarbonate solution (3×75 ml), water (2×75 ml), dried over anhydrous sodium sulfate, and concentrated in vacuo. The residue was crystallized from isopropyl ether-tetrahydrofuran giving 26.5 g (83%). A 3.0-g sample was twice recrystallized from isopropyl ether-tetrahydrofuran to give 2.4 g of a white needles, mp 98°–100° C.

Analysis: Calculated for $C_{15}H_{16}N_4O_3$: C, 59.99; H, 5.37; N, 18.66. Found: C, 59.86; H, 5.40; N, 18.62.

PREPARATION 27

N-[3-[[4-(Trifluoromethyl)benzoyl]amino]-2-pyridinyl]glycine ethyl ester

Under a nitrogen atmosphere, triethylamine (7.4 g, 0.073 mole) and 4-trifluoromethylbenzoyl chloride (15.2 g, 0.073 mole) were added simultaneously (dropwise) to a stirred and chilled (10°–15° C.) solution of freshly prepared N-(3-amino-2-pyridinyl)glycine ethyl ester (0.073 mole), obtained by 5% palladium on carbon hydrogenation of N-(3-nitro-2-pyridinyl) glycine ethyl ester at room temperature, in dry tetrahydrofuran (200 ml). The reaction mixture was stirred at room temperature for 2½ hr and filtered. The filtrate was evaporated to dryness and the residue dissolved in methylene chloride (500 ml). The solution was washed with saturated sodium bicarbonate solution (2×100 ml), water (100 ml), dried over anhydrous sodium sulfate, and concentrated in vacuo, giving 24.9 g (93%) of solid. A 2.0-g sample was recrystallized from isopropyl alcohol-isopropyl ether to give white solid, mp 155°–156° C.

Analysis: Calculated for $C_{17}H_{16}N_3O_3F_3$: C, 55.59; H, 4.39; N, 11.44. Found: C, 55.52; H, 4.40; N, 11.38.

PREPARATION 28

N-[3-[(3,4-Dichlorobenzoyl)amino]-2-pyridinyl]glycine ethyl ester

A solution of N-(3-nitro-2-pyridinyl)glycine ethyl ester (22.5 g, 0.1 mole) in 250 ml of tetrahydrofuran was hydrogenated in a small Parr bottle over 5% palladium on carbon (2.5 g) at room temperature for 1 hr. The reaction mixture was dried over magnesium sulfate and filtered through a Celite pad. Under nitrogen atmosphere, 3,4-dichlorobenzoyl chloride (20.95 g, 0.1 mole) and triethylamine (11.1 g, 0.11 mole) were added dropwise simultaneously to the above stirred filtrate at room temperature. After stirring overnight, the reaction mixture was filtered and the filtrate was evaporated to dryness. The residue was treated with acetone and water to obtain a crystalline solid, which was refrigerated overnight. The solid was collected by filtration, washed with water, and dried under high vacuum at 50° C. overnight (37.1 g). A 4-g sample was recrystallized from acetone/water and dried under high vacuum at 50° C. for 2 days to give 2.66 g of title compound, mp 137°–38° C.

Analysis: Calculated for $C_{16}H_{15}N_3O_3Cl_2$: C, 52.19; H, 4.11; N, 11.41. Found: C, 52.09; H, 4.13; N, 11.44.

PREPARATION 29

N-[3-[(4-Nitrobenzoyl)amino]-2-pyridinyl]glycine ethyl ester

Under a nitrogen atmosphere, triethylamine (14.9 g, 0.148 mole) and 4-nitrobenzoyl chloride (27.5 g, 0.148 mole) in tetrahydrofuran (25 ml) were added simultaneously (dropwise) to a stirred and chilled (5°–10° C.) solution of freshly prepared N-(3-amino-2-pyridinyl)glycine ethyl ester (0.14 mole), obtained by 5% palladium on carbon hydrogenation of N-(3-nitro-2-pyridinyl) glycine ethyl ester at room temperature, in dry tetrahydrofuran (140 ml). The reaction mixture was stirred at room temperature under nitrogen overnight and the solvent was evaporated under reduced pressure. The resulting solid was triturated in water (200 ml) and saturated sodium bicarbonate solution (200 ml). The solid was filtered off, rinsed with water and dried under vacuum at 50° C. to give 50.5 g (95%) of yellow solid. A 2.0-g sample was recrystallized from isopropyl alcohol to give 1.5 g of yellow solid, mp. 151°–154° C.

Analysis: Calculated for $C_{16}H_{16}N_4O_5$: C, 55.81; H, 4.68; N, 16.27. Found: C, 55.81; H, 4.67; N, 16.28.

PREPARATION 30

(S)-N-(3-Nitro-2-pyridinyl)alanine hydrochloride [1:1]

A suspension of 2-chloro-3-nitropyridine (68.6 g, 0.434 mole), (S)-alanine ethyl ester hydrochloride (100 g, 0.651 mole) and triethylamine (103.7 g, 1.03 mole) in 95% ethanol was heated at reflux for 4.5 hours, during which time a dark yellow solution formed. The reaction mixture was stirred at room temperature overnight and then refluxed for an additional 2 hours. The solvents were evaporated under reduced pressure, and the resulting solid was triturated in ethyl acetate, filtered, and rinsed with additional ethyl acetate. The filtrate and washings were combined and washed three times with water, dried over sodium sulfate, filtered, and evaporated to an oil weighing 107 g (quantitative yield). The oil was eluted through 600 g of silica gel, using ethyl acetate as the eluent, and evaporated to an oil. A 3.5-g portion of the oil was dissolved in isopropyl alcohol and acidified with ethereal hydrogen chloride. The mixture was evaporated and redissolved in acetonitrile. Addition of isopropyl ether caused a solid to precipitate. The solid was collected by filtration and its mother liquor was evaporated and the residue was triturated in ethereal hydrogen chloride. A yellow solid formed which was collected by filtration. Upon standing, more solid formed in the mother liquor. This solid was collected by filtration, rinsed with diethyl ether and dried under high vacuum to give 0.14 g of title compound, mp >260° C. (darkens 178°–185° C.).

Analysis: Calculated for $C_8H_{10}N_3O_4Cl$: C, 38.80; H, 4.07; N, 16.97. Found: C, 39.14; H, 4.19; N, 16.74.

PREPARATION 31

(S)-N-[3-[(4-Chlorobenzoyl)amino]-2-pyridinyl]alanine ethyl ester hydrochloride[1:1]

A solution of (S)-N-(3-nitro-2-pyridinyl)alanine ethyl ester (5.0 g, 0.0209 mole) in tetrahydrofuran (60 ml) was hydrogenated over 5% palladium on carbon (0.5 g) keeping the temperature of the solution at approximately room temperature to give (S)-N-(3-amino-2-pyridinyl) alanine ethyl ester. The solution of the reduction product was cooled in an ice bath and dried over magnesium sulfate under nitrogen. The solution was filtered and 4-chlorobenzoyl chloride (3.84 g, 0.022 mole) and triethylamine (2.22 g, 0.022 mole) were added simultaneously, dropwise, to the cooled and stirred solution. The reaction mixture was stirred at room temperature overnight under nitrogen and the solvents were removed under reduced pressure. The residue was partitioned between water (50 ml) and ethyl acetate (50 ml). The layers were separated and the aqueous layer was extracted again with ethyl acetate. The combined organic layers were washed twice with water, dried over magnesium sulfate, treated with charcoal, filtered and evaporated to an oil weighing 6.2 g (85% yield). A 2.2-g portion of the oil was dissolved in isopropyl alcohol and the solution was acidified with ethereal hydrogen chloride. The resulting solid was filtered and dried under high vacuum to give 1.70 g of title compound, mp 172°–177° C. with decomposition.

Analysis: Calculated for $C_{17}H_{19}N_3O_3Cl_2$: C, 53.14; H, 4.98; N, 10.94. Found: C, 53.11; H, 5.02; N, 10.91.

PREPARATION 32

N,N,N'-Trimethyl-1,4-benzenediamine hydrochloride[1:2]

Formic acid (95–97%, 15 g, 0.326 mole) was added dropwise to acetic anhydride (27 g, 0.264 mole) at 0° C. under a nitrogen atmosphere. The resulting solution was heated at 55° C. for 3 hours under a nitrogen atmosphere, then cooled to −20° C. and a solution of N,N-dimethyl-1,4-phenylenediamine (13.6 g, 0.100 mole) in dry tetrahydrofuran (40 ml) was added. After stirring at −20° C. for 30 minutes, the solvents were removed under reduced pressure. The dark residue was dissolved in dry tetrahydrofuran (50 ml) and the solution was cooled in an ice bath. Over 30 minutes, a solution of borane-methyl sulfide in tetrahydrofuran (2.0M, 125 ml, 0.25 mole) was added dropwise. The ice bath was removed, and upon warming, a vigorous reaction commenced. Upon its cessation, the solution was heated to reflux for 3 hours, stirred at room temperature overnight and cooled in ice. Methanol (40 ml) was added. After the mixture was stirred at 0° C. for one hour, 200 ml of methanolic hydrogen chloride solution was added to pH ≦2. The reaction mixture was refluxed for one hour and cooled to room temperature. Evaporation of the solvents under reduced pressure gave a dark solid residue. Water (200 ml) and sodium hydroxide pellets were added to pH ≧12 and the product was extracted into 3 (200-ml) portions of diethyl ether. The combined ether layers were washed with water (200 ml (3×)), dried over magnesium sulfate, charcoaled, and filtered. Evaporation of the solvents under reduced pressure gave an oily liquid (12.1 g, 80.7% yield). A 7.9-g sample of the oil was dissolved in absolute ethanol and the solution was acidified with hydrogen chloride in methanol and hydrogen chloride in isopropyl alcohol. A solid precipitated and was collected by filtration, rinsed with isopropyl alcohol-isopropyl ether and then isopropyl ether. Drying under high vacuum gave 8.92 g of title compound, mp 207°-210° C.

Analysis: Calculated for $C_9H_{16}N_2Cl_2$: C, 48.44; H, 7.23; N, 12.55. Found: C, 48.44; H, 7.41; N, 12.38.

PREPARATION 33

2-(4-Chlorophenyl)-3H-imidazo[4,5-b]pyridine

A mixture of 2,3-diaminopyridine (10.9 g, 0.1 mole), p-chlorobenzoic acid (16.0 g, 0.102 mole), and 150 g of polyphosphoric acid was heated at 180° C. in an oil bath for 3½ hr. The reaction mixture was neutralized with concentrated ammonium hydroxide and bisified with sodium hydroxide. The precipitate was filtered and washed with water. The solid was treated with dilute sodium hydroxide, filtered, washed with water, and dried under high vacuum at 60° C. overnight. A 3-g sample was dissolved in hot methanol, and the solution was treated with 3 g of charcoal, and filtered through a Celite pad. The product crystallized from the filtrate upon cooling. The precipitate was filtered, washed with methanol-water (2:1), and dried under high vacuum at 70° C. to give 1.0 g of the title compound, mp 305°-8° C. with sublimation.

Analysis: Calculated for $C_{12}N_8N_3Cl$: C, 62.76; H, 3.51; N, 18.30. Found: C, 62.34; H, 3.48; N, 18.25.

PREPARATION 34

(S)-N-(3-Nitro-2-pyridinyl)alanine ethyl ester

Under a nitrogen atmosphere, triethylamine (82.1 g, 0.813 mole) was added to a stirred suspension of 2-chloro-3-nitropyridine (51.4 g, 0.325 mole) and (S)-alanine ethyl ester hydrochloride (75 g, 0.488 mole) in absolute ethanol (500 ml). After refluxing for 10.5 hr. and stirring at room temperature overnight, the solvents were evaporated under reduced pressure. The residue was triturated in 500 ml of ethyl acetate, filtered, and the filter cake was rinsed with ethyl acetate. The filtrate was washed three times with water, dried over sodium sulfate, filtered and evaporated to an oil weighing 85.6 g. A 1.25-g sample of the oil was eluted through 20 g of silica gel with isopropyl ether as the eluting solvent to give a pure fraction. The solvent was evaporated and the residual oil was dissolved in methylene chloride, filtered, and evaporated to an oil which was dried under high vacuum at 50° C. overnight to give 0.9 g of title compound.

Analysis: Calculated for $C_{10}H_{13}N_3O_4$: C, 50.21; H, 5.48; N, 17.56. Found: C, 49.91; H, 5.45; N, 17.34.

PREPARATION 35

1-[(3-Nitro-2-pyridinyl)amino]-2-propanol

A mixture of 2-chloro-3-nitropyridine (10.0 g, 0.063 mole), DL-1-amino-2-propanol (7.1 g, 0.095 mole), and triethylamine (8.75 ml, 0.063 mole) in absolute ethanol was heated at reflux for 1½ hours. The reaction mixture was evaporated to dryness and the residue was partitioned between water and methylene chloride. The water layer was separated and extracted with methylene chloride (2×). The combined methylene chloride layers were extracted with water and dried over sodium sulfate. The filtrate was evaporated to a yellow oil. The oil was purified on a silica gel column (200 g) eluting first with methylene chloride, followed by 5%, 10%, 25% (500 ml each), and finally 50% ethyl acetate/methylene chloride. The appropriate fractions (TLC using ethyl acetate) were combined and evaporated to an oil. A sample of the oil was dried at 50°-60° C., then at 70° C. for 6 hours to give 11.9 g (96%) of a yellow oil.

Analysis: Calculated for $C_8H_{11}N_3O_3$: C, 48.73; H, 5.62; N, 21.31. Found: C, 48.48; H, 5.63; N, 21.31.

PREPARATION 36

4-Chlorobenzoic acid ester with 4-chloro-N-[2-[(2-hydroxypropyl)amino]3-pyridinyl]benzamide A mixture of 1-[(3-nitro-2-pyridinyl)amino]-2-propanol (9.9 g, 0.05 mole) and 5% palladium on carbon (1.0 g) in 150 ml of tetrahydrofuran was hydrogenated in a glass Parr apparatus for ½ hour. The mixture was dried over magnesium sulfate and filtered through a Celite pad to give a colorless filtrate. p-Chlorobenzoyl chloride (8.79 g, 0.05 mole) and triethylamine (6.98 ml, 0.05 mole) were added dropwise to the stirred filtrate at 12°-15° C. (ice bath). The reaction mixture was allowed to warm to ambient temperature overnight. The reaction mixture was filtered, and the filtrate was evaporated to dryness. The residue was recrystallized from isopropyl alcohol and water. The solid was collected by filtration, then treated with boiling methanol. The insoluble solid was collected by filtration, washed with methanol, and dried under high vacuum overnight to give 1.4 g of solid, mp. 186°-188° C.

Analysis: Calculated for $C_{22}H_{19}N_3O_3Cl_2$: C, 59.47; H, 4.31; N, 9.46. Found: C, 59.11; H, 4.70; N, 9.36.

PREPARATION 37

N-[2-[(2-Hydroxypropyl)amino]-3-pyridinyl]-4-chlorobenzamide hydrochloride[1:1]

A mixture of 1-[(3-nitro-2-pyridinyl)amino]-2-propanol (9.9 g, 0.05 mole) and 5% palladium on carbon (1.0 g) in 150 ml of tetrahydrofuran was hydrogenated in a glass Parr apparatus for ½ hour. The mixture was dried over magnesium sulfate and filtered through a Celite pad to give a colorless filtrate. The p-chlorobenzoyl chloride (8.79 g, 0.05 mole) and triethylamine (6.98 ml, 0.05 mole) were added dropwise to the stirred filtrate at 12°-15° C. (ice bath). The reaction mixture was allowed to warm to ambient temperature overnight. The reaction mixture was filtered, and the filtrate was evaporated to dryness. The residue was recrystallized from isopropyl alcohol and water. The solid was collected by filtration, then treated with boiling methanol. The insoluble solid was collected by filtration, and the filtrate was evaporated to dryness, azetroped with benzene, and dried under high vacuum. The residue was partitioned between water and methylene chloride. The methylene chloride was extracted with 5% potassium hydroxide and water. The methylene chloride layer was dried, filtered, and evaporated to a foam. A 1.5-g sample was dissolved in ethyl acetate, acidified with ethereal and methanolic hydrogen chloride, and seeded. The crystalline solid was collected by filtration, washed with ethyl acetate, and dried under high vacuum to give 1.2 g of solid, mp 178°-180° C.

Analysis: Calculated for $C_{15}H_{16}N_3O_2Cl \cdot HCl$: C, 52.65; H, 5.01; N, 12.28. Found: C, 52.45; H, 5.24; N, 12.19.

PREPARATION 38

α-[(3-Nitro-2-pyridinylamino)methyl]benzenemethanol

A mixture of 2-chloro-3-nitropyridine (20.0 g, 0.13 mole), 2-amino-1-phenylethanol (20.74 g, 0.15 mole), and triethylamine (17.5 ml, 0.13 mole) in 200 ml of absolute ethanol was heated to reflux for 1½ hours. The reaction mixture was filtered and evaporated to dryness. The residue was partitioned between water and methylene chloride (2x). The methylene chloride layers were combined and extracted with water. The methylene chloride layers were dried, filtered, and evaporated to a solid (30.8 g, 94.5%). A 2.4-g sample was recrystallized from methanol and water to give a yellow solid, which was collected by filtration, washed with water, and dried under high vacuum overnight to give 1.8 g of the compound, mp 101°–103° C.

Analysis: Calculated for $C_{13}H_{13}N_3O_3$: C, 60.23; H, 5.05; N, 16.21. Found: C, 59.99; H, 5.26; N, 16.18.

PREPARATION 39

N-[3-[(5-Bromo-2-furanylcarbonyl)amino]-2-pyridinyl]glycine ethyl ester hydrate[1:1]

Under a nitrogen atmosphere, triethylamine (32.12 g, 0.32 mole) and 5-bromofuranoyl chloride (70.0 g, 0.33 mole) in tetrahydrofuran (200 ml) were added simultaneously, dropwise, to a stirred and chilled solution of freshly prepared N-[[3-amino]-2-pyridinyl]glycine ethyl ester (0.318 mole) in dry tetrahydrofuran (~1 liter), obtained by 5% palladium on carbon reduction of N-[[3-nitro]-2-pyridinyl]glycine ethyl ester (71.95 g, 0.318 mole) at room temperature. The reaction mixture was stirred at room temperature under nitrogen overnight and the solvent was evaporated under reduced pressure. The residue was partitioned between water and ethyl acetate, the layers separated and the aqueous layer was again extracted with ethyl acetate. The combined organic layers were washed with a saturated sodium chloride solution and with water. It was dried over magnesium sulfate, charcoaled, filtered, and the solvent was evaporated under reduced pressure to give a residue weighing 115.5 g (99%). A 5.0-g sample was recrystallized twice from isopropyl alcohol/water and dried under high vacuum overnight to give 3.14 g of title compound, mp 78°–81° C.

Analysis: Calculated for $C_{14}H_{16}N_3O_5Br$: C, 43.54; H, 4.18; N, 10.88. Found: C, 43.47; H, 4.18; N, 10.62.

PREPARATION 40

(R)-N-(3-Nitro-2-pyridinyl)alanine methyl ester

A suspension of 2-chloro-3-nitropyridine (37.76 g, 0.239 mole), (R)-alanine methyl ester hydrochloride (50 g, 0.358 mole) and triethylamine (60.3 g, 0.597 mole) in methanol (370 ml) was refluxed overnight under nitrogen. The solvents were removed under reduced pressure and the resulting solid was triturated in ethyl acetate (300 ml), filtered, and rinsed with additional ethyl acetate. The filtrate and washings were combined and washed once with water. The aqueous wash was extracted with ethyl acetate and the combined organic layers were washed several times with water, dried over sodium sulfate, filtered and evaporated under reduced pressure to given an oil weighing 45.6 g (85%). Elution of a portion of the oil with 1:6 tetrahydrofuran/hexane through a silica gel column gave 3.2 g of product after evaporation of solvent. Drying of a portion of the solid under high vacuum at room temperature gave 0.98 g of title compound, mp 39°–40° C.

Analysis: Calculated for $C_9H_{11}N_3O_4$: C, 48.00; H, 4.92; N, 18.66. Found: C, 47.90; H, 4.90; N, 18.54.

PREPARATION 41

N-(3-Nitro-4-pyridinyl)glycine ethyl ester

Under a nitrogen atmosphere, a mixture of 4-chloro-3-nitropyridine (5.3 g, 0.033 mole) and ethyl glycinate hydrochloride (4.67 g, 0.033 mole) in 50 ml of tetrahydrofuran was treated with triethylamine (4.6 ml, 0.033 mole). The reaction mixture was allowed to stir at room temperature for 1½ hours before treating with additional triethylamine (4.6 ml, 0.033 mole). The tetrahydrofuran was evaporated and the residue was partitioned between water and methylene chloride. The aqueous layer was separated and extracted with methylene chloride. The combined methylene chloride extracts were dried over magnesium sulfate and evaporated to dryness. NMR indicated only 26% product, and the remainder starting material.

The residue was dissolved in 50 ml of dioxane and treated with triethylamine (9.2 ml, 0.066 mole) and ethyl glycinate hydrochloride (4.67 g, 0.033 mole). The reaction mixture was allowed to stir at room temperature overnight. The reaction mixture was partitioned between water and methylene chloride. The aqueous layer was separated and extracted with methylene chloride (2×). The combined methylene chloride layers were extracted with water, dried over magnesium sulfate, and evaporated to an oil. A portion of the oil was purified by liquid chromatography (silica gel) and elution with ethyl acetate/hexanes (1:1). The appropriate fraction by TLC (ethyl acetate) was evaporated to an oil, which crystallized. The solid was dried under high vacuum over the weekend to give yellow solid, 1.1 g, mp 81.5°–83° C. Total yield by HPLC and silica gel filtration was 69%.

Analysis: Calculated for $C_9H_{11}N_3O_4$: C, 48.00; H, 4.92; N, 18.66. Found: C, 48.11; H, 4.95; N, 18.90.

PREPARATION 42

N-[3-[(5-Methyl-2-thienylcarbonyl)amino]-2-pyridinyl]glycine ethyl ester

Under a nitrogen atmosphere, triethylamine (31.41 g, 0.311 mole) and 5-methyl-2-thiophenecarbonyl chloride (50 g, 0.311 mole) were added simultaneously, dropwise, to a stirred and chilled solution of freshly prepared N-[[3-amino]-2-pyridinyl] glycine ethyl ester (0.296 mole) by palladium carbon reduction of N-[[3-nitro]-2-pyridinyl]glycine ethyl ester (66.98 g, 0.296 mole) in dry tetrahydrofuran (~1 liter). The reaction mixture was stirred at room temperature overnight and the solvent was evaporated under reduced pressure. The residue was partitioned between water and ethyl acetate, the layers separated and the aqueous layer was again extracted with ethyl acetate. The combined organic layers were washed twice with a 5% potassium hydroxide solution, twice with a saturated sodium bicarbonate solution, twice with water, dried over magnesium sulfate, treated with charcoal, filtered, and evaporated under reduced pressure to give 95.3 g of a tan solid in quantitative yield. A 1.5-g portion of the solid was dissolved in hot absolute ethanol, filtered while hot, and brought to its cloud point by addition of water.

Cooling to room temperature gave a solid which was collected by filtration, rinsed with water, and dried under high vacuum at room temperature overnight to give 1.11 g of title compound, mp 112°–115° C.

Analysis: Calculated for $C_{15}H_{17}N_3O_3S$: C, 56.41; H, 5.36; N, 13.16. Found: C, 56.58; H, 5.36; N, 13.02.

PREPARATION 43

N,N-Dimethyl-2-[(3-nitro-4-pyridinyl)amino]acetamide

Condensed dimethylamine (20 ml) was added in portions to a solution of crude N-(3-nitro-4-pyridinyl)glycine ethyl ester (4.0 g, 0.018 mole) in absolute ethanol (10 ml). The reaction was allowed to stir at ambient temperature over the weekend. The mixture was diluted with petroleum ether and the solid was collected by filtration. The solid 3-g was dissolved in tetrahydrofuran, filtered and diluted with isopropyl ether to produce a dark amorphous solid which was filtered off. The filtrate was further diluted with petroleum ether and placed in the freezer to produce a dark orange crystalline solid. The solid (2.5 g) was dissolved in methylene chloride, treated with Florisil ©, and the filtrate was evaporated to a yellow solid. which was dried under high vacuum at 70° C. to give 1.8 g (45%), mp 142°–143° C.

Analysis: Calculated for $C_9H_{12}N_4O_3$: C, 48.21; H, 5.39; N, 24.99. Found: C, 48.03; H, 5.36; N, 24.89.

PREPARATION 44

N-[3-[(4-Fluorobenzoyl)amino]-2-pyridinyl]glycine ethyl ester

Under a nitrogen atmosphere, triethylamine (31.8 g, 0.315 mole) and 4-fluorobenzoyl chloride (50 g, 0.315 mole) were added simultaneously, dropwise, to a stirred and chilled solution of freshly prepared N-[[3-amino]-2-pyridinyl]glycine ethyl ester (0.33 mole) by palladium/carbon reduction of N-[[3-nitro]-2-pyridinyl] glycine ethyl ester, (75.3 g, 0.33 mole) in dry tetrahydrofuran (~800 ml). The reaction mixture was stirred at room temperature overnight and the solvent was evaporated under reduced pressure. The residue was partitioned between ethyl acetate (300 ml) and water (300 ml), the insoluble material was filtered off, the layers were separated and the aqueous layer was extracted again with ethyl acetate. The combined organic layer was washed three times with water, dried over magnesium sulfate, treated with charcoal, filtered and evaporated to give 76.8 g of crude solid (77% yield). A 6.8-g portion of the solid was recrystallized from isopropyl alcohol and water to give 5.63 g of title compound, mp 127°–128.5° C.

Analysis: Calculated for $C_{16}H_{16}N_3O_3F$: C, 60.56; H, 5.08; N, 13.24. Found: C, 60.19; H, 5.10; N, 13.09.

PREPARATION 45

Following the procedure of preparation 33 but substituting the following for 2,3-diaminopyridine:
a. 2,3-diamino-4-chloropyridine (C.A. 72, 12687d),
b. 2,3-diamino-5-chloropyridine (C.A. 72, 78970x),
c. 2,3-diamino-4,6-dichloropyridine (C.A. 72, 12687d),
d. 2,3-diamino-5-nitropyridine (C.A. 72, 3431p),
e. 2,3-diamino-6-methoxypyridine (C.A. 72, 61408x),
f. 2,3-diamino-5,6-dichloropyridine (C.A. 54, 5683d),
g. 2,3-diamino-5-bromopyridine (C.A. 61, 651a),
h. 2,3-diamino-6-chloropyridine (C.A., 61, 7763d),
i. 2,3-pyridinediamine-4-methylpyridine (U.S. Pat. No. 3,985,891),
j. 2,3-pyridinediamine-5-methylpyridine (U.S. Pat. No. 3,985,891) and
k. 2,3-pyridinediamine-6-methylpyridine (U.S. Pat. No. 3,985,891).

there are obtained:
a. 2-(4-chlorophenyl)-7-chloro-3H-imidazo[4,5-b]pyridine,
b. 2-(4-chlorophenyl)-6-chloro-3H-imidazo[4,5-b]pyridine,
c. 2-(4-chlorophenyl)-5,7-dichloro-3H-imidazo[4,5-b]pyridine,
d. 2-(4-chlorophenyl)-6-nitro-3H-imidazo[4,5-b]pyridine,
e. 2-(4-chlorophenyl)-5-methoxy-3H-imidazo[4,5-b]pyridine,
f. 2-(4-chlorophenyl)-5,6-dichloro-3H-imidazo[4,5-b]pyridine,
g. 2-(4-chlorophenyl)-6-bromo-3H-imidazo[4,5-b]pyridine,
h. 2-(4-chlorophenyl)-5-chloro-3H-imidazo[4,5-b]pyridine,
i. 2-(4-chlorophenyl)-7-methyl-3H-imidazo[4,5-b]pyridine,
j. 2-(4-chlorophenyl)-7-methyl-3H-imidazo[4,5-b]pyridine and
k. 2-(4-chlorophenyl)-5-methyl-3H-imidazo[4,5-b]pyridine.

PREPARATION 46

Following the procedure of preparation 33 but substituting the following for 2,3-diaminopyridine:
a. 3,4-diamino-2-methoxypyridine (C.A. 75, 62924m),
b. 3,4-diamino-5-bromo-6-chloropyridine (C.A. 58, 5676a),
c. 3,4-diaminopyridine (C.A. 66, 75975t),
d. 3,4-diamino-2-chloropyridine (C.A. 63, 5628e),
e. 3,4-diamino-2,6-dichloropyridine (C.A. 63, 5628e),
f. 3,4-diamino-5-nitropyridine (C.A. 62, 16231h),
g. 3,4-diamino-6-bromo-2-chloropyridine (C.A. 58, 5676a),
h. 3,4-diamino-5-bromopyridine (C.A. 58, 5675h) and
i. 4,5-diamino-2-chloropyridine (C.A. 63, 5628e).
there are obtained:
a. 2-(4-chlorophenyl)-4-methoxy-3H-imidazo[4,5-c]pyridine,
b. 2-4-chlorophenyl)-6-chloro-7-bromo-3H-imidazo[4,5c]pyridine,
c. 2-(4chlorophenyl)3H-imidazo[4,5-c]pyridine,
d. 2-(4-chlorophenyl)-4-chloro-3H-imidazo[4,5-c]pyridine,
e. 2-(4-chlorophenyl)-4,6-dichloro-3H-imidazo[4,5-c]pyridine,
f. 2-(4-chlorophenyl)-7-nitro-3H-imidazo[4,5-c]pyridine,
g. 2-(4-chlorophenyl)-4-chloro-6-bromo-3H-imidazo[4,5-c]pyridine,
h. 2-(4-chlorophenyl)-7-bromo-3H-imidazo[4,5-c]pyridine and
i. 2-(4-chlorophenyl)-6-chloro-1H-imidazo[4,5-c]pyridine.

PREPARATION 47

Following the procedure of preparation 1 but substituting the following for 2-chloro-3-nitropyridine:
a. 2-chloro-3-nitro-4-methylpyridine (C.A. 94, 15636b),
b. 2-chloro-3nitro-5-methylpyridine (C.A. 89, 6192y),
c. 2-chloro-3-nitro-6-methylpyridine (C.A. 89, 43036w), d. 2-chloro-3-nitro-5,6-dimethylpyridine (C.A. 90, 121359r),
e. 4-chloro-6-diethylamino-2-methyl-5-nitropyridine (C.A. 88, 6799f),
f. 4-chloro-2-methyl-3-nitropyridine (C.A. 91, 20266y) and
g. 2-chloro-6-methoxy-3-nitropyridine (C.A. 77, 148422g).

there are obtained:
a. N-(4-methyl-3-nitro-2-pyridinyl)glycine ethyl ester,
b. N-(5-methyl-3-nitro-2-pyridinyl)glycine ethyl ester,
c. N-(6-methyl-3-nitro-2-pyridinyl)glycine ethyl ester,
d. N-(5,6-dimethyl-3-nitro-2-pyridinyl)glycine ethyl ester,
e. N-(6-diethylamino-2-methyl-5-nitro-4-pyridinyl)glycine ethyl ester,
f. N-(2-methyl-3-nitro-4-pyridinyl)glycine ethyl ester and
g. N-(6-methoxy-3-nitro-2-pyridinyl)glycine ethyl ester.

PREPARATION 48 a-g

Following the procedure of preparation 13 but substituting the following for N-(3-nitro-2-pyridinyl) glycine ethyl ester:
a. N-(4-methyl-3-nitro-2-pyridinyl)glycine ethyl ester,
b. N-(5-methyl-3-nitro-2-pyridinyl)glycine ethyl ester,
c. N-(6-methyl-3-nitro-2-pyridinyl)glycine ethyl ester,
d. N-(5,6-dimethyl-3-nitro-2-pyridinyl)glycine ethyl ester,
e. N-(6-diethylamino-2-methyl-5-nitro-4-pyridinyl)glycine ethyl ester,
f. N-(2-methyl-3-nitro-4-pyridinyl)glycine ethyl ester and
g. N-(6-methoxy3-nitro-2-pyridinyl)glycine ethyl ester.

there are obtained:
a. N-[3-(4-chlorobenzoylamino)-4-methyl-2-pyridinyl]glycine ethyl ester,
b. N-[3-(4-chlorobenzoylamino)-5-methyl-2-pyridinyl]glycine ethyl ester,
c. N-[3-(4-chlorobenzoylamino)-6-methyl-2-pyridinyl]glycine ethyl ester,
d. N-[3-(4-chlorobenzoylamino)-5,6-dimethyl-2-pyridinyl] glycine ethyl ester,
e. N-[5-(4-chlorobenzoylamino)-6-diethylamino-2-methyl-4-pyridinyl]glycine ethyl ester,
f. N-[3-(4-chlorobenzoylamino)-2-methyl-4-pyridinyl] glycine ethyl ester and
g. N-[3-(4-chlorobenzoylamino)-6-methoxy-2-pyridinyl] glycine ethyl ester.

PREPARATION 49

(R)-N-[3-[(4-Chlorobenzoyl)amino]-2-pyridinyl]alanine methyl ester

A solution of (R)-N-(3-nitro-2-pyridinyl)alanine methyl ester (21.0 g, 0.0933 mole) in tetrahydrofuran (300 ml) was hydrogenated over 5% palladium on carbon (2.1 g) keeping the temperature of the solution at approximately room temperature. The solution of the reduction product was cooled in an ice-bath and dried over magnesium sulfate under nitrogen. The solution was filtered and 4-chlorobenzoyl chloride (17.2 g, 0.0982 mole) and triethylamine (9.9 g, 0.0982 mole) were added simultaneously, dropwise, to the cooled and stirred solution. After stirring at room temperature overnight, the solvents were removed under reduced pressure and the residue was partitioned between ethyl acetate (200 ml) and water (200 ml). The layers were separated and the aqueous layer was extracted again with ethyl acetate (100 ml). The combined organic layers were washed three times with water, dried over magnesium sulfate, treated with charcoal, filtered and evaporated to give 30.9 g (99%) of product. A 3.5-g portion of the product was dissolved in hot isopropyl alcohol, treated with charcoal and filtered while hot. Petroleum ether was added to the cool solution and upon stirring, solid precipitated, which was collected by filtration and dried under high vacuum to give 0.68 g of title compound, mp 125°–134° C.

Analysis: Calculated for $C_{16}H_{16}N_3O_3Cl$: C, 57.58; H, 4.83; N, 12.59. Found: C, 57.52; H, 4.85; N, 12.52.

PREPARATION 50

4-Chloro-N-(4-chlorobenzoyl)-N-[4-[[2-(dimethylamino)-2-oxoethyl]amino]-3-pyridinyl]benzamide hydrate [1:1]

A mixture of N,N-dimethyl-2-[(3-nitro-4-pyridinyl)amino]acetamide (11.0 g, 0.05 mole) and 5% palladium on carbon catalyst (1.1 g) in 250 ml of tetrahydrofuran was hydrogenated in a small Parr apparatus while heating at 50° C. The reaction mixture was heated with methanol and filtered through a Celite pad. The pad was washed with boiling methanol. The filtrate was evaporated to a solid. The solid was dissolved in acetonitrile (500 ml) and treated with p-chlorobenzoyl chloride (5.97 ml, 0.047 mole) and triethylamine (6.52 ml, 0.047 mole). The reaction mixture was stirred at ambient temperature overnight. The reaction mixture was filtered and the filtrate was evaporated. The solid residue was partitioned between methylene chloride and water (2×). The methylene chloride layer was dried and evaporated to dryness. The residue was dissolved in ethyl acetate, treated with charcoal, filtered through Celite, and concentrated. A crystalline precipitate was collected by filtration, washed with isopropyl ether and dried at 50° C. under high vacuum to give 4.65 g of solids (40%), mp 175°–176° C.

Analysis: Calculated for $C_{23}H_{20}N_4O_3Cl_2 \cdot H_2O$: C, 56.45; H, 4.53; N, 11.45. Found: C, 56.03; H, 4.47; N, 11.55.

The filtrate was evaporated to dryness to give 9.24 g of crude title compound.

PREPARATION 51

4-Chloro-N-[2-[(2-hydroxy-2-phenylethyl)amino]-3-pyridinyl]benzamide

A mixture of α-[(3-nitro-2-pyridinylamino)methyl]benzene methanol (30.8 g, 0.12 mole) and 5% palladium on carbon catalyst in 450 ml of tetrahydrofuran was hydrogenated in a large glass Parr bottle at room temperature. The reaction mixture was dried over magnesium sulfate and filtered through a Celite pad. p-Chlorobenzoyl chloride (15.1 ml, 0.12 mole) and triethylamine (16.5 ml, 0.12 mole) were added simultaneously dropwise to the stirred filtrate at 12°–15° C. (ice-water bath) and the mixture was allowed to stir at ambient temperature overnight. The reaction mixture was filtered and the filtrate was evaporated to dryness. The residue was partitioned between methylene chloride and water. The methylene chloride layer was separated and extracted with water (1×), 5% potassium hydroxide (2×), and water (2×). The methylene chloride layer was separated, dried, and evaporated to dryness. The residue was purified on a silica gel column (400 g) by eluting with 50% ethyl acetate/50% hexanes. Total recovery:

18.2 g (41.6% yield). A 5-g sample was recrystallized from ethyl acetate/hexanes to give 2.71 g of solid, mp. 157°–159° C.

Analysis: Calculated for $C_{20}H_{18}N_3O_2Cl$: C, 65.31; H, 4.93; N, 11.42. Found: C, 65.19; H, 4.95; N, 11.41.

PREPARATION 52

N-(6-Chloro-3-nitro-2-pyridinyl)glycine ethyl ester

To suspenson of 2,6-dichloro-3-nitropyridine (1.0 g, 0.00518 mole) and glycine ethyl ester hydrochloride (0.725 g, 0.00518 mole) in absolute ethanol (10 ml) was added triethylamine (1.05 g, 0.0104 mole). The resulting solution was stirred overnight at room temperature under nitrogen. An additional portion of absolute ethanol (10 ml) was added and the suspension was filtered and the solid was washed with 3°–10 ml portions of absolute ethanol. The combined filtrate and washings were evaporated under reduced pressure at room temperature to give a yellow solid which was triturated in water (30 ml) collected by filtration, and rinsed with additional water. The solid was recrystallized from isopropyl ether/light petroleum ether, and the resulting solid was purified by column chromatography (10 g of silica gel) with 1:1 isopropyl ether/light petroleum ether as the eluting solvent. The appropriate fraction was recrystallized from isopropyl ether and dried under high vacuum to give the title compound, mp. 77.5°–80° C.

Analysis: Calculated for $C_9H_{10}N_3O_4Cl$: C, 41.63; H, 3.88, N, 16.18. Found: C, 41.61; H, 3.85; N, 16.10.

PREPARATION 53

N-[6-Chloro-3-[(4-chlorobenzoyl)amino]-2-pyridinyl]glycine ethyl ester

A solution of N-(6-chloro-3-nitro-2-pyridinyl) glycine ethyl ester (5.0 g, 0.0193 mole) in tetrahydrofuran (100 ml) was hydrogenated over platinum dioxide (0.5 g) at room temperature. After ⅔ of the theoretical amount of hydrogen had been absorbed, the mixture was filtered and a fresh portion of platinum dioxide (0.5 g) was added. The hydrogenation was continued until the theoretical amount of hydrogen was absorbed. The reaction mixture was cooled in ice, dried over magnesium sulfate and filtered. Triethylamine (2.05 g, 0.0203 mole) and 4-chlorobenzoyl chloride (3.55 g, 0.0203 mole) were added simultaneously, dropwise, to the cooled and stirred solution. After stirring at room temperature for 1.75 hours, the mixture was evaporated under reduced pressure and partitioned between water (100 ml) and ethyl acetate (100 ml). The layers were separated and the aqueous layer was re-extracted with ethyl acetate. The combined ethyl acetate layers were washed three times with saturated sodium chloride solution, dried over magnesium sulfate, charcoaled, filtered, and evaporated under reduced pressure. The resulting solid was dissolved in hot isopropyl alcohol, filtered hot and cooled to room temperature to give a solid which was collected by filtration and rinsed with isopropyl ether to give 2.2 g of title compound (31% yield). A 0.5 g portion was dissolved in hot isopropyl alcohol, filtered hot, isopropyl ether was added, and the mixture was cooled. The resulting suspension was filtered, the filtrate was evaporated under reduced pressure, and the residue was recrystallized from isopropyl alcohol/water and dried under high vacuum at 60° C. to give 0.37 g of the title compound, mp 157°–158.5° C.

Analysis: Calculated for $C_{16}H_{15}N_3O_3Cl_2$: C, 52.19; H, 4.11, N, 11.41. Found: C, 52.28; H, 4.05; N, 11.09.

EXAMPLE 1

2-(4-Chloro-2-pyridinyl)-3H-imidazo[4,5-b]pyridine-3-acetic acid

A mixture of 2-(4-chloro-2-pyridinyl)-3H-imidazo[4,5-b]pyridine-3-acetic acid ethyl ester (1.6 g, 0.005 mole), and crushed sodium hydroxide (0.2 g, 0.005 mole) in aqueous ethanol (5 ml water and 4 ml ethanol) was heated at reflux for ½ hr. The reaction mixture was diluted with water (10 ml) and extracted with ether (2×). The aqueous layer was acidified with 3N hydrochloric acid. The precipitate was collected, washed with water, and dried under high vacuum at 50° C. overnight to give 0.84 g of crystals, mp 218°–20° C. with decomposition.

Analysis: Calculated for $C_{13}H_9N_4O_2Cl$: C, 54.09, H, 3.14, N, 19.41. Found: C, 53.94; H, 3.23; N, 19.09.

EXAMPLE 2

2-(4-Chlorophenyl)-3H-imidazo[4,5-b]pyridine-3-acetic acid

A mixture of 14.6 g (0.04 mole) of 2-(4-chlorophenyl)-3H-imidazo[4,5-b]pyridine-3-acetic acid ethyl ester, 2.9 g (0.073 mole) of sodium hydroxide pellets, and 150 ml of ethanol/water (1:1) was refluxed for 45 min. The reaction mixture was poured into a 250-ml of water, acidified with concentrated hydrochloric acid; and filtered, giving 12.8 g (97%) of a white solid. A 2-g portion was recrystallized from methanol-water to give 1.2 g of white needles, mp 271°–273° C. with decomposition.

Analysis: Calculated for $C_{14}H_{10}N_3O_2Cl$: C, 58.45; H, 3.50; N, 14.61. Found: C, 58.30; H, 3.50; N, 14.57.

EXAMPLE 3

2-(2-Chlorophenyl)-3-H-imidazo[4,5-b]pyridine-3-acetic acid.

A mixture of 9.7 g (0.0308 mole) of 2-(2-chlorophenyl)-3H-imidazo[4,5-b]pyridine-3-acetic acid ethyl ester, 2.5 g (0.0339 mole) of sodium hydroxide (pellets), and 100 ml of ethanol-water (1:1) was refluxed for 1 hr. The ethanol was evaporated and the residual aqueous solution was extracted with methylene chloride (2×30 ml). The aqueous layer was acidified with concentrated hydrochloric acid and filtered. The filter cake was recrystallized from ethanol-water to give 7.0 g (79%). A 2.0-g portion was recrystallized from ethanol-isopropyl ether to give white needles, mp 227°–228° C.

Analysis: Calculated for $C_{14}H_{10}N_3O_2Cl$: C, 58.45; H, 3.50; N, 14.61. Found: C, 58.55; H, 3.54; N, 14.54.

EXAMPLE 4

2-(3-Chlorophenyl)-3H-imidazo[4,5-b]pyridine-3-acetic acid

A mixture of 2-(3-chlorophenyl)-3H-imidazo[4,5-b]pyridine-3acetic acid ethyl ester (6.0 g, 0.019 mole), sodium hydroxide pellets (0.9 g, 0.023 mole), and 50 ml of ethanol-water (2:1) was refluxed for 1 hour. The reaction mixture was cooled and the ethanol evaporated in vacuo. The residual aqueous mixture was diluted with water (40 ml) and extracted with diethyl ether (2×25 ml). The aqueous portion was acidified with concentrated hydrochloric acid to a pH of 5–6. After precipitation was complete, the solid was collected by filtration, giving 5.9 g (100%). Recrystallization from ethanol gave 4.7 g of cream colored needles, mp 214°–216° C.

Analysis: Calculated for $C_{14}H_{10}N_3O_2Cl$: C, 58.45; H, 3.50; N, 14.61. Found: C, 58.25; H, 3.51; N, 14.55.

EXAMPLE 5

2-(3-Fluorophenyl)-3H-imidazo[4,5-b]pyridine-3-acetic acid

A mixture of N-[3-[(3-fluorobenzoyl)amino]-2-pyridinyl] glycine ethyl ester (20.44 g, 0.065 mole), and ethylene glycol (75 ml) was heated at 195° C. for 40 minutes. Water was added to the cooled reaction mixture and the solid was collected by filtration. The solid was suspended in water (2×100 ml) and collected by filtration to give 17.75 g of crude 2-(3-fluorophenyl)-3H-imidazo[4,5-b]pyridine-3-acetic acid ethyl ester. A portion of this solid (6.0 g, 0.02 mole) together with sodium hydroxide pellets (0.9 g, 0.0231 mole), and 50 ml of ethanol-water (1:1) was refluxed for 1 hour. The ethanol was evaporated. The residual aqueous mixture was cooled, diluted with water (50 ml) and extracted with diethyl ether (2×25 ml). The aqueous portion was acidified to a pH of 3 with concentrated hydrochloric acid. After precipitation was complete, the solid was collected by filtration. The filter cake was suspended in ethanol and filtered, giving 4.94 g (91%). Recrystallization of a 1.2-g sample from tetrahydrofuran gave 1.1 g of an off-white solid, mp 243°–245° C. with decomposition.

Analysis: Calculated for $C_{14}H_{10}N_3O_2F$: C, 61.99; H, 3.72; N, 15.49. Found: C, 61.95; H, 3.73; N, 15.44.

EXAMPLE 6

2-(4-Bromophenyl)-3H-imidazo[4,5-b]pyridine-3-acetic acid

A mixture of 2-(4-bromophenyl)-3H-imidazo[4,5-b]pyridine-3-acetic acid ethyl ester (7.00 g, 0.0194 mole) sodium hydroxide pellets (0.88 g, 0.0220 mole), and 95% ethanol (100 ml) was refluxed for 1 hr. The reaction mixture was cooled and filtered. The filter cake (7.3 g) was dissolved in warm water, acidified with concentrated hydrochloric acid, and chilled. The precipitated solid was collected by filtration and the filter cake was rinsed with water, giving 5.6 g (87%) of crystals. Recrystallization from tetrahydrofuran-methanol gave 5.4 g of white needles, mp 264°–267° C.

Analysis: Calculated for $C_{14}H_{10}N_3O_2Br$: C, 50.63; H, 3.03; N, 12.65. Found: C, 50.38; H, 2.97; N, 12.70.

EXAMPLE 7

2-(4-Fluorophenyl)-3H-imidazo[4,5-b]pyridine-3-acetic acid

A solution of N-[3-[(4-fluorobenzoyl)amino]-2-pyridinyl] glycine ethyl ester (70.0 g, 0.2205 mole) in ethylene glycol was refluxed for 2 hours, cooled and 14% of the solution was removed. To the remaining solution (0.19 mole) was added 88 ml of water and solid potassium hydroxide pellets (21.4 g, 0.38 mole). The solution was heated at reflux for an additional 1¼ hours, filtered into ice water (2 liter) and acidified with 3N hydrochloric acid. The resulting solid was collected by filtration, washed with water and dried under high vacuum at 60° C. overnight to give 45.5 g of crude title compound (88% yield). A 3.5-g portion of the solid was dissolved in hot methanol and filtered while hot, and water was added to the cloud point. Upon cooling to room temperature, solid precipitated which was collected and recrystallized again from methanol/water to give 2.00 g of title compound after drying under high vacuum at 50° C., mp >250° C.

Analysis: Calculated for $C_{14}H_{10}N_3O_2F$: C, 61.99; H, 3.72; N, 15.49. Found: C, 61.83; H, 3.71; N, 15.39.

EXAMPLE 8

2-(3-Bromophenyl)-3H-imidazo[4,5-b]pyridine-3-acetic acid

A solution of 2-(3-bromophenyl)-3H-imidazo[4,5-b]pyridine-3-acetic acid ethyl ester (4.8 g, 0.0133 mole), 95% ethanol (50 ml), sodium hydroxide pellets (0.6 g, 0.014 mole), and water (5 ml) was refluxed for 2 hrs. The ethanol was evaporated and water (50 ml) added. Glacial acetic acid was added dropwise until precipitation began (pH neutral). The precipitated solid was collected by filtration and recrystallized from ethanol-tetrahydrofuran, giving 3.9 g (88% yield) of white needles, mp 247°–249° C.

Analysis: Calculated for $C_{14}H_{10}N_3O_2Br$: C, 50.63; H, 3.03; N, 12.65. Found: C, 50.70; H, 3.02; N, 12.80.

EXAMPLE 9

2-(2-Pyridinyl)-3H-imidazo[4,5-b]pyridine-3-acetic acid

A solution of 2-(2-pyridinyl)-3H-imidazo[4,5-b]pyridine-3-acetic acid ethyl ester (18.0 g, 0.064 mole), potassium hydroxide pellets (5.6 g, 0.100 mole), 95% ethanol (250 ml) and water (10 ml) was refluxed for 1½ hr. The solution was evaporated to ⅓ volume and then diluted with water (50 ml) and acidified with glacial acetic acid. Water (200 ml) was added and the mixture filtered after precipitation was complete, giving 15.5 g (96%) of a granular solid. Recrystallization of a 2.0-g portion twice from ethanol-water gave 1.5 g of an off-white granular solid, mp 224°–225° C. with decomposition.

Analysis: Calculated for $C_{13}H_{10}N_4O_2$: C, 61.41; H, 3.96; N, 22.04. Found: C, 61.28; H, 3.94; N, 21.98.

EXAMPLE 10

2-[3-Trifluoromethyl)phenyl]-3H-imidazo[4,5-b]pyridine-3-acetic acid

A mixture of N-[3-[[3-(trifluoromethyl)benzoyl]amino]-2 2-pyridinyl]glycine ethyl ester (22.0 g, 0.06 mole) and ethylene glycol (100 ml) was heated at reflux for 40 minutes. The reaction mixture was poured into water (300 ml) and cooled. The solid was collected by filtration, washed with water (200 ml), and dried. The solid was recrystallized from isopropyl ether/tetrahydrofuran to give in 2 crops 18.4 g (0.053 mole) of crude 2-(3-trifluoromethylphenyl)-3H-imidazo[4,5-b]pyridine-3-acetic acid ethyl ester. This solid together with potassium hydroxide pellets (4.7 g, 0.084 mole), 95% ethanol (150 ml), and water (10 ml) was refluxed for 2½ hrs. The reaction mixture was cooled to room temperature and concentrated in vacuo. The residue was dissolved in water (100 ml) and extracted with methylene chloride (2×30 ml). The aqueous portion was acidified with glacial acetic acid and filtered after precipitation was complete. The filter cake was suspended in water (200 ml) and filtered. Recrystallization from tetrahydrofuran-isopropyl ether gave 15.3 g (91%). A 1.6-g sample was recrystallized from tetrahydrofuranisopropyl ether to give 1.0 g of an off-white solid, mp 240°–241.5° C.

Analysis: Calculated for $C_{15}H_{10}N_3O_2F_3$: C, 56.08; H, 3.12; N, 13.08. Found: C, 55.72; H, 3.16; N, 12.76.

EXAMPLE 11

2-[4-(Trifluoromethyl)phenyl]-3H-imidazo[4,5-b]pyridine-3-acetic acid

A solution of 2-[4-(trifluoromethyl)phenyl]-3H-imidazo[4,5-b] pyridine-3-acetic acid ethyl ester (17.7 g, 0.051 mole), potassium hydroxide pellets (4.5 g, 0.080 mole), 95% ethanol (150 ml), and water (10 ml) was refluxed for 2½ hrs. The ethanol was evaporated in vacuo, the residue acidified with glacial acetic acid, and the mixture filtered. The filter cake was suspended in water (300 ml) and filtered. The filter cake was air dried (17 g) and recrystallized from ethanol-water to give 12.21 g (75%) of a white solid, mp 240°–241° C.

Analysis: Calculated for $C_{15}H_{10}N_3O_2F_3$: C, 56.08; H, 3.14; N, 13.08. Found: C, 56.02; H, 3.11; N, 13.07.

EXAMPLE 12

2-(3,4-Dichlorophenyl)-3H-imidazo[4,5-b]pyridine-3-acetic acid

A mixture of N-[3-[(3,4-dichlorobenzoyl)amino]-2-pyridinyl] glycine ethyl ester (33 g, 0.09 mole) and 167 ml of ethylene glycol was heated at reflux for 1½ hr. After cooling, potassium hydroxide (8.4 g) in 40 ml of water was added and the reaction mixture was heated at reflux for 1 hr. The solution was filtered to remove yellow insoluble precipitate, the filtrate was diluted with 650 ml of water, and acidified with ethanolic hydrogen chloride. The solid, which formed, was collected by filtration, washed with water, and dried under high vacuum first at 50° C. overnight, then at 70° C. for 2½ days to give 25.3 g (98%), mp 248°–49° C.

Analysis: Calculated for $C_{14}H_9N_3O_2Cl_2$: C, 52.20; H, 2.82; N, 13.04. Found: C, 52.15; H, 2.85; N, 12.92.

EXAMPLE 13

2-(4-Methoxyphenyl)-3H-imidazo[4,5-b]pyridine-3-acetic acid

A mixture of N-[3-[(4-methoxybenzoyl)amino]-2-pyridinyl] glycine ethyl ester (32 g, 0.1 mole) and 167 ml of ethylene glycol was heated at reflux for 1½ hr. After cooling, potassium hydroxide (8.4 g) in 40 ml of water was added, and the reaction mixture was heated at reflux for 1 hr. The solution was filtered to remove yellow precipitate, the filtrate was diluted with 650 ml of water, and acidified with 3N hydrochloric acid. The solid which formed, was collected by filtration, washed with water, and dried under high vacuum at 50° C. overnight to give 25.5 g (90.1% yield). A 0.5-g sample was recrystallized from ethanol, collected by filtration, washed with cold ethanol and water, and dried under high vacuum at 70° C. over 2 days to give 0.47 g of crystals, mp 260°–63° C.

Analysis: Calculated for $C_{15}H_{13}N_3O_3$: C, 63.60; H, 4.63; N, 14.83. Found: C, 63.52; H, 4.63; N, 14.74.

EXAMPLE 14

2-(4-Chlorophenyl)-3H-imidazo[4,5-b]pyridine-3-propanoic acid

3-[[3-[(4-Chlorobenzoyl)amino]-2-pyridinyl]amino]-propanoic acid ethyl ester, (142 g, 0.409 mole) was refluxed in ethylene glycol (725 ml) under a nitrogen atmosphere for 2 hr until a solution formed. Solid potassium hydroxide (31.9 g, 0.57 mole) and water (125 ml) were added to the hot solution and a solid precipitated. After the suspension was refluxed for an additional 1.5 hours, it was poured into ice water (2 liters) and acidified with a 3N hydrochloric acid solution. The solid was collected by filtration and dried under high vacuum at 70° C. to give 96.9 g of a solid. 'H NMR of the solid showed it to contain a mixture of the titled product and 2-(4-chlorophenyl)-3H-imidazo[4,5-b]pyridine. The solid was triturated in pyridine (500 ml) at room temperature and filtered to remove 2-(4-chlorophenyl)-3H-imidazo[4,5-b]pyridine. The solid was rinsed well with water. The filtrate and washings were evaporated at reduced pressure until an aqueous suspension was left. The solid was collected by filtration and rinsed with water to give 45.5 g of solid (37% yield). A 2.0-g sample of the solid was dissolved in hot methanol and the solution was filtered hot. Upon cooling to room temperature, solid precipitated. The solid was collected by filtration and dried under high vacuum at room temperature to give 0.65 g of solid, mp 232°–234° C.

Analysis: Calculated for $C_{15}H_{12}N_3O_2Cl$: C, 59.71; H, 4.01; N, 13.93. Found: C, 59.44; H, 4.04; N, 14.05.

EXAMPLE 15

2-(4-Chlorophenyl)-1H-imidazo[4,5-b]pyridine-1-acetic acid hydrate [1:1]

A mixture of 2-(4-chlorophenyl)-1H-imidazo[4,5-b]pyridine-1-acetic acid ethyl ester (8.4 g, 0.027 mole) and potassium hydroxide (2.25 g, 0.04 mole) in 95% ethanol (75 ml) and water (5 ml) was heated at reflux for 2.5 hours. The mixture was evaporated to dryness. The residue was dissolved in water and acidified with glacial acetic acid. The precipitate was collected by filtration, washed with water, and dried under high vacuum overnight at 60° C. to give 7.4 g (95% yield). A 1.4-g sample was dissolved in ~450 ml of boiling methanol, and the solution was treated with Florisil ® and filtered. The filtrate was concentrated and diluted with water. A crystalline precipitate was collected by filtration, washed with water, and dried under high vacuum at 60° C. for 4 hours, then at room temperature over the weekend to give 0.16 g of solids, mp. 194°–96° C.

Analysis: Calculated for $C_{14}H_{10}N_3O_2Cl \cdot H_2O$: C, 55.00; H, 3.96; N, 13.74. Found: C, 54.95; H, 3.98; N, 13.45.

EXAMPLE 16

2-(4-Bromo-2-furanyl)-3H-imidazo[4,5-b]pyridine-3-acetic acid

A solution of N-[3-[(5-bromo-2-furanylcarbonyl)amino]2-pyridinyl]glycine ester (110 g, 0.30 mole) in ethylene glycol (510 ml) was refluxed under nitrogen for two hours. The solution was cooled to room temperature and water (100 ml) and potassium hydroxide pellets (23.25 g, 0.41 mole) was added. The solution was refluxed for an additional 1.5 hours and then filtered, while hot, into ice water (2 liters). A 3N hydrochloric acid solution was added until the suspension was acidic. After stirring overnight, the solid was collected by filtration and rinsed with water. Most of the wet material was dried at 56° C. overnight under high vacuum to give 79.5 g of crude material (82% yield). A portion (3.0 g of wet material) was dissolved in hot methanol, filtered, and cooled to room temperature. Addition of water caused a solid to precipitate which was collected by filtration, rinsed with water, and dried at high vacuum at 56° C. to give 1.59 g of title compound, mp 229°-231° C.

Analysis: Calculated for $C_{12}H_8N_3O_3Br$: C, 44.74; H, 2.50; N, 13.04. Found: C, 44.83; H, 2.42; N, 12.92.

EXAMPLE 17

2-(4-Nitrophenyl)-3H-imidazo[4,5-b]pyridine-3-acetic acid hydrate [1:1]

Under a nitrogen atmosphere, a suspension of N-[3-[(4-nitrobenzoyl)amino]-2-pyridinyl]glycine ethyl ester (47.4 g, 0.138 mole) in ethylene glycol (235 ml) was refluxed, with stirring for 1.5 hr. A solution was formed during heating. The solution was cooled and water (41.5 ml) and potassium hydroxide pellets (10.6 g, 0.189 mole) were added. Solid precipitated, but upon heating, a solution was again formed. The solution was refluxed for 2 hr, cooled, and poured into 750 ml of ice water. Upon acidification with a 3N hydrochloric acid solution, a yellow solid precipitated. The solid was collected by filtration and rinsed with water. The solid was dissolved in hot methanol, filtered hot and cooled to room temperature. Addition of water caused solid to precipitate. The solid was collected by filtration and dried under high vacuum to give 16.4 g of orange solid (40% yield). 1.0 g of the solid was dissolved in hot methanol, and the solution was treated with charcoal, filtered hot, and cooled to room temperature, causing a solid to precipitate. The solid was collected by filtration, rinsed with water and dried under high vacuum at room temperature overnight to give 0.61 g of title compound, mp. 249°-251° C.

Analysis: Calculated for $C_{14}H_{12}N_4O_5$: C, 53.17; H, 3.82; N, 17.71. Found: C, 52.86; H, 3.64; N, 17.49.

EXAMPLE 18

(S)-2-(4-Chlorophenyl)-α-methyl-3H-imidazo[4,5-b]pyridine-3-acetic acid

A mixture of (S)-N-[3-[(4-chlorophenyl)amino]-2-pyridinyl]alanine ethyl ester (4.0 g, 0.016 mole), and ethylene glycol (20 ml) was heated at reflux for 1½ hr. To the cooled reaction mixture was added water (4 ml) and solid potassium hydroxide (0.9 g, 0.016 mole). The mixture was refluxed for 2.75 hours and then filtered into ice water (70 ml). Solid precipitated upon acidification with concentrated hydrochloric acid. The solid was collected by filtration, rinsed with water, dissolved in hot methanol and the solution was treated with magnesium sulfate and charcoal while hot. The mixture was filtered while hot. Upon cooling to room temperature, a solid formed, which was collected by filtration and dried under high vacuum to give 1.20 g of solid. The solid was redissolved in hot methanol, and the solution was filtered hot, and cooled to room temperature which caused a solid to precipitate. Water was added and the solid was collected by filtration, rinsed with water, and dried under high vacuum at 50° C. to give the title compound, mp. 226°-229° C.

Analysis: Calculated for $C_{15}H_{12}N_3O_2Cl$: C, 59.71; H, 4.01; N, 13.93. Found: C, 59.82; H, 3.98; N, 14.02.

EXAMPLE 19

2-Phenyl-3H-imidazo[4,5-b]pyridine-3-acetic acid ethyl ester

N-[3-(benzoylamino)-2-pyridinyl]glycine ethyl ester, 10.32 g (0.034 mole) in two divided portions was heated in glass in a Wood's metal bath at 190° C. under a flow of nitrogen, one portion for 15 min and the other for 7 min. The green glassy residues were dissolved in methylene chloride, combined, and stirred together with 90 g of Florisil ® for 1 hr. The mixture was filtered, and the filtrate evaporated to an oil, which crystallized. The solid was recrystallized from hexanes to give a crystalline solid, which was dried under high vacuum at room temperature overnight to give 3.67 g (39%) of crystals, m.p. 93°-95° C.

Analysis: Calculated for $C_{16}H_{15}N_3O_2$: C, 68.31; H, 5.37; N, 14.94. Found: C, 68.40; H, 5.35; N, 14.88.

EXAMPLE 20

2-Phenyl-3H-imidazo[4,5-b]pyridine-3-acetamide

A 7.62-g (0.028 mole) sample of N-[2-[[(aminocarbonyl)methyl]amino]-3-pyridinyl]benzamide was heated in glass in a Wood's metal bath under a flow of nitrogen at 200° C. for 7 minutes. The green solid residue was broken up with a glass rod in methanol and the solid was filtered off. The filtrate was concentrated and the precipitate which formed, was separated by filtering twice. The solids were combined and recrystallized from boiling water to give 3.19 g (45%) of white needles which were dried under high vacuum at room temperature overnight, mp. 226°-7° C.

Analysis: Calculated for $C_{14}H_{12}N_4O$: C, 66.66; H, 4.79; N, 22.21. Found: C, 66.63; H, 4.75; N, 22.25.

EXAMPLE 21

2-(2-Pyridinyl)-3H-imidazo[4,5-b]pyridine-3-acetamide

Solid N-[2-[(2-amino-2-oxoethyl)amino]-3-pyridinyl]-2-pyridinecarboxamide (5.14 g, 0.019 mole) was heated in glass at 210°-15° C. in a Wood's metal bath while stirring with a glass rod for 4½ minutes. The dark green residue was triturated with methylene chloride (125 ml) and the insoluble material was filtered off. This green solid was dissolved in 450 ml of methanol, treated with 0.9 g of charcoal, and filtered through Celite. The yellow filtrate was concentrated on a rotary evaporator to produce a yellow crystalline solid. The solid was filtered and recrystallized from methanol (3 crops by progressive concentration). The crops were combined and recrystallized from methanol-water to produce a precipitate which was collected and dried under high vacuum at room temperature overnight to give 2.26 g (47%) of pale-yellow crystals, mp 275°-78° C.

Analysis: Calculated for $C_{13}H_{11}N_5O$: C, 61.65; H, 4.38; N, 27.65. Found: C, 61.33; H, 4.30; N, 27.27.

EXAMPLE 22

2-(2-Pyridinyl)-3H-imidazo[4,5-b]pyridine-3-acetic acid ethyl ester

Solid N-[3-[(2-pyridinylcarbonyl)amino]-2-pyridinyl]glycine ethyl ester (21.9 g, 0.069 mole) was heated in glass at 210°-220° C. using a heating mantle for 7½ minutes. The residue was dissolved in methylene chloride, treated with 25.6 g of charcoal, and filtered through a Celite pad. The filtrate was evaporated to a dark residue, which was taken up in ethyl acetate and filtered to remove an insoluble brown solid. The concentrated ethyl acetate filtrate was applied to a silica gel column (400 g) and eluted with ethyl acetate. The appropriate fractions were combined and evaporated to a solid, which was placed under high vacuum for several hours. The solid residue (6.9 g) was recrystallized from ethanol-water and refrigerated overnight. The crystalline precipitate was filtered, washed with water, and dried under high vacuum at room temperature overnight to give 6.34 g of title compound (31%), mp 109°–111° C.

Analysis: Calculated for $C_{15}H_{14}N_4O_2$: C, 63.82; H, 5.00; N, 19.85. Found: C, 64.06; H, 5.00; N, 2026.

EXAMPLE 23

2-(4-Chloro-2-pyridinyl)-3H-imidazo[4,5-b]pyridine-3-acetic acid ethyl ester

The cyclization was effected by heating 12.3 g (0.037 mole) of N-[3-[[(4-chloro-2-pyridinyl)carbonyl]amino]-2-pyridinyl]glycine ethyl ester at 200°–210° C. (oil bath) for 15 minutes. The dark residue was dissolved in methylene chloride and filtered. The filtrate was treated with Florisil®, filtered, and evaporated to an oil, which crystallized upon standing. The solid was recrystallized from methanol-water, washed with 50% aqueous methanol, and dried under high vacuum at 50° C. overnight to give 2.44 g (21%) of title compound, mp 99°–101° C.

Analysis: Calculated for $C_{15}H_{13}N_4O_2Cl$: C, 56.88; H, 4.14; N, 17.69. Found: C, 56.88; H, 4.13; N, 17.64.

EXAMPLE 24

2-(3-Chlorophenyl)-3H-imidazo[4,5-b]pyridine-3-acetic acid ethyl ester

Solid N-[3-[(3-chlorobenzoyl)amino]-2-pyridinyl]glycine ethyl ester, 12.84 g (0.038 mole) was heated in glass at 210°–20° C. in a Wood's metal bath for 7 minutes. The residue was dissolved in methylene chloride, treated with charcoal, and filtered through a Celite pad. The orange filtrate was treated with Florisil ® to give a pink filtrate. The filtrate was evaporated to give a solid, which was recrystallized from tetrahydrofuran-petroleum ether. The solid was collected, washed with petroleum ether, and dried under high vacuum at 50° C. for 5 hours to give 5.3 g (44%) of title compound, mp 98°–99.8° C.

Analysis: Calculated for $C_{16}H_{14}N_3O_2Cl$: C, 60.86; H, 4.47; N, 13.31. Found: C, 60.92; H, 4.54; N, 13.24.

EXAMPLE 25

2-(4-Chlorophenyl)-3H-imidazo[4,5-b]pyridine-3-acetic acid ethyl ester

Solid N-[3-[(4-chlorobenzoyl)amino]-2-pyridinyl]glycine ethyl ester, 15.5 g (0.04 mole) was heated in glass at 210°–20° C. in a Wood's metal bath for 8 minutes. The residue was dissolved in methylene chloride, treated with charcoal, and filtered through a Celite pad. The filtrate (red) was treated with Florisil ® to give a colorless filtrate. The filtrate was evaporated to give a solid, which was recrystallized from tetrahydrofuran-petroleum ether. The solid was collected, washed with petroleum ether (along with a small amount of tetrahydrofuran), and dried under high vacuum at 50° C. overnight to give 7.0 g (48%) of title compound, mp 123°–24° C.

Analysis: Calculated for $C_{16}H_{14}N_3O_2Cl$: C, 60.86; H, 4.47; N, 13.31. Found: C, 60.91; H, 4.48; N, 13.34.

EXAMPLE 26

2-(4-Methoxyphenyl)-3H-imidazo[4,5-b]pyridine-3-acetic acid ethyl ester

Solid N-[3-[(4-methoxybenzoyl)amino]-2-pyridinyl]glycine ethyl ester, 12.8 g (0.039 mole) was heated in glass in a Wood's metal bath at 210°–220° C. for 6 minutes. The residue was dissolved in methylene chloride, treated with charcoal, and filtered through a Celite pad. The filtrate (dark orange) was treated with Florisil ® to give a pale orange filtrate. The filtrate was evaporated to a solid, which was recrystallized from tetrahydrofuran-petroleum ether. The solid was collected, washed with tetrahydrofuranpetroleum ether and dried under high vacuum at 50° C. overnight to give 3.58 g (29.5%) of title compound, mp 107°–8° C.

Analysis: Calculated for $C_{17}N_{17}N_3O_3$: C, 65.58; H, 5.50; N, 13.50. Found: C, 65.69; H, 5.53; N, 13.46.

EXAMPLE 27

2-(2-Chlorophenyl)-3H-imidazo[4,5-b]pyridine-3-acetic acid ethyl ester

Solid N-[3-[(2-chlorobenzoyl)amino]-2-pyridinyl]glycine ethyl ester, 15.0 g (0.045 mole) was heated in a Wood's metal bath at 210°–20° C. for 9 minutes. The residue was dissolved in methylene chloride, treated with Florisil ® (90 g), and filtered. The filtrate was treated with decolorizing charcoal and filtered through a Celite pad to give a yellow filtrate. The filtrate was evaporated to an oil, which crystallized upon standing. The solid (3.0 g) was recrystallized from petroleum ether-tetrahydrofuran (minimum) by cooling in a freezer overnight. The solid was collected, washed with petroleum ether-tetrahydrofuran and dried under high vacuum at room temperature to give 1.62 g (11%) of title compound, mp 64°–66° C.

Analysis: Calculated for $C_{16}H_{14}N_3O_2Cl$: C, 60.86; H, 4.47; N, 13.30. Found: C, 61.07; H, 4.52; N, 13.30.

EXAMPLE 28

2-(2-Methoxyphenyl)-3H-imidazo[4,5-b]pyridine-3-acetic acid ethyl ester hydrochloride [1:1]

Solid N-[3-[(2-methoxybenzoyl)amino]-2-pyridinyl]glycine ethyl ester, 13.75 g (0.042 mole) was heated in glass in a Wood's metal bath at 210°–20° C. for 2 minutes, then at 215°–20° C. for 2 minutes. The residue was dissolved in methylene chloride, treated with activated charcoal, and filtered through a Celite pad. The filtrate (dark orange) was treated with Florisil ® to give a dark filtrate, which was evaporated to give an oil. The oil was dissolved in isopropyl alcohol, filtered and the filtrate acidified with methanolic hydrogen chloride and diluted with isopropyl ether. The crystalline crop was collected, washed with isopropyl etherisopropyl alcohol (minimum), and dried under high vacuum at room temperature overnight to give 1.6 g (11%) of title compound, mp 177°–80° C.

Analysis: Calculated for $C_{17}H_{18}N_3O_3Cl$: C, 58.71; H, 5.22; N, 12.08. Found: C, 58.64; H, 5.24; N, 12.06.

EXAMPLE 29

2-(4-Chloro-2-pyridinyl)-3-[2-(4-methyl-2-piperazinyl)-2-oxoethyl]-3H-imidazo[4,5-b]pyridine A solution of ethyl chloroformate (0.66 g, 0.0061 mole) in 20 ml of methylene chloride was added slowly to a solution of 2-(4-chloro-2-pyridinyl)-3H-imidazo[4,5-b]pyridine acetic acid (1.75 g, 0.006 mole) and triethylamine (0.68 g, 0.0067 mole) in 75 ml of methylene chloride. After the solution was allowed to stir at room temperature for 2 hrs, a solution of N-methylpiperazine (0.61 g, 0.0061 mole) in methylene chloride was added slowly at room temperature and allowed to stir overnight. The reaction mixture was filtered and the filtrate was evaporated to dryness. The residue was partitioned between dilute hydrochloric acid and diethyl ether. The aqueous layer was separated and extracted with diethyl ester (2×) and methylene chloride (3×). The aqueous layer was neutralized (pH 7) and refrigerated. The small amount of precipitate was removed by filtration. The aqueous filtrate was basified and extracted with methylene chloride (3×). The methylene chloride extracts were combined and evaporated to a gum. The gummy residue was purified by alumina column chromatography (Brockman activity 1, 80–200 mesh, 40 g) by elution with 20% acetone/80% benzene. The appropriate fractions (TLC) were combined and evaporated. The residue was crystallized from acetone/petroleum ether (bp 50°–110° C.). The crystalline solid was collected, washed with petroleum ether and isopropyl ether, and dried under high vacuum at room temperature to give 0.54 g (24%) of title compound, mp 174°–75° C.

Analysis: Calculated for $C_{18}H_{19}N_6OCl$: C, 58.30; H, 5.16; N, 22.66. Found: C, 58.29; H, 5.21; N, 22.53.

EXAMPLE 30

2-(4-Chlorophenyl)-3H-imidazo[4,5-b]pyridine-3-acetamide

A mixture of N-[2-[(2-amino-2-oxoethyl)amino]-3-pyridinyl]4-chlorobenzamide (6.0 g, 0.03 mole) in 150 ml of ethylene glycol was heated at 190° C. for 40 minutes. The precipitate, which formed, was filtered off and washed with water. The filtrate was diluted with water to produce a second crop. The first crop was heated to boiling in 300 ml of methanol, filtered through a Celite pad, seeded, and refrigerated overnight. The crystalline precipitate was filtered, washed with cold methanol, and dried under high vacuum at 60° C. overnight to give 1.42 g (25%) of title compound, mp 270°–1° C.

Analysis: Calculated for $C_{14}H_{11}N_4OCl$: C, 58.65; H, 3.87; N, 19.54. Found: C, 58.38; H, 3.86; N, 19.56.

EXAMPLE 31

2-(2-Chlorophenyl)-3H-imidazo[4,5-b]pyridine-3-acetamide hydrochloride [1:1]

The solid N-[2-[(2-amino-2-oxoethyl)amino]-3-pyridinyl]2-chlorobenzamide (7.1 g, 0.023 mole) was heated in glass at 210° C. in a Wood's metal bath for 6 min. The residue was dissolved in methanol (800 ml) and treated with 5.25 g of charcoal. The mixture was filtered through Celite and the filtrate was evaporated to dryness to give 6.3 g residue (85%) crude yield). A 2-g sample was dissolved in 150 ml of ethyl acetate and filtered. The filtrate was acidified with ethereal hydrogen chloride to produce a gummy precipitate which was solubilized by the addition of methanolic hydrogen chloride. The crystalline precipitate, which formed, was filtered, washed with acetonitrile, and dried under high vacuum at room temperature overnight. The solid was recrystallized from methanol (minimum)/ethyl acetate to give a pale yellow solid which was dried under high vacuum at room temperature over the weekend to give 1.2 g of title compound, mp 250°–55° C. with decomposition.

Analysis: Calculated for $C_{14}H_{11}N_4OCl.HCl$: C, 52.03; H, 3.74; N, 17.33. Found: C, 51.77; H, 3.75; N, 17.02.

EXAMPLE 32

2-(3-Chlorophenyl)-3-[2-(4-methyl-1-piperazinyl)-2-oxoethyl]3H-imidazo[4,5-b]pyridine fumarate [2:3]

A stream of nitrogen gas was bubbled through a stirred solution of 2-(3-chlorophenyl)-3H-imidazo[4,5-b]pyridine-3-acetic acid (3.68 g, 0.0128 mole), 1,1'-carbonyldiimidazole (2.07 g, 0.0128 mole), and anhydrous tetrahydrofuram (70 ml) for 2½ hrs. at room temperature. A solution of N-methylpiperazine in 10 ml of tetrahydrofuran was added (rapid drop) and stirring was continued for 4 hrs. at room temperature. The tetrahydrofuran was evaporated and the residue was dissolved in methylene chloride (75 ml). The methylene chloride solution was washed with water (2×30 ml), dried over sodium sulfate, and concentrated in vacuo. The residue was converted to the sesquifumarate salt and crystallized from isopropyl alcohol-isopropyl ether. Recrystallization twice from isopropyl alcohol-isopropyl ether gave 3.2 g (46%) of a white solid, mp 190°–193° C. with decomposition.

Analysis: Calculated for $C_{25}H_{26}N_5O_7Cl$: C, 55.20; H, 4.82; N, 12.87. Found: C, 55.44; H, 4.96; N, 13.23.

EXAMPLE 33

2-(3-[2-(4-methyl-1-piperazinyl)-2-oxoethyl]3H-imidazo[4,5-b]pyridine, fumarate [2:3]

A stream of nitrogen gas was bubbled through a stirred suspension of 2-(3-fluorophenyl)-3H-imidazo[4,5-b]pyridine-3-acetic acid (4.2 g, 0.0151 mole), 1,1'-carbonyldiimidazole (2.5 g, 0.0151 mole) and anhydrous tetrahydrofuran (100 ml) for 2 hrs. at room temperature. A solution of N-methylpiperazine (1.5 g, 0.0151 mole) in tetrahydrofuran (5 ml) was added dropwise, and the reaction solution was stirred 3½ hrs at room temperature. The tetrahydrofuran was evaporated and the residue dissolved in 75 ml of methylene chloride. The methylene chloride solution was washed with water (2×20 ml), dried over sodium sulfate, and concentrated in vacuo. The residue was converted to the sesquifumarate salt and crystallized from isopropyl alcohol-isopropyl ether. Recrystallization twice from isopropyl alcohol-isopropyl ether gave 5.2 g (22%) of white solid, mp 183°–185° C.

Analysis: Calculated for $C_{25}H_{26}N_5O_7F$: C, 56.92; H, 4.97; N, 13.28 Found: C, 57.20; H, 5.08; N, 13.61

EXAMPLE 34

2-(4-Fluorophenyl)-3-[2-(4-methyl-1-piperazinyl)-2-oxoethyl]3H-imidazo[4,5-b]pyridine, fumarate [1:1]

A stream of nitrogen gas was bubbled through a stirred suspension of 2-(4-fluorophenyl)-3H-imidazo[4,5-b]pyridine-3-acetic acid (3.6 g, 0.0133 mole), 1,1'-carbonyldiimidazole (2.2 g, 0.133 mole) and anhydrous tetrahydrofuran (50 ml) for 3 hrs. at room temperature. A solution of N-methylpiperazine (1.3 g, 0.133 mole) in 10 ml of tetrahydrofuran was added dropwise and the solution was stirred for 18 hrs. at room temperature. The tetrahydrofuran was evaporated and the residue was dissolved in methylene chloride (75 ml). The methylene chloride solution was washed with water (3×25 ml), dried over sodium sulfate, and concentrated in vacuo. The residue was converted to the fumarate salt and crystallized from isopropyl alcohol-isopropyl ether, giving 5.3 g (85%). Recrystallization from isopropyl alcohol-isopropyl ether gave 5.1 g of white solid, mp 187°–188.5° C.

Analysis: Calculated for $C_{23}H_{24}N_5O_5F$: C, 58.84; H, 5.15; N, 14.92. Found: C, 58.49; H, 5.23; N, 14.75.

EXAMPLE 35

2-(4-Chlorophenyl)-3-[2-(4-methyl-1-piperazinyl)-2-oxoethyl]3H-imidazo[4,5-b]pyridine, fumarate [1:1]

A stream of nitrogen gas was bubbled through a stirred suspension of 2-(4-chlorophenyl)-3H-imidazo[4,5-b]pyridine-3-acetic acid (2.32 g, 0.0081 mole), 1,1'-carbonyldiimidazole (1.31 g, 0.0081 mole) and anhydrous tetrahydrofuran (50 ml) for 3 hrs. at room temperature. A solution of N-methylpiperazine (0.81 g, 0.0081 mole) in 10 ml of tetrahydrofuran was added and the solution was stirred at room temperature overnight. The tetrahydrofuran was evaporated and the residue was dissolved in methylene chloride (75 ml). The methylene chloride solution was washed with water (3×25 ml), dried over sodium sulfate and concentrated in vacuo. The residue was converted to the fumarate salt and crystallized from isopropyl alcohol-isopropyl ether, to give 3.52 g (89%) slightly impure title compound. Recrystallization from isopropyl alcohol-isopropyl ether gave 2.5 g of title compound, white solid, mp 190°–196° C.

Analysis: Calculated for $C_{23}H_{24}N_5O_5Cl$: C, 56.85; H, 4.98; N, 14.41. Found: C, 57.10; H, 5.24; N, 14.35.

EXAMPLE 36

2-(4-Bromophenyl)-3-[2-(4-methyl-1-piperazinyl)-2-oxoethyl]-3H-imidazo[4,5-b]pyridine fumarate [1:1]

A suspension of 4.4 g (0.0133 mole) of 2-(4-bromophenyl)3H-imidazo[4,5-b]pyridine-3-acetic acid, 2.2 g (0.0133 mole) of 1,1'-carbonyldiimidazole, and anhydrous tetrahydrofuran (100 ml) was stirred at room temperature with a stream of nitrogen bubbling through the mixture for 3 hours. To the resulting solution was added dropwise a solution of 1.3 g (0.0133 mole) of N-methylpiperazine in 10 ml of tetrahydrofuran. The reaction mixture was stirred at room temperature for 18 hours. The tetrahydrofuran was evaporated and the residue taken up in methylene chloride (75 ml) was washed with water (3×25 ml). The methylene chloride solution was dried over sodium sulfate and concentrated in vacuo. The residue was converted to the fumarate salt and crystallized from ethanol-ethyl acetate, giving 6.5 g. Recrystallization from ethanol-ethyl acetate and then from isopropyl alcohol-isopropyl ether gave 3.2 g (45%) of white solid, mp 203°–203.5° C. with decomposition.

Analysis: Calculated for $C_{23}H_{24}N_5O_5Br$: C, 52.09; H, 4.56; N, 13.20. Found: C, 51.91; H, 4.62; N, 13.26.

EXAMPLE 37

2-(3-Chlorophenyl)-3H-imidazo[r,t-b]pyridine-3-acetamide

A suspension of N-[2-[(2-amino-2-oxoethyl)amino]-3-pyridinyl]3-chlorobenzamide (8.7 g, 0.029 mole) in 200 ml of ethylene glycol was heated at 190° C. for 40 minutes. The reaction mixture was allowed to cool to room temperature and filtered. The filtrate was diluted with water to produce a white precipitate. The mixture was refrigerated and the precipitate was filtered, washed with water, and dried under high vacuum at room temperature overnight, then at 60° C. for 6 hrs. The sample was recrystallized from methanol-water (~40/60-) and refrigerated. The crystalline precipitate was filtered, washed with water, and dried under high vacuum at room temperature overnight. The sample was redried under high vacuum at 60° C. overnight to give 5.48 g (66%) of title compound, mp. 245°–47° C.

Analysis: Calculated for $C_{14}H_{11}N_4OCl$: C, 58.65; H, 3.87; N, 19.54. Found: C, 58.44; H, 3.86; N, 19.56.

EXAMPLE 38

2-(4-Chlorophenyl)-3H-imidazo[4,5-pyridine-3-propanoic acid ethyl ester

Solid 3-[[3-[(4-chlorobenzoyl)amino]-2-pyridinyl]amino]propanoic acid ethyl ester, (14.5 g, 0.042 mole) was heated in glass at 202°–205° C. in a Woods metal bath for 5¼ minutes. The residue was purified on a silica gel column (400 g) by elution with 5% methanol/95% toluene. The appropriate frictions were pooled and evaporated to an oil which crystallized upon standing (10.7 g). A 3-g sample was recrystallized from methanol-water. The solid was filtered, washed with water, and dried under high vacuum at room temperature overnight to give 1.45 g (~37%) of title compound, mp 57°–59° C.

Analysis: Calculated for $C_{17}H_{16}N_3O_2Cl$: C, 61.91; H, 4.89; N, 12.74. Found: C, 62.07; H, 4.92; N, 12.88.

EXAMPLE 39

2-(3-Bromophenyl)-3H-imidazo[4,5-b]pyridine-3-acetic acid ethyl ester

A solution of 0.080 mole of 3-bromobenzoyl chloride (freshly prepared) in 30 -ml methylene chloride was added dropwise to a stirred and chilled (10°–15° C.) solution of 14.4 g (0.075 mole) of N-[[3-amino]-2-pyridinyl]glycine ethyl ester in dry tetrahydrofuran (100 ml) and dry methylene chloride (100 ml) while adding simultaneously (dropwise) a solution of 8.1 g, (0.080 mole) of triethylamine and methylene chloride (30 ml). The reaction mixture was stirred for 16 hrs at room temperature. The mixture was filtered and the filtrate concentrated in vacuo. The residue was dissolved in methylene chloride (250 ml) and washed with water (50 ml), 5% aqueous sodium hydroxide solution (2×50 ml) water (2×50 ml), dried over sodium sulfate, and concentrated in vacuo.

The residue (21 g) was dissolved in ethanol and heated on a hot plate to recrystallize. The ethanol evaporated, and continued heating for an undetermined length of time effected cyclodehydration. The melt was cooled and dissolved in methylene chloride (200 ml) and the solution treated with Florisil®. The mixture was filtered, rising the Florisil® with a mixture of methylene chloride-tetrahydrofuram. The filtrate was concentrated in vacuo and the residue recrystallized from isopropyl alcohol-isopropyl ether, giving 6.6 g (24%). A 1.6-g sample was dissolved in methylene chloride and again treated with Florisil®. The mixture was filtered and the filtrate concentrated in vacuo. The residue was recrystallized from isopropyl alcohol-isopropyl ether to give 1.0 g of a white solid, mp 87°–90° C.

Analysis: Calculated for $C_{16}H_{14}N_3O_2Br$: C, 53.35; H, 3.92; N, 11.67. Found: C, 53.60; H, 3.94; N, 11.92.

EXAMPLE 40

2-(4-Chlorophenyl)-3-[4-morpholinyl)-2-oxoethyl]-3H-imidazo[4,5-b]pyridine

A stream of nitrogen gas was bubbled through a stirred suspension of 2-(4-chlorophenyl)-3H-imidazo[4,5-b]pyridine-3-acetic acid (5.96 g, 0.0208 mole), 1,1'-carbonyldiimidazole (3.37 g, 0.0208 mole), and anhydrous tetrahydrofuran (100 ml) at room temperature for 3 hrs. To the resulting solution was added dropwise a solution of morpholine (1.81 g, 0.0208 mole) in tetrahydrofuran (10 ml). The reaction mixture was stirred overnight at room temperature. The tetrahydrofuran was evaporated and the crystalline residue suspended in water and filtered, giving 5.35 g (72%). Recrystallization from 95% ethanol gave 4.9 g of white flakes, mp 213°–216° C.

Analysis: Calculated for $C_{18}H_{17}N_4O_2Cl$: C, 60.59; H, 4.80; N, 15.70. Found: C, 60.84; H, 4.84; N, 15.94.

EXAMPLE 41

2-(4-Chlorophenyl)-N-[2-(dimethylamino)ethyl]-3H-imidazo[4,5-b]pyridine-3-acetamide A stream of nitrogen was bubbled through a stirred suspension of 2-(4-chlorophenyl)-3H-imidazo[4,5-pyridine-3-acetic acid (4.50 g, 0.0157 mole), 1,1'-carbonyldiimidazole (2.54 g, 0.0157 mole) and anhydrous methylene chloride (100 ml) for 2 hrs at room temperature. A solution of N,N-dimethylethylenediamine (1.50 g, 0.0170 mole) in 10 ml of methylene chloride was added dropwise and the reaction mixture was stirred overnight at room temperature. The methylene chloride was washed with water (2×30 ml), 5% sodium hydroxide (2×30 ml), water (30 ml), dried over sodium sulfate and concentrated. The residue (4.5 g) was recrystallized from isopropyl alcohol to give 3.5 g (62%) of white flakes, mp 195°–196.5° C.

Analysis: Calculated for $C_{18}H_{20}N_5OCl$: C, 60.42; H, 5.63; N, 19.57. Found: C, 60.57; H, 5.68; N, 19.87.

EXAMPLE 42

2-(4-Chlorophenyl)-N-[2-(dimethylamino)ethyl]-3H-imidazo[4,5-b] pyridine-3-acetamide hydrochloride [1:2]

2-(4-Chlorophenyl)-N-[2-(dimethylamino)ethyl]-3H-imidazo[4,5-b]pyridine-3-acetamide (0.5 g, 0.0014 mole) was dissolved in acetone, acidified with ethanolic hydrogen chloride, and seeded to initiate crystallization. The solid was collected by filtration, washed with diethyl ether, and dried under high vacuum at room temperature overnight to give 0.60 g (quantitative yield), m.p. 222°–25° C.

Analysis: Calculated for $C_{18}H_{22}N_5OCl_2$: C, 50.19; H, 5.15; N, 16.26. Found: C, 50.00; H, 5.25; N, 16.16.

EXAMPLE 43

2-(4-Chlorophenyl)-N-(3-pyridinyl)-3H-imidazo[4,5-b]pyridine-3-acetamide hydrate [1:0.5]

Under a nitrogen atmosphere, oxalyl chloride (2.41 g, 0.0190 mole) was added dropwise to a stirred suspension of 2-(4-chlorophenyl)-3H-imidazo[4,5-b]pyridine-3-acetic acid (5.28 g, 0.0184 mole) in anhydrous dimethylformamide (70 ml). The resulting solution was stirred at room temperature for 3 hrs and was then added dropwise to a stirred and chilled (15°–20° C.) solution of 3-aminopyridine (1.79 , 0.0190 mole), triethylamine (1.92 , 0.0190 mole) and dimethylformamide (30 ml). The reaction mixture was stirred at room temperature overnight and then poured into 300 ml of water. The mixture was filtered. The filter cake was suspended between methylene chloride (200 ml) and 5% sodium hydroxide (100 ml) and the methylene chloride was separated. The aqueous portion was extracted with methylene chloride (100 ml). The combined methylene chloride layers were washed with 5% sodium hydroxide (2×50 ml), water (50 ml), dried over sodium sulfate, and concentrated. The residue (4.3 g, 66%) was twice recrystallized from isopropyl alcohol-isopropyl ether to give 3.2 g of a white granular solid, mp 217°–218° C.

Analysis: Calculated for $C_{19}H_{15}N_5O_{1.5}Cl$: C, 61.21; H, 4.06; N, 18.78. Found: C, 60.93; H, 4.11; N, 19.04.

EXAMPLE 44

2-(4-Chlorophenyl)-N-(3-pyridinyl)-3H-imidazo[4,5-b]pyridine-3-acetamide hydrochloride hydrate [1:2:1.5]

Solid 2-(4-chlorophenyl)-N-(3-pyridinyl)-3H-imidazo[4,5-b]pyridine-3-acetamide (0.50 g) was dissolved in isopropyl alcohol and acidified with excess ethereal hydrogen chloride to produce a crystalline precipitate. The solid was collected, washed with ether, and dried under high vacuum at room temperature overnight to give 0.58 g (91%), mp 189°–91° C.

Analysis: Calculated for $C_{19}H_{19}N_5O_{2.5}Cl_3$: C, 49.21; H, 4.13; N, 15.10. Found: C, 49.20; H, 4.06; N, 15.07.

EXAMPLE 45

2-(3-Bromophenyl)-3-[2-(4-methyl-1-piperazinyl)-2-oxoethyl]-3H-imidazo[4,5-b]pyridine fumarate [2:3]

A suspension of 2-(3-bromophenyl)-3H-imidazo[4,5-b]pyridine-3-acetic acid (3.00 g, 0.0090 mole), 1,1'-carbonyldiimidazole (1.46 g, 0.0090 mole) and anhydrous tetrahydrofuran (50 ml) was stirred at room temperature with a stream of nitrogen bubbling through the mixture for 3 hrs. A solution of N-methylpiperazine (0.90 g, 0.0090 mole) in 10 ml of tetrahydrofuran (dry) was added and stirring continued at room temperature overnight. The tetrahydrofuran was evaporated and the residue dissolved in methylene chloride (50 ml) and washed with water (3×25 ml), dried over sodium sulfate, and concentrated in vacuo. The residue (3.0 g) was converted to the 1½ fumarate salt and recrystallized twice from isopropyl alcohol-isopropyl ether, giving 2.36 g (45%) of an off-white granular solid, mp 192°–194° C. with decomposition.

Analysis: Calculated for $C_{25}H_{26}N_5O_7Br$: C, 51.03; H, 4.45; N, 11.90. Found: C, 51.01; H, 4.46; N, 12.11.

EXAMPLE 46

2-(4-Chlorophenyl)-3-[2-oxo-2-[4-[3-(trifluoromethyl)phenyl]-1-piperazinyl]ethyl]-3H-imidazo[4,5-b]pyridine A suspension of 2-(4-chlorophenyl)-3H-imidazo[4,5-b]pyridine-3-acetic acid (4.0 g, 0.014 mole), 1,1'-carbonyldiimidazole (2.3 g, 0.014 mole), and anhydrous tetrahydrofuran (100 ml) was stirred at room temperature with a stream of nitrogen bubbling through the mixture for 2½ hrs. A solution of N-(α, α, α-trifluoro-m-tolyl)-piperazine (3.2 g, 0.014 mole) in dry tetrahydrofuran (10 ml) was added and the reaction mixture was stirred at room temperature for 4½ hrs. The tetrahydrofuran was evaporated and the residue dissolved in methylene chloride (75 ml). The methylene chloride solution was extracted with 5% potassium hydroxide solution (2×30 ml), water (30 ml), brine (25 ml), dried over sodium sulfate, and concentrated in vacuo. The residue (6.6 g) was twice recrystallized from isopropyl alcohol-isopropyl ether to give 3.3 g (47%) of white needles, mp 185°–186.5° C.

Analysis: Calculated for $C_{25}N_{21}N_5OClF_3$: C, 60.06; H, 4.24; N, 14.01. Found: C, 59.95; H, 4.16; N, 13.92.

EXAMPLE 47

2-(4-Chlorophenyl)-N-methyl-3H-imidazo[4,5-b]pyridine-3-acetamide

Under a nitrogen atmosphere, a suspension of 2-(4-chlorophenyl)3H-imidazo[4,5-b]pyridine-3-acetic acid, 6.0 g (0.021 mole) and 1,1'-carbonyldiimidazole (3.39 g, 0.021 mole) in tetrahydrofuran (150 ml) was refluxed, with stirring, for 2.5 hrs. The mixture was cooled to room temperature and a solution of 3.6 g (0.116 mole) of monomethylamine in tetrahydrofuran (60 ml) was added dropwise and the reaction mixture was stirred in room temperature overnight. The tetrahydrofuran was evaporated and the residue was triturated in water (150 ml). The solid was filtered and rinsed with water. The solid was dissolved in hot isopropyl alcohol, treated with charcoal, filtered, and allowed to cool. Solid formed, and water was added to precipitate more. The solid was filtered and dried under vacuum to give 3.0 g (47.5%) of title compound, mp 238°–238.5° C.

Analysis: Calculated for $C_{15}H_{13}N_4OCl$: C, 59.91; H, 4.36; N, 18.63. Found: C, 59.76; H, 4.37; N, 18.43.

EXAMPLE 48

2-(4-Chlorophenyl)-N,N-dimethyl-3H-imidazo[4,5-b]pyridine-3-acetamide

A suspension of 2-(4-chlorophenyl)-3H-imidazo[4,5-b]pyridine-3-acetic acid (3.0 g, 0.010 mole) 1,1'-carbonyldiimidazole (1.7 g, 0.010 mole) and dry tetrahydrofuran (150 ml) was stirred for 3 hrs. at room temperature with a stream of nitrogen bubbling through it. A solution of 1.0 g of dimethylamine in 25 ml of tetrahydrofuran was added and the reaction container was stoppered and the mixture was stirred overnight at room temperature. The tetrahydrofuran was evaporated and the residue triturated in water (50 ml) and filtered. The filter cake was recrystallized from isopropyl alcohol and then from ethanol, giving 2.4 g (32%) of white needles, mp 212°–213° C.

Analysis: Calculated for $C_{16}H_{15}N_4OCl$: C, 61.05; H, 4.80; N, 17.80. Found: C, 60.78; H, 4.76; N, 17.67.

EXAMPLE 49

2-(4-Chlorophenyl)-N,N-dimethyl-3H-imidazo[4,5-b]pyridine-3-acetamide hydrochloride[1:1]

A mixture of 2-(4-chlorophenyl)-3H-imidazo[4,5-b]pyridine-3-acetic acid (6.0 g, 0.021 mole) and 1,1'-carbonyldiimidazole (3.39 g, 0.021 mole) in 150 ml of tetrahydrofuran was stirred at room temperature for 3 hours with nitrogen bubbling through it. A solution of dimethylamine in tetrahydrofuran (84 ml of 1M solution, 0.042 mole) was added dropwise at room temperature to the stirred solution and the reaction mixture was allowed to stir at room temperature overnight. The tetrahydrofuran was evaporated and the solid was triturated with water. The solid was collected and dried under high vacuum overnight. The solid was dissolved in tetrahydrofuran and acidified with ethereal hydrogen chloride to produce a crystalline precipitate, which was collected, washed with tetrahydrofuran, and dried under high vacuum overnight at room temperature to give 5.3 g, (73%), mp 216°–219.5° C.

Analysis: Calculated for $C_{16}H_{16}N_4OCl_2$: C, 54.71; H, 4.59; N, 15.95. Found: C, 54.58; H, 4.64; N, 15.88.

EXAMPLE 50

2-(3-Chlorophenyl)-3H-imidazo[4,5-b]pyridine-3-propanoic acid ethyl ester hydrochloride[1:1]

N-[[3-[(3-Chlorobenzoyl)amino]-2-pyridinyl]amino]-propanoic acid ethyl ester (17.3 g, 0.05 mole) was heated at 205° C. in glass in a Wood's metal bath for 12–13 minutes. The residue was dissolved in ethyl acetate, filtered to remove small amounts of insoluble material, and evaporated to dryness. The residue was purified on a silica gel column (400 g) by elution with 5% methanol/95% toluene. The appropriate fractions were combined and evaporated. Latter fractions containing product were treated with Florisil ® to remove color. Total yield of free base was 13.0 g (79%). A 2.5-g sample was dissolved in tetrahydrofuran, acidified with excess ethereal hydrogen chloride, and allowed to slowly crystallize. The solid was collected, washed with anhydrous ether, and dried under high vacuum at room temperature overnight to give 2.45 g of product in 2 crops, mp 144°–46° C.

Analysis: Calculated for $C_{17}H_{16}N_3O_2Cl \cdot HCl$: C, 55.75; H, 4.68; N, 11.47. Found: C, 55.84; H, 4.66; N, 11.44.

EXAMPLE 51

2-(2-Chlorophenyl)-3H-imidazo[4,5-b]pyridine-3-propanoic acid ethyl ester hydrochloride[1:1]

3-[[3-[(2-Chlorobenzoyl)amino]-2-pyridinyl]-amino]-propanoic acid ethyl ester (12.36 g, 0.036 mole) was heated at 220°–225° C. in glass in a Wood's metal bath for 13 minutes. The residue was purified on a silica gel column (400 g) by elution with 5% methanol/95% toluene. The appropriate fractions were combined and evaporated to an oil. Latter fractions containing product plus red color were treated with Florisil ® to remove the color. Total yield of free base was 64%. A 2.1-g sample of the oil was dissolved in tetrahydrofuran, acidified with ethereal hydrogen chloride, and allowed to slowly crystallize. The crystalline precipitate was collected, washed with cold tetrahydrofuran and diethyl ether, and dried under high vacuum at room temperature overnight to give 1.65 g, mp 173°–76° C.

Analysis: Calculated for $C_{17}N_{16}N_3O_2Cl \cdot HCl$: C, 55.75; H, 4.68; N, 11.47. Found: C, 55.66; H, 4.68; N, 11.38.

EXAMPLE 52

2-(4-Chlorophenyl)-3H-imidazo[4,5-b]pyridine-3-acetic acid 1,1-dimethyl ethyl ester Under a nitrogen atmosphere, N,N-dimethylformamide-ditert-butyl acetal (8.0 g, 0.044 mole) was added dropwise over a 20-minute period to a stirred and refluxing suspension of 2-(4-chlorophenyl)-3H-imidazo[4,5-b]pyridine-3-acetic acid (3.11 g, 0.011 mole) in dry benzene (50 ml). Refluxing was continued for 4 hrs. The cooled solution was washed with dilute sodium bicarbonate solution (3×25 ml), water (25 ml), dried over sodium sulfate, and concentrated in vacuo. The residue, 3.6 g (24%) was twice recrystallized from isopropyl ether to give an off-white solid, mp 89°–92° C.

Analysis: Calculated for $C_{18}H_{18}N_3O_2Cl$: C, 62.88; H, 5.28; N, 12.22. Found: C, 62.91; H, 5.33; N, 12.36.

EXAMPLE 53

2-(4-Chlorophenyl)-3H-imidazo[4,5-b]pyridine-3-ethanethioamide hydrate[1:0.5]

A mixture of 2-(4-chlorophenyl)-3H-imidazo [4,5-b]pyridine-3-acetamide (3.44 g, 0.012 mole) and phosphorus pentasulfide (1.47 g, 0.0033 mole) in 150 ml of dry acetonitrile (dried over molecular sieves) was heated at reflux for 3 hr. The reaction mixture was filtered and washed with boiling acetonitrile. The solid residue in the flask was treated with boiling methanol and filtered. The methanol and acetonitrile filtrates were combined and evaporated to dryness. The residue was treated with acetone and filtered through a silica gel filter funnel. The filtrate was treated with Florisil ®, filtered, and evaporated to dryness. The residue was treated with acetone, applied to a silica gel column (7×15 cm), and eluted with acetone. The appropriate fractions were combined and evaporated. The residue was dissolved in hot methanol, treated with activated charcoal, and filtered through a Celite pad. The filtrate was concentrated to initiate crystallization. The mixture was diluted with water and ice, then filtered to collect the precipitate which was washed with water. The solid was dried under high vacuum overnight at room temperature, then at 55° C. for 5 hr. to give 0.31 g product (8.3%), mp 226°–29° C. with decomposition.

Analysis: Calculated for $C_{14}H_{11}SN_4Cl.\frac{1}{2}H_2O$: C, 53.93; H, 3.88; N, 17.97. Found: C, 54.26; H, 3.83; N, 17.68.

EXAMPLE 54

2-(4-Chlorophenyl)-3H-imidazo[4,5-b]pyridine-3-acetic acid methyl ester

A solution of 2-(4-chlorophenyl)-3H-imidazo[4,5-b]pyridine3-acetic acid (3.1 g, 0.1011 mole), methanol (100 ml) and concentrated sulfuric acid (3 ml) was refluxed overnight under a Dean-Stark trap. Another 2 ml of concentrated sulfuric acid and methanol (50 ml) was added and reflux continued for 12 hr. The methanol was evaporated, water (50 ml) was added, and sodium bicarbonate (solid) added until basic. The mixture was extracted with ethyl acetate (3×25 ml). The combined ethyl acetate extracts were washed with water (25 ml), dried over sodium sulfate, and concentrated in vacuo. The residue (2.5 g) was combined with a sample obtained previously and recrystallized from isopropyl ether-isopropyl alcohol to give 3.0 g (56%) of white needles, mp 198°–200° C.

Analysis: Calculated for $C_{15}H_{12}N_3O_2Cl$: C, 59.71; H, 4.01; N, 13.93. Found: C, 59.64; H, 3.98; N, 13.85.

EXAMPLE 55

2-(4-Chlorophenyl)-3H-imidazol[4,5-b]pyridine-3-acetic acid 1-methylethyl ester

A solution of 2-(4-chlorophenyl)-3H-imidazo[4,5-b]pyridine3-acetic acid (3.1 g, 0.0108 mole), isopropanol (50 ml), benzene (50 ml), and concentrated sulfuric acid (5 ml) was refluxed under a Dean-Stark trap for 24 hrs. The reaction mixture was concentrated and the residue partitioned between 5% potassium hydroxide solution (50 ml) and ethyl acetate (50 ml). The layers were separated and the aqueous portion extracted with ethyl acetate (2×25 ml). The organic layers were combined and washed with 5% potassium hydroxide (25 ml), water (25 ml), dried over sodium sulfate, and concentrated in vacuo to give 2.0 g (56%) of a solid, mp 118°–120° C. Recrystallization from isopropyl ether gave 1.7 g of off-white needles, mp 117.5°–119° C.

Analysis: Calculated for $C_{17}H_{16}N_3O_2Cl$: C, 61.92; H, 4.89; N, 12.74. Found: C, 61.87; H, 4.84; N, 12.67.

EXAMPLE 56

N,N-Dimethyl-2-[4-(trifluoromethyl)phenyl]-3H-imidazo [4,5-b]pyridine-3-acetamide A suspension of 2-(4-trifluoromethylphenyl)-3H-imidazo [4,5-b]pyridine-3-acetic acid (10.0 g, 0.031 mole), 1,1'-carbonyldiimidazole (6.0 g, 0.037 mole), and dry tetrahydrofuran (200 ml) was stirred at room temperature for 2 hr. with a stream of nitrogen bubbling through it. The suspension was heated at 50° C. under nitrogen for 2 hr, cooled in ice and treated with a solution of dimethylamine in tetrahydrofuran (4.22 g of dimethylamine in 40 ml of tetrahydrofuran.) The solution was stirred at room temperature overnight, more dimethylamine (0.071 mole in 30 ml of tetrahydrofuran) was added, and the reaction mixture was heated at 45° C. for 3 hr. The reaction mixture was concentrated under reduced pressure; the resulting solid was triturated in water, filtered, rinsed twice with water, twice with 5% potassium hydroxide solution and then twice again with water. The solid was dissolved in hot isopropyl alcohol, filtered hot, and cooled. Water was added and the solid filtered and dried at 80° C. under vacuum to yield 3.55 g (33%) of white solid, mp. 181°–183° C.

Analysis: Calculated for $C_{17}H_{15}N_4OF_3$: C, 58.62; H, 4.32; N, 16.08. Found: C, 58.76; H, 4.37; N, 16.07.

EXAMPLE 57

3-[2-(4-Methyl-1-piperazinyl)-2-oxoethyl]-2-(2-pyridinyl)-3H-imidazo[4,5-b]pyridine fumarate[1:1]

A solution of (2-(2-pyridinyl)-3H-imidazo[4,5-b]pyridine-3-acetic acid (3.00 g, 0.012 mole), 1,1'-carbonyldiimidazole (1.94 g, 0.012 mole), and anhydrous tetrahydrofuran (50 ml) was stirred at room temperature with a stream of nitrogen bubbling through it for 2½ hours. The nitrogen flow was stopped, N-methylpiperazine (1.2 g, 0.012 mole) added, and the reaction mixture was stoppered and stirred over the weekend. The tetrahydrofuran was evaporated, water (100 ml) added, and the mixture basified with 10% sodium hydroxide solution. The mixture was extracted with ethyl acetate (4×25 ml). The combined organic extracts were washed with water (25 ml), dried over sodium sulfate, and concentrated in vacuo. The residue (1.3 g) was converted to the fumarate salt and crystallized from isopropyl alcohol-isopropyl ether-water, giving 1.4 g (26%). Recrystallization from isopropyl alcohol-isopropyl ether gave 1.2 g of a white solid, mp 212°–213° C.

Analysis: Calculated for $C_{22}H_{24}N_6O_5$: C, 58.40; H, 5.35; N, 18.57. Found: C, 58.10; H, 5.34; N, 18.33.

EXAMPLE 58

2-(2-Pyridinyl)-3H-imidazo[4,5-b]pyridine-3-acetic acid methyl ester hydrochloride[1:1]

A solution of 2-(2-pyridinyl)-3H-imidazo[4,5-b]pyridine-3-acetic acid (2.50 g, 0.010 mole), methanol (50 ml), concentrated sulfuric acid (5 ml), and benzene (50 ml) was refluxed overnight with a Dean-Stark trap. The reaction was concentrated in vacuo, diluted with water (50 ml), and basified with 10% potassium carbonate solution. The mixture was extracted with methylene chloride (3×25 ml). The combined organic extracts were washed with water (25 ml), dried over sodium sulfate, and concentrated in vacuo. The residue was dissolved in tetrahydrofuran and treated with excess ethereal hydrogen chloride, giving 2.35 g (77%). Recrystallization twice from tetrahydrofuran-methanol gave 1.0 g of a white solid, mp 188°–190° C.

Analysis: Calculated for $C_{14}H_{13}N_4O_2Cl$: C, 55.18; H, 4.30; N, 18.38. Found: C, 55.56; H, 4.30; N, 18.49.

EXAMPLE 59

N,N-Dimethyl-2-[3-(trifluoromethyl)phenyl]-3H-imidazo[4,5-b] pyridine-3-acetamide A suspension of 2-[(3-trifluoromethyl)phenyl]-3H-imidazo[4,5-b] pyridine3-acetic acid (3.0 g, 0.0093 mole), 1,1'-carbonyldiimidazole (1.5 g, 0.0093 mole) and anhydrous tetrahydrofuran (75 ml) was stirred at room temperature for 4½ hours with a stream of nitrogen bubbling through. A solution (25 ml) of dimethylamine in tetrahydrofuran (2 g/100 ml) was added and the reaction mixture was stoppered and stirred overnight. The resulting solution was concentrated in vacuo and the residue was triturated in water (30 ml) and filtered. The filter cake was again triturated in water (30 ml) and filtered, giving 2.6 g (80%), mp 136°–137.5° C. Recrystallization from tetrahydrofuran-petroleum ether gave 2.0 g of a white solid, mp 138°–139° C.

Analysis: Calculated for $C_{17}H_{15}N_4OF_3$: C, 58.62; H, 4.34; N, 16.08; Found: C, 58.44; H, 4.26; N, 16.00.

EXAMPLE 60

N,Methyl-2-(2-pyridinyl)-3H-imidazo[4,5-b]pyridine-3-acetamide

A solution of 2-(2-pyridinyl)-3H-imidazo[4,5-b]pyridine-3-acetic acid (2.44 g, 0.0096 mole), 1,1'-carbonyldiimidazole (1.56 g, 0.0096 mole), and anhydrous tetrahydrofuran (100 ml) was stirred at room temperature with a stream of nitrogen bubbling through it for 5 hours. A solution of 1M monomethylamine in tetrahydrofuran (15 ml) was added and the reaction stoppered and stirred overnight. The tetrahydrofuran was evaporated in vacuo and the residue triturated in water (30 ml) and filtered. The filter cake was again triturated in water (30 ml) and filtered, giving 1.94 g (76%) of solid, mp 228°–230° C. Recrystallization from tetrahydrofuran-methanol gave 1.49 g of a white solid, mp 228.5°–230° C.

Analysis: Calculated for $C_{14}H_{13}N_5O$: C, 62.91; H, 4.90; N, 26.20. Found: C, 62.62; H, 4.84; N, 26.12.

EXAMPLE 61

2-(2-Pyridinyl)-3H-imidazo[4,5-b]pyridine-3-acetic acid 1,1-dimethylethyl ester

Under a nitrogen atmosphere, N,N-dimethylformamide-ditert-butyl acetal (8.12 g, 0.040 mole) was added dropwise over a 20-minute period to a stirred, refluxing suspension of 2-(2-pyridyl)-3H-imidazo[4,5-b]pyridine-3-acetic acid (2.54 g, 0.010 mole) in anhydrous benzene (50 ml). The resulting solution was refluxed for 1 hour and allowed to cool to room temperature. The reaction mixture was washed with 10% potassium carbonate solution (2×25 ml), water (25 ml), dried over sodium sulfate and concentrated in vacuo. The residue (3.5 g) was dissolved in tetrahydrofuran and treated with excess ethereal hydrogen chloride. The crystalline solid was recrystallized from tetrahydrofuran, giving 1.5 g (43%). Drying in vacuo at 65° C. for 8 hours and then at 78° C. overnight gave 1.4 g of the compound as the free base, mp 124°–125.5° C.

Analysis: Calculated for $C_{17}H_{18}N_4O_2$: C, 65.79; H, 5.84; N, 18.05. Found: C, 65.44; H, 5.84; N, 17.99.

EXAMPLE 62

2-(4-Chlorophenyl)-N,N-dipropyl-3H-imidazo[4,5-b]pyridine-3-acetamide

A mixture of 2-(4-chlorophenyl)-3H-imidazo[4,5-b]pyridine3-acetic acid (6.0 g, 0.021 mole) and 1,1'-carbonyldiimidazole (3.39 g, 0.021 mole) in 150 ml of tetrahydrofuran was stirred at room temperature for 2 hours with a stream of nitrogen bubbling through it. A solution of di-n-propylamine (1.94 g, 0.063 mole) in tetrahydrofuran was added dropwise at room temperature to the stirred solution and the reaction mixture was allowed to stir at room temperature overnight. The tetrahydrofuran was evaporated and the solid residue was triturated with water. The solid was collected by filtration and dried under high vacuum overnight. The solid was recrystallized from isopropyl alcohol-water, collected by filtration, washed with water, and dried under high vacuum at room temperature over the weekend to give 3.79 g (59%) in 2 crops, mp 156°–57° C.

Analysis: Calculated for $C_{20}H_{23}N_4OCl$: C, 64.77; H, 6.25; N, 15.11. Found: C, 64.60; H, 6.26; N, 15.08.

EXAMPLE 63

2-(3-Chlorophenyl)-N-methyl-3H-imidazo[4,5-b]pyridine-3-acetamide hydrochloride[1:1]

A suspension of 2-(3-chlorophenyl)-3H-imidazo[4,5-b] pyridine-3-acetic acid (2.89 g, 0.010 mole), 1,1'-carbonyldiimidazole (1.62 g, 0.010 mole), and anhydrous tetrahydrofuran (125 ml) was stirred at room temperature with a stream of nitrogen bubbling through it for 4½ hours. A solution of 1M methylamine in tetrahydrofuran (15 ml, 0.015 mole) was added and the resulting solution was stoppered and stirred overnight at room temperature. The reaction mixture was concentrated in vacuo and the residue triturated twice in water (2×75 ml) and filtered. The filter cake (mp 186°–189° C.) was dissolved in isopropyl alcohol and treated with excess ethereal hydrogen chloride, giving 1.6 g (47%) of a white flocculent solid which melted from 195°–199° C. after a few crystals had melted between 185°–190° C. It was also observed that prolonged heating decreases the melting point.

Analysis: Calculated for $C_{15}H_{14}N_4OCl_2$: C, 53.43; H, 4.18; N, 16.61.Found: C, 53.48; H, 4.20; N, 16.60.

EXAMPLE 64

2-(4-Chlorophenyl)-N,N-diethyl-3H-imidazo[4,5-b]pyridine-3-acetamide hydrate[1:0.5]

A mixture of 2-(4-chlorophenyl)-3H-imidazo[4,5-b]pyridine-3-acetic acid (5.64 g, 0.020 mole) and 1,1'-carbonyldiimidazole (3.18 g, 0.02 mole) in 150 ml of tetrahydrofuran was stirred at room temperature for 2 hours with a stream of nitrogen bubbling through it. A solution of diethylamine (2.87 g, 0.04 mole) in tetrahydrofuran was added dropwise at room temperature to the stirred solution and the mixture was allowed to stir overnight. The tetrahydrofuran was evaporated and the solid residue was triturated with water. The solid was collected by filtration and dried under high vacuum overnight. The solid was recrystallized from isopropyl alcohol-water, collected by filtration, washed with water, and dried under high vacuum at room temperature over the weekend to give 3.83 g (57%) mp 155°–56° C.

Analysis: Calculated for $C_{18}H_{19}N_4OCl.\frac{1}{2}H_2O$: C, 61.45; H, 5.73; N, 15.92. Found: C, 61.34; H, 5.46; N, 15.96.

EXAMPLE 65

2-(4-Chlorophenyl)-N-(1-methylethyl)-3H-imidazo[4,5-b]pyridine-3-acetamide

A mixture of 2-(4-chlorophenyl)-3H-imidazo[4,5-b]pyridine3-acetic acid (5.0 g, 0.017 mole) and 1,1′-carbonyldiimidazole (2.82 g, 0.017 mole) in 150 ml of tetrahydrofuran was stirred at room temperature for 2 hours with a stream of nitrogen bubbling through it. A solution of isopropylamine (2.06 g, 0.035 mole) in tetrahydrofuran was added dropwise and the reaction mixture was allowed to stir at room temperature overnight. The tetrahydrofuran was evaporated and the solid residue was triturated with water. The solid was collected and dried under high vacuum overnight. The solid was crystallized from isopropyl alcohol with cooling in the freezer, collected by filtration, washed with water, and dried under high vacuum at 50° C. overnight to give 4.0 g (70%), mp 248°–9° C.

Analysis: Calculated for $C_{17}H_{17}N_4OCl$: C, 62.10; H, 5.21; N, 17.04. Found: C, 61.95; H, 5.23; N, 17.05.

EXAMPLE 66

2-(4-Chlorophenyl)-N-(1-ethyl-3-piperidinyl)-3H-imidazo[4,5-b] pyridine-3-acetamide hydrochloride hydrate [1:2:1]

A mixture of 2-(4-chlorophenyl)-3H-imidazo[4,5-b]pyridine3-acetic acid (5.0 g, 0.0174 mole) and 1,1′-carbonyldiimidazole (2.82 g, 0.0174 mole) in 150 ml of tetrahydrofuran was stirred at room temperature for 3 hrs having a stream of nitrogen bubbling through it. 3-Amino-N-ethylpiperidine (4.46 g, 0.0348 mole) was added dropwise and the reaction mixture was allowed to stir at room temperature overnight.

The tetrahydrofuran was evaporated and the residue was partitioned between methylene chloride and water. The methylene chloride layer was separated and extracted with dilute sodium hydroxide then with water. The methylene chloride layer was separated, dried, and evaporated. The residue was dried under high vacuum to give 5.2 g of solid.

The solid was dissolved in acetone, acidified with ethanolic and ethereal hydrogen chloride and seeded. The solid was collected by filtration, washed with tetrahydrofuran, and dried under high vacuum at room temperature overnight. The solid was converted to the free base with dilute sodium hydroxide and extracted with methylene chloride (3×). The combined methylene chloride extracts were washed with water, dried, and evaporated. The solid was dissolved in acetone, acidified with ethanolic and ethereal hydrogen chloride, and seeded. The crystalline solid was collected by filtration, washed with tetrahydrofuran, and dried under high vacuum at room temperature overnight, then at 50° C. for 2 hrs to give 2.24 g (27%) of title product, mp 208°–210° C.

Analysis: Calculated for $C_{21}H_{24}N_5OCl.2HCl.H_2O$: C, 51.60; H, 5.77; N, 14.33. Found: C, 51.85; H, 5.66; N, 14.32.

EXAMPLE 67

1-[2-(4-Chlorophenyl)-1H-imidazo[4,5-b]pyridin-1-yl]-2-propanone hydrochloride[1:1]

The 2-(4-chlorophenyl)-3H-imidazo[4,5-b]pyridine (2.29 g, 0.01 mole), was added to a suspension of sodium hydride (0.44 g of 60% sodium hydride/oil, 0.01 mole, washed once with hexanes) in 50 ml of dimethylformamide. The mixture was heated to 70° C. for 1 hr before the addition of chloroacetone (0.93 g, 0.01 mole) at room temperature. The reaction mixture was stirred at room temperature overnight, then poured into 300 ml of water. The precipitate was collected by filtration, washed with water, and dried under high vacuum at 50° C. overnight. The solid was recrystallized from methanol-water and dried under high vacuum at 50° C. overnight. The solid was dissolved in methanol, treated with charcoal, and filtered through Celite to give a pale yellow filtrate. The filtrate was concentrated and diluted with water to initiate crystallization. The precipitate was collected by filtration, washed with water, and dried under high vacuum overnight. The solid was dissolved in isopropyl alcohol, acidified with ethereal hydrogen chloride, diluted with isopropyl ether, and seeded to initiate crystallization. The crystalline solid was collected by filtration, washed with isopropyl ether, and dried under high vacuum overnight to give 1.6 g, (50%), m.p. 220°–22° C.

Analysis: Calculated for $C_{15}H_{13}N_3OCl_2$: C, 55.92; H, 4.07; N, 13.04. Found: C, 55.49; H, 4.13; N, 13.06.

EXAMPLE 68

N-[[2-(4-Chlorophenyl)-3H-imidazo[4,5-b]pyridin-3-yl]acetyl] glycine ethyl ester Under nitrogen bubbling, a mixture of 2-(4-chlorophenyl)-3H-imidazo[4,5-b]pyridine-3-acetic acid, 5.0 g (0.0174 mole) and 1,1′-carbonyldiimidazole (2.82 g, 0.0174 mole) in 150 ml of tetrahydrofuran was stirred at room temperature for 3 hrs. The ethyl glycinate (2.65 g, 0.019 mole) and triethylamine (1.92 g, 0.019 mole) were added dropwise and the reaction was allowed to stir at room temperature overnight.

The tetrahydrofuran was evaporated and the residue was partitioned between methylene chloride and water. The methylene chloride layer was separated and extracted with dilute sodium hydroxide then with water. The methylene chloride layer was separated, dried, and evaporated. A 2-g sample was recrystallized from ethanol-water. The crystalline solid was collected by filtration, washed with water, and dried under high vacuum overnight to give 1.02 g (~43%) of title compound, m.p. 191°–192° C.

Analysis: Calculated for $C_{18}H_{17}N_4O_3Cl$: C, 57.99; H, 4.60; N, 15.03. Found: C, 58.04; H, 4.46; N, 15.00.

EXAMPLE 69

2-(4-Chlorophenyl)-N-propyl-3H-imidazo[4,5-b]pyridine-3-acetamide

A mixture of 2-(4-chlorophenyl)-3H-imidazo[4,5-b]pyridine3-acetic acid 5.0 g (0.0174 mole) and 1,1′-carbonyldiimidazole (2.82 g, 0.0174 mole) in 150 ml of tetrahydrofuran was stirred at room temperature for 2.5 hrs with a stream of nitrogen bubbling through it. The n-propylamine (2.06 g, 0.0348 mole) was added dropwise and the reaction mixture was allowed to stir at room temperature under nitrogen atmosphere overnight. The tetrahydrofuran was evaporated and the residue was triturated with water. The solid was collected and dried under high vacuum at 50° C. overnight. The solid was dissolved in isopropyl alcohol, filtered, diluted with water, and placed in the freezer overnight. The crystalline precipitate was collected by filtration, washed with water, and dried at 50° C. under high vacuum overnight to give 3.6 g (63%), m.p. 220°-21° C.

Analysis: Calculated for $C_{17}H_{17}N_4OCl$: C, 62.10; H, 5.21; N, 17.04. Found: C, 61.99; H, 5.22; N, 17.05.

EXAMPLE 70

N-[[2-(3-Chlorophenyl)-3H-imidazo[4,5-]pyridin-3-yl]acetyl]glycine ethyl ester A solution of 2-(3-chlorophenyl)-3H-imidazo[4,5-b]pyridine-3-acetic acid (9.50 g, 0.033 mole), 1,1'-carbonyldiimidazole (5.35 g, 0.033 mole) and anhydrous tetrahydrofuran (300 ml) was stirred at room temperature for 2 hrs with a stream of nitrogen bubbling through it. To the resulting suspension was added glycine ethyl ester (8.0 g, 0.078 mole) and the solution stirred over the weekend. The reaction mixture was filtered and the filtrate concentrated in vacuo. The residue was partitioned between ethyl acetate (150 ml) and potassium bicarbonate solution (75 ml). The organic layer was washed with potassium bicarbonate solution (2×50 ml), water (50 ml), brine (25 ml), dried over sodium sulfate, and concentrated in vacuo. The residue (10 g) was recrystallized from tetrahydrofuran-isopropyl ether to give 6.93 g (56%) of an off-white solid, m.p. 144°-145° C.

Analysis: Calculated for $C_{18}H_{17}N_4O_3Cl$: C, 57.99; h, 4.60; N, 15.03. Found: C, 58.00; H, 4.62; N, 15.03.

EXAMPLE 71

2-(4-Chlorophenyl)-N-[(1-ethyl-2-pyrrolidinyl)methyl]-3-imidazo[4,5-b]pyridine-3-acetamide hydrochloride[1:2]

A mixture of 2-(4-chlorophenyl)-3H-imidazo[4,5-b]pyridine-3-acetic acid 5.0 g (0.0174 mole) and 1,1'-carbonyldiimidazole (2.82 g, 0.0174 mole) in 150 ml of tetrahydrofuran was stirred at room temperature for 3 hrs with a stream of nitrogen bubbling through it. The 2-(aminomethyl)-1-ethylpyrrolidine (4.46 g, 0.0348 mole) was added dropwise and the reaction mixture was allowed to stir at room temperature overnight.

The tetrahydrofuran was evaporated and the residue was partitioned between methylene chloride and water. The methylene chloride layer was separated and extracted with dilute sodium hydroxide, then with water. The methylene chloride layer was separated, dried, and evaporated. The residue was dried under high vacuum overnight. The solid was dissolved in isopropyl alcohol, acidified with ethereal hydrogen chloride, and seeded. The crystalline material was collected, washed with tetrahydrofuran and dried under high vacuum overnight. The solid was converted to the free base with dilute sodium hydroxide and extracted with methylene chloride (3×). The combined methylene chloride extracts were washed with water, dried, evaporated, and dried under high vacuum overnight. The solid was dissolved in isopropyl alcohol, acidified with ethanolic and ethereal hydrogen chloride, and seeded. The crystalline material was collected, washed with diethyl ether, and dried under high vacuum at 50° C. for 2 hrs, then at room temperature overnight. The sample was redried under high vacuum at 50° C. overnight, at 70° C. overnight, and at room temperature overnight to give 5.0 g (61%) of title compound, m.p. 199°-202° C.

Analysis: Calculated for $C_{21}H_{24}N_5OCl.2HCl$: C, 53.57; H, 5.67; N, 14.60. Found: C, 53.10; H, 5.61; N, 14.62.

EXAMPLE 72

N-[[2-(4-Chlorophenyl)-3H-imidazo[4,5-b]pyridin-3-yl]acetyl]glycine potassium salt hydrate [1:1:2]

A mixture of N-[[2-(4-chlorophenyl)-3H-imidazo[4,5-b] pyridin-3-yl]acetyl]glycine ethyl ester (4.0 g, 0.0108 mole), potassium hydroxide (0.62 g, 0.011 mole), and 100 ml of 95% ethyl alcohol was heated at reflux for 2 hrs. The hot solution was filtered and allowed to cool to initiate crystallization. The solid was diluted with 95% ethyl alcohol, filtered, and washed with a little 95% ethyl alcohol. The solid was dried under high vacuum at room temperature overnight to give 2.5 g (55%) of title compound, m.p. >300° C.

Analysis: Calculated for $C_{16}H_{12}N_4O_3Cl.K.2H_2O$: C, 45.88; H, 3.85; N, 13.38. Found: C, 45.58; H, 3.80; N, 13.33.

EXAMPLE 73

2-(4-Chlorophenyl)-N-phenyl-3H-imidazo[4,5-b]pyridine-3-acetamide

Under nitrogen atmosphere, oxalyl chloride, 1.73 g (0.0137 mole) was added dropwise to a stirred, chilled (10°-15° C.) suspension of 2-(4-chlorophenyl)-3H-imidazo[4,5-b]pyridine-3-acetic acid (3.7 g, 0.013 mole) in 50 ml of dimethylformamide dried over molecular sieves. The reaction mixture was heated at 60° C. for 5 hrs.

The solution of the acyl chloride prepared above was added dropwise under nitrogen atmosphere to a stirred and chilled (10°-15° C.) solution of aniline (1.31 g, 0.014 mole), triethylamine (1.42 g, 0.014 mole), and 75 ml of dry dimethylformamide. The reaction mixture was stirred at room temperature overnight. The reaction mixture was poured into 200 ml of water and the solid was collected by filtration, washed with water, and dried under high vacuum overnight. The solid was recrystallized from isopropyl alcohol with refrigeration overnight. The crystalline material was collected by filtration, washed with water, and dried under high vacuum at 70° C. overnight to give 3.11 g of title compound (66%), m.p. 240°-42° C.

Analysis: Calculated for $C_{20}H_{15}N_4OCl$: C, 66.21; H, 4.17; N, 15.44. Found: C, 66.17; H, 4.25; N, 15.34.

EXAMPLE 74

2-(4-Chlorophenyl)-N-(1-ethyl-3-pyrrolidinyl)-3H-imidazo[4,5-b] pyridine-3-acetamide hydrochloride hydrate [1:2:1]

A mixture of 2-(4-chlorophenyl)-3H-imidazo[4,5-b]pyridine-3-acetic acid, (5.0 g, 0.0174 mole) and 1,1,'-carbonyldiimidazole (2.82 g, 0.0174 mole) in 150 ml of tetrahydrofuran was stirred at room temperature for 3 hrs. 3-Amino-N-ethylpyrrolidine (2.18 g, 0.019 mole) was added dropwise and the reaction mixture was allowed to stir at room temperature overnight.

The tetrahydrofuran was evaporated and the residue was partitioned between methylene chloride and water. The methylene chloride layer was separated and extracted with dilute sodium hydroxide, then with water. The methylene chloride layer was separated, dried, and evaporated. The residue was triturated with water and dried under high vacuum overnight. The solid was dissolved in acetone, acidified with ethanolic hydrogen chloride, diluted with ethereal hydrogen chloride to the cloud point and seeded. The crystalline material was collected by filtration, washed with acetone, and dried under high vacuum at 70° C. overnight to give 5.83 g (71%) of crystals, m.p. 170°–72°C.

Analysis: Calculated for $C_{20}H_{22}N_5OCl.2$ HCl.1 $H_2O$: C, 50.59; H, 5.52; N, 14.75. Found: C, 50.69; H, 5.57; N, 14.73.

EXAMPLE 75

4-[[[2-(4-Chlorophenyl)-3H-imidazo[4,5-b]pyridin-3-yl]acetyl]amino]butanoic acid ethyl ester A mixture of 2-(4-chlorophenyl)-3H-imidazo[4,5-b]pyridine-3-acetic acid (5.0 g, 0.0174 mole) and 1,1'-carbonyldiimidazole (2.82 g, 0.0174 mole) in 150 ml of tetrahydrofuran was stirred at room temperature for 3 hrs. Then, under nitrogen atmosphere, 4-aminobutyric acid ethyl ester hydrochloride (3.19 g, 0.019 mole) and triethylamine (1.92 g, 0.019 mole) were added simultaneously and the reaction mixture was allowed to stir at room temperature overnight. The tetrahydrofuran was evaporated to dryness and the residue was partitioned between methylene chloride and water. The combined methylene chloride layers were extracted with dilute sodium hydroxide, then with water. The methylene chloride layer was separated, dried, and evaporated to dryness (5.3 g) (76% crude yield). A 2-g sample was recrystallized from absolute ethanol, and dried under high vacuum overnight to give 1.47 g, mp. 169°–71° C.

Analysis: Calculated for $C_{20}H_{21}N_4O_3Cl$: C, 59.93; H, 5.28; N, 13.98. Found: C, 59.76; H, 5.28; N, 13.94.

EXAMPLE 76

2-(3-Chlorophenyl)-N-(3-pyridinyl)-3H-imidazo[4,5-b]pyridine-3-acetamide hydrochloride [1:2]

Under a nitrogen atmosphere, oxalyl chloride (1.41 ml, 0.015 mole) was added dropwise (slowly) to a stirred and chilled (25°–30° C.) solution of 2-(3-chlorophenyl)-3H-imidazo[4,5-b] pyridine-3-acetic acid (4.00 g, 0.0138 mole) in anhydrous dimethylformamide (75 ml). The reaction mixture was heated at 55°–60° C. for 3½ hrs, cooled to room temperature, and added dropwise to a stirred and chilled (15°–20° C.) solution of 3-aminopyridine (1.50 g, 0.016 mole) and triethylamine (1.62 g, 0.016 mole) in anhydrous dimethylformamide (25 ml). The reaction mixture was stirred at room temperature overnight, filtered, and poured into ice water (500 ml). The mixture was extracted with ethyl acetate (3×75 ml). The combined organic portions were washed with 5% potassium hydroxide solution (2×50 ml), water (50 ml), brine (25 ml), dried over sodium sulfate and concentrated in vacuo. The residue was dissolved in tetrahydrofuran and treated with excess ethereal hydrogen chloride and isopropyl ether giving 2.5 g (41%). Recrystallization from isopropyl alcohol-ethanol-isopropyl ether gave 0.82 g. This was combined with a second crop of 0.43 g to give an off-white solid which underwent a phase change from 157°–163° C. and then decomposed at 186°–192° C.

Analysis: Calculated for $C_{19}H_{16}N_5OCl_3$: C, 52.26; H, 3.69; N, 16.04. Found: C, 52.16; H, 3.84; N, 15.92.

EXAMPLE 77

2-(3-Chlorophenyl)-N-[3-(dimethylamino)propyl]-3H-imidazo [4,5-b]pyridine-3-acetamide hydrochloride [1:2]

A solution of 2-(3-chlorophenyl)-3H-imidazo[4,5-b]pyridine-3-acetic acid (5.76 g, 0.020 mole), 1,1'-carbonyldiimidazole (3.24 g, 0.020 mole), and anhydrous tetrahydrofuran (250 ml) was stirred at room temperature with a stream of nitrogen bubbling through it for 2 hrs. The nitrogen flow was stopped and a solution of 3-dimethylaminopropylamine (2.04 g, 0.020 mole) in dry tetrahydrofuran (50 ml) was added. The solution was stoppered and stirred at room temperature over the weekend. The reaction mixture was concentrated in vacuo and partitioned between ethyl acetate (100 ml) and 5% potassium hydroxide (50 ml). The layers were separated and the aqueous portion washed with ethyl acetate (50 ml). The combined organic portions were washed with 5% potassium hydroxide solution (25 ml), water (25 ml), brine (25 ml), dried over sodium sulfate, and concentrated in vacuo. The solid residue was converted to the dihydrochloride salt and crystallized from acetone-ethanol-tetrahydrofuran to give 3.23 g (36%) of a white granular solid, mp. 203°–209° C. with decomposition.

Analysis: Calculated for $C_{19}H_{24}N_5OCl_3$: C, 51.31; H, 5.44; N, 15.74. Found: C, 51.26; H, 5.49; N, 15.70.

EXAMPLE 78

2-(3-Chlorophenyl)-N-(1-ethyl-2-pyrrolidinylmethyl)-3H-imidazo [4,5-b]pyridine-3-acetamide hydrochloride [1:2]

A solution of 2-(3-chlorophenyl)-3H-imidazo[4,5-b]pyridine-3-acetic acid (5.76 g, 0.020 mole), 1,1'-carbonyldiimidazole (3.24 g, 0.020 mole), and anhydrous tetrahydrofuran (250 ml) was stirred at room temperature with a stream of nitrogen bubbling through for 2 hrs. The nitrogen flow was stopped and a solution of 2-(aminomethyl)-1-ethyl pyrrolidine (2.56 g, 0.02 mole) in dry tetrahydrofuran (50 ml) was added. The solution was stoppered and stirred at room temperature over the weekend. The reaction was concentrated in vacuo and partitioned between ethyl acetate (100 ml) and 5% potassium hydroxide soluton (50 ml). The layers were separated and the aqueous portion washed with ethyl acetate (50 ml), water (25 ml), brine (25 ml), dried over sodium sulfate, and concentrated in vacuo. The solid residue was converted to the dihydrochloride salt and crystallized from isopropyl alcohol-diethyl ether. Recrystallization from isopropyl alcohol-isopropyl ether gave 1.38 g (15%) of an off-white solid, mp 186°–190° C. with decomposition.

Analysis: Calculated for $C_{21}H_{26}N_5OCl_3$: C, 53.57; H, 5.57; N, 14.87. Found: C, 53.56; H, 5.60; N, 14.86.

EXAMPLE 79

2-(3-Chlorophenyl)-N-(1-ethyl-3-piperidinyl)-3H-imidazo[4,5-b]pyridine-3-acetamide hydrochloride [1:1]

A solution of 2-(3-chlorophenyl)-3H-imidazo[4,5-b]pyridine-3-acetic acid (5.76 g, 0.020 mole), 1,1'-carbonyldiimidazole (3.24 g, 0.020 mole), and anhydrous tetrahydrofuran (250 ml) was stirred at room temperature with a stream of nitrogen bubbling through it for 2½ hrs. The nitrogen flow was stopped and a solution of 3-amino-N-ethylpiperidine (2.56 g, 0.020 mole) in dry tetrahydrofuran (50 ml) was added. The solution was stoppered and stirred at room temperature for 2 hrs. The reaction was concentrated in vacuo and partitioned between ethyl acetate (150 ml) and potassium bicarbonate solution (50 ml). The layers were separated and the organic portion was washed with potassium bicarbonate solution (2×50 ml), water (50 ml), brine (25 ml), dried over sodium sulfate, and concentrated in vacuo. The solid residue (3.4 g) was converted to the hydrochloride salt and twice recrystallized from acetone-tetrahydrofuran-ethanol to give 2.7 g (31%) of a white solid, mp. 275°–276° C. with decomposition.

Analysis: Calculated for $C_{21}H_{25}N_5OCl_2$: C, 58.07; H, 5.80; N, 16.12 Found: C, 57.92; H, 5.90; N, 15.88

EXAMPLE 80

2-(3-Chlorophenyl)-N-[4-(dimethylamino)phenyl]-3H-imidazo [4,5-b]pyridine-3-acetamide hydrochloride[1:1]

Under a nitrogen atmosphere, oxalyl chloride (2.8 ml, 0.032 mole) was added dropwise (slowly) to a stirred and chilled solution of 2-(3-chlorophenyl)-3H-imidazo[4,5-b]pyridine-3-acetic acid (8.0 g, 0.028 mole) in anhydrous dimethylformamide (100 ml). The reaction was heated at 55°–60° C. for 3 hrs, cooled to room temperature, and added dropwise to a stirred and chilled (5°–10° C.) suspension of N,N-dimethyl-p-phenylenediamine dihydrochloride (6.7 g, 0.032 mole) and triethylamine (12.9 g, 0.128 mole) in anhydrous dimethylformamide (200 ml). The reaction was stirred at room temperature over the weekend, filtered, and poured into ice water (600 ml). The mixture was filtered and the filter cake recrystallized from ethanol giving 6.6 g (58%). The solid was converted to the hydrochloride salt in isopropyl alcohol and concentrated hydrochloric acid to give 6.6 g of a white granular solid, mp. 229°–231° C. with decomposition.

Analysis: Calculated for $C_{22}H_{21}N_5OCl_2$: C, 59.74; H, 4.78; N, 15.83. Found: C, 59.94; H, 4.86; N, 15.78.

EXAMPLE 81

2-(4-Chlorophenyl)-N-[2-(1-piperidinyl)ethyl]-3H-imidazo[4,5-b] pyridine-3-acetamide hydrochloride hydrate [1:1:0.5]

Under nitrogen bubbling, a mixture of 2-(4-chlorophenyl)3H-imidazo[4,5-b]pyridine-3-acetic acid (5.0 g, 0.0174 mole) and 2.82 g (0.0174 mole) of 1,1'-carbonyldiimidazole in 150 ml of tetrahydrofuran was stirred at room temperature for 3 hrs. N-(2-aminoethyl)piperidine (4.46 g, 0.0348 mole) was added dropwise and the reaction mixture was allowed to stir at room temperature overnight.

The tetrahydrofuran was evaporated and the residue was partitioned between methylene chloride and water. The methylene chloride layer was separated and extracted with dilute sodium hydroxide, then with water. The methylene chloride layer was separated, dried, and evaporated. The residue was dried under high vacuum for 4–5 hrs (7.0 g).

A 4.8-g sample of the solid residue was dissolved in acetone, acidifed with ethanolic and ethereal hydrogen chloride to produce a solid, which was collected by filtration, washed with tetrahydrofuran, and dried under high vacuum overnight. The solid was converted to the free base with dilute sodium hydroxide and extracted with methylene chloride (3×). The combined methylene chloride extracts were washed with water (1×), dried, and evaporated to a solid, which was triturated with water. The solid was collected by filtration and placed under high vacuum overnight. The solid was dissolved in isopropyl alcohol, acidified with ethanolic hydrogen chloride, diluted with isopropyl ether, and seeded to initiate crystallization. The crystalline precipitate was collected by filtration, washed with cold isopropyl alcohol, and dried under high vacuum at 50° C. over the weekend to give 2.7 g (~56%) of title compound, mp. 188°–90° C.

Analysis: Calculated for $C_{21}H_{24}N_5OCl.HCl.\frac{1}{2} H_2O$: C, 56.89; H, 5.91; N, 15.80. Found: C, 56.54; H, 5.81; N, 15.79.

EXAMPLE 82

2-(4-Chlorophenyl)-N-[3-(dimethylamino)propyl]-3H-imidazo [4,5-b]pyridine-3-acetamide hydrochloride hydrate [1:2:1]

Under nitrogen bubbling, a mixture of 2-(4-chlorophenyl)3H-imidazo[4,5-b]pyridine-3-acetic acid (5.0 g, 0.0174 mole) and 1,1'-carbonyldiimidazole (2.82 g, 0.0174 mole) in 150 ml of tetrahydrofuran was stirred at room temperature for 3 hrs. Under a nitrogen atmosphere, N,N-dimethylaminopropylamine (1.94 g, 0.019 mole) was added dropwise and the reaction was allowed to stir at room temperature overnight. The tetrahydrofuran was evaporated to dryness and the residue was treated with ice water. The solid was collected by filtration and dried under high vacuum. The solid was dissolved in isopropyl alcohol, acidified with ethereal hydrogen chloride, and seeded. The crystalline material was collected by filtration, washed with cold isopropyl alcohol, and dried under high vacuum at 50° C. over the weekend to give 2.78 g (34.5%), mp. 188°–90° C.

Analysis: Calculated for $C_{19}H_{22}N_5OCl.2HCl.H_2O$: C, 49.31; H, 5.66; N, 15.13. Found: C, 49.34; H, 5.69; N, 15.20.

EXAMPLE 83

N-[2-(Acetylamino)ethyl]-2-(4-chlorophenyl)-3H-imidazo[4,5-b]pyridine-3-acetamide hydrate [1:0.5]

A suspension of 2-(4-chlorophenyl)-3H-imidazo[4,5-b]pyridine-3-acetic acid (5.0 g, 0.0174 mole), 1,1'-carbonyldiimidazole (2.82 g, 0.0174 mole) and dry tetrahydrofuran (100 ml) was stirred at room temperature for two hours with nitrogen bubbling through it. Solid N-acetylethylenediamine (4.44 g, 0.0435 mole) was added as well as 100 ml of tetrahydrofuran. A solid formed. After stirring overnight under nitrogen, the reaction mixture was evaporated to a white solid which was triturated in water (200 ml) overnight. The solid was collected by filtration, rinsed with water, dissolved in hot isopropyl alcohol and filtered hot. Water was added and the entire mixture was evaporated to a solid which was rinsed several times with light petroleum ether. The solid was dissolved in hot isopropyl alcohol and water was added to the cloud point. Upon cooling, solid precipitated, which was collected by filtration, and recrystallized again from isopropyl alcohol. Upon addition of water, the solid dissolved. All of the solvents were again evaporated under reduced pressure, and the resulting solid was again recrystallized from isopropyl alcohol to give 1.20 g (18%) of title compound, mp 247°–249° C.

Analysis: Calculated for $C_{18}H_{19}N_5O_{2.5}Cl$: C, 56.77; H, 5.03; N, 18.39. Found: C, 57.15; H, 5.00; N, 18.14.

EXAMPLE 84

4-[[[2-(3-Chlorophenyl)-3H-imidazo[4,5-b]pyridin-3-yl]acetyl]amino]butanoic acid ethyl ester A solution of 2-(3-chlorophenyl)-3H-imidazo[4,5-b]pyridine-3-acetic acid (8.0 g, 0.028 mole), 1,1'-carbonyldiimidazole (4.5 g, 0.028 mole), and anhydrous tetrahydrofuran (100 ml) was stirred at room temperature with a stream of nitrogen bubbling through it for 3 hours. The nitrogen flow was stopped and triethylamine (6.3 g, 0.062 mole) and ethyl 4-aminobutyrate hydrochloride (5.2 g, 0.031 mole) was added all at once. The reaction mixture was stirred under nitrogen over the weekend. The tetrahydrofuran was evaporated and the solid residue triturated in water (100 ml) and filtered off to give 4.7 g (42%) of cake. A 2.3-g portion of the filter cake was recrystallized from isopropyl ether-ethanol to give 1.9 g of white solid, mp 127°–129° C.

Analysis: Calculated for $C_{20}H_{21}N_4O_3Cl$: C, 59.93; H, 5.28; N, 13.98. Found: C, 59.89; H, 5.28; N, 14.08.

EXAMPLE 85

2-(3-Chlorophenyl)-N-[2-(dimethylamino)ethyl]-3H-imidazo[4,5-b]pyridine-3-acetamide A solution of 2-(3-chlorophenyl)-3H-imidazo[4,5-b]pyridine-3-acetic acid (6.7 g, 0.00233 mole), 1,1'-carbonyldiimidazole (4.0 g, 0.0245 mole), and anhydrous tetrahydrofuran (150 ml) was stirred at room temperature with a stream of nitrogen bubbling through for 2½ hours. The nitrogen flow was stopped and a solution of N,N-dimethylethylenediamine (2.3 g, 0.0257 mole) in dry tetrahydrofuran (50 ml) was stirred at room temperature under nitrogen for 2 hours. The reaction was concentrated in vacuo and partitioned between methylene chloride (75 ml) and water (75 ml). The layers were separated and the aqueous portion washed with methylene chloride (25 ml). The combined organic portions were washed with potassium bicarbonate solution (2×50 ml), water (25 ml), dried over sodium sulfate, and concentrated in vacuo. The solid residue, 5.7 g (68%) was recrystallized from isopropyl alcohol-isopropyl ether to give 4.0 g of off-white granular solid, mp 124°–125° C.

Analysis: Calculated for $C_{18}H_{20}N_5OCl$: C, 60.42; H, 5.63; N, 19.57. Found: C, 60.52; H, 5.69; N, 19.69.

EXAMPLE 86

2-(3-Chlorophenyl)-3-[2-oxo-2-(1-piperidinyl)ethyl]-3H-imidazo[4,5-b]pyridine

A solution of 2-(3-chlorophenyl)-3H-imidazo[4,5-b]pyridine-3-acetic acid (5.0 g, 0.017 mole), 1,1'-carbonyldiimidazole (3.0 g, 0.018 mole), and anhydrous tetrahydrofuran (100 ml) was stirred at room temperature with a stream of nitrogen bubbling through it for 3 hours. The nitrogen flow was stopped and a solution of piperidine (1.6 g, 0.019 mole) in dry tetrahydrofuran (50 ml) was added. The solution was stirred at room temperature under nitrogen for 2 hours. The reaction was concentrated in vacuo and the residue triturated in water (100 ml) and the mix was filtered. The filter cake was recrystallized from isopropyl alcohol-isopropyl ether to give 3.4 g (56%) of off-white flakes, mp 149°–150° C.

Analysis: Calculated for $C_{19}H_{19}N_4OCl$: C, 64.31; H, 5.40; N, 15.79. Found: C, 64.18; H, 5.32; N, 15.73.

EXAMPLE 87

2-(4-Bromophenyl)-N,N-dimethyl-3H-imidazo[4,5-b]pyridine-3-acetamide

A suspension of 2-(4-bromophenyl)-3H-imidazo[4,5-b]pyridine-3-acetic acid (5.5 g, 0.0166 mole), 1,1'-carbonyldiimidazole (2.7 g, 0.0166 mole), and anhydrous tetrahydrofuran (100 ml) was stirred at room temperature with a stream of nitrogen bubbling through it for 2½ hours. The nitrogen flow was stopped and a solution of dimethylamine (0.5M in tetrahydrofuran) (66 ml) was added. The solution was stirred at room temperature, stoppered, for 16 hours. The reaction mixture was concentrated in vacuo and the residue triturated in water (100 ml) and filtered. The filter cake was recrystallized from ethanol to give 3.78 g (63%) of white needles, mp 224°–225° C.

Analysis: Calculated for $C_{16}H_{15}N_4OBr$: C, 53.50; H, 4.21; N, 15.60. Found: C, 53.55; H, 4.19; N, 15.68.

EXAMPLE 88

2-(4-Chlorophenyl)-N-(2-propenyl)-3H-imidazo[4,5-b]pyridine-3-acetamide

Under nitrogen bubbling, a mixture of 2-(4-chlorophenyl)-3H-imidazo[4,5-b]pyridine-3-acetic acid (4.0 g, 0.014 mole) and 1,1'-carbonyldiimidazole (2.27 g, 0.014 mole) in 130 ml tetrahydrofuran was stirred at room temperature for 3 hours. Under a nitrogen atmosphere, N-allylamine (1.60 g, 0.028 mole) was added and the reaction mixture was allowed to stir at room temperature overnight. The tetrahydrofuran was evaporated to a solid, which was placed under high vacuum over the weekend. The solid residue was dissolved in isopropyl alcohol, filtered, and diluted with water to initiate crystallization, then refrigerated overnight. The solid was collected by filtration, washed with water, and dried under high vacuum at 50° C. overnight to give 3.0 g (66%) of title compound, mp 208°–9° C.

Analysis: Calculated for $C_{17}H_{15}N_4OCl$: C, 62.48; H, 4.63; N, 17.14. Found: C, 62.53; H, 4.64; N, 17.18.

EXAMPLE 89

2-(4-Bromophenyl)-3H-imidazo[4,5-b]pyridine-3-acetic acid ethyl ester

N-[3-[(4-bromobenzoyl)amino]-2-pyridinyl]glycine ethyl ester (4.6 g, 0.012 mole) was heated in glass in a 190° C. oil bath for ½ hour. The melt was cooled and methylene chloride (150 ml) added. The solution was twice treated with 25 g of Florisil ® and filtered. The filtrate was concentrated in vacuo and the residue recrystallized from isopropyl ether-ethanol to give 2.1 g (49%) of a white flocculent solid, mp 138°–139° C.

Analysis: Calculated for $C_{16}H_{14}N_3O_2Br$: C, 53.35; H, 3.92; N, 11.66. Found: C, 55.16; H, 3.92; N, 11.70.

EXAMPLE 90

2-(4-Bromophenyl)-N-methyl-3H-imidazo[4,5-b]pyridine-3-acetamide

A solution of 2-(4-bromophenyl)-3H-imidazo[4,5-b]pyridine-3-acetic acid (5.5 g, 0.0166 mole) and 1,1'-carbonyldiimidazole (2.7 g, 0.0166 mole) in anhydrous tetrahydrofuran (100 ml) was stirred at room temperature with a stream of nitrogen bubbling through it for 2½ hours. The nitrogen flow was stopped and a solution of monomethylamine (1M in tetrahydrofuran) (33 ml) was added. The solution was stoppered and stirred at room temperature for 16 hours. The reaction mixture was concentrated in vacuo and the residue triturated in water (100 ml) and filtered. The filter cake (5.5 g, 96%) was recrystallized from tetrahydrofuran-ethanol to give 3.0 g of a white flocculent solid, mp 258°–259° C. after forming a polymorph from 250°–255° C.

Analysis: Calculated for $C_{15}H_{13}N_4OBr$: C, 52.19; H, 3.80; N, 16.23. Found: C, 52.22; H, 3.78; N, 16.28.

EXAMPLE 91

2-(4-Bromophenyl)-N-methyl-3H-imidazo[4,5-b]pyridine-3-acetamide hydrochloride [1:1]

A suspension of 2-(4-bromophenyl)-3H-imidazo[4,5-b]pyridine-3-acetic acid (5.5 g, 0.0166 mole) 1,1'-carbonyldiimidazole (2.7 g, 0.0166 mole) and anhydrous tetrahydrofuran (100 ml) was stirred at room temperature with a stream of nitrogen bubbling through for 2½ hours. The nitrogen flow was stopped and a solution of methylamine (1M in tetrahydrofuran) (33 ml, 0.0332 mole) was added. The solution was stirred at room temperature under nitrogen for 2 hours. The reaction mixture was concentrated in vacuo and the residue triturated in water (100 ml) and filtered. The filter cake (5.5 g) was recrystallized from tetrahydrofuran-ethanol to give 3.0 g (52%) of the free base of the title compound. The free base was converted to the hydrochloride salt in isopropyl alcohol/isopropyl ether and the salt was recrystallized from isopropyl alcohol-isopropyl ether to give white solid, mp 230°–232° C.

Analysis: Calculated for $C_{15}H_{14}N_4OBrCl$: C, 47.20; H, 3.70; N, 14.68. Found: C, 47.27; H, 3.76; N, 14.52.

EXAMPLE 92

4-[[[2-(4-Chlorophenyl)-3H-imidazo[4,5-b]pyridin-3-yl]acetyl]amino]butanoic acid potassium salt hydrate [1:1:1]

A mixture of 4-[[[2-(4-chlorophenyl)-3H-imidazo[4,5-b]pyridin-3-yl]acetyl]amino]butanoic acid ethyl ester (3.3 g, 0.008 mole), potassium hydroxide (0.5 g, 0.009 mole), and 80 ml of 95% ethyl alcohol was heated at reflux for 1¾ hours. The hot reaction mixture was filtered, washed with absolute ethanol, and the filtrate was evaporated to a solid residue. The solid was triturated with acetone and filtered. The solid was dissolved in hot tert-butanol and allowed to cool with seeding. The crystalline precipitate was collected by filtration, washed with tert-butyl alcohol and dried under high vacuum at 50° C. overnight to give 1.2 g (35%) of title compound, mp 263°–264° C.

Analysis: Calculated for $C_{18}H_{16}N_4O_3ClK \cdot H_2O$: C, 50.14; H, 4.23; N, 13.06. Found: C, 49.99; H, 4.05; N, 13.02.

EXAMPLE 93

2-(4-Chlorophenyl)-3-[2-oxo-2-(1-piperidinyl)ethyl]-3H-imidazo [4,5-b]pyridine

Under nitrogen bubbling, a mixture of 2-(4-chlorophenyl)-3H-imidazo[4,5-b]pyridine-3-acetic acid (4.0 g, 0.014 mole) and 1,1'-carbonyldiimidazole (2.27 g, 0.014 mole), in 150 ml of tetrahydrofuran was stirred at room temperature for 3 hours. Then, under nitrogen atmosphere, piperidine (1.31 g, 0.015 mole) was added and the reaction mixture was allowed to stir at room temperature overnight. The tetrahydrofuran was evaporated to give a solid which was triturated with water and dried under high vacuum over the weekend at 50° C. The solid was recrystallized from isopropyl alcohol and refrigerated overnight. The crystalline material was collected by filtration, washed with cold isopropyl alcohol, and dried under high vacuum at 50° C. overnight to give 2.95 g (59%) of title compound, mp 176°–178° C.

Analysis: Calculated for $C_{19}H_{19}N_4OCl$: C, 64.31; H, 5.40; N, 15.79. Found: C, 64.14; H, 5.39; N, 15.95.

EXAMPLE 94

2-(4-Chlorophenyl)-N-(phenylmethyl)-3H-imidazo[4,5-b]pyridine-3-acetamide

Under nitrogen bubbling, a mixture of 2-(4-chlorophenyl)-3H-imidazo[4,5-b]pyridine-3-acetic acid (4.0 g, 0.014 mole) and 1,1'-carbonyldiimidazole (2.27 g, 0.014 mole) in 150 ml of tetrahydrofuran was stirred at room temperature for 3 hours. Then, under nitrogen atmosphere, benzylamine (1.58 g, 0.0147 mole) was added and the reaction was allowed to stir at room temperature overnight. The tetrahydrofuran was evaporated, to give a solid. The solid was recrystallized from isopropyl alcohol, collected by filtration, washed with cold isopropyl alcohol and water, and dried under high vacuum at 50° C. overnight to give 3.43 g (65%) of title compound, mp 200°–200.5° C.

Analysis: Calculated for $C_{21}H_{17}N_4OCl$: C, 66.93; H, 4.55; N, 14.88. Found: C, 66.98; H, 4.57; H, 15.06.

EXAMPLE 95

2-(4-Chlorophenyl)-N-cyclopropyl-3H-imidazo[4,5-b]pyridine-3-acetamide

Under nitrogen bubbling, a mixture of 2-(4-chlorophenyl)-3H-imidazo[4,5-b]pyridine-3-acetic acid (4.0 g, 0.014 mole) and 1,1'-carbonyldiimidazole (2.27 g, 0.014 mole) in 150 ml of tetrahydrofuran was stirred at room temperature for 3 hours. Then, under nitrogen atmosphere, cyclopropylamine (2.40 g, 0.042 mole) was added and the reaction mixture was allowed to stir at room temperature overnight. The tetrahydrofuran was evaporated and the residue was recrystallized from isopropyl alcohol with refrigeration. The solid was collected by filtration, washed with cold isopropyl alcohol and water, and dried under high vacuum at 50° C. over the weekend to give 2.4 g (53%) of title compound, mp 231°–232° C.

Analysis: Calculated for $C_{17}H_{15}N_4OCl$: C, 62.48; H, 4.63; N, 17.14. Found: C, 62.61; H, 4.68; N, 17.10.

EXAMPLE 96

2-(4-Chlorophenyl)-3-[2-oxo-2-(1-pyrrolidinyl)ethyl]-3H-imidazo [4,5-b]pyridine

Under nitrogen bubbling, a mixture of 2-(4-chlorophenyl)-3H-imidazo[4,5-b]pyridine-3-acetic acid (4.0 g, 0.014 mole) and 1,1'-carbonyldiimidazole (2.27 g, 0.014 mole) in 150 ml of tetrahydrofuran was stirred at room temperature for 3 hours. Then, under nitrogen atmosphere, pyrrolidine (1.99 g, 0.028 mole) was added and the reaction mixture was allowed to stir at room temperature over the weekend. The precipitate which had formed was filtered and the filtrate was evaporated to dryness. The solid residue was triturated with water and dried under high vacuum at 50° C. overnight. The solid was recrystallized from isopropyl alcohol with refrigeration. The precipitate was collected by filtration, washed with cold isopropyl alcohol and water, and dried under high vacuum at room temperature overnight to give 2.84 g (60%) of title compound, mp 224°–225° C.

Analysis: Calculated for $C_{18}H_{17}N_4OCl$: C, 63.44; H, 5.03; N, 16.44. Found: C, 63.57; H, 5.04; N, 16.56.

EXAMPLE 97

2-(4-Bromophenyl)-N-(1-ethyl-3-pyrrolidinyl)-3H-imidazo[4,5-b]pyridine-3-acetamide A suspension of 2-(4-bromophenyl)-3H-imidazo[4,5-b]pyridine-3-acetic acid (5.0 g, 0.0151 mole), 1,1'-carbonyldiimidazole (2.45 g, 0.0151 mole), and anhydrous tetrahydrofuran (100 ml) was stirred at room temperature with a stream of nitrogen bubbling through it for 3 hours. The nitrogen flow was stopped and a solution of 1-ethyl-3-aminopyrrolidine (1.89 g, 0.0166 mole) in dry tetrahydrofuran (25 ml) was added. The solution was stirred at room temperature under nitrogen for 2 hours. The reaction mixture was concentrated in vacuo and the residue triturated in water (100 ml) and filtered. The filter cake was recrystallized from isopropyl alcohol-isopropyl ether to give 4.64 g (72%) of white needles, mp 202.5°–204° C.

Analysis: Calculated for $C_{20}H_{22}N_5OBr$: C, 56.08; H, 5.18; N, 16.35. Found: C, 56.34; H, 5.20; N, 16.44.

EXAMPLE 98

2-(4-Bromophenyl)-N-(1-ethyl-3-pyrrolidinyl)-3H-imidazo[4,5-b]pyridine-3-acetamide hydrochloride hydrate [1:1:1]

A suspension of 2-(4-bromophenyl)-3H-imidazo[4,5-b]pyridine-3-acetic acid (5.0 g, 0.0151 mole), 1,1'-carbonyldiimidazole (2.45 g, 0.0151 mole), and anhydrous tetrahydrofuran (100 ml) was stirred at room temperature with a stream of nitrogen bubbling through it for 3 hours. The nitrogen flow was stopped and a solution of 1-ethyl-3-aminopyrrolidine (1.89 g, 0.0166 mole) in dry tetrahydrofuran (25 ml) was added. The solution was stirred at room temperature under nitrogen for 2 hours. The reaction mixture was concentrated in vacuo and the residue triturated in water (100 ml) and filtered. The filter cake was recrystallized from isopropyl alcohol-isopropyl ether to give 4.64 g (72%) of the free base of the title compound. The organic filtrate was concentrated in vacuo, combined with 2.6 g of the free base obtained in Example 97, converted to the hydrochloride salt and crystallized from isopropyl alcohol-isopropyl ether to give 2.6 g of an off-white solid, mp 177°–180° C., with decomposition after a phase change at 170°–173° C.

Analysis: Calculated for $C_{20}H_{25}N_5O_2BrCl$: C, 49.76; H, 5.22; N, 14.50. Found: C, 49.36; H, 5.06; N, 14.25.

EXAMPLE 99

2-(4-Bromophenyl)-N-[2-(1-piperidinyl)ethyl]-3H-imidazo[4,5-b]pyridine-3-acetamide A suspension of 2-(4-bromophenyl)-3H-imidazo[4,5-b]pyridine-3-acetic acid (6.0 g, 0.018 mole), 1,1'-carbonyldiimidazole (2.9 g, 0.018 mole) and anhydrous tetrahydrofuran (100 ml) was stirred at room temperature with a stream of nitrogen bubbling through for 3 hours. The nitrogen flow was stopped and a solution of 1-(2-aminoethyl)piperidine (2.3 g, 0.018 mole) in dry tetrahydrofuran (25 ml) was added. The solution was stirred at room temperature under nitrogen for 2 hours. The reaction mixture was concentrated in vacuo and the residue triturated in potassium bicarbonate solution (100 ml) and filtered. The filter cake was washed with water and recrystallized from isopropyl alcohol-isopropyl ether to give 5.8 g (73%) of off-white needles, mp 178°–179° C.

Analysis: Calculated for $C_{21}H_{24}N_5OBr$: C, 57.02; H, 5.47; N, 15.83. Found: C, 57.34; N, 5.52; N, 15.98.

EXAMPLE 100

2-(4-Bromophenyl)-N-[2-(1-piperidinyl)ethyl]-3H-imidazo[4,5-b]pyridine-3-acetamide hydrochloride hydrate [1:2:1]

2-(4-Bromophenyl)-N-[2-(1-piperidinyl)ethyl]-3H-imidazo[4,5-b]pyridine-3-acetamide (3.5 g, 0.0079 mole) was converted to the hydrochloride salt in isopropyl alcohol-isopropyl ether, using concentrated hydrochloric acid to acidify. Recrystallization from isopropyl alcohol-isopropyl ether gave 3.5 g (83%) of a white solid, mp 150°–153° C.

Analysis: Calculated for $C_{21}H_{28}N_5O_2BrCl_2$: C, 47.30; H, 5.29; N, 13.13. Found: C, 47.63; H, 5.35; N, 13.21.

EXAMPLE 101

2-(4-Bromophenyl)-N-(1-ethyl-3-piperidinyl)-3H-imidazo[4,5-b]pyridine-3-acetamide A suspension of 2-(4-bromophenyl)-3H-imidazo[4,5-b]pyridine-3-acetic acid (6.0 g, 0.018 mole), 1,1'-carbonyldiimidazole (3.1 g, 0.019 mole), and anhydrous tetrahydrofuran (100 ml) was stirred at room temperature with a stream of nitrogen bubbling through it for 3 hours. The nitrogen flow was stopped and a solution of 3-amino-N-ethylpiperidine (2.6 g, 0.020 mole) in dry tetrahydrofuran (25 ml) was added. The solution was stirred at room temperature under nitrogen for 2 hours. The reaction mixture was concentrated in vacuo and the residue triturated in potassium bicarbonate solution (100 ml) and filtered. The filter cake was washed with water and recrystallized from isopropyl alcohol to give 4.9 g, (62%) of a white solid, mp 190°–192° C.

Analysis: Calculated for $C_{21}H_{24}N_5OBr$: C, 57.02; H, 5.47; N, 15.83. Found: C, 57.38; H, 5.52; N, 15.98.

EXAMPLE 102

2-(4-Bromophenyl)-N-(1-ethyl-3-piperidinyl)-3H-imidazo[4,5-b]pyridine-3-acetamide hydrochloride hydrate [1:2:1]

A sample of 2-(4-bromophenyl)-N-(1-ethyl-3-piperidinyl)-3H-imidazo[4,5-b]pyridine-3-acetamide (4.8 g, 0.011 mole) was converted to the hydrochloride salt using concentrated hydrochloric acid in isopropyl alcohol. Recrystallization from ethanol-isopropyl ether gave 3.58 g (61%) of white solid, mp 179°–183° C. after a phase change at 168°–172° C.

Analysis: Calculated for $C_{21}H_{28}N_5O_2BrCl_2$: C, 47.30; H, 5.29; N, 13.13. Found: C, 47.32; H, 5.41; N, 12.85.

EXAMPLE 103

N-[[2-(3-Chlorophenyl)-3H-imidazo[4,5-b]pyridin-3-yl]acetyl]glycine potassium salt hydrate [1:1:2]

A solution of N-[[2-(3-chlorophenyl)-3H-imidazo[4,5-b]pyridin-3-yl]acetyl]glycine ethyl ester (4.90 g, 0.0132 mole), and potassium hydroxide pellets (0.9 g, 0.0161 mole) in ethanol (100 ml) was refluxed for 2 hours. The reaction mixture was filtered and the filtrate volume reduced to 50 ml, giving 4.6 g (83%). Recrystallization from ethanol gave a white flocculent solid which, after drying overnight at 98° C. in vacuo, was shown by NMR spectroscopy to be the hemihydrate of the potassium salt. When exposed to atmospheric moisture for 2 hours, the dihydrate formed, mp 295°–301° C.

Analysis: Calculated for $C_{16}H_{16}N_4O_5ClK$: C, 45.88; H, 3.85; N, 13.38. Found: C, 45.92; H, 3.67; N, 13.47.

EXAMPLE 104

2-(4-Chlorophenyl)-N-(2-pyridinyl)-3H-imidazo[4,5-b]pyridine-3-acetamide

Under a nitrogen atmosphere, oxalyl chloride (1.73 g, 0.014 mole) was added slowly to a stirred and chilled (10°–15° C.) suspension of 2-(4-chlorophenyl)-3H-imidazo[4,5-b]pyridine-3-acetic acid (3.7 g, 0.013 mole) in 50 ml of dry dimethylformamide. The reaction mixture was heated between 60°–90° C. for 5 hours. The solution of the acyl chloride was added dropwise under a nitrogen atmosphere to a stirred, chilled (10°–15° C.) solution of 2-aminopyridine (1.77 g, 0.019 mole), and triethylamine (1.90 g, 0.019 mole) in 75 ml of dry dimethylformamide. The reaction mixture was stirred at room temperature overnight. The reaction mixture was poured into water, diluted with water to the cloud point, and seeded. The crystalline solid was collected by filtration, washed with water, and dried under high vacuum at 70° C. for 2 hours, then at 60° C. overnight to give 1.0 g (20%) of crystals, mp 190°–191° C.

Analysis; Calculated for $C_{19}H_{14}N_5OCl$: C, 62.73; H, 3.88; N, 19.25. Found: C, 62.54; H, 3.95; N, 18.94.

EXAMPLE 105

2-(4-Chlorophenyl)-N-cyclopentyl-3H-imidazo[4,5-b]pyridine-3-acetamide

Under nitrogen bubbling, a mixture of 2-(4-chlorophenyl)-3H-imidazo [4,5-b]pyridine-3-acetic acid (4.0 g, 0.014 mole) and 1,1'-carbonyldiimidazole (2.27 g, 0.014 mole) in 150 ml of tetrahydrofuran was stirred at room temperature for 3 hours. Cyclopentylamine (2.38 g, 0.028 mole) was added and the reaction mixture was allowed to stir at room temperature overnight. The tetrahydrofuran was evaporated to dryness and the residue was treated with water. The solid was collected by filtration, washed with water, and dried under high vacuum overnight. The solid was recrystallized from isopropyl alcohol-ethanol, collected by filtration, washed with cold isopropyl alcohol, and dried under high vacuum over the weekend to give 3.67 g (74%) of crystals, mp 260°–261° C.

Analysis: Calculated for $C_{19}H_{19}N_4OCl$: C, 64.31; H, 5.40; N, 15.79. Found: C, 64.16; H, 5.39; N, 15.84.

EXAMPLE 106

2-(4-Chlorophenyl)-N-(cyclopropylmethyl)-3H-imidazo[4,5-b]pyridine-3-acetamide

Under nitrogen bubbling, a mixture of 2-(4-chlorophenyl)-3H-imidazo[4,5-b]pyridine-3-acetic acid (4.0 g, 0.014 mole) and 1,1'-carbonyldiimidazole (2.27 g, 0.014 mole) in 150 ml of tetrahydrofuran was stirred at room temperature for 4 hours. Aminomethylcyclopropane hydrochloride (3.01 g, 0.028 mole) and triethylamine (2.83 g, 0.028 mole) were added and the reaction mixture was allowed to stir at room temperature overnight. The tetrahydrofuran was evaporated to dryness and the residue was treated with water. The solid was collected by filtration, washed with water, and dried under high vacuum overnight. The solid was recrystallized from isopropyl alcohol with cooling. The crystalline precipitate was collected by filtration, washed with cold isopropyl alcohol and water, and dried under high vacuum at 60° C. overnight to give 3.92 g (82%) of crystals, mp 228°–229° C.

Analysis: Calculated for $C_{18}H_{17}N_4OCl$: C, 63.44; H, 5.03; N, 16.44. Found: C, 63.28; H, 5.00; N, 16.54.

EXAMPLE 107

2-(4-Chlorophenyl)-N-cyclohexyl-3H-imidazo[4,5-b]pyridine-3-acetamide

Under nitrogen bubbling, a mixture of 2-(4-chlorophenyl)-3H-imidazo[4,5-b]pyridine-3-acetic acid (4.0 g, 0.014 mole) and 1,1'-carbonyldiimidazole (2.27 g, 0.014 mole) in 150 ml of tetrahydrofuran was stirred at room temperature for 3 hours. Cyclohexylamine (2.77 g, 0.028 mole) was added and the reaction mixture was allowed to stir at room temperature overnight. The tetrahydrofuran was evaporated to dryness and the residue was treated with water. The solid was collected by filtration, washed with water, and dried under high vacuum over the weekend. The solid was recrystallized from isopropyl alcohol-95% ethanol, collected by filtration, washed with water, and dried under high vacuum at 50° C. overnight to give 3.75 g (73%) of crystals, mp 240°–241° C.

Analysis: Calculated for $C_{20}H_{21}N_4OCl$: C, 65.12; H, 5.74; N, 15.19. Found: C, 65.18; H, 5.72; N, 15.28.

EXAMPLE 108

2-(3-Chlorophenyl)-N-(1-ethyl-3-pyrrolidinyl)-3H-imidazo[4,5-b]pyridine-3-acetamide hydrochloride hydrate [1:2:0.5]

A solution of 2-(3-chlorophenyl)-3H-imidazo[4,5-b]pyridine-3-acetic acid (5.0 g, 0.0174 mole), 1,1'-carbonyldiimidazole (2.82 g, 0.0174 mole) and anhydrous tetrahydrofuran (100 ml) was stirred at room temperature with a stream of nitrogen bubbling through it for 3 hours. The nitrogen flow was stopped and a solution of 1-ethyl-3-aminopyrrolidine (2.18 g, 0.0192 mole) in dry tetrahydrofuran (25 ml) was added. The solution was stirred at room temperature under nitrogen for 1 hour. The reaction mixture was concentrated in vacuo and the residue triturated in potassium bicarbonate solution (75 ml) and filtered. The filter cake was washed with water and recrystallized from isopropyl alcohol-isopropyl ether to give 2.25 g (28%) of beige solid, mp 154°–157° C.

Analysis: Calculated for $C_{20}H_{22}N_5OCl$: C, 51.57; H, 5.41; N, 15.03.2HCl. 0.5H$_2$O Found: C, 51.49; H, 5.55; N, 14.90.

EXAMPLE 109

2-(4-Bromophenyl)-N-[2-(dimethylamino)ethyl]-3H-imidazo[4,5-b]pyridine-3-acetamide A suspension of 2-(4-bromophenyl)-3H-imidazo[4,5-b]pyridine-3-acetic acid (5.0 g, 0.0151 mole), 1,1'-carbonyldiimidazole (2.45 g, 0.0151 mole), and anhydrous tetrahydrofuran (100 ml) was stirred at room temperature with a stream of nitrogen bubbling through it for 3 hours. The nitrogen flow was stopped and a solution of N,N-dimethylethylenediamine (1.46 g, 0.0166 mole) in dry tetrahydrofuran (25 ml) was added. The solution was stirred at room temperature under nitrogen for 2 hours. The reaction mixture was concentrated in vacuo and the residue triturated in water (100 ml) and filtered. The filter cake was recrystallized from ethanolisopropyl ether-tetrahydrofuran to give 4.45 g (73%) of white flakes, mp 195°–197° C.

Analysis: Calculated for $C_{18}H_{20}N_5OBr$: C, 53.74; H, 5.01; N, 17.41. Found: C, 53.63; H, 5.04; N, 17.57.

EXAMPLE 110

2-(4-Bromophenyl)-N-[2-(dimethylamino)ethyl]-3H-imidazo[4,5-b]pyridine-3-acetamide hydrochloride hydrate [1:2:0.5]

2-(4-Bromophenyl)-N-[2-(dimethylamino)ethyl]-3H-imidazo[4,5-b]pyridine-3-acetamide (2.25 g, 0.0056 mole) was treated with concentrated hydrochloric acid and isopropyl alcohol to give 2.4 g precipitate. Recrystallization from isopropyl alcohol gave 1.9 g (70%) of white solid, mp 160.5°–162° C.

Analysis: Calculated for $C_{18}H_{23}N_5O_{1.5}BrCl_2$: C, 44.65; H, 4.79; N, 14.46. Found: C, 44.68; H, 5.01; N, 14.52.

EXAMPLE 111

2-(3-Chlorophenyl)-N-phenyl-3H-imidazo[4,5-b]pyridine-3-acetamide

Under a nitrogen atmosphere, oxalyl chloride (4.6 g, 0.037 mole) was added dropwise (slowly) to a stirred and chilled (10°–15° C.) solution of 2-(3-chlorophenyl)-3H-imidazo[4,5-b]pyridine-3-acetic acid (10.0 g, 0.035 mole) in anhydrous dimethylformamide (100 ml). The reaction mixture was heated at 55°–60° C. for 5 hours, cooled to room temperature, and added dropwise to a stirred and chilled (10°–15° C.) solution of aniline (3.5 g, 0.038 mole) and triethylamine (7.6 g, 0.076 mole) in anhydrous dimethylformamide (75 ml). The reaction was stirred at room temperature overnight, poured into water (500 ml), allowed to precipitate, and filtered. The filter cake was twice suspended in potassium bicarbonate solution (250 ml) and filtered. The filter cake was washed with water, air dried, and recrystallized from ethanol, giving 4.74 g (37%) of off-white needles, mp 211°–212° C.

Analysis: Calculated for $C_{20}H_{15}N_4OCl$: C, 66.28; H, 4.17; N, 15.44, Found: C, 66.00; H, 4.23; N, 15.43,

EXAMPLE 112

N-(2-Chlorophenyl)-2-(4-chlorophenyl)-3H-imidazo[4,5-b]pyridine3-acetamide

Under a nitrogen atmosphere, oxalyl chloride (1.73 g, 0.014 mole) was added slowly to a stirred and chilled (10°–15° C.) suspension of 2-(4-chlorophenyl)-3H-imidazo[4,5-b]pyridine-3-acetic acid (3.7 g, 0.013 mole) in 50 ml of dimethylformamide. The reaction mixture was heated at 60° C. for 5 hours. The solution of the acyl chloride prepared above was added dropwise under nitrogen atmosphere to a stirred and chilled (10°–15° C.) solution of o-chloroaniline (1.79 g, 0.014 mole), triethylamine (1.42 g, 0.014 mole), and 75 ml of dimethylformamide. After the addition, the reaction mixture was allowed to stir at room temperature overnight. The reaction mixture was poured into 200 ml of water. The crystalline solid was collected by filtration, washed with water, and dried under high vacuum overnight to give 2.76 g (54%) of crystals, mp 232°–235.5° C.

Analysis: Calculated for $C_{20}H_{14}N_4OCl_2$: C, 60.47; H, 3.55; N, 14.10, Found: C, 60.37; H, 3.58; N, 14.09,

EXAMPLE 113

2-(3-Chlorophenyl)-N-[2-(1-piperidinyl)ethyl]-3H-imidazo[4,5-b]pyridine-3-acetamide A solution of 2-(3-chlorophenyl)-3H-imidazo[4,5-b]pyridine-3-acetic acid (5.4 g, 0.0188 mole), 1,1'-carbonyldiimidazole (3.0 g, 0.0188 mole) in anhydrous tetrahydrofuran (150 ml) was stirred at room temperature with a stream of nitrogen bubbling through it for 2½ hours. The nitrogen flow was stopped and a solution of 1-(2-aminoethyl)piperidine (2.4 g, 0.0188 mole) in dry tetrahydrofuran (50 ml) was added. The solution was stirred at room temperature under nitrogen for 2 hours. The reaction mixture was concentrated in vacuo and the residue partitioned between methylene chloride (75 ml) in water (75 ml). The layers were separated and the aqueous portion washed with methylene chloride (25 ml). The organic layers were combined and washed with potassium bicarbonate solution (2×50 ml), water (25 ml), dried over sodium sulfate, and concentrated in vacuo. The residue (6.6 g) was recrystallized from isopropyl alcohol-isopropyl ether to give 3.5 g (47%). Recrystallization from isopropyl alcohol-isopropyl ether gave 2.5 g of cream colored solid, mp 114°–115° C.

Analysis: Calculated for $C_{21}H_{24}N_5OCl$: C, 63.39; H, 6.08; N, 17.60. Found: C, 63.34; H, 6.16; N, 17.69.

EXAMPLE 114

2-(4-Bromophenyl)-3-[2-oxo-2-(1-piperidinyl)ethyl]-3H-imidazo [4,5-b]pyridine

A suspension of 2-(4-bromophenyl)-3H-imidazo[4,5-b]pyridine-3-acetic acid (6.0 g, 0.018 mole), 1,1'-carbonyldiimidazole (3.1 g, 0.019 mole), and anhydrous tetrahydrofuran (100 ml) was stirred at room temperature with a stream of nitrogen bubbling through for 3 hours. The nitrogen flow was stopped and a solution of piperidine (1.7 g, 0.020 mole) in dry tetrahydrofuran (25 ml) was added. The solution was stirred at room temperature under nitrogen for 2 hours. The reaction mixture was concentrated in vacuo and the residue triturated in potassium bicarbonate solution (100 ml) and filtered. The filter cake was washed with water and recrystallized from isopropyl alcohol-isopropyl ether to give 5.9 g (82%) of white flakes, mp 175°–176° C.

Analysis: Calculated for $C_{19}H_{19}N_4OBr$: C, 57.15; H, 4.80; N, 14.03. Found: C, 57.22; H, 4.83; N, 14.15.

EXAMPLE 115

2-(4-Chlorophenyl)-N-methyl-N-(phenylmethyl)-3H-imidazo[4,5-b]pyridine-3-acetamide Under nitrogen bubbling, a mixture of 2-(4-chlorophenyl)-3H-imidazo[4,5-b]pyridine-3-acetic acid (4.0 g, 0.014 mole) and 1,1'-carbonyldiimidazole (2.27 g, 0.014 mole) in 150 ml of tetrahydrofuran was stirred at room temperature for 3 hours. The benzylmethylamine (1.95 g, 0.016 mole) was added and the reaction mixture was allowed to stir at room temperature for 3 hours. The tetrahydrofuran was evaporated to dryness and the residue was partitioned between methylene chloride and saturated sodium bicarbonate. The aqueous layer was separated and extracted with methylene chloride (2×). The methylene chloride extracts were combined and extracted with water (1×). The methylene chloride layer was dried over magnesium sulfate, evaporated to dryness, and placed under high vacuum at room temperature overnight. The oil was dissolved in hot isopropyl alcohol, diluted with water, and seeded to produce crystalline needles, then refrigerated. The solid was collected by filtration, washed with water, and dried at 50° C. overnight under high vacuum to give 4.08 g (75%) of title compound, mp 87°–89° C.

Analysis: Calculated for $C_{22}H_{19}N_4OCl$: C, 67.60; H, 4.90; N, 14.33. Found: C, 67.47; H, 4.85; N, 14.39.

EXAMPLE 116

2-(4-Bromophenyl)-N-(2-chlorophenyl)-3H-imidazo[4,5-b]pyridine-3-acetamide

Under a nitrogen atmosphere, oxalyl chloride (3.2 g, 0.025 mole) was added dropwise (slowly) to a stirred and chilled (5°–10° C.) solution of 2-(4-bromophenyl)-3H-imidazo[4,5-b]pyridine-3-acetic acid (8.0 g, 0.024 mole) in anhydrous dimethylformamide (50 ml). The reaction mixture was heated at 55°–60° C. for 4 hrs, cooled to room temperature, and added dropwise to a stirred and chilled (10°–15° C.) solution of 2-chloroaniline (3.2 g, 0.25 mole) and triethylamine (2.5 g, 0.025 mole) in anhydrous dimethylformamide (100 ml). The reaction mixture was stirred at room temperature overnight, filtered, and poured into water (350 ml). The mixture was allowed to precipitate and filtered. The filter cake was twice suspended in water (250 ml) and filtered. The filter cake was air dried and twice recrystallized from tetrahydrofuran to give 4.22 g (40%) of a white solid, mp. 230.5°–232° C.

Analysis: Calculated for $C_{20}H_{14}N_4OBrCl$: C, 54.38; H, 3.19; N, 12.68. Found: C, 54.29; H, 3.18; N, 12.65.

EXAMPLE 117

2-(4-Bromophenyl)-N-(3-pyridinyl)-3H-imidazo[4,5-b]pyridine-3-acetamide hydrochloride [1:2]

Under a nitrogen atmosphere, oxalyl chloride (3.4 g, 0.0267 mole) was added dropwise (slowly) to a stirred and chilled (10° C.) solution of 2-(4-bromophenyl)-3H-imidazo[4,5-b]pyridine-3-acetic acid (8.4 g, 0.0254 mole) in anhydrous dimethylformamide (50 ml). The reaction was heated at 55°–60° C. for 4 hrs, cooled to room temperature, and added dropwise to a stirred and chilled (10° C.) solution of 3-aminopyridine (2.6 g, 0.0279 mole) and triethylamine (5.4 g, 0.0534 mole) in anhydrous dimethylformamide (100 ml). The reaction was stirred at room temperature overnight and then 100 ml of dimethylformamide was distilled off at 100 mm Hg. The residue was cooled and triturated in potassium bicarbonate solution (2×50 ml) and filtered. The filter cake was rinsed with water (2×50 ml) and recrystallized from isopropyl alcohol-isopropyl ether, giving 5.64 g (53%). Recrystallization from isopropyl alcohol-isopropyl ether gave 2.3 g of the free base hemihydrate of the title compound. The organic filtrates were combined and excess etherealhydrogen chloride added, giving 3.72 g. Recrystallization from isopropyl alcohol-isopropyl ether gave 3.0 g of an off-white solid, mp. 180°–186° C. after a phase change at 176–178° C.

Analysis: Calculated for $C_{19}H_{16}N_5OBrCl_2$: C, 47.43; H, 3.35; N, 14.55. Found: C, 47.26; H, 3.55; N, 14.50;

EXAMPLE 118

2-(4-Bromophenyl)-N-(3-pyridinyl)-3H-imidazo[4,5-b]pyridine-3-acetamide hydrate [1:0.5]

Under a nitrogen atmosphere, oxalyl chloride (3.4 g, 0.0267 mole) was added dropwise (slowly) to a stirred and chilled (10° C.) solution of 2-(4-bromophenyl)-3H-imidazo[4,5-b]pyridine-3-acetic acid (8.4 g, 0.0254 mole) in anhydrous dimethylformamide (50 ml). The reaction was heated at 55°–60° C. for 4 hrs, cooled to room temperature, and added dropwise to a stirred and chilled (10° C.) solution of 3-aminopyridine (2.6 g, 0.0279 mole) and triethylamine (5.4 g, 0.0534 mole) in anhydrous dimethylformamide (100 ml). The reaction mixture was stirred at room temperature overnight and then 100 ml of dimethylformamide was distilled off at 100 mm Hg. The residue was cooled and triturated in potassium bicarbonate solution (2×50 ml) and filtered. The filter cake was rinsed with water (2×50 ml) and recrystallized from isopropyl alcohol-isopropyl ether, giving 5.64 g (53%) of solids. Recrystallization from isopropyl alcoholisopropyl ether gave 2.3 g of an off-white solid, mp. 215°–217° C.

Analysis: Calculated for $C_{19}H_{15}N_5O_{1.5}Br$: C, 54.69; H, 3.62; N, 16.78. Found: C, 54.75; H, 3.72; N, 16.72.

EXAMPLE 119

N,N-Dimethyl-2-(2-pyridinyl)-3H-imidazo[4,5-b]pyridine-3-acetamide hydrochloride hydrate [1:1:0.5]

A suspension of 2-(2-pyridyl)-3H-imidazo[4,5-b]pyridine-3-acetic acid (2.44 g, 0.0096 mole), 1,1'-carbonyldiimidazole (1.56 g, 0.0096 mole), and anhydrous tetrahydrofuran (75 ml) was stirred at room temperature with a stream of nitrogen bubbling through for 4½ hrs. The nitrogen flow was stopped and 25 ml of a solution of dimethylamine (2 g, 100 ml) in dry tetrahydrofuran (25 ml of 0.44M) was added. The solution was stirred at room temperature under nitrogen for 12 hrs. The reaction mixture was concentrated in vacuo and the residue dissolved in ethyl acetate (50 ml). The solution was washed with 5% potassium carbonate solution (2×25 ml), water (25 ml), dried over sodium sulfate, and concentrated in vacuo. The residue (1.1 g) was dissolved in tetrahydrofuran-isopropyl ether and treated with excess ethereal hydrogen chloride giving 1.0 g. The aqueous portions were combined, acidified with acetic acid, saturated with sodium chloride and filtered. The filter cake was dissolved in tetrahydrofuran and treated with excess ethereal hydrogen chloride, giving 0.9 g. This was combined with the 1.0-g sample and recrystallized from tetrahydrofuran-methanol. Trituration in tetrahydrofuran-isopropyl ether-ethereal hydrogen chloride gave 1.4 g (45%) of a white solid, mp. 171°–174° C. with decomposition.

Analysis: Calculated for $C_{15}H_{17}N_5O_{1.5}Cl$: C, 55.18; H, 5.24; N, 21.45. Found: C, 55.42; H, 5.16; N, 21.56.

EXAMPLE 120

2-(4-Chlorophenyl)-N,N-dimethyl-3H-imidazo[4,5-b]pyridine-3-acetamide-4-oxide

A mixture of 2-(4-chlorophenyl)-N,N-dimethyl-3H-imidazo[4,5-b]pyridine-3-acetamide (0.3 g, 0.00096 mole), glacial acetic acid (2.5 ml), and m-chloroperbenzoic acid (0.66 g, 0.00384 mole) was heated at 60° C. for a total of 4 hrs. The reaction mixture was diluted with water and the organic acid which precipitated was filtered. The aqueous filtrate was neutralized for peroxides with 10% sodium sulfite. The aqueous solution was evaporated to dryness and the residue was dissolved in methylene chloride. The methylene chloride was extracted with a minimum of saturated sodium bicarbonate. The methylene chloride was dried and evaporated to a residue which crystallized upon standing. The solid was recrystallized from tetrahydrofuran-hexanes with refrigeration overnight. The solid was collected by filtration and dried under high vacuum overnight to give 0.28 g (88 %) of the title compound, mp 200°-201.5° C.

Analysis: Calculated for $C_{16}H_{15}N_4O_2Cl$: C, 58.10; H, 4.57; N, 16.94. Found: C, 58.04; H, 4.60; N, 16.86;

EXAMPLE 121

2-(4-Chlorophenyl)-3H-imidazo[4,5-b]pyridine-3-acetamide-4-oxide

A mixture of 2-(4-chlorophenyl)-3H-imidazo[4,5-b]pyridine-3-acetamide (1.84 g, 0.0064 mole), glacial acetic acid, and m-chloroperbenzoic acid (4.4 g, 0.0256 mole) was heated at 60° C. for a total of 4 hrs. The reaction mixture was diluted with water and the organic acid which precipitated was filtered. The aqueous filtrate was neutralized for peroxides with 10% sodium sulfite. The aqueous solution was evaporated to dryness and the residue was treated with methylene chloride/saturated sodium bicarbonate. The insoluble precipitate was filtered, washed with methylene chloride and water, and dried at 50° C. under high vacuum overnight to give 1.0 g (52%) of title compound, mp. 272°-75° C. with decomposition.

Analysis: Calculated for $C_{14}H_{11}N_4O_2Cl$: C, 55.55; H, 3.66; N, 18.51. Found: C, 55.55; H, 3.64; N, 18.29.

EXAMPLE 122

2-4-Chlorophenyl)-N,N-dibutyl-3H-imidazo[4,5-b]pyridine-3-acetamide

Under nitrogen bubbling, a mixture of 2-(4-chlorophenyl)-3H-imidazo[4,5-b]pyridine-3-acetic acid (5.0 g, 0.0174 mole) and 1,1'-carbonyldiimidazole (2.82 g, 0.0174 mole) in 150 ml of tetrahydrofuran was stirred at room temperature for 3 hrs. The di-n-butylamine (2.59 g, 0.02 mole) was added and the reaction mixture was heated at 60° C. for 3 hrs.

The tetrahydrofuran was evaporated to dryness and the residue was partitioned between methylene chloride and saturated sodium bicarbonate. The aqueous layer was separated and extracted with methylene chloride. (2×). The methylene chloride extracts were combined and extracted with water (1×). The methylene chloride layer was dried, evaporated, and dried under high vacuum overnight. The solid was recrystallized from isopropyl alcohol-water. The solid was collected by filtration, washed with water, and dried under high vacuum at 50° C. overnight to give 3.33 g of title compound (48%), mp. 99°-101° C.

Analysis: Calculated for $C_{22}H_{27}N_4OCl$: C, 66.24; H, 6.82; N, 14.04. Found: C, 66.09; H, 6.80; N, 14.07.

EXAMPLE 123

2-(4-Bromophenyl)-N-(2-pyridinyl)-3H-imidazo[4,5-b]pyridine-3-acetamide

Under a nitrogen atmosphere, oxalyl chloride (3.4 g, 0.027 mole) was added dropwise (slowly) to a stirred and chilled (10° C.) suspension of 2-(4-bromophenyl)-3H-imidazo[4,5-b]pyridine-3-acetic acid (8.4 g, 0.025 mole) in anhydrous dimethylformamide (50 ml). The reaction mixture was heated at 55°-60° C. for 4 hours, cooled to room temperature, and added dropwise to a stirred and chilled (10° C.) solution of 2-aminopyridine (2.6 g, 0.028 mole) and triethylamine (5.4 g, 0.0053 mole) in anhydrous dimethylformamide (100 ml). The reaction was stirred at room temperature overnight. Dimethylformamide (100 ml) was distilled off at 100 mm Hg. The residue was cooled, triturated in potassium bicarbonate solution (2×50 ml), and filtered. The filter cake was rinsed with water (2×50 ml) and recrystallized from ethanolisopropyl ether to give 4.8 g (47%) of white solid, mp 191.5°-195° C.

Analysis: Calculated for $C_{19}H_{14}N_5OBr$: C, 55.90; H, 3.46; N, 17.15. Found: C, 55.68; H, 3.76; N, 16.79.

EXAMPLE 124

2-(4-Chlorophenyl)-N-[bis(2-propenyl)]-3H-imidazo[4,5-b]pyridine-3-acetamide

Under nitrogen bubbling, a mixture of 2-(4-chlorophenyl)-3H-imidazo[4,5-b]pyridine-3-acetic acid (5.0 g, 0.017 mole) and 1,1'-carbonyldiimidazole (2.82 g, 0.017 mole) in 150 ml of tetrahydrofuran was stirred at room temperature for 3 hours. Then, under nitrogen atmosphere, diallylamine (1.94 g, 0.02 mole) was added and the reaction mixture was allowed to stir at room temperature overnight. The tetrahydrofuran was evaporated and the residue was partitioned between methylene chloride and dilute sodium bicarbonate. The separated aqueous layer was extracted with methylene chloride (2×). The combined methylene chloride extracts were extracted with water, dried over magnesium sulfate, and evaporated to dryness. The residue was dried under high vacuum over the weekend. The solid was recrystallized from isopropyl alcohol-water with refrigeration overnight. The solid was collected by filtration, washed with water, and dried under high vacuum at 50° C. overnight to give 4.17 g (65%) of title compound, mp, 143°-145° C.

Analysis: Calculated for $C_{20}H_{19}N_4OCl$: C, 65.48; H, 5.22; N, 15.27. Found: C, 65.08; H, 5.20; N, 15.25.

EXAMPLE 125

2-(4-Bromophenyl)-N-phenyl-3H-imidazo[4,5-b]pyridine-3-acetamide

Under a nitrogen atmosphere, oxalyl chloride (2.6 g, 0.020 mole) was added dropwise (slowly) to a stirred and chilled (5°-10° C.) suspension of 2-(4-bromophenyl)-3H-imidazo[4,5-b]pyridine-3acetic acid (6.4 g, 0.019 mole) in anhydrous dimethylformamide (50 ml). The reaction mixture was heated at 55°-60° C. for 5 hours, cooled to room temperature, and added dropwise to a stirred and chilled (10°-15° C.) solution of aniline (1.9 g, 0.020 mole) and triethylamine (2.1 g, 0.020 mole) in anhydrous dimethylformamide (100 ml). The reaction mixture was stirred at room temperature overnight, filtered, and poured into ice water (500 ml). The mixture was allowed to precipitate and was filtered. The filter cake was triturated in potassium bicarbonate solution (100 ml), filtered, and the cake washed with water (100 ml). Recrystallization from tetrahydrofuran-isopropyl ether and then isopropyl alcohol-ethanoltetrahydrofuran gave 3.8 g (49%) of an off-white solid, mp 242°-243.5° C.

Analysis: Calculated for $C_{20}H_{15}N_4OBr$: C, 58.98; H, 3.71; N, 13.76. Found: C, 58.90; H, 3.69; N, 13.71;

EXAMPLE 126

2-(3-Bromophenyl)-N-methyl-3H-imidazo[4,5-b]pyridine-3-acetamide

A suspension of 2-(3-bromophenyl)-3H-imidazo[4,5-b]pyridine-3-acetic acid (6.0 g, 0.018 mole) 1,1'-carbonyldiimidazole (2.9 g, 0.018 mole), and anhydrous tetrahydrofuran (200 ml) was stirred at room temperature with a stream of nitrogen bubbling through for 4 hours. The nitrogen flow was stopped and a solution of methylamine in tetrahydrofuran (36 ml of 1M) was added. The solution was stirred at room temperature under nitrogen for ½ hour. The reaction mixture was filtered and concentrated in vacuo and the residue triturated in water (100 ml) and filtered. The filter cake was recrystallized from tetrahydrofuran-isopropyl ether, giving 4.6 g (74%). Recrystallization from isopropyl alcohol-isopropyl ether gave 4.4 g of off-white needles, mp 199°–201° C.

Analysis: Calculated for $C_{15}H_{13}N_4OBr$: C, 52.19; H, 3.80; N, 16.23. Found: C, 52.13; H, 3.75; N, 16.15.

EXAMPLE 127

2-(3-Bromophenyl)-N,N-dimethyl-3H-imidazo[4,5-b]pyridine-3-acetamide

A suspension of 2-(3-bromophenyl)-3H-imidazo[4,5-b]pyridine-3-acetic acid (6.0 g, 0.018 mole), and 1,1'carbonyldiimidazole (2.9 g, 0.018 mole), in anhydrous tetrahydrofuran (175 ml) was stirred at room temperature with a stream of nitrogen bubbling through it for 4 hours. The nitrogen flow was stopped and a solution of dimethylamine in tetrahydrofuran (72 ml of 0.5M) was added. The solution was stirred at room temperature under nitrogen for ½ hour. The reaction mixture was filtered, concentrated in vacuo and the residue triturated in water (100 ml) and filtered. The filter cake was recrystallized from tetrahydrofuran-isopropyl ether, giving 4.5 g (70%). Recrystallization from isopropyl alcohol-isopropyl ether gave 4.0 g of cream colored needles, mp 144°–146° C.

Analysis: Calculated for $C_{16}H_{15}N_4OBr$: C, 53.50; H, 4.21; N, 15.60. Found: C, 53.38; H, 4.14; N, 15.57;

EXAMPLE 128

N,N-Dipropyl-2-[4-(trifluoromethyl)phenyl]-3H-imidazo[4,5-b]pyridine-3-acetamide A suspension of 2-(4-trifluoromethylphenyl)-3H-imidazo[4,5-b]pyridine-3-acetic acid (3.21 g, 0.010 mole), and 1,1'-carbonyldiimidazole (1.62 g, 0.010 mole), in anhydrous tetrahydrofuran (75 ml) was stirred at room temperature with a stream of nitrogen bubbling through for 3 hours. The nitrogen flow was stopped and a solution of dipropylamine (1.31 g, 0.013 mole) in dry tetrahydrofuran (25 ml) was added. The solution was stirred at room temperature under nitrogen for 1 hour. The reaction mixture was concentrated in vacuo and the residue triturated in potassium bicarbonate solution (50 ml) and filtered. The filter cake was washed with water and recrystallized twice from isopropyl ether-petroleum ether, giving 1.26 g (31%) of a white solid, mp 138°–139° C.

Analysis: Calculated for $C_{21}H_{23}N_4OF_3$: C, 62.37; H, 5.73; N, 13.85. Found: C, 62.20; H, 5.66; N, 13.84.

EXAMPLE 129

N-(Phenylmethyl)-2-[4-(trifluoromethyl)phenyl]-3H-imidazo[4,5-b]pyridine-3-acetamide A suspension of 2-(4-trifluoromethylphenyl)-3H-imidazo[4,5-b]pyridine-3-acetic acid (3.21 g, 0.010 mole), 1,1'-carbonyldiimidazole (1.62 g, 0.010 mole), and anhydrous tetrahydrofuran (75 ml) was stirred at room temperature with a stream of nitrogen bubbling through for 3 hours. The nitrogen flow was stopped and a solution of benzylamine (1.39 g, 0.013 mole) in dry tetrahydrofuran (25 ml) was added. The solution was stirred at room temperature under nitrogen for 1 hour. The reaction mixture was concentrated in vacuo and the residue triturated in potassium bicarbonate solution (50 ml) and filtered. The filter cake was washed with water and recrystallized from isopropyl alcohol-isopropyl ether, giving 2.8 g (68%). Recrystallization from isopropyl alcohol-isopropyl ether gave 2.3 g of white flakes, mp 224°–225° C.

Analysis: Calculated for $C_{22}H_{17}N_4OF_3$: C, 64.39; H, 4.18; N, 13.65. Found: C, 64.27; H, 4.11; N, 13.51;

EXAMPLE 130

2-(4-Bromophenyl)-N-[4-(dimethylamino)phenyl]-3H-imidazo[4,5-b]pyridine-3-acetamide hydrochloride hydrate [1:2:1.5]

A 0.7-g sample (0.00155 mole) of 2-(4-bromophenyl)-N-[4-(dimethylamino) phenyl]-3H-imidazo[4,5-b]pyridine-3-acetamide obtained in Example 244, was dissolved in acetonitrile (150 ml), acidified with ethereal hydrogen chloride, and refrigerated overnight with seeding. The solid was collected by filtration, washed with diethyl ether-acetonitrile, and dried under high vacuum overnight. The solid was sublimed under high vacuum at 70° C. to give 0.47 g (55%) of title compound, 180° C. (effervescence).

Analysis: Calculated for $C_{22}H_{20}N_5OBr \cdot 2HCl \cdot 1.5\text{-}H_2O$: C, 48.02; H, 4.58; N, 12.73. Found: C 47.88; H, 4.58; N, 12.63.

EXAMPLE 131

N-Methyl-N-phenyl-2-[4-(trifluoromethyl)phenyl]-3H-imidazo[4,5-b]pyridine-3-acetamide Under a nitrogen atmosphere, oxalyl chloride (1.91 g, 0.015 mole) was added dropwise (slowly) to a stirred and chilled (5°–10° C.) solution of 2-(4-trifluoromethylphenyl)-3H-imidazo[4,5-b]pyridine-3-acetic acid (4.5 g, 0.014 mole) and anhydrous dimethylformamide (50 ml). The reaction mixture was heated at 55°–60° C. for 4 hours, cooled, and added dropwise to a stirred and chilled (5°–10° C.) solution of N-methylaniline (1.60 g, 0.015 mole), triethylamine (1.52 g, 0.015 mole), and anhydrous dimethylformamide (50 ml). The reaction mixture was stirred at room temperature overnight and then poured into water (300 ml). The mixture was extracted with methylene chloride (3×50 ml). The combined organic extracts were washed with potassium bicarbonate solution (2×30 ml), water (30 ml), dried over sodium sulfate and concentrated in vacuo. Recrystallization twice from isopropyl ether-petroleum ether gave 1.5 g (24%) of off-white needles, mp 158°–159° C.

Analysis: Calculated for $C_{22}H_{17}N_4OF_3$: C, 64.39; H, 4.18; N, 13.65. Found: C, 64.45; H, 4.18; N, 13.58;

EXAMPLE 132

N,N-Diethyl-2-[4(trifluoromethyl)phenyl]-3H-imidazo[4,5-b]pyridine-3-acetamide

A suspension of 2-(4-trifluoromethylphenyl)-3H-imidazo[4,5-b]pyridine-3-acetic acid (10.0 g, 0.0312 mole), 1,1'-carbonyldiimidazole (6.1 g, 0.0374 mole), and dry tetrahydrofuran (250 ml) was stirred at room temperature for 3 hr with a stream of nitrogen bubbling through it. An additional 6.1 g (0.0374 mole) of 1,1'-carbonyldiimidazole was added, and the suspension was stirred at room temperature under nitrogen overnight. The suspension was heated at 50° C. for 2 hours and then treated with diethylamine (7.07 g, 0.097 mole) in dry tetrahydrofuran (10 ml). The reaction mixture was heated at 50° C. for 5 hr and allowed to stand at room temperature over the weekend. The solvent was evaporated under reduced pressure, the resulting solid was triturated in water (200 ml) and filtered. The solid was dissolved in hot isopropyl alcohol, treated with charcoal and filtered while hot. Upon cooling, a solid precipitated. The solid was filtered and rinsed with isopropyl ether to give 6.4 g (55%) of white solid, mp. 140.5°–142.5° C.

Analysis: Calculated for $C_{19}H_{19}N_4OF_3$: C, 60.63; H, 5.09; N, 14.88. Found: C, 60.77; H, 5.09; N, 14.88.

EXAMPLE 133

N-Methyl-N-(phenylmethyl)-2-[4-(trifluoromethyl)-phenyl]-3H-imidazo[4,5-b]pyridine-3-acetamide hydrate [1:0.5]

Under nitrogen bubbling, a mixture of 2-(4-trifluoromethylphenyl)-3H-imidazo[4,5-b]pyridine-3-acetic acid (3.21 g, 0.01 mole) and 1,1'-carbonyldiimidazole (1.62 g, 0.01 mole) in 150 ml of tetrahydrofuran was stirred at room temperature for 3 hrs. N-methylbenzylamine (1.33 g, 0.011 mole) was added, and the reaction mixture was allowed to stir at room temperature for 1 hr.

The tetrahydrofuran was evaporated to dryness. The residue was triturated with aqueous potassium bicarbonate, collected by filtration, and washed with water. The solid was recrystallized from ethanol-isopropyl ether to give 2.3 g, then from isopropyl alcohol-isopropyl ether-petroleum ether to give 2.0 g which was dried under high vacuum at 79° C. for 4 hrs, then overnight at room temperature. The solid was recrystallized from isopropyl ether-petroleum ether and dried overnight under high vacuum at 65° C. The solid was triturated with isopropyl ether-petroleum ether, collected by filtration, and dried under high vacuum at room temperature overnight to give 1.5 g (35%) of title compound, mp 125.5°–127° C.

Analysis: Calculated for $C_{23}H_{19}N_4OF_3 \cdot \tfrac{1}{2}H_2O$: C, 63.74; H, 4.65; N, 12.93. Found: C, 63.43; H, 4.35; N, 12.86.

EXAMPLE 134

N-[Bis(1-methylethyl)]-2-(4-chlorophenyl)-3H-imidazo[4,5-b]pyridine-3-acetamide

Under nitrogen bubbling, a mixture of 2-(4-chlorophenyl)-3H-imidazo[4,5-b]pyridine-3-acetic acid (5.0 g, 0.0174 mole) and 1,1'-carbonyldiimidazole (2.82 g, 0.0174 mole) in 150 ml of tetrahydrofuran was stirred at room temperature for 2 hrs. The di-isopropylamine (2.02 g, 0.02 mole) was added, and the reaction mixture was allowed to stir at room temperature overnight. The reaction mixture was heated at 60° C. for 8 hrs.

The tetrahydrofuran was evaporated to dryness, and the residue was partitioned between methylene chloride and dilute sodium bicarbonate. The aqueous layer was separated and extracted with methylene chloride (2×). The combined methylene chloride layers were extracted with water and dried over magnesium sulfate. The filtrate was evaporated to a solid, which was dried under high vacuum overnight. The solid was recrystallized twice from isopropyl alcohol-water, collected by filtration, washed with water, and dried under high vacuum overnight to give 0.8 g (12.4%) of title compound, mp 218°–20° C.

Analysis: Calculated for $C_{20}H_{23}N_4OCl$: C, 64.77; H, 6.25; N, 15.11. Found: C, 64.26; H, 6.23; N, 14.98;

EXAMPLE 135

2-(3-Chlorophenyl)-N,N-dimethyl-3H-imidazo[4,5-b]pyridine-3-acetamide hydrate [1:0.5]

Under nitrogen bubbling, a mixture of 2-(3-chlorophenyl)-3H-imidazo[4,5-b]pyridine-3-acetic acid (4.0 g, 0.0138 mole) and 1,1'-carbonyldiimidazole (2.24 g, 0.0138 mole) in 150 ml of tetrahydrofuran was stirred at room temperature for 4 hrs. A solution of dimethylamine in tetrahydrofuran (42 ml of 0.5M solution) was added, and the reaction mixture was allowed to stir at room temperature for ½ hr.

The tetrahydrofuran was evaporated to dryness, and the residue was partitioned between water and ethyl acetate. The water layer was extracted with ethyl acetate (2×). The combined ethyl acetate layers were extracted with water (25 ml), dried over magnesium sulfate, and evaporated to dryness. The solid was dissolved in isopropyl alcohol and acidified with ethanolic hydrogen chloride. The solution was diluted first with isopropyl ether, then with tetrahydrofuran to initiate crystallization. The solid was collected, recrystallized from tetrahydrofuran-isopropyl alcohol, and dried under high vacuum at 65° C. for 3 hrs, then at room temperature overnight. The hydrochloride salt was added to water, which converted it to the crystalline free base, which was collected by filtration, washed with water and dried under high vacuum for 2 days to give 1.0 g (22%) of crystals, mp 68°–70° C. (melted and resolidified), 107° C. (melted and resolidified), 125°–26° C.

Analysis: Calculated for $C_{16}H_{15}N_4OCl \cdot \tfrac{1}{2}H_2O$: C, 59.35; H, 4.98; N, 17.30. Found: C, 59.72; H, 4.94; N, 17.43.

EXAMPLE 136

N,N-Dibutyl-2-[4-(trifluoromethyl)phenyl]-3H-imidazo[4,5-b]pyridine-3-acetamide

Under nitrogen bubbling, a mixture of 2-(4-trifluoromethylphenyl)-3H-imidazo[4,5-b]pyridine-3-acetic acid (3.21 g, 0.01 mole) and 1,1'-carbonyldiimidazole (1.62 g, 0.01 mole) in 100 ml of tetrahydrofuran was stirred at room temperature for 3 hrs. The di-n-butylamine (1.68 g, 0.013 mole) was added, and the reaction was allowed to stir at room temperature for 1 hr.

The tetrahydrofuran was evaporated to dryness. The residue was triturated with aqueous potassium bicarbonate solution (50 ml), collected by filtration, and washed with water. The solid was triturated with diethyl ether, collected by filtration, and crystallized from isopropyl ether-isopropyl alcohol. The solid was recrystallized first from isopropyl ether-petroleum ether to give 0.81 g, followed by isopropyl alcohol-water to give 0.56 g (13%) after drying under high vacuum for 2 days, mp 116°–117.5° C.

Analysis: Calculated for $C_{23}H_{27}N_4OF_3$: C, 63.88; H, 6.29; N, 12.95. Found: C, 63.76; H, 6.25; N, 12.91.

EXAMPLE 137

2-(3-Chlorophenyl)-N-(2-pyridinyl)-3H-imidazo[4,5-b]pyridine-3-acetamide

Under a nitrogen atmosphere, oxalyl chloride (2.38 g, 0.019 mole) was added slowly dropwise to a stirred and chilled (15°–20° C.) solution of 2-(3-chlorophenyl)-3H- imidazo[4,5-b]pyridine-3-acetic acid (4.70 g, 0.016 mole) in 50 ml of dimethylformamide. The reaction mixture was stirred at ambient temperature for ½ hr., then warmed to 60°-65° C. for 5 hrs. This acylchloride solution was added dropwise under nitrogen to a stirred and chilled (15°-20° C.) solution of 2-aminopyridine (1.76 g, 0.019 mole), triethylamine (1.89 g, 0.019 mole), and 30 ml of dimethylformamide. The reaction mixture was stirred at room temperature over the weekend. The reaction mixture was poured into 400 ml of ice water and extracted with ethyl acetate (3×). The ethyl acetate layers were washed with 5% potassium hydroxide (2×50 ml), water (2×50 ml), dried, and filtered. The residue was treated with isopropyl alcohol and excess ethereal hydrogen chloride to give solid which was recrystallized twice from isopropyl alcohol-isopropyl ether and once from isopropyl alcohol. The solid was collected by filtration, washed with cold isopropyl alcohol, then isopropyl alcohol-water, and dried under high vacuum for 2 days to give 0.92 g (15.8%) of title compound, mp 165°-66° C.

Analysis: Calculated for $C_{19}H_{14}N_5OCl$: C, 62.73; H, 3.88; N, 19.25. Found: C, 62.53; H, 3.88; N, 19.08.

EXAMPLE 138

2-(4-Chlorophenyl)-N-methyl-N-phenyl-3H-imidazo[4,5-b]pyridine-3-acetamide

Under nitrogen atmosphere, oxalyl chloride (2.21 g, 0.0174 mole) was added slowly dropwise to a stirred and chilled (~10° C.) suspension of 2-(4-chlorophenyl)-3H-imidazo[4,5-b]pyridine-3-acetic acid (5.0 g, 0.0174 mole) in 75 ml of dimethylformamide. After the addition was complete, the reaction was heated at 60° C. for 5 hrs. This acylchloride solution was added dropwise to a stirred and cooled (~10° C.) solution of N-methylaniline (2.02 g, 0.019 mole), triethylamine (1.88 g, 0.019 mole), and 74 ml of dimethylformamide. The reaction was stirred at room temperature overnight. The reaction mixture was poured into 200 ml of water and diluted with water until the cloud point. The mixture was seeded and refrigerated overnight. The solid was collected by filtration and dried under high vacuum. The solid was suspended in dilute sodium bicarbonate, collected by filtration, washed with water, and dried under high vacuum at 50° C. The solid was recrystallized from isopropyl alcohol-water, collected by filtration, washed with water, and dried under high vacuum first at 56° C., then at 98° C. for 2 days to give 3.0 g (45.7%) of crystals, mp 170°-171° C.

Analysis: Calculated for $C_{21}H_{17}N_4OCl$: C, 66.93; H, 4.55; N, 14.87 Found: C, 66.57; H, 4.56; N, 14.81.

EXAMPLE 139

2-(4-Chlorophenyl)-N-[4-(dimethylamino)phenyl]-3H-imidazo[4,5-b]pyridine-3-acetamide Under a nitrogen atmosphere, oxalyl chloride (2.21 g, 0.0174 mole) was added slowly dropwise to a stirred and cooled (0°-10° C.) suspension of 2-(4-chlorophenyl)-3H-imidazo[4,5-b]pyridine-3-acetic acid (5.0 g, 0.0174 mole) in 50 ml of dimethylformamide. After the addition was complete, the reaction solution was heated at 60° C. for 5 hrs. This acylchloride solution was added dropwise to a stirred and cooled (<10° C.) suspension of N,N-dimethyl-1,4-phenylenediamine dihydrochloride (3.64 g. 0.0174 mole), triethylamine (5.27 g, 0.052 mole), and 75 ml of dimethylformamide. The reaction mixture was stirred at room temperature overnight. The reaction mixture was poured into 1800 ml of water and refrigerated overnight. The solid was collected by filtration and dried. The solid was recrystallized twice from isopropyl alcohol, collected by filtration, washed with water, and dried under high vacuum at 98° C. overnight to give 0.9 g (12.7%) of crystals, mp 245°-246° C.

Analysis: Calculated for $C_{22}H_{20}N_5OCl$: C, 65.10; H, 4.97; N, 17.25. Found: C, 64.81; H, 4.98; N, 17.24.

EXAMPLE 140

2-(4-Methoxyphenyl)-N,N-dimethyl-3H-imidazo[4,5-b]pyridine-3-acetamide

Under nitrogen bubbling, a mixture of 2-(4-methoxyphenyl-3H-imidazo[4,5-b]pyridine-3-acetic acid (4.2 g, 0.0148 mole) and 1,1'-carbonyldiimidazole (2.43 g, 0.015 mole) in 120 ml of tetrahydrofuran was stirred at room temperature for 3½ hrs. A solution of dimethylamine in tetrahydrofuran (60 ml of 0.5M) was added, and the reaction was allowed to stir at room temperature overnight.

The tetrahydrofuran was evaporated to dryness, and the residue was treated with water. The solid was collected by filtration, washed with water, and dried under high vacuum overnight. The solid was recrystallized from isopropyl alcohol, collected by filtration, washed with water, and dried under high vacuum at 70° C. over 2 days to give 1.16 g (25.3%) of crystals, mp 156°-58° C.

Analysis: Calculated for $C_{17}H_{18}N_4O_2$: C, 65.79; H, 5.85; N, 18.05. Found: C, 65.66; H, 5.84; N, 17.98;

EXAMPLE 141

2-(3,4-Dichlorophenyl)-3H-imidazo[4,5-b]pyridine-3-acetic acid ethyl ester

A mixture of N-[3-[(3,4-dichlorobenzoyl)amino]-2-pyridinyl]glycine ethyl ester (33 g, 0.09 mole) and 167 ml of ethylene glycol was heated at reflux for 1¼ hr. The material crystallized upon cooling. A small portion of the solid was collected by filtration, washed with water, and dried under high vacuum. The solid was recrystallized from ethanol with refrigeration, collected by filtration, washed with ethanol/water mixture, and dried under high vacuum at 70° C. over 2 days to give 2.0 g, mp 141°-42° C.

Analysis: Calculated for $C_{16}H_{13}N_3O_2Cl_2$: C, 54.88; H, 3.74 N, 12.00. Found: C, 54.59; H, 3.75; N, 11.90.

EXAMPLE 142

4-[[[(3-Chlorophenyl)-3H-imidazo[4,5-b]pyridin-3-yl]acetyl]amino]butanoic acid hydrate [1:0.5]

A mixture of 4-[[(2-(3-chlorophenyl)-3H-imidazo[4,5-b]pyridine-3-yl]acetyl]amino]butanoic acid ethyl ester (2.4 g, 0.006 mole) and potassium hydroxide (0.5 g) in 100 ml of ethanol was heated at reflux for 2 hrs. The reaction mixture was evaporated to dryness. The residue was dissolved in water, filtered, and the filtrate was acidified with acetic acid. The precipitate, which had formed, was collected by filtration, washed with water, and dried. The solid was recrystallized from ethanol-water, collected by filtration, washed with water, and dried under high vacuum at 78° C. over 2 days to give 0.93 g (42%), mp 207°-8° C.

Analysis: Calculated for $C_{18}H_{17}N_4O_3Cl.\frac{1}{2}H_2O$: C, 56.62; H, 4.75; N, 14.67. Found: C, 56.87; H, 4.71; N, 14.61;

EXAMPLE 143

2-(4-Methoxyphenyl)-N,N-dipropyl-3H-imidazo[4,5-b]pyridine-3-acetamide

Under nitrogen bubbling, a mixture of 2-(4-methoxyphenyl)-3H-imidazo[4,5-b]pyridine-3-acetic acid (4.2 g, 0.015 mole) and 1,1'-carbonyldiimidazole (2.43 g, 0.015 mole) in 120 ml of tetrahydrofuran was stirred at room temperature for 3 hrs. The dipropylamine (3.04 g, 0.03 mole) was added and the reaction mixture was allowed to stir at room temperature overnight, then heated at reflux for 8 hrs. The reaction mixture was filtered and the filtrate was evaporated to dryness, then placed under high vacuum over the weekend. The residue was treated with water, and dried under high vacuum. The solid was dissolved in 100 ml of isopropyl alcohol, filtered, and the filtrate concentrated to 50 ml. The filtrate was diluted with water, seeded, and placed in a freezer overnight. The solid was collected by filtration, washed with water, and dried under high vacuum at 50°–60° C. overnight to give 1.8 g (33%) of title compound, mp 127°–29° C.

Analysis: Calculated for $C_{21}H_{26}N_4O_2$: C, 68.83; H, 7.15; N, 15.29. Found: C, 68.74; H, 7.15; N, 15.18.

EXAMPLE 144

2-(4-Methoxyphenyl)-3-[2-oxo-2-(1-piperidinyl)ethyl]-3H-imidazo[4,5-b]pyridine Under nitrogen bubbling, a mixture of 2-(4-methoxyphenyl)-3H-imidazo[4,5-b]pyridine-3-acetic acid (4.2 g, 0.015 mole) and 1,1'-carbonyldiimidazole (2.43 g, 0.015 mole) in 120 ml of tetrahydrofuran was stirred at room temperature for 3 hrs. Then, under nitrogen atmosphere, piperidine (1.92 g, 0.022 mole) was added and the reaction mixture was allowed to stir at room temperature overnight. The reaction mixture was filtered and the filtrate was evaporated to dryness, then placed under high vacuum for 3-4 hrs. The residue was treated with water and solid was collected by filtration, washed with water, and dried under high vacuum at 50°–60° C. overnight. The solid was recrystallized from isopropyl alcohol with refrigeration overnight. The solid was collected by filtration, washed with cold isopropyl alcohol and water, and dried under high vacuum at 50°–60° C. overnight to give 3.21 g (62%) of title compound, mp 153°–55° C.

Analysis: Calculated for $C_{20}H_{22}N_4O_2$: C, 68.55; H, 6.33; N, 15.99. Found: C, 68.53; H, 6.34; N, 16.00.

EXAMPLE 145

N,N-Diethyl-2-(4-methoxyphenyl)-3H-imidazo[4,5-b]pyridine-3-acetamide hydrate [1:0.5]

Under nitrogen bubbling, a mixture of 2-(4-methoxyphenyl)-3H-imidazo[4,5-b]pyridine-3-acetic acid (4.2 g, 0.015 mole) and 1,1'-carbonyldiimidazole (2.43 g, 0.015 mole) in 150 ml of tetrahydrofuran was stirred at room temperature for 3 hrs. The diethylamine (2.19 g, 0.03 mole) was added and the reaction mixture was allowed to stir at room temperature overnight, then heated at reflux for 3 hrs. The tetrahydrofuran was evaporated to dryness. The residue was treated with hot water, filtered through a Celite pad, and allowed to crystallize upon cooling. The solid was collected by filtration, washed with water, and dried under high vacuum at 50°–60° C. overnight to give 1.0 g, mp (softens at 55° C., resolidified) 133°–35° C. Total yield in 2 crops was 1.9 g (38%).

Analysis: Calculated for $C_{19}H_{22}N_4O_2.0.5H_2O$: C, 65.69; H, 6.67; N, 16.13. Found: C, 65.48; H, 6.43; N, 16.13.

EXAMPLE 146

2-(3,4-Dichlorophenyl)-N,N-dipropyl-3H-imidazo[4,5-b]pyridine-3-acetamide hydrate [1:0.5]

Under nitrogen bubbling, a mixture of 2-3,4-dichlorophenyl)-3H-imidazo[4,5-b]pyridine-3-acetic acid (3.5 g, 0.011 mole) and 1,1'-carbonyldiimidazole (1.95 g, 0.011 mole) in 120 ml of tetrahydrofuran was stirred at room temperature for 3½ hrs. Then, under nitrogen atmosphere, dipropylamine (2.43 g, 0.024 mole) was added at room temperature and the reaction mixture was heated at reflux for 6 hrs. The reaction mixture was filtered, and the filtrate was evaporated to dryness. The residue was treated with water and refrigerated. The solid was collected by filtration, washed with water, and dried under high vacuum at 50°–60° C. overnight. The solid was recrystallized from isopropyl alcohol-water, collected, washed with water, and dried under high vacuum at 50°–60 ° C. overnight. Two crops gave 1.9 g (43%) of crystals, mp 122°–123° C.

Analysis: Calculated for $C_{20}H_{22}N_4OCl_2.0.5H_2O$: C, 57.98; H, 5.60; N, 13.52. Found: C, 57.81; H, 5.34; N, 13.54.

EXAMPLE 147

2-[4-(Trifluoromethyl)phenyl]-3H-imidazo[4,5-b]pyridine-3-acetic acid ethyl ester The solid N-[3-[(4-trifluoromethylbenzoyl)amino]-2-pyridinyl] glycine ethyl ester (5.0 g, 0.014 mole) was heated in a siliconoil bath at 240° C. for 5 min. The residue was sublimed at 140° C. under high vacuum to give a white solid, 0.7 g (15%), mp 147°–48° C.

Analysis: Calculated for $C_{17}H_{14}N_3O_2F_3$: C, 58.45; H, 4.04; N, 12.03 Found: C, 58.43; H, 3.98; N, 12.09.

EXAMPLE 148

2-(3-Bromophenyl)-3-[2-oxo-2-(1-piperidinyl)ethyl]-3H-imidazo[4,5-b]pyridine Under nitrogen bubbling, a mixture of 2-(3-bromophenyl)-3H-imidazo[4,5-b]pyridine-3-acetic acid (4.98 g, 0.015 mole) and 1,1'-carbonyldiimidazole (2.59 g, 0.016 mole) in 120 ml of tetrahydrofuran was stirred at room temperature for 4 hrs. The piperidine (2.55 g, 0.03 mole) was added and the reaction mixture was allowed to stir at room temperature overnight. The reaction mixture was filtered and the filtrate was evaporated to dryness, then placed under high vacuum for 3 hrs. The solid was treated with water, collected by filtration, washed with water, and dried at 50° C. under high vacuum over the weekend to give 3.93 g (66%) of title compound, mp 157°–58° C.

Analysis: Calculated for $C_{19}H_{19}N_4OBr$: C, 57.15; H, 4.80; N, 14.03. Found: C, 56.98; H, 4.76; N, 14.00.

EXAMPLE 149

2-(3-Bromophenyl)-N,N-dipropyl-3H-imidazo[4,5-b]pyridine-3-acetamide

Under nitrogen bubbling, a mixture of 2-(3-bromophenyl)-3H-imidazo[4,5-b]pyridine-3-acetic acid (4.98 g, 0.015 mole) and 1,1'-carbonyldiimidazole (2.59 g, 0.016 mole) in 120 ml of tetrahydrofuran was stirred at room temperature for 4 hrs. The di-n-propylamine (3.04 g, 0.03 mole) was added and the reaction mixture was heated at reflux for (65° C.) for 8-9 hrs. The reaction mixture was filtered and the filtrate was evaporated to an oil, which was placed under high vacuum for 3 hrs. The solid residue was treated with water, collected by filtration, washed with water, and dried under high vacuum. The solid was recrystallized from isopropyl alcohol-water, collected by filtration, washed with water, and dried under high vacuum to give 3.2 g (52%), mp 125°-27° C.

Analysis: Calculated for $C_{20}H_{23}N_4OBr$: C, 57.84; H, 5.58; N, 13.49. Found: C, 57.89; H, 5.57; N, 13.48.

EXAMPLE 150

2-(3-Chlorophenyl)-N-methyl-N-[3-(4-methyl-1-piperazinyl)propyl]-3H-imidazo[4,5-b]pyridine-3-acetamide Under nitrogen bubbling, a mixture of 2-(3-chlorophenyl)-3H-imidazo[4,5-b]pyridine-3-acetic acid (2.38 g, 0.008 mole) and 1,1'-carbonyldiimidazole (1.34 g, 0.008 mole) was stirred at room temperature for 3 hours. The N,4-dimethyl-1piperazinepropanamine (1.42 g, 0.008 mole) was added and the reaction mixture was allowed to stir at room temperature for 2 hours. The reaction mixture was evaporated to dryness. The residue was partitioned between methylene chloride and aqueous potassium bicarbonate. The aqueous layer was separated and extracted with methylene chloride. The methylene chloride layers were combined, extracted with aqueous potassium bicarbonate and water and dried over sodium sulfate. The filtrate was evaporated and the solid residue was recrystallized as a fumarate salt from ethyl alcohol-isopropyl ether. Recrystallization from isopropyl alcohol-acetonitrile-isopropyl ether did not improve the analysis. The solid was converted to the free base. The free base was treated with boiling hexanes and allowed to cool to room temperature. The solid was collected by filtration, washed with hexane, and dried under high vacuum overnight to give 0.7 g of title compound, mp 114°-17° C.

Analysis: Calculated for $C_{23}H_{29}N_6OCl$: C, 62.65; H, 6.63; N, 19.06. Found: C, 62.56; H, 6.61; N, 18.70.

EXAMPLE 151

2-(4-Chlorophenyl)-N-(2-methoxyethyl-3H-imidazo[4,5-b]pyridine-3-acetamide

Under nitrogen bubbling, a mixture of 2-(4-chlorophenyl)-3H-imidazo[4,5-b]pyridine-3-acetic acid (4.37 g, 0.015 mole) and 1,1'-carbonyldiimidazole (2.59 g, 0.016 mole) in 150 ml of tetrahydrofuran was stirred at room temperature for 4 hrs. 2-Methoxyethylamine (1.71 g, 0.023 mole) was added and the reaction mixture was allowed to stir at room temperature overnight.

The tetrahydrofuran was evaporated to dryness and the residue was placed under high vacuum overnight. The solid was recrystallized from hot isopropyl alcohol. The solid was collected by filtration, washed with water, and dried under high vacuum at 50° C. overnight to give 4.0 g (76 %) of title compound, mp 180°-81° C.

Analysis: Calculated for $C_{17}H_{17}N_4O_2Cl$: C, 59.22; H, 4.97; N, 16.25. Found: C, 59.24; H, 4.97; N, 16.32;

EXAMPLE 152

2-(3,4-Dichlorophenyl)-3-[2-oxo-2-(1-piperidinyl)ethyl]-3H-imidazo[4,5-b]pyridine Under nitrogen bubbling, a mixture of 2-(3,4-dichlorophenyl)-3H-imidazo[4,5-b]pyridine-3-acetic acid (3.5 g, 0.011 mole) and 1,1'-carbonyldiimidazole (1.95 g, 0.011 mole) in 150 ml of tetrahydrofuran was stirred at room temperature for 4 hrs. Piperidine (1.87 g, 0.022 mole) was added and the reaction was allowed to stir at room temperature overnight.

The reaction mixture was filtered and the filtrate was evaporated to dryness, then placed under high vacuum. The solid was recrystallized from isopropyl alcohol, collected by filtration, washed with water, and dried under high vacuum to give 2.58 g (60.2%) of title compound, mp 194°-96° C.

Analysis: Calculated for $C_{19}H_{18}N_4OCl_2$: C, 58.62; H, 4.66; N, 14.39. Found: C, 58.28; H, 4.58; N, 14.35.

EXAMPLE 153

2-(3,4-Dichlorophenyl)-N-[2-(dimethylamino)ethyl]-3H-imidazo[4,5-b]pyridine-3-acetamide hydrochloride [1:2]

Under nitrogen bubbling, a mixture of 2-(3,4-dichlorophenyl)-3H-imidazo[4,5-b]pyridine-3-acetic acid (3.5 g, 0.011 mole) and 1,1'-carbonyldiimidazole (1.95 g, 0.011 mole) in 150 ml of tetrahydrofuran was stirred at room temperature for 2 hrs, then heated at 60°-65° C. for 2 hrs. N,N-Dimethylaminoethylamine (1.06 g, 0.012 mole) was added and the reaction mixture was allowed to stir at room temperature. The reaction mixture was filtered and the filtrate was evaporated to dryness, then placed under high vacuum overnight. The solid was treated with ice water, collected by filtration, washed with water, and dried under high vacuum at 50° C. overnight. The solid was dissolved in acetone and acidified with ethanolic hydrogen chloride. The crystalline precipitate was collected by filtration, washed with cold acetone, and dried under high vacuum to give 3.61 g. The solid was dissolved in 1.2 liters of acetone and concentrated to 600 ml to initiate crystallization. The solid was collected by filtration, washed with acetone, and dried under high vacuum overnight at 50° C. to give 1.9 g of title compound, mp 120°-122° C.

Analysis: Calculated for $C_{18}H_{19}N_5OCl_2.2HCl$: C, 46.47; H, 4.55; N, 15.05; Found; C, 46.60; H, 4.86; N, 14.87.

EXAMPLE 154

2-(4-Chlorophenyl)-N,N-diphenyl-3H-imidazo[4,5-b]pyridine-3-acetamide

Under a nitrogen atmosphere, oxalyl chloride (1.73 g, 0.0137 mole) was added dropwise, slowly, to a stirred and chilled (10° C.) solution of 2-(4-chlorophenyl)-3H-imidazo[4,5-b]pyridine-3-acetic acid (3.7 g, 0.013 mole) in anhydrous dimethylformamide (50 ml). The reaction mixture was heated at 60° C. for 4 hr under nitrogen, cooled and added dropwise to a stirred and chilled (10° C.) solution of diphenylamine (2.37 g, 0.014 mole) and triethylamine (1.42 g, 0.014 mole) in anhydrous dimethylformamide (75 ml). The reaction mixture was stirred at room temperature overnight and then poured into water (400 ml). The mixture was extracted with ethyl acetate (2×75 ml). The aqueous layer was saturated with sodium chloride and extracted again with ethyl acetate (75 ml). The combined organic layers were washed with 5% potassium hydroxide solution (2×50 ml), water (50 ml) and saturated sodium chloride solution (50 ml). The combined layers were dried over sodium sulfate, filtered and concentrated under reduced pressure to give 4.0 g of an oil (70%). The oil was crystallized from isopropyl ether-isopropyl alcohol to give 2.2 g (39%) of a white solid, mp. 176°–178° C.

Analysis: Calculated for $C_{26}H_{19}N_4OCl$: C, 71.15; H, 4.36; N, 12.76. Found: C, 70.87; H, 4.38; N, 12.68;

EXAMPLE 155

N-[2-Dimethylamino)ethyl]-2-[4-(trifluoromethyl)-phenyl]-3H-imidazo[4,5-b]pyridine-3-acetamide A suspension of 2-[4-(trifluoromethyl)phenyl]-3H-imidazo[4,5-b]pyridine-3-acetic acid (5.0 g, 0.0156 mole) 1,1'-carbonyldiimidazole (3.0 g, 0.0185 mole) and dry tetrahydrofuran (125 ml) was stirred at room temperature for 2 hours with nitrogen bubbling through it. The reaction mixture was then heated at 50° C. under nitrogen for 2 hours. The solution was cooled and a solution of N,N-dimethylethylenediamine (4.2 g, 0.047 mole) in tetrahydrofuran (5 ml) was added. The reaction mixture was stirred at room temperature overnight under nitrogen and evaporated under reduced pressure. The residue was triturated in water, and the solid was collected by filtration, washed once with water, twice with 5% potassium hydroxide solution and then twice again with water to yield 3.0 g (49%) of product. A 0.7-g sample of the solid was dissolved in hot isopropyl ether with a little isopropyl alcohol added to aid solubility, filtered, and cooled to room temperature to yield 0.4 g of a white solid, mp 196°–197° C.

Analysis: Calculated for $C_{19}H_{20}N_5F_3O_1$: C, 58.31; H, 5.15; N, 17.89. Found: C, 58.62; H, 5.18; N, 18.11.

EXAMPLE 156

N-[2-(Dimethylamino)ethyl]-2-[4-(trifluoromethyl)-phenyl]-3H-imidazo[4,5-b]pyridine-3-acetamide hydrochloride [1:2]

A solution of 2.3 g of N-[2-(dimethylamino)ethyl]-2-]4-(trifluoromethyl)phenyl]-3H-imidazo[4,5-b]pyridine-3-acetamide in hot isopropyl alcohol was acidified with concentrated hydrochloric acid. The solvents were evaporated under reduced pressure and the residue redissolved in hot isopropyl alcohol and methanol, filtered, and while still hot, isopropyl ether was added to the cloud point. Solid precipitated upon cooling to room temperature. The solid was collected by filtration to give 1.8 g of a white solid, mp 230°–234° C.

Analysis: Calculated for $C_{19}H_{22}N_5F_3O_1Cl_2$: C, 49.15; H, 4.78; H, 15.08. Found: C, 48.83; H, 4.96; N, 14.69.

EXAMPLE 157

2-(4-Chlorophenyl)-N,N-dipropyl-3H-imidazo[4,5-b]pyridine-3-propanamide

A suspension of 2-(4-chlorophenyl)-3H-imidazo[4,5-b]pyridine-3-propanoic acid 5.0 g, 0.0166 mole) 1,1'-carbonyldiimidazole (3.21 g, 0.0198 mole) and dry tetrahydrofuran (100 ml) was stirred at room temperature for 1 hour with nitrogen bubbling through it. The reaction mixture was then heated at reflux for 1 hour under nitrogen during which a solution formed. A solution of dipropylamine (5.04 g, 0.050 mole) in tetrahydrofuran (7 ml) was added and the reaction mixture was heated at 50° C. overnight under nitrogen. The reaction mixture was evaporated under reduced pressure and the residue was partitioned between water and ethyl acetate (100 ml of each). The two layer mixture was filtered to remove an insoluble solid and the layers were separated. The aqueous layer was re-extracted once with ethyl acetate and the combined organic layers were washed once with a 5% potassium hydroxide solution (100 ml), dried over sodium sulfate, filtered, and evaporated to a residue weighing 8.9 g. The residue was dissolved in hot isopropyl alcohol, filtered, cooled to room temperature, and water was added. Solid formed which was collected by filtration to give 4.84 g (76%) of a white solid, after drying under vacuum overnight, mp 104°–105.5° C.

Analysis: Calculated for $C_{21}H_{25}N_4O_1Cl_1$: C, 65.53; H, 6.55; N, 14.56. Found: C, 65.35; H, 6.59; N, 14.53;

2-(4-Chlorophenyl)-N-[2-(dimethylamino)ethyl]-3H-imidazo[4,5-b]pyridine-3-propanamide hydrochloride [1:2]

A solution of 3.9 g of crude 2-(4-chlorophenyl)-N-[2-(dimethylamino)ethyl]-3H-imidazo[4,5-b]pyridine-3-propanamide in hot isopropyl alcohol-methanol was filtered and acidified with ethereal hydrogen chloride. Isopropyl ether was added to precipitate a solid. The entire mixture was evaporated under reduced pressure, redissolved in hot isopropyl alcohol and precipitated with isopropyl ether. The solid was collected by filtration and dried under high vacuum. The solid melted. The resulting glass was combined with a second crop of solid and recrystallized from isopropyl alcohol-/acetone/diethyl ether to give a white solid which after drying under high vacuum at room temperature and then at 50° C. gave a white solid, mp 202°–205° C.

Analysis: Calculated for $C_{19}H_{24}N_5O_1Cl_3$: C, 51.31; H, 5.44; N, 15.74. Found: C, 51.14; H, 5.48; N, 15.78.

EXAMPLE 159

2-(4-Chlorophenyl)-N-[2-(dimethylamino)ethyl]-3H-imidazo[4,5-b]pyridine-3-propanamide A suspension of 2-(4-chlorophenyl)-3H-imidazo[4,5-b]pyridine-3-propanoic acid (5.0 g, 0.0166 mole), 1,1'-carbonyldiimidazole (3.21 g, 0.0198 mole) and dry tetrahydrofuran (100 ml) was stirred at room temperature for 2 hours with nitrogen bubbling through it. The reaction mixture was then heated at 55° C. for 2 hours under nitrogen and cooled to room temperature. A solution of N,N-dimethylethylenediamine (4.41 g, 0.050 mole) in tetrahydrofuran (5.5 ml) was added and the reaction mixture was stirred at room temperature under nitrogen over the weekend. The reaction mixture was evaporated to a white solid and triturated with water (100 ml). The solid was collected by filtration, rinsed once with a 5% potassium hydroxide solution, and washed twice more with water to give 4.9 g of a white solid (79%). A second crop of white solid was obtained from the mother liquor of the above solid. The second crop was dried under high vacuum at 70° C. to give a white solid, mp 141.5°–143° C.

Analysis: Calculated for $C_{19}H_{22}N_5O_1Cl_1$: C, 61.37; H, 5.96; N, 18.83. Found: C, 61.64; H, 6.04; N, 19.12.

EXAMPLE 160

3-[2-(1-Azetidinyl)-2-oxoethyl]-2-(4-chlorophenyl)-3H-imidazo[4,5-b]pyridine

A suspension of 2-(4-chlorophenyl)-3H-imidazo[4,5-b]pyridine-3-acetic acid (6.72 g, 0.0234 mole), 1,1'-carbonyldiimidazole (3.78 g, 0.0234 mole) and dry tetrahydrofuran (85 ml) was stirred at room temperature for 2 hours with nitrogen bubbling through and was then stirred at room temperature under nitrogen overnight. A solution of azetidine (2.0 g, 0.0350 mole) in tetrahydrofuran (10 ml) was added. The resulting suspension was stirred at room temperature under nitrogen for 3.5 hours, evaporated to a white solid, triturated with water (75 ml), the solid filtered and rinsed twice with water. The solid was dissolved in hot isopropyl alcohol, filtered, and cooled to room temperature to yield a white solid. The solid was collected by filtration, rinsed once with isopropyl alcohol, twice with isopropyl ether and dried under high vacuum at room temperature to give 5.34 g (70%) of a white solid, mp 195.5°–197° C.

Analysis: Calculated for $C_{17}H_{15}N_4O_1Cl_1$: C, 62.48; H, 4.63; N, 17.14. Found: C, 62.29; H, 4.57; N, 17.23.

EXAMPLE 161

2-(4-Chlorophenyl)-N-[4-(dimethylamino)phenyl]-3H-imidazo[4,5-b]pyridine-3-propanamide hydrochloride [1:2]

A solution of 0.9 g of 2-(4-chlorophenyl)-N-[4-(dimethylamino)phenyl]-3H-imidazo[4,5-b]pyridine-3-propanamide (obtained in Example 245), in hot isopropyl alcohol was acidified with ethereal hydrogen chloride. Isopropyl ether was added and a pink solid formed. The solid was collected by filtration, rinsed with isopropyl ether and then recrystallized from isopropyl alcohol:isopropyl ether to give 0.81 g of a lavender solid. After drying at high vacuum, mp 215.5°–217° C.

Analysis: Calculated for $C_{23}H_{24}N_5O_1Cl_3$: C, 56.05; H, 4.91; N, 14.21. Found: C, 55.94; H, 5.09; N, 13.94.

EXAMPLE 162

2-(4-Chlorophenyl)-N-[2-(diethylamino)ethyl]-3H-imidazo[4,5-b]pyridine-3-acetamide A suspension of 2-(4-chlorophenyl)-3H-imidazo[4,5-b]pyridine-3-acetic acid (6.0 g, 0.021 mole), 1,1'-carbonyldiimidazole (3.39 g, 0.021 mole) and dry tetrahydrofuran (100 ml) was stirred at room temperature for 3 hours with nitrogen bubbling through it. A solution of N,N-diethylethylenediamine (7.32 g, 0.063 mole) in tetrahydrofuran (10 ml) was added and the reaction mixture was stirred at room temperature under nitrogen overnight. The reaction mixture was evaporated to a solid. The solid was triturated with water (50 ml), filtered, and the filter cake was rinsed twice with water, twice with a 5% potassium hydroxide solution and twice with water. The resulting solid was dissolved in hot isopropyl alcohol, filtered hot and cooled to room temperature. Addition of water caused a white solid to form. The solid was collected by filtration and rinsed with water to give 4.21 g (52%) of a white solid. A 1.0-g sample of the solid was dried under high vacuum at room temperature to give a white solid, mp 142°–143° C.

Analysis: Calculated for $C_{20}H_{24}N_5O_1Cl_1$: C, 62.25; H, 6.27; N, 18.15. Found: C, 62.15; H, 6.28; N, 18.30;

EXAMPLE 163

2-(4-Chlorophenyl)-N-[2-(diethylamino)ethyl]-3H-imidazo[4,5-b]pyridine-3-acetamide hydrochloride hydrate [1:2:0.5]

A solution of crude 2-(4-chlorophenyl)-N-[2-(diethylamino)ethyl]-3H-imidazo[4,5-b]pyridine-3-acetamide (3.21 g, 0.0112 mole) in hot isopropyl alcohol was treated with ethereal hydrogen chloride until acidic. The solution was evaporated to dryness, the residue dissolved in hot isopropyl alcohol and the solution was filtered while hot. Solid precipitated upon cooling to room temperature. Isopropyl ether was added and the solid was collected by filtration and rinsed with isopropyl ether. The solid was dried under high vacuum to give 4.4 g (84%) of title compound, mp. 193°–196° C.

Analysis: Calculated for $C_{20}H_{27}N_5O_{1.5}Cl_3$: C, 51.35; H, 5.82; N, 14.96. Found: C, 51.23; H, 5.72; N, 14.94.

EXAMPLE 164

2-(4-Chlorophenyl)-N-[3-(diethylamino)propyl]-3H-imidazo[4,5-b]pyridine-3-acetamide A suspension of 2-(4-chlorophenyl)-3H-imidazo[4,5-b]pyridine-3-acetic acid (5.0 g, 0.0174 mole), 1,1'-carbonyldiimidazole (2.82 g, 0.0174 mole) and dry tetrahydrofuran (100 ml) was stirred at room temperature for 2 hours with nitrogen bubbling through it. A solution of 3-diethylaminopropylamine (6.8 g, 0.0522 mole) in tetrahydrofuran (10 ml) was added and the reaction mixture was stirred at room temperature overnight under nitrogen. The reaction mixture was evaporated under reduced pressure to give a white solid. The solid was triturated with water (50 ml), filtered and rinsed twice with water, twice with a 5% potassium hydroxide solution and twice with water to yield a white solid. The solid was dissolved in hot isopropyl alcohol and filtered. Addition of water and cooling to room temperature gave a white solid which was collected by filtration and rinsed with water to give 4.33 g (61%) of a solid. A 1.0-g sample of the solid was dried at high vacuum, mp 172°–174° C.

Analysis: Calculated for $C_{21}H_{26}N_5O_1Cl_1$: C, 63.07; H, 6.55; N, 17.51. Found: C, 63.11; H, 6.58; N, 17.74.

EXAMPLE 165

2-(4-Chlorophenyl)-N-[3-(diethylamino)propyl]-3H-imidazo[4,5-b]pyridine-3-acetamide hydrochloride [1:2]

Approximately 5.7 g of crude 2-(4-chlorophenyl)-N-[3-(diethylamino)propyl]-3H-imidazo[4,5-b]pyridine-3-acetamide was dissolved in hot isopropyl alcohol and acidified with ethereal hydrogen chloride. The solvents were removed under reduced pressure. The residue was redissolved in hot isopropyl alcohol and cooled to room temperature while a solid formed. The solid was collected by filtration, rinsed with an isopropyl alcohol-isopropyl ether solution and finally rinsed with isopropyl ether. Drying under high vacuum gave a white solid weighing 5.0 g, mp 173°–177° C.

Analysis: Calculated for $C_{21}H_{28}N_5O_1Cl_3$: C, 53.34; H, 5.97; N, 14.81. Found: C, 52.97; H, 5.98; N, 14.80.

EXAMPLE 166

2-(4-Chlorophenyl)-N-(4,5-dihydro-2-thiazolyl)-3H-imidazo[4,5-b]pyridine-3-acetamide A suspension of 2-(4-chlorophenyl-3H-imidazo[4,5-b]pyridine-3-acetic acid (5.0 g, 0.0174 mole) 1,1'-carbonyldiimidazole (2.82 g, 0.0174 mole) and dry tetrahydrofuran (100 ml) was stirred at room temperature for 3.5 hours with a stream of nitrogen bubbling through it. Solid 2-amino-2-thiazoline (2.67 g, 0.0261 mole) was added to the reaction mixture. The resulting suspension was allowed to stir at room temperature overnight. The solvent was evaporated under reduced pressure to give a white solid. The solid was triturated in water (200 ml), filtered, and the filter cake was rinsed twice more with water. The resulting solid was heated in boiling isopropyl alcohol to dissolve most of it, filtered while hot, and cooled to room temperature. A white precipitate formed. Water was added, and the white solid was filtered and rinsed once with isopropyl alcohol and twice with isopropyl ether. A 1.0-g sample of the resulting 3.3 g of white solid was dried at high vacuum to give 0.6 g (29%) of title compound, mp. 227°–229° C.

Analysis: Calculated for $C_{17}H_{14}N_5SOCl$: C, 54.91; H, 3.80; N, 18.83. Found: C, 54.94; H, 3.74; N, 18.85.

EXAMPLE 167

2-(4-Chlorophenyl)-N,N-dimethyl-3H-imidazo[4,5-b]pyridine-3-propanamide hydrochloride [1:1]

A suspension of 2-(4-chlorophenyl)-3H-imidazo[4,5-b]pyridine-3-propanoic acid (5.0 g, 0.0166 mole), 1,1'-carbonyldiimidazole (3.21 g, 0.0198 mole) and dry tetrahydrofuran (100 ml) was stirred at room temperature for one hour with nitrogen bubbling through it and then refluxed for one hour under a nitrogen atmosphere. The solution which had formed was cooled and a solution of dimethylamine in tetrahydrofuran (21.4 ml of 2.3M solution, 0.05 mole) was added. The reaction mixture was stirred at room temperature under nitrogen overnight. The solvent was removed under reduced pressure and the resulting oil was partitioned between water (100 ml) and ethyl acetate (100 ml). The layers were separated and the suspended solid was removed by filtration. The aqueous layer was extracted once more with ethyl acetate (100 ml) and the combined organic layer was washed once with a 5% potassium hydroxide solution (100 ml). The organic layer was dried over sodium sulfate, filtered, and evaporated under reduced pressure to give 6.3 g of crude product. Attempts to crystallize the pure free base failed (due to imidazole contamination and trapping of solvents by the solid). The impure product, after triturations in water to remove imidazole, was dissolved in hot isopropyl alcohol, filtered while hot and acidified with hydrogen chloride in isopropyl alcohol. Isopropyl ether was added to precipitate the solid. Filtration and drying under high vacuum gave 1.84 g of the title compound, mp. 203°–205° C.

Analysis: Calculated for $C_{17}H_{18}N_4OCl_2$: C, 55.90; H, 4.97; N, 15.34. Found: C, 55.89; H, 4.92; N, 15.37;

EXAMPLE 168

2-(4-Chlorophenyl)-N-methyl-N-phenyl-3H-imidazo[4,5-b]pyridine-3-propanamide hydrochloride [1:1]

Under nitrogen atmosphere, oxalyl chloride (2.18 g, 0.0172 mole) was added dropwise, slowly, to a stirred and chilled (10° C.) suspension of 2-(4-chlorophenyl)-3H-imidazo[4,5-b]pyridine-3-propanoic acid (5.0 g, 0.0166 mole) in anhydrous dimethylformamide (75 ml). The reaction mixture was stirred at room temperature for 1.5 hours and then additional oxalyl chloride (0.73 g, 0.00573 mole) was added. After stirring at room temperature for 0.5 hour, the reaction mixture was cooled in ice and methylaniline (1.91 g, 0.0178 mole) was added. The reaction mixture was stirred at room temperature for 2.25 hours and then poured into ice water (400 ml) with stirring. Addition of triethylamine (6 ml) precipitated a solid. The solution was decanted from the gum and the gum was dissolved in hot isopropyl alcohol, treated with charcoal and filtered hot. Attempts to crystallize the free base failed. The product, in isopropyl alcohol, was treated with hydrogen chloride in isopropyl alcohol until acidic. Addition of isopropyl ether caused a tan solid to precipitate. The solid was filtered, rinsed with isopropyl ether and dried under high vacuum to give 1.93 g of title compound, mp. 178°–183° C.

Analysis: Calculated for $C_{22}H_{20}N_4OCl_2$: C, 61.84; H, 4.72; N, 13.11. Found: C, 61.47; H, 4.75; N, 12.84.

EXAMPLE 169

2-(4-Chlorophenyl)-3-[2-oxo-2-(3-thiazolidinyl)ethyl]-3H-imidazo[4,5-b]pyridine

A suspension of 2-(4-chlorophenyl)-3H-imidazo[4,5-b]pyridine-3-acetic acid (5.0 g, 0.0174 mole), 1,1'-carbonyldiimidazole (2,82 g, 0.0174 mole) and dry tetrahydrofuran (100 ml) was stirred at room temperature for 3.5 hours while nitrogen was bubbled through it. Solid thiazolidine (2.33 g, 0.0261 mole) was added and the reaction mixture was stirred at 55° C., under nitrogen overnight. The solvent was removed under reduced pressure. The resulting white solid was triturated with water (100 ml), filtered, rinsed with water, twice with 5% potassium hydroxide solution and twice more with water. The resulting solid was heated in boiling isopropyl alcohol and filtered hot. Upon cooling to room temperature, a white solid precipitated. The solid was collected by filtration and dried under high vacuum to give 3.08 g (49.4%) of title compound, mp. 215°–218° C.

Analysis: Calculated for $C_{17}H_{15}N_4OClS$: C, 56.90; H, 4.21; N, 15.61. Found: C, 56.72; H, 4.30; N, 15.34.

EXAMPLE 170

2-(4-Chlorophenyl)-N-(2-thiazolyl)-3H-imidazo[4,5-b]pyridine-3-acetamide

A suspension of 2-(4-chlorophenyl)-3H-imidazo[4,5-b]pyridine-3-acetic acid (5.0 g, 0.0174 mole), 1,1'-carbonyldiimidazole (2.82 g, 0.0174 mole) and dry tetrahydrofuran (100 ml) was stirred at room temperature for 3.5 hours with nitrogen bubbling through it. A solution formed, and solid 2-aminothiazole (2.61 g, 0.0261 mole) was added. The suspension was stirred overnight at room temperature under nitrogen. The solvents were evaporated under reduced pressure to give a white solid which was triturated in water (100 ml), filtered, and the filter cake rinsed with water, 2 portions of 5% potassium hydroxide solution and 2 additional portions of water. The white solid was dissolved in hot methanol, filtered hot and allowed to cool to give 2.70 g (42% yield) of white solid. The solid was suspended in hot isopropyl alcohol and treated with isopropyl alcohol-hydrogen chloride. A solution formed. Addition of isopropyl ether and cooling to room temperature gave a white solid. This solid was dissolved in hot methanol and isopropyl alcohol, filtered hot and cooled. The resulting solid was dried under high vacuum at 92° C. overnight which caused the hydrogen chloride to be driven off leaving 1.0 g of title compound, mp >260° C.

Analysis: Calculated for $C_{17}H_{12}N_5OClS$: C, 55.21; H, 3.27; N, 18.94. Found: C, 55.11; H, 3.27; N, 18.82;

EXAMPLE 171

(S)-2-(4-Chlorophenyl)-N,N,α-trimethyl-3H-imidazo[4,5-b]pyridine-3-acetamide

A solution of (S)-2-(4-chlorophenyl)-α-methyl-3H-imidazo[4,5-b]pyridine-3-acetic acid (5.0 g, 0.0166 mole), 1,1'-carbonyldiimidazole (3.21 g, 0.0198 mole)

and dry tetrahydrofuran (100 ml) was stirred at room temperature for 3 hours with nitrogen bubbling through it. A solution of dimethylamine (2.26 g, 0.050 mole) in tetrahydrofuran (20 ml) was added and the reaction mixture was stirred at room temperature under nitrogen overnight. The mixture was evaporated to an oil and partitioned between ethyl acetate (50 ml) and water (50 ml). The layers were separated and the aqueous layer was re-extracted with ethyl acetate. The combined organic layers were washed once with water (50 ml), twice with 5% potassium hydroxide solution (50 ml portions), and once more with water (50 ml). Drying over magnesium sulfate, treatment with charcoal, filtration and evaporation of the solvents gave a residue which upon recrystallization from hot isopropyl ether and drying under high vacuum gave 3.20 g (59%) of title compound, mp 124°–126° C.

Analysis: Calculated for $C_{17}H_{17}N_4OCl$: C, 62.10; H, 5.21; N, 17.04. Found: C, 62.11; H, 5.21; N, 17.06.

EXAMPLE 172

(S)-2-(4-Chlorophenyl)-α-methyl-N,N-dipropyl-3H-imidazo[4,5-b]pyridine-3-acetamide A solution of (S)-2-(4-chlorophenyl)-α-methyl-3H-imidazo[4,5-b]pyridine-3-acetic acid (5.0 g, 0.0166 mole), 1,1'-carbonyldiimidazole (3.21 g, 0.0198 mole) and dry tetrahydrofuran (100 ml) was stirred at room temperature for 3 hours with nitrogen bubbling through it. A solution of dipropylamine (5.04 g, 0.050 mole) in tetrahydrofuran (7 ml) was added and the solution was heated at 50° C. overnight under nitrogen. The solvents were evaporated under reduced pressure and the resulting oil was partitioned between ethyl acetate (50 ml) and water (50 ml). The layers were separated and the aqueous layer was re-extracted with ethyl acetate (50 ml). The combined organic layers were washed once with water (50 ml) followed by two (50 ml) portions of 5% potassium hydroxide solution and then by water again (50 ml). The organic layer was dried over magnesium sulfate, charcoaled, filtered and evaporated to an oil which was crystallized from hot isopropyl ether. The solid was collected by filtration, and dried under high vacuum at room temperature to give 3.33 g (52%) of title compound, mp 96°–99° C.

Analysis: Calculated for $C_{21}H_{25}N_4OCl$: C, 65.53; H, 6.55; N, 14.56. Found: C, 65.44; H, 6.54; N, 14.56.

EXAMPLE 173

(S)-2-(4-Chlorophenyl)-N,α-dimethyl-N-phenyl-3H-imidazo[4,5-b]pyridine-3-acetamide Under a nitrogen atmosphere, oxalyl chloride (2.18 g, 0.0172 mole) was added slowly, dropwise, to a stirred and chilled (10° C.) suspension of (S)-2-(4-chlorophenyl)-α-methyl-3H-imidazo[4,5-b]pyridine-3-acetic acid (5.0 g, 0.0166 mole) in dry dimethylformamide (75 ml). The mixture was stirred at room temperature for 3 hours, heated at 50° C. for one hour and cooled to room temperature. An additional 0.0057 mole of oxalyl chloride was added and the mixture was stirred at room temperature for 30 minutes. N-Methylaniline (1.92 g, 0.0179 mole) was added and the reaction mixture was stirred at room temperature under nitrogen overnight. The mixture was poured into 400 ml of ice water and triethylamine (6 ml) was added. The precipitated solid was collected by filtration, rinsed with water, redissolved in hot isopropyl alcohol, treated with charcoal, filtered hot and allowed to cool. Addition of water caused a solid to form. The solid was collected by filtration, rinsed with water and dried under high vacuum overnight to give 4.2 g (65%) of title compound, mp 174°–177° C.

Analysis: Calculated for $C_{22}H_{19}N_4OCl$: C, 67.60; H, 4.90; N, 14.33. Found: C, 67.41; H, 4.91; N, 14.24;

EXAMPLE 174

2-(4-Chlorophenyl)-N-[2-(dimethylamino)ethyl]-N-methyl-3H-imidazo[4,5-b]pyridine-3-acetamide A suspension of 2-(4-chlorophenyl)-3H-imidazo[4,5-b]pyridine-3-acetic acid (5.0 g, 0.0174 mole) 1,1'-carbonyldiimidazole (2.82 g, 0.0174 mole) and dry tetrahydrofuran (100 ml) was stirred at room temperature for 2 hours with nitrogen bubbling through it, during which time a solution formed. A solution of N,N,N'-trimethylenediamine (3.56 g, 0.0348 mole) in tetrahydrofuran (4.5 ml) was added and the solution was refluxed overnight under a nitrogen atmosphere. The solvents were removed under reduced pressure and the resulting oil was partitioned between water (100 ml) and ethyl acetate (100 ml). The layers were separated, the aqueous layer was re-extracted with ethyl acetate, and the combined organic layers were washed once with water, twice with 5% potassium hydroxide solution and twice with water. The organic layer was dried over sodium sulfate and evaporated under reduced pressure. The residue was recrystallized from isopropyl ether to give 3.5 g of product. A 1.0-g portion was dried at high vacuum overnight to give 0.63 g of title compound, mp 120°–122° C.

Analysis: Calculated for $C_{19}H_{22}N_5OCl$: C, 61.37; H, 5.96; N, 18.83. Found: C, 61.23; H, 5.95; N, 18.82.

EXAMPLE 175

2-(4-Chlorophenyl)-N-[2-(dimethylamino)ethyl]-N-methyl-3H-imidazo[4,5-b]pyridine-3-acetamide hydrochloride [1:2]

A solution of crude 2-(4-chlorophenyl)-N-[2-(dimethylamino)-ethyl]-N-methyl-3H-imidazo[4,5-b]pyridine-3-acetamide (2.5 g, 0.0067 mole) in hot isopropyl alcohol was treated with hydrogen chloride in isopropyl alcohol until the solution was acidic. Upon addition of isopropyl ether, solid precipitated. After cooling to room temperature, the solid was collected by filtration, rinsed with isopropyl ether, and dried under high vacuum to give 2.23 g (75%) of title compound, mp 239°–242° C.

Analysis: Calculated for $C_{19}H_{24}N_5OCl_3$: C, 51.31; H, 5.44; N, 15.74. Found: C, 50.99; H, 5.57; N, 15.45.

EXAMPLE 176

(S)-2-(4-Chlorophenyl)-N-[2-(dimethylamino)ethyl]-α-methyl-3H-imidazo[4,5-b]pyridine-3-acetamide A solution of (S)-2-(4-chlorophenyl)-α-methyl-3H-imidazo[4,5-b]pyridine-3-acetic acid (5.0 g, 0.0166 mole), 1,1'-carbonyldiimidazole (3.21 g, 0.0198 mole) in tetrahydrofuran (100 ml) was stirred at room temperature for two hours with nitrogen bubbling through it. A solution of N,N-dimethylethylenediamine (4.41 g, 0.050 mole) in tetrahydrofuran (5.5 ml) was added and the reaction mixture was stirred at room temperature under nitrogen overnight. The solvents were removed under reduced pressure and the solid was triturated in water (100 ml). The solid was collected by filtration, rinsed once with water, twice with 5% potassium hydroxide solution and twice with water. The solid was recrystallized from hot isopropyl ether to give 1.99 g (32%) of a solid. A 0.5-g sample was dried under high vacuum to give 0.49 g of title compound, mp 130°-133° C.

Analysis: Calculated for $C_{19}H_{22}N_5OCl$: C, 61.37; H, 5.96; H, 18.83. Found: C, 61.36; H, 5.97; N, 18.83.

EXAMPLE 177

(S)-2-(4-Chlorophenyl)-N-[2-(dimethylamino)ethyl]-α-methyl-3H-imidazo[4,5-b]pyridine-3-acetamide hydrochloride hydrate [1:2:0.5]

A solution of crude (S)-2-(4-chlorophenyl)-N-[2-(dimethylamino)ethyl]-α-methyl-3H-imidazo[4,5-b]pyridine-3-acetamide (1.49 g, 0.00335 mole) in hot isopropyl alcohol was treated with hydrogen chloride in isopropyl alcohol until the solution was acidic. Upon addition of isopropyl ether, solid precipitated. After cooling to room temperature, the solid was collected by filtration, rinsed with isopropyl ether, and dried under high vacuum to give 1.64 g of title compound, mp 252°-255° C.

Analysis: Calculated for $C_{19}H_{25}N_5O_{1.5}Cl_3$: C, 50.29; H, 5.55; N, 15.43. Found: C, 50.64; H, 5.58; N, 15.32.

EXAMPLE 178

2-(4-Chlorophenyl)-N-methyl-N-(2-propenyl)-3H-imidazo[4,5-b]pyridine-3-acetamide A suspension of 2-(4-chlorophenyl)-3H-imidazo[4,5-b]pyridine-3-acetic acid (5.0 g, 0.0174 mole), 1,1'-carbonyldiimidazole (2.82 g, 0.0174 mole) and dry tetrahydrofuran (100 ml) was stirred at room temperature for 2 hours with nitrogen bubbling through it. A solution formed. A solution of N-allylmethylamine (3.71 g, 0.0522 mole) in tetrahydrofuran (5.0 ml) was added and the reaction mixture was stirred at 40°-50° C. overnight under nitrogen. The solvents were removed under reduced pressure and the residue was triturated in water (100 ml). The solid was collected by filtration, rinsed once with water, twice with 5% potassium hydroxide solution, and twice again with water. The solid was recrystallized from hot isopropyl ether, collected by filtration, rinsed with isopropyl ether, and dried under high vacuum to give 2.01 g (34%) of title compound, mp 124°-127° C.

Analysis: Calculated for $C_{18}H_{17}N_4OCl$: C, 63.44; H, 5.03; N, 16.44. Found: C, 63.22; H, 5.00; N, 16.52.

EXAMPLE 179

2-(4-Chlorophenyl)-N-(1,2-diethyl-4-pyrazolidinyl)-3H-imidazo [4,5-b]pyridine-3-acetamide hydrochloride hydrate [1:2:0.5]

A suspension of 2-(4-chlorophenyl)-3H-imidazo[4,5-b]pyridine-3-acetic acid (5.0 g, 0.0174 mole), 1,1'carbonyldiimidazole (2.82 g, 0.0174 mole) and dry tetrahydrofuran (100 ml) was stirred at room temperature for two hours with nitrogen bubbling through it. A solution of 4-amino-1,2-diethyl-pyrazolidine (7.5 g, 0.0522 mole) in tetrahydrofuran (6 ml) was added and the reaction mixture was stirred at room temperature overnight under nitrogen. The reaction mixture was evaporated under reduced pressure to an oil. Water (200 ml) was added, and the resulting suspension was stirred. The solid was collected by filtration, rinsed twice with water, twice with 5% potassium hydroxide solution and twice again with water. The solid was dissolved in hot isopropyl alcohol, filtered hot, and acidified with hydrogen chloride in isopropyl alcohol. Isopropyl ether was added to the cloud point, and upon cooling to room temperature, a solid precipitated. The solid was collected by filtration, rinsed with isopropyl ether, and dried under high vacuum to give 4.8 g (56%) of title compound, mp 220° C. (darkens), 228°-230° C. (melts).

Analysis: Calculated for $C_{21}H_{28}N_6O_{1.5}Cl_3$: C, 50.97; H, 5.70; N, 16.98. Found: C, 51.05; H, 5.61; N, 16.59.

EXAMPLE 180

N-(1-Azabicyclo[2.2.2]oct-3-yl)-2-(4-chlorophenyl)-3H-imidazo [4,5-b]pyridine-3-acetamide hydrochloride hydrate [1:2:1]

A suspension of 2-(4-chlorophenyl)-3H-imidazo[4,5-b]pyridine-3-acetic acid (5.0 g, 0.0174 mole), 1,1'-carbonyldiimidazole (2.82 g, 0.0174 mole) and dry tetrahydrofuran (100 ml) was stirred at room temperature for three hours with nitrogen bubbling through it. 3-Aminoquinuclidine dihydrochloride (20.8 g, 0.104 mole) and sodium methoxide (freshly prepared from 5.28 g of sodium metal in 50 ml of methanol) were stirred at room temperature for one hour. This second suspension was filtered and evaporated to an oil. The oil was extracted into boiling light petroleum ether (1500 ml) and the petroleum ether was then removed under reduced pressure to give 6.6 g of 3-aminoquinuclidine. The 3-aminoquinuclidine was dissolved in tetrahydrofuran (20 ml) and added to the solution containing the product resulting from the first suspension. The reaction mixture was stirred at room temperature under a nitrogen atmosphere overnight.

The solvents were removed under reduced pressure to give a white solid which was triturated in water (200 ml), collected by filtration, and rinsed twice with water, twice with 5% potassium hydroxide solution and twice again with water. The resulting solid was dissolved in hot isopropyl alcohol, filtered hot, and acidified with hydrogen chloride in isopropyl alcohol. Isopropyl ether was added to the cloud point and upon cooling to room temperature, a solid precipitated. The solid was collected by filtration, rinsed with isopropyl ether and dried under high vacuum overnight to give 5.3 g (62%) of title compound, mp 240°-245° C.

Analysis: Calculated for $C_{21}H_{26}N_5O_2Cl_3$: C, 51.81; H, 5.38; N, 14.38. Found: C, 51.44; H, 5.33; N, 14.16.

EXAMPLE 181

2-(4-Chlorophenyl)-N-[2-(1-methyl-2-pyrrolidinyl)ethyl]-3H-imidazo [4,5-b]pyridine-3-acetamide hydrochloride hydrate [1:2:1]

A solution of crude 2-(4-chlorophenyl)-N-[2-(1-methyl-2-pyrrolidinyl)ethyl]-3H-imidazo[4,5-b]pyridine-3-acetamide (3.96 g, 0.0100 mole) in hot isopropyl alcohol was acidified with hydrogen chloride in isopropyl alcohol. Isopropyl ether was added to the cloud point. Upon cooling to room temperature, a solid precipitated. The solid was collected by filtration, rinsed with isopropyl ether, and dried under high vacuum to give 4.2 g (86%) of title compound, mp 171°-175° C.

Analysis: Calculated for $C_{21}H_{28}N_5O_2Cl_3$: C, 51.60; H, 5.77; N, 14.33. Found: C, 51.38; H, 5.67; N, 14.19.

EXAMPLE 182

2-(4-Chlorophenyl)-N-[2-(1-methyl-2-pyrrolidinyl)ethyl]-3H-imidazo[4,5-b]pyridine-3-acetamide A suspension of 2-(4-chlorophenyl)-3H-imidazo[4,5-b]pyridine-3-acetic acid (5.0 g, 0.0174 mole), 1,1'-carbonyldiimidazole (2.82 g, 0.0174 mole) and dry tetrahydrofuran (100 ml) was stirred at room temperature for two hours with nitrogen bubbling through it. A solution of 2-(2-aminoethyl)-1-methylpyrrolidine (5.6 g, 0.0435 mole) in tetrahydrofuran (6 ml) was added and the reaction mixture was stirred at room temperature overnight under a nitrogen atmosphere. The solvents were removed under reduced pressure. The resulting solid was triturated in water (200 ml), collected by filtration, rinsed twice with water, twice with 5% potassium hydroxide solution and twice again with water. The solid was dissolved in hot isopropyl alcohol, filtered hot, and water was added. Upon cooling, a solid precipitated. The solid was collected by filtration and air dried to give 4.46 g (64%) of solid. A 0.5-g sample was dried under high vacuum to give 0.40 g of title compound, mp 170°–172° C.

Analysis: Calculated for $C_{21}H_{24}N_5OCl$: C, 63.39; H, 6.08; N, 17.60. Found: C, 63.02; H, 6.03; N, 17.38.

EXAMPLE 183

2-(4-Chlorophenyl)-N-[4-(dimethylamino)phenyl]-N-methyl-3H-imidazo[4,5-b]pyridine-3-acetamide A suspension of 2-(4-chlorophenyl)-3H-imidazo[4,5-b]pyridine-3-acetic acid (5.0 g, 0.0174 mole) in dry dimethylformamide (75 ml) was cooled in an ice bath and oxalyl chloride (2.2 g, 0.0172 mole) was added dropwise, with stirring, under nitrogen. The reaction mixture was stirred at room temperature for 3.5 hours and then N,N,N'-trimethyl-1,4-benzenediamine (2.9 g, 0.0193 mole) was added dropwise. The reaction mixture was stirred at room temperature under nitrogen overnight, poured into 400 ml of ice water and made basic with triethylamine (6 ml). The resulting white solid was collected by filtration, dissolved in hot isopropyl alcohol, treated with charcoal, and filtered while hot. Water was added to the cloud point and upon cooling, a solid precipitated. The gray solid was collected by filtration and rinsed with water to yield 6.6 g (92%) of product. A 1.0-g sample was dried under high vacuum to give 0.6 g of title compound, mp 152°–155° C.

Analysis: Calculated for $C_{23}H_{22}N_5OCl$: C, 65.79; H, 5.28; N, 16.68. Found: C, 65.79; H, 5.31; N, 16.57.

EXAMPLE 184

2-(4-Chlorophenyl)-N-[4-(dimethylamino)phenyl]-N-methyl-3-H-imidazo [4,5-b]pyridine-3-acetamide hydrochloride hydrate [1:2:2.5].

A solution of 2-(4-chlorophenyl)-N-[4-(dimethylamino)phenyl]-N-methyl-3H-imidazo[4,5-b]pyridine-3-acetamide (5.6 g, 0.0133 mole) in hot isopropyl alcohol was acidified with hydrogen chloride in isopropyl alcohol. Isopropyl ether was added to precipitate a solid. The solid was collected by filtration, rinsed with isopropyl ether, and dried under high vacuum to give 3.74 g (52%) of title compound, mp 120°–132° C. (shrinks), 150°–155° C. (melts).

Analysis: Calculated for $C_{23}H_{29}N_5O_{3.5}Cl_3$: C, 51.36; H, 5.43; N, 13.02. Found: C, 51.48; H, 5.10; N, 12.83.

EXAMPLE 185

4-[[2-(4-Chlorophenyl)-3-H-imidazo[4,5-b]pyridin-3-yl]acetyl]-1-piperazinecarboxylic acid ethyl ester A suspension of 2-(4-chlorophenyl)-3H-imidazo[4,5-b]pyridine-3-acetic acid (5.0 g, 0.0174 mole), 1,1'-carbonyldiimidazole (2.82 g, 0.0174 mole), and dry tetrahydrofuran (100 ml) was stirred at room temperature for two hours with nitrogen bubbling through it. A solution of ethyl-1-piperazine carboxylate (6.9 g, 0.0435 mole) in tetrahydrofuran (6 ml) was added dropwise and the reaction mixture was stirred at 50° C. overnight under nitrogen. The solvents were removed under reduced pressure and the residual oil was triturated in water (100 ml) overnight. The resulting solid was collected by filtration, rinsed with water, dissolved in hot isopropyl alcohol, and filtered hot. Water was added to the cloud point and upon cooling to room temperature, a solid precipitated, which was collected by filtration, rinsed with water, and dried under high vacuum to give 4.66 g (63%) of title compound, mp 184°–186° C.

Analysis: Calculated for $C_{21}H_{22}N_5O_3Cl$: C, 58.95; H, 5.18; N, 16.37. Found: C, 58.87; H, 5.14; N, 16.32.

EXAMPLE 186

2-(4-Chlorophenyl)-N,N-dipropyl-1H-imidazo[4,5-b]pyridine-1-acetamide hydrate [1:0.5].

Under nitrogen bubbling, a mixture of 2-(4-chlorophenyl)-1H-imidazo[4,5-b]pyridine-1-acetic acid (3.83 g, 0.013 mole) and 1,1'-carbonyldiimidazole (2.11 g, 0.013 mole) in 150 ml of tetrahydrofuran was stirred at room temperature for 4 hrs. Dipropylamine (2.63 g, 0.026 mole) was added and the reaction mixture was heated at reflux for 2 hrs, followed by standing at room temperature over the weekend. The tetrahydrofuran was evaporated to dryness and placed under high vacuum overnight. The residue was dissolved in isopropyl alcohol, filtered, and diluted with water to produce a crystalline product upon refrigeration. The solid was collected by filtration, washed with water, and dried under high vacuum overnight to give 1.22 g. A recrystallization from isopropyl alcohol-water gave 0.91 g of title compound after drying under high vacuum at 50° C. over the weekend, mp 139°–141° C.

Analysis: Calculated for $C_{20}H_{23}N_4OCl \cdot \frac{1}{2}H_2O$: C, 63.23; H, 6.37; N, 14.75. Found: C, 62.92; H, 6.53; N, 14.54.

EXAMPLE 187

2-(4-Chlorophenyl)-1H-imidazo[4,5-b]pyridine-1-acetic acid ethyl ester hydrochloride [1:1]

Under a nitrogen flow, sodium hydride (1.76 g, 0.044 mole, 60% in oil) was with hexanes (~75 ml) and decanted. Dimethylformamide (150 ml) was added and the 2-(4-chlorophenyl)-3H-imidazo [4,5-b]pyridine (9.16 g, 0.04 mole) was added in portions. The reaction mixture was heated at 70°–85° C. for 1½ hours. Ethyl bromoacetate (6.68 g, 0.04 mole) was added dropwise and the reaction mixture was allowed to stir at room temperature over the weekend. The reaction mixture was poured into water and the precipitate was collected by filtration, washed with water, and dried under high vacuum at 50° C. overnight (78.6% crude yield). A 1.5-g sample was dissolved in ethyl acetate, acidified with ethereal hydrogen chloride, and the crystalline precipitate was collected by filtration, washed with ethyl acetate, and dried under high vacuum to give 1.55 g. The sample was recrystallized from acetonitrile to give 1.16 g after drying under high vacuum at 75° C. over the weekend, mp 199°–200° C. with decomposition.

Analysis: Calculated for $C_{26}H_{14}N_3O_2Cl \cdot HCl$: C, 54.56; H, 4.29; N, 11.93. Found: C, 54.29; H, 4.25; N, 12.05.

EXAMPLE 188

2-(4-Chlorophenyl)-1H-imidazo[4,5-b]pyridine-1-acetamide

Under nitrogen flow, sodium hydride (0.96 g, 0.0234 mole, 60% in oil) was washed with hexanes (~70 ml) and decanted. Dimethylformamide was added (100 ml) and the 2-(4-chlorophenyl)-3-H-imidazo[4,5-b]pyridine (5.0 g, 0.022 mole) was added in portions. The reaction mixture was heated at 70°–85° C. for 1½ hours. Chloroacetamide (2.06 g, 0.022 mole) was added and the reaction mixture was stirred overnight at room temperature. The reaction mixture was added to water (~600 ml) and the precipitate was collected by filtration, washed with water, and dried under high vacuum overnight at 50° C. NMR indicated a 14% yield of the isomer: 2-(4-chlorophenyl)-3H-imidazo[4,5-b]pyridine-3-acetamide and an 86% yield of the title compound. The solid was dissolved in pyridine, filtered, and diluted with water to produce crystalline product with refrigeration. The solid was collected by filtration, washed with water and dried under high vacuum at 90° C. overnight to give 2.3 g (36.5%) of the title compound, mp 280°–283° C. with decomposition.

Analysis: Calculated for $C_{14}H_{11}N_4OCl$: C, 58.65; H, 3.87; N, 19.54. Found: C, 58.38; H, 3.88; N, 19.26.

EXAMPLE 189

2-(4-Bromophenyl)-N,N-dipropyl-3-H-imidazo[4,5-b]pyridine-3-acetamide

Under nitrogen bubbling, a mixture of 2-(4-bromophenyl)-3H-imidazo[4,5-b]pyridine-3-acetic acid (13.28 g, 0.04 mole) and 1,1' carbonyldiimidazole (7.14 g, 0.044 mole) in 300 ml of tetrahydrofuran was stirred at room temperature for 6 hrs. Then, under nitrogen atmosphere, dipropylamine (12.12 g, 0.12 mole) was added and the reaction mixture was heated at reflux for 3 hrs. The reaction mixture was filtered and the filtrate was evaporated to dryness. The solid was dried under high vacuum overnight and was recrystallized from isopropyl alcohol-water. The crystalline solid was collected by filtration, washed with water, and dried under high vacuum over the weekend to give 9.0 g (54%), mp 153°–55° C.

Analysis: Calculated for $C_{20}H_{23}N_4OBr$: C, 57.84; H, 5.58; N, 13.49. Found: C, 57.65; H, 5.55; N, 13.43.

EXAMPLE 190

2-(4-Chlorophenyl)-N-(4-pyridinyl)-3H-imidazo[4,5-b]pyridine-3-acetamide hydrate [1:0.5]

Under a nitrogen atmosphere, oxalyl chloride (2.43 g, 0.01914 mole) was added dropwise, slowly, to a stirred and chilled solution of 2-(4-chlorophenyl)-3H-imidazo[4,5-b]pyridine-3-acetic acid (4.0 g, 0.014 mole) in dimethylformamide (60 ml). The reaction mixture was stirred at room temperature for 1.5 hour. An additional portion of oxalyl chloride (0.5 ml, 0.0057 mole) was added. After additional stirring at room temperature for 0.5 hr, a solution of 4-aminopyridine (1.81 g, 0.0192 mole) in dimethylformamide (10 ml) was added and the mixture was stirred at room temperature overnight. The mixture was poured into ice water (400 ml) and the resulting solid was collected by filtration, dissolved in hot isopropyl alcohol, filtered hot, and cooled to room temperature at give a solid. The solid was collected by filtration, rinsed with water, and dried under high vacuum to give 1.0 g of title compound, mp>250° C.

Analysis: Calculated for $C_{19}H_{15}N_5O_{1.5}Cl$: C, 61.21; H, 4.06; N, 18.78. Found: C, 61.23; H, 4.04; N, 18.67.

EXAMPLE 191

2-(4-Nitrophenyl)-3H-imidazo[4,5-b]pyridine-3-acetic acid ethyl ester

A suspension of crude 2-(4-nitrophenyl)-3H-imidazo[4,5-b]pyridine-3-acetic acid (1.5 g, 0.00503 mole) in absolute ethanol was acidified with 0.5 ml of concentrated sulfuric acid and refluxed under nitrogen for three days. The solution was evaporated to approximately one-third of its original volume (reduced pressure), and saturated sodium bicarbonate solution and ethyl acetate were added. The layers were separated, the aqueous layer was re-extracted with ethyl acetate and the combined organic layers were washed twice with water, dried over sodium sulfate, filtered, and evaporated under reduced pressure to give a solid. The solid was dissolved in hot absolute ethanol and filtered hot. Upon cooling to room temperature, a solid formed which was collected by filtration, rinsed with water, and dried under high vacuum at 50° C. overnight to give 1.17 g (71%) of title compound, mp 191.5°–193.5° C.

Analysis: Calculated for $C_{16}H_{14}N_4O_4$: C, 58.89; H, 4.32; N, 17.17. Found: C, 58.85; H, 4.28; N, 17.13.

EXAMPLE 192

(S)-2-(4-Chlorophenyl)-α-methyl-3H-imidazo[4,5-b]pyridine-3-acetic acid ethyl ester A suspension of crude (S)-2-(4-chlorophenyl)-α-methyl-3H-imidazo[4,5-b]pyridine-3-acetic acid (2.0 g, 0.00663 mole) in absolute ethanol was stirred at room temperature while 4 drops of concentrated sulfuric acid was added. The reaction mixture was refluxed for three days. Approximately ½ to ⅔ of the solvent was removed under reduced pressure. Saturated sodium bicarbonate solution (20 ml) was added to the remaining solution. The product was extracted into two portions of ethyl acetate and the combined organic layers were washed twice with water, dried over sodium sulfate, filtered and evaporated to an oil which was dissolved in hot absolute ethanol. Water was added to the cloud point and upon cooling to room temperature, a solid precipitated. The solid was collected by filtration, rinsed with water and dried under high vacuum at 50° C. to give 1.48 g (68%) of title compound, mp 103°–106° C.

Analysis: Calculated for $C_{17}H_{16}N_3O_2Cl$: C, 61.92: H, 4.89; N, 12.74. Found: C, 61.89; H, 4.86; N, 12.77.

EXAMPLE 193

3-[2-(4-Acetyl-1-piperazinyl)-2-oxoethyl]-2-(4-chlorophenyl)-3H-imidazo[4,5-b]pyridine A suspension of 2-(4-chlorophenyl)-3H-imidazo[4,5-b]pyridine-3-acetic acid (4.0 g, 0.014 mole), 1,1'-carbonyldiimidazole (2.26 g, 0.014 mole) and dry tetrahydrofuran (80 ml) was stirred at room temperature for 3 hr with a stream of nitrogen bubbling through it. A solution of 1-acetylpiperazine (4.49 g, 0.035 mole) in tetrahydrofuran (10 ml) was added and the resulting suspension was heated at 60° C. overnight. The solvent was evaporated under reduced pressure and the residue was triturated in water (100 ml), filtered, and the filter cake rinsed with water. The solid was dissolved in hot isopropyl alcohol, filtered hot, and allowed to cool to room temperature. The resulting solid was collected by filtration and dried under high vacuum at 50° C. to yield 3.18 g (57%) of title compound, mp 217°–219° C.

Analysis: Calculated for $C_{20}H_{20}N_5O_2Cl$: C, 60.38; H, 5.07; N, 17.60. Found: C, 60.40; H, 5.06; N, 17.60.

EXAMPLE 194

2-(4-Chlorophenyl)-N-[2-(1-methyl-1H-pyrrol-2-yl)ethyl]-3H-imidazo[4,5-b]pyridine-3-acetamide A suspension of 2-(4-chlorophenyl)-3H-imidazo[4,5-b]pyridine-3-acetic acid (5.0 g, 0.0174 mole), 1,1'-carbonyldimidazole (2.82 g, 0.0174 mole) and dry tetrahydrofuran (100 ml) was stirred at room temperature for 3 hr with a stream for nitrogen bubbling through it. A solution of 2-(2-aminoethyl)-1-methylpyrrole (5.40 g, 0.0435 mole) in tetrahydrofuran (6 ml) was added and the mixture was stirred at room temperature under nitrogen overnight. The solvent was evaporated under reduced pressure and the resulting oil was triturated in water (100 ml) which caused a solid to form. The solid was collected by filtration, rinsed twice with water, twice with 5% potassium hydroxide solution and twice again with water. The solid was dissolved in hot isopropyl alcohol and filtered hot. Water was added to the cloud point. Upon cooling, a solid precipitated which was collected by filtration, rinsed with water, and dried under high vacuum at 50° C. overnight to give 4.31 g (63%) of title compound, mp 171°–172.5° C.

Analysis: Calculated for $C_{21}H_{20}N_5OCl$: C, 64.04; H, 5.12; N, 17.78. Found: C, 63.97; H, 5.09; N, 17.75.

EXAMPLE 195

2-(4-Chlorophenyl)-N-[3-(dimethylamino)phenyl]-3H-imidazo[4,5-b]pyridine-3-acetamide hydrate[1:1]

Under a nitrogen atmosphere, oxalyl chloride (2.03 g, 0.016 mole) was added dropwise, slowly, to a stirred and chilled solution of 2-(4-chlorophenyl)-3H-imidazo[4,5-b]pyridine-3-acetic acid (4.0 g, 0.014 mole) in dry dimethylformamide (60 ml). The reaction mixture was stirred at room temperature for 1.5 hr, and then an additional 0.3 ml of oxalyl chloride was added. After stirring for an additional 0.5 hr, the solution was added dropwise to a stirred mixture of N,N-dimethyl-1,3-benzenediamine dihydrochloride (3.35 g, 0.016 mole) and triethylamine (6.46 g, 0.064 mole) in dimethylformamide (130 ml). The resultant mixture was stirred at room temperature overnight and poured into 400 ml of ice water. The solid which precipitated was collected by filtration, dissolved in hot isopropyl alcohol, and filtered hot. Upon cooling to room temperature, solid precipitated. Water was added and the solid was collected by filtration and rinsed with water. A 0.5-g sample was dried under high vacuum at room temperature to give 0.34 g of title compound, mp 215°–217° C.

Analysis: Calculated for $C_{22}H_{22}N_5O_2Cl$: C, 62.34; H, 5.23; N, 16.52. Found: C, 62.31; H, 5.19; N, 16.53.

EXAMPLE 196

2-(4-Chlorophenyl)-N-[3-(dimethylamino)phenyl]-3H-imidazo[4,5-b]pyridine-3-acetamide hydrochloride hydrate [1:2:0.5]

A solution of 2-(4-chlorophenyl)-N-[3-(dimethylamino) phenyl]-3H-imidazo[4,5-b]pyridine-3-acetamide in hot isopropyl alcohol was acidified with hydrogen chloride/isopropyl alcohol. Isopropyl ether was added to the cloud point. Upon cooling to room temperature, solid formed which was collected by filtration, rinsed with isopropyl ether, and dried under high vacuum at 50° C. overnight to give 1.9 g of title compound, mp 166°–170° C. (shrinks), 183°–187° C. (melts).

Analysis: Calculated for $C_{22}H_{23}N_5O_{1.5}Cl_3$: C, 54.17; H, 4.75; N, 14.36. Found: C, 54.29; H, 4.72; N, 14.42.

EXAMPLE 197

2-(4-Nitrophenyl)-N,N-dipropyl-3H-imidazo[4,5-b]pyridine-3-acetamide

A suspension of crude 2-(4-nitrophenyl)-3H-imidazo[4,5-b]pyridine-3-acetic acid (3.0 g, 0.0101 mole), 1,1'-carbonyldi imidazole (1.63 g, 0.0101 mole) and dry tetrahydrofuran (100 ml) was stirred at room temperature for three hours with nitrogen bubbling through it and then refluxed under nitrogen overnight. The mixture was cooled to room temperature and a solution of dipropylamine (3.06 g, 0.0302 mole) in tetrahydrofuran (5 ml) was added. The suspension was refluxed over the weekend under nitrogen. The solvents were removed under reduced pressure and the solid residue was triturated in water (100 ml) overnight. The solid was collected by filtration, rinsed twice with water, twice with 5% potassium hydroxide solution and then twice more with water. The solid was dissolved in hot isopropyl alcohol, filtered while hot, and cooled to room temperature to precipitate a solid. Water was added and the solid was collected by filtration, rinsed with water and dried under high vacuum at 70° C. to give 1.23 g (32%) of title compound, mp. 205°–208° C.

Analysis: Calculated for $C_{20}H_{23}N_5O_3$: C, 62.98; H, 6.08; N, 18.36. Found: C, 62.63; H, 6.02; N, 18.34.

EXAMPLE 198

N-Methyl-2-(4-nitrophenyl)-3H-imidazo[4,5-b]pyridine-3-acetamide

A suspension of crude 2-(4-nitrophenyl)-3H-imidazo[4,5-b]pyridine-3-acetic acid (3.0 g, 0.0101 mole), 1,1'-carbonyldiimidazole (1.63 g, 0.0101 mole) and dry tetrahydrofuran (100 ml) was stirred at room temperature for three hours with a stream of nitrogen bubbling through it and then refluxed overnight under nitrogen. It was cooled to room temperature and a solution of methylamine (0.94 g, 0.0302 mole) in tetrahydrofuran (10 ml) was added and the reaction mixture was stirred at room temperature over the weekend. The solvents were removed under reduced pressure and the resulting solid was triturated in water, collected by filtration, rinsed once with water, once with 5% potassium hydroxide solution and once with water. The solid was dissolved in hot isopropyl alcohol, filtered hot cooled in the refrigerator to precipitate a solid. Water was added and the solid was collected by filtration and dried under high vacuum at 70° C. to give 0.42 g (13%) of title compound, mp. >260° C.

Analysis: Calculated for $C_{15}H_{13}N_5O_3$: C, 57.88; H, 4.21; N, 22.50. Found: C, 57.66; H, 4.23; N, 22.30.

EXAMPLE 199

2-(5-Bromo-2-furanyl)-N,N-dimethyl-3H-imidazo[4,5-b]pyridine-3-acetamide hydrate [1:0.5]

A suspension of 2-(5-bromo-2-furanyl)-3H-imidazo[4,5-b]pyridine-3-acetic acid (5.0 g, 0.0155 mole), and 1,1'-carbonyldiimidazole (2.52 g, 0.0155 mole) in dry tetrahydrofuran (100 ml) was stirred at room temperature for two hours with a stream of nitrogen bubbling through it. A solution of dimethylamine in tetrahydrofuran (40.6 ml of a 2.29M solution, 0.093 mole) was added, and the resulting solution was heated at 45° C. overnight under a nitrogen atmosphere. The reaction mixture was evaporated to a solid which was triturated in water (100 ml), collected by filtration, and rinsed twice with water, twice with a 5% potassium hydroxide solution, and twice again with water. The solid was dissolved in hot isopropyl alcohol, filtered, and allowed to cool to room temperature. Addition of water caused a precipitate to form which was collected by filtration, rinsed with water, and dried at high vacuum to give 3.16 g (58%) of title compound, mp 182°–185° C.

Analysis: Calculated for $C_{14}H_{14}N_4O_{2.5}Br$: C, 46.94; H, 3.94; N, 15.64. Found: C, 46.91; H, 4.12; N, 15.63.

EXAMPLE 200

2-(5-Bromo-2-furanyl)-N-methyl-3H-imidazo[4,5-b]pyridine-3-acetamide

A suspension of 2-(5-bromo-2-furanyl)-3H-imidazo[4,5-b]pyridine acetic acid (5.0 g, 0.0155 mole) and 1,1'-carbonyldiimidazole (2.52 g, 0.0155 mole) in dry tetrahydrofuran (100 ml) was stirred at room temperature for two hours with a stream of nitrogen bubbling through it. A solution of methylamine in tetrahydrofuran (31 ml of a 3.03M solution, 0.093 mole) was added, and the suspension was stirred at room temperature overnight under a nitrogen atmosphere. The reaction mixture was evaporated under reduced pressure, and the residue was triturated in water. The resulting solid was collected by filtration and rinsed twice with water, twice with a 5% potassium hydroxide solution, and twice again with water. The solid was dissolved in hot isopropyl alcohol and filtered, and the solution was allowed to cool to room temperature. Addition of water caused a precipitate to form which was collected by filtration and dried under high vacuum to give 2.95 g (57%) of title compound, mp. 187°–191° C.

Analysis: Calculated for $C_{13}H_{11}N_4O_2Br$: C, 46.59; H, 3.31; N, 16.72. Found: C, 46.05; H, 3.59; N, 16.44.

EXAMPLE 201

N,N-Dimethyl-2-(4-nitrophenyl)-3H-imidazo[4,5-b]pyridine-3-acetamide

A suspension of 2-(4-nitrophenyl)-3H-imidazo[4,5-b]pyridine-3-acetic acid (3.0 g, 0.0101 mole), 1,1'-carbonyldiimidazole (1.6 g, 0.0101 mole), and dry dimethylformamide (10 ml) in tetrahydrofuran (100 ml) was stirred at room temperature for two hours with nitrogen bubbling through it. A solution of dimethylamine in tetrahydrofuran (26.4 ml of a 2.29M solution, 0.0606 mole) was added. The resulting solution was heated at 45° C. overnight under nitrogen. The solvents were evaporated under reduced pressure. The residue was triturated in water (300 ml), and the resulting solid was collected by filtration, rinsed with water, 5% potassium hydroxide solution and again with water. The solid was dissolved in hot isopropyl alcohol, filtered, and allowed to cool to room temperature. A solid precipitated which was collected by filtration and dried under high vacuum to give 1.26 g (38%) of title compound, mp 204°–207° C.

Analysis: Calculated for $C_{16}H_{15}N_5O_3$: C, 59.07; H, 4.65; N, 21.53. Found: C, 58.86; H, 4.85; N, 21.54.

EXAMPLE 202

2-(4-Chlorophenyl)-N-methyl-N-propyl-3H-imidazo[4,5-b]pyridine-3-acetamide hydrate [1:2]

A suspension of 2-(4-chlorophenyl)-3H-imidazo[4,5-b]pyridine-3-acetic acid (5.0 g, 0.0174 mole), 1,1'-carbonyldiimidazole (2.82 g, 0.0174 mole) and dry tetrahydrofuran (100 ml) was stirred at room temperature for 2.5 hours with a stream of nitrogen bubbling through it. A solution of methylpropylamine (3.81 g, 0.0522 mole) in tetrahydrofuran (4 ml) was added, and the reaction mixture was heated at 45° C. for 15 hours, then stirred at room temperature. The solvents were evaporated under reduced pressure, and the resulting oil was triturated in water (100 ml) which caused a solid to form. The solid was collected by filtration and washed with water, twice with a 5% potassium hydroxide solution, and twice again with water. The solid was dissolved in hot isopropyl alcohol, filtered, and cooled to room temperature. Addition of water to the cloud point caused crystals to form. The solid was collected by filtration, rinsed with water, and dried at high vacuum to give 3.60 g (60%) of title compound, mp 130°–133° C.

Analysis: Calculated for $C_{18}H_{23}N_4O_3Cl$: C, 57.06; H, 6.12; N, 14.79. Found: C, 57.27; H, 5.95; N, 14.80.

EXAMPLE 203

2-(5-Bromo-2-furanyl)-N,N-dipropyl-3H-imidazo[4,5-b]pyridine-3-acetamide

A suspension of 2-(5-bromo-2-furanyl)-3H-imidazo[4,5-b]pyridine acetic acid (5.0 g, 0.0155 mole), 1,1'-carbonyldiimidazole (2.52 g, 0.0155 mole) and dry tetrahydrofuran (100 ml) was stirred at room temperature for 2.5 hours with a stream of nitrogen bubbling through it. A solution of dipropylamine 4.71 g, 0.046 mole) in tetrahydrofuran (6 ml) was added and the reaction mixture was refluxed for 15 hours, then stirred at room temperature. The solvents were removed under reduced pressure, and the resulting oil was partitioned between ethyl acetate (100 ml) and water (100 ml). The layers were separated, and the aqueous layer was re-extracted with ethyl acetate. The combined organic layers were washed with water, twice with a 5% potassium hydroxide solution and twice again with water, dried with magnesium sulfate, charcoaled, and filtered. The solvent was removed under reduced pressure to give an oil which crystallized upon trituration with isopropyl ether. The solid was collected by filtration and dried under high vacuum to give 2.0 g (32%) of title compound, mp 102°–104° C.

Analysis: Calculated for $C_{18}H_{21}N_4O_2Br$: C, 53.34; H, 5.22; N, 13.82. Found: C, 53.63; H, 5.25; N, 13.48.

EXAMPLE 204

(R)-2-(4-Chlorophenyl)-N,α-dimethyl-3H-imidazo[4,5-b]pyridine-3-acetamide

A solution of (R)-2-(4-chlorophenyl)-α-methyl-3H-imidazo [4,5-b]pyridine-3-acetic acid (5.0 g, 0.0166 mole), 1,1'carbonyldiimidazole (2.69 g, 0.0166 mole), and dry tetrahydrofuran (100 ml) was stirred at room temperature for 1.75 hours with a stream of nitrogen bubbling through it. A solution of methylamine in tetrahydrofuran (33 ml of a 3.03M solution, 0.996 mole) was added and the reaction mixture was stirred at room temperature overnight under nitrogen. The solvents were removed under reduced pressure and the resulting solid was triturated in water, collected by filtration, rinsed twice with water, twice with 5% potassium hydroxide solution, and twice again with water. The solid was dissolved in hot isopropyl alcohol, charcoaled, and filtered while hot. Water was added to the cloud point, and upon cooling, solid precipitated. The solid was collected by filtration and dried under high vacuum at 50° C. overnight to give 3.21 g (62%) of title compound, mp 217°–218° C.

Analysis: Calculated for $C_{16}H_{15}N_4O_1Cl$: C, 61.05; H, 4.80; N, 17.80. Found: C, 60.84; H, 4.95; N, 17.64.

EXAMPLE 205

(S)-2-(4-Chlorophenyl)-N,α-dimethyl-3H-imidazo[4,5-b]pyridine-3-acetamide

A solution of (S)-2-(4-chlorophenyl)-α-methyl-3H-imidazo [4,5-b]pyridine-3-acetic acid (3.0 g, 0.00995 mole), 1,1'-carbonyldiimidazole (1.61 g, 0.00995 mole) and dry tetrahydrofuran (60 ml) was stirred at room temperature for 1.75 hours with a stream of nitrogen bubbling through it. A solution of methylamine in tetrahydrofuran (20 ml of a 3.03M solution, 0.060 mole) was added and the reaction mixture was stirred at room temperature overnight under nitrogen. The solvents were removed under reduced pressure and the resulting solid was triturated in water, collected by filtration, rinsed twice with water, twice with 5% potassium hydroxide solution, and twice again with water. The solid was dissolved in hot isopropyl alcohol and filtered hot. Upon cooling to room temperature, solid precipitated which was collected by filtration and dried under high vacuum at 50° C. overnight to give 0.86 g (28%) of title compound, mp 218°–220° C.

Analysis: Calculated for $C_{16}H_{15}N_4OCl$: C, 61.05; H, 4.80; N, 17.80. Found: C, 60.97; H, 4.96; N, 17.89.

EXAMPLE 206

(S)-2-(4-Chlorophenyl)-N-[4-(dimethylamino)phenyl]-α-methyl-3H-imidazo[4,5-b]pyridine-3-acetamide hydrochloride hydrate[1:2:1]

Under a nitrogen atmosphere, oxalyl chloride (2.41 g, 0.019 mole) was added dropwise, slowly, to a stirred and chilled (10° C.) suspension of (S)-2-(4-chlorophenyl)-α-methyl-3H-imidazo [4,5-b]pyridine-3-acetic acid (5.0 g, 0.0166 mole) in anhydrous dimethylformamide (75 ml). The suspension was stirred at room temperature for 30 minutes and then an additional portion of oxalyl chloride (0.73 g, 0.0057 mole) was added. The resulting solution was stirred at room temperature for 45 minutes and then added slowly to a suspension of N,N-dimethyl-1,4-benzenediamine dihydrochloride (3.97 g, 0.0019 mole) and triethylamine (7.7 g, 0.076 mole) in anhydrous dimethylformamide (150 ml). The reaction mixture was stirred at room temperature overnight under nitrogen and protected from light. The solution was then poured into 400 ml of ice water. The resulting solid was collected by filtration, rinsed with water, dissolved in hot isopropyl alcohol, filtered, and cooled to room temperature. Upon addition of water, solid precipitated. The solid was collected by filtration, dissolved in hot tetrahydrofuran, and made acidic with ethereal hydrogen chloride. The solid was collected by filtration, rinsed with isopropyl ether, and dried under high vacuum at 50° C. to give 4.0 g (47%) of title compound, mp 186°–190° C.

Analysis: Calculated for $C_{23}H_{26}N_5O_2Cl_3$: C, 54.08; H, 5.13; N, 13.71. Found: C, 54.49; H, 4.95; N, 13.39.

EXAMPLE 207

(R)-2-(4-Chlorophenyl)-N,N,α-trimethyl-3H-imidazo[4,5-b]pyridine-3-acetamide

A solution of (R)-2-(4-chlorophenyl)-α-methyl-3H-imidazo [4,5-b]pyridine-3-acetic acid (5.0 g, 0.0166 mole), 1,1'-carbonyldiimidazole (2.69 g, 0.0166 mole) and dry tetrahydrofuran (100 ml) was stirred at room temperature for 2.25 hours with a stream of nitrogen bubbling through it. A solution of dimethylamine in tetrahydrofuran (22 ml of a 2.29M solution, 0.050 mole) was added and the reaction mixture was heated at 45° C. for two days under nitrogen. The solvents were removed under reduced pressure and the residue was partitioned between water and ethyl acetate. The ethyl acetate layer was washed twice with water, twice with a 5% potassium hydroxide solution and twice again with water. It was then dried over magnesium sulfate, charcoaled, filtered, and evaporated to a residue which was dissolved in hot isopropyl ether, filtered, and cooled to room temperature. The resulting solid was collected by filtration and dried under high vacuum at 50° C. to give 2.61 g (48%) of title compound, mp 124°–127° C.

Analysis: Calculated for $C_{17}H_{17}N_4OCl$: C, 62.10; H, 5.21; N, 17.04. Found: C, 62.18; H, 5.09; N, 17.10.

EXAMPLE 208

(R)-2-(4-Chlorophenyl)-α-methyl-N,N-dipropyl-3H-imidazo[4,5-b]pyridine-3-acetamide A solution of (R)-2-(4-chlorophenyl)-α-methyl-3H-imidazo [4,5-b]pyridine-3-acetic acid (5.0 g, 0.0166 mole), 1,1'-carbonyldiimidazole (2.69 g, 0.0166 mole) and dry tetrahydrofuran (100 ml) was stirred at room temperature for 2.25 hours with nitrogen bubbling through it. A solution of dipropylamine (5.04 g, 0.050 mole) in tetrahydrofuran (7 ml) was added and the reaction mixture was refluxed under nitrogen for two days. The solvents were removed under reduced pressure and the residue was partitioned between water and ethyl acetate. The ethyl acetate layer was washed twice with water, twice with a 5% potassium hydroxide solution, and twice again with water. It was then dried over magnesium sulfate, charcoaled, filtered, and evaporated to an oil which crystallized upon trituration with isopropyl ether. The solid was collected by filtration and dried under high vacuum at 50° C. overnight to give 1.96 g (31%) of title compound, mp 95°–97° C.

Analysis: Calculated for $C_{21}H_{25}N_4OCl$: C, 65.53; H, 6.55; N, 14.56. Found: C, 65.52; N, 6.51; N, 14.54.

EXAMPLE 209

1-[2-(4-Chlorophenyl)-3H-imidazo[4,5-b]pyridine-3-yl]propanone

The free base of 2-(4-chlorophenyl)-α-methyl-3H-imidazo [4,5-b]pyridine-3-ethanol (6.3 g, 0.019 mole) was prepared by partitioning its hydrochloride salt between methylene chloride and dilute aqueous base. The methylene chloride layer was separated and the aqueous basic layer was extracted with methylene chloride (2×). The methylene chloride layers were combined, extracted with saturated sodium chloride, and dried over anhydrous sodium sulfate. The methylene chloride filtrate was evaporated and dried under high vacuum overnight.

Under nitrogen atmosphere, the free base from above in 25 ml of methylene chloride was added in one portion to a magnetically stirred suspension of pyridinium chlorochromate (6.28 g, 0.029 mole) in 50 ml of methylene chloride. After two hours, a 50-ml portion of diethyl ether was added to the reaction mixture and the supernatant liquid was decanted from a black gum. The insoluble residue was triturated with boiling methylene chloride (3×). The combined organic solvents were treated with Florisil®, filtered, and evaporated to a solid (4.4 g). NMR indicated 50% starting material/50% product.

Under nitrogen atmosphere, the 4.4 g of solid in 25 ml of methylene chloride was added to a magnetically stirred suspension of pyridinium chlorochromate (5.0 g, 0.023 mole) in50 ml of methylene chloride. Allowed to stir at ambient temperature overnight. The reaction solvent was decanted and the residue was triturated with hot methylene chloride (3×). The combined organic solvents were treated with Florisil®, filtered, and evaporated to a solid. NMR indicated complete oxidation to ketone. The solid was recrystallized from isopropyl alcohol with refrigeration. The product was collected by filtration, washed with water, and dried under high vacuum first at room temperature overnight, then at 50° C. for ½ day to give crystalline solid, 2.2 g (40%), mp 172°–173.5° C.

Analysis: Calculated for $C_{15}H_{12}N_3OCl$: C, 63.05; H, 4.23; N, 14.71. Found: C, 62.89; H, 4.15; N, 14.63.

EXAMPLE 210

(R)-2-(4-Chlorophenyl)-α-methyl-3H-imidazo[4,5-b]pyridine-3-acetic acid 2-hydroxyethyl ester hydrochloride [1:1]

A solution of (R)-N-[3-[(4-chlorobenzoyl)amino]-2-pyridinyl]alanine methyl ester (42.5 g, 0.0127 mole) in ethylene glycol (250 ml) was refluxed under nitrogen for one hour. The solution was cooled to room temperature and approximately 5 ml of the solution was added to water. Ethyl acetate was added and the layers were separated. The aqueous layer was extracted with two additional portions of ethyl acetate and the combined organic layers were washed three times with a saturated sodium chloride solution. The ethyl acetate layer was dried over sodium sulfate, filtered, and evaporated to an oil under reduced pressure. The oil was dissolved in isopropyl alcohol and was made acidic with hydrogen chloride/isopropyl alcohol. Addition of isopropyl ether to the cloud point gave a solid. The solid was collected by filtration, rinsed with isopropyl ether and dried under high vacuum at room temperature to give 0.25 g of title compound, mp 191°–195° C.

Analysis: Calculated for $C_{17}H_{17}N_3O_3Cl_2$: C, 53.42; H, 4.48; N, 10.99. Found: C, 53.24; H, 4.50; N, 10.78.

EXAMPLE 211

2-(4-Chlorophenyl)-α-methyl-3H-imidazo[4,5-b]pyridine-3-ethanol hydrochloride [1:1]

The solid 4-chloro-N-[2-[(2-hydroxypropyl)amino]-3-pyridinyl]benzamide monohydrochloride (12.3 g, 0.04 mole) was heated in a glass beaker at 180°–185° C. with a Wood's metal bath under nitrogen flow for twelve minutes. The residue was dissolved in tetrahydrofuran, filtered, and the filtrate was acidified with ethereal hydrogen chloride. The crystalline solid was collected by filtration, washed with tetrahydrofuran and dried under high vacuum overnight. A portion of the solid was recrystallized from methanol and diethyl ether and dried under high vacuum at 50° C. overnight to give 1.6 g (total crude yield 8.55 g, 66%), mp 206°–211° C.

Analysis: Calculated for $C_{15}H_{14}N_3OCl\cdot HCl$: C, 55.57; H, 4.66; N, 12.96. Found: C, 55.44; H, 4.79; N, 13.10.

EXAMPLE 212

2-(5-Methyl-2-thienyl)-3H-imidazo[4,5-b]pyridine-3-acetic acid

A suspension of N-[3-[(5-methyl-2-thienylcarbonyl)amino]-2-pyridinyl]glycine ethyl ester (93.8 g, 0.293 mole) was refluxed in ethylene glycol (500 ml) for 45 minutes. The solution was cooled and water (200 ml) and solid potassium hydroxide pellets (23.25 g, 0.41 mole) were added. The resulting solution was refluxed for one hour and then filtered hot into ice water (2 liters) and acidified with 3N hydrochloric acid to give a solid which was collected by filtration and dried to give 52.3 g of crude title compound (65% yield). A 2.0-g portion was dissolved in hot methanol, treated with charcoal, filtered while hot, and cooled to room temperature. Addition of water caused a precipitate to form which was collected by filtration and dried under high vacuum at room temperature overnight to give 0.68 g of title compound, mp>250° C.

Analysis: Calculated for $C_{13}H_{11}N_3O_2S$: C, 57.13; H, 4.00; N, 15.37. Found: C, 57.12; H, 3.99; N, 15.24.

EXAMPLE 213A (S)-2-(4-Chlorophenyl)-α-methyl-3H-imidazo[4,5-b]pyridine-3-acetic acid 2-hydroxyethyl ester A solution of crude (S)-N-[3-[(4-chlorobenzoyl)amino]-2-pyridinyl]alanine ethyl ester (37 g, 0.11 mole) was refluxed in ethylene glycol (200 ml) for 1.5 hours and cooled. Approximately ⅓ of the volume was removed, added to water (800 ml) and extracted twice into ethyl acetate. The combined organic layer was washed three times with water, dried over magnesium sulfate, treated with charcoal, filtered and evaporated under reduced pressure to an oil which crystallized upon standing. It was triturated in isopropyl alcohol and filtered, and the mother liquor was evaporated to give 8.0 g of a residue (66% yield). The residue was dissolved in hot isopropyl ether, treated with charcoal, filtered while hot and cooled to room temperature. A solid precipitated which was collected by filtration and recrystallized from hot isopropyl ether to give 2.03 g of title compound, mp 114°–118° C.

Analysis: Calculated for $C_{17}H_{16}N_3O_3Cl$: C, 59.05; H, 4.66; N, 12.15. Found: C, 58.79; H, 4.60; N, 12.06.

EXAMPLE 213B (S)-2-(4-Chlorophenyl)-α-methyl-3H-imidazo[4,5-b]pyridine-3-acetic acid 2-hydroxyethyl ester A solution of (S)-2-(4-chlorophenyl)-α-methyl-3H-imidazo[4,5-b]pyridine-3-acetic acid (3.0 g, 0.00995 mole) and concentrated sulfuric acid (4 drops) in ethylene glycol (50 ml) was refluxed under nitrogen for three hours, and then poured into a saturated sodium bicarbonate solution (200 ml). Water (50 ml) was added and the product was extracted into two portions of ethyl acetate. The combined organic layers were washed twice with water and once with a saturated sodium chloride solution, dried over magnesium sulfate, treated with charcoal and filtered. Evaporation of the solvents under reduced pressure gave 1.9 g (56% yield) of solid which was dissolved in hot isopropyl ether (with a little isopropyl alcohol added). The solution was stirred and cooled to room temperature to precipitate a solid. The mixture was cooled in the freezer, the solid was collected by filtration, rinsed with isopropyl ether and dried under high vacuum at room temperature overnight to give 1.44 g of title compound, mp 112°–113.5° C.

Analysis: Calculated for $C_{17}H_{16}N_3O_3Cl$: C, 59.05; H, 4.66; N, 12.15. Found: C, 58.98; H, 4.65; N, 12.11.

EXAMPLE 214

N,N-Dimethyl-2-(5-methyl-2-thienyl)-3H-imidazo[4,5-b]pyridine-3-acetamide

A solution of 2-(5-methyl-2-thienyl)-3H-imidazo[4,5-b]pyridine-3-acetic acid (5.0 g, 0.0183 mole) and 1,1'-carbonyldiimidazole (2.97 g, 0.0183 mole) in tetrahydrofuran (100 ml) was stirred at room temperature for 3¾ with a stream of nitrogen bubbling through it. A solution of dimethylamine (48 ml of a 2.29M solution in tetrahydrofuran, 0.1098 mole) was added and the mixture was heated at 40° C. overnight under nitrogen. The solvents were removed under reduced pressure and the residue was partitioned between water and ethyl acetate. The layers were separated and the aqueous layer was extracted again with ethyl acetate. The combined organic layer was washed twice with a saturated sodium chloride solution, twice with a 5% potassium hydroxide solution and twice again with a saturated sodium chloride solution. The organic layer was dried over magnesium sulfate, treated with charcoal, filtered and evaporated under reduced pressure to give a residue which was dissolved in hot isopropyl alcohol and brought to the cloud point by addition of isopropyl ether. Upon cooling to room temperature, a solid precipitated which was collected by filtration, rinsed with isopropyl ether, and dried under high vacuum at room temperature to give 1.13 g of title compound (20%), mp 193°–197° C.

Analysis: Calculated for $C_{15}H_{16}N_4OS$: C, 59.98; N, 5.37; N, 18.65. Found: C, 59.66; H, 5.32; N, 18.46.

EXAMPLE 215

N-Methyl-2-(5-methyl-2-thienyl)-3H-imidazo[4,5-b]pyridine-3-acetamide

A solution of 2-(5-methyl-2-thienyl)-3H-imidazo[4,5-b]pyridine-3-acetic acid (5.0 g, 0.0183 mole) and 1,1'-carbonyldiimidazole (2.97 g, 0.0183 mole) in tetrahydrofuran (100 ml) was stirred at room temperature for 3¾ hours with a stream of nitrogen bubbling through it. A solution of methylamine (36 ml of a 3.03M solution in tetrahydrofuran, 0.1098 mole) was added and the reaction mixture was stirred at room temperature overnight under nitrogen. The solvents were removed under reduced pressure and the resulting solid was triturated in water (100 ml), collected by filtration, and rinsed twice with water, twice with a 5% potassium hydroxide solution, and twice again with water. The solid was dissolved in hot isopropyl alcohol, and filtered while hot. Addition of isopropyl ether caused solid to precipitate. The solid was collected by filtration, rinsed with isopropyl ether, and dried under high vacuum at room temperature overnight to give 3.12 g (60%) of title compound, mp 213°–216° C.

Analysis: Calculated for $C_{14}H_{14}N_4OS$: C, 58.72; H, 4.93; N, 19.56. Found: C, 58.56; H, 4.93; N, 19.43.

EXAMPLE 216

2-(4-Fluorophenyl)-3H-imidazo[4,5-b]pyridine-3-acetic acid 2-hydroxyethyl ester

A solution of N-[3-[(4-fluorobenzoyl)amino]-2-pyridinyl]glycine ethyl ester (70.0 g, 0.2205 mole) in ethylene glycol was refluxed for 2 hours, cooled, and 14% for the solution (0.030 mole) was removed. Water (550 ml) was added to this aliquot, causing a solid to precipitate. The product was extracted into ethyl acetate twice and the combined organic layers were washed once with water and three times with a saturated sodium chloride solution, dried over magnesium sulfate, treated with charcoal, filtered, and evaporated to give 7.0 g of a white solid consisting of a mixture of title compound and 2-(4-fluorophenyl)-3H-imidazo[4,5-b]pyridine-3-acetic acid ethyl ester. This was dissolved in methylene chloride and purified using a silica gel column (100 g) and 1:1 methylene chloride/ethyl acetate and also 15% absolute ethanol in ethyl acetate as eluting solvents. The fraction containing pure title compound was evaporated under reduced pressure to give 1.98 g (21%) of title compound, mp 166.5°–168.5° C.

Analysis: Calculated for $C_{16}H_{14}N_3O_3F$: C, 60.95; H, 4.48; N, 13.33. Found: C, 60.99; H, 4.48; N, 13.31.

EXAMPLE 217

2-(4-Fluorophenyl)-3H-imidazo[4,5-b]pyridine-3-acetic acid ethyl ester

A solution N-[3-[(4-fluorobenzoyl)amino]-2-pyridinyl]glycine ethyl ester (70.0 g, 0.02205 mole) in ethylene glycol was refluxed for 2 hours, cooled, and 14% of the solution (0.30 mole) was removed. Water (550 ml) was added to this aliquot, causing a solid to precipitate. The product was extracted into ethyl acetate twice and the combined organic layers were washed once with water and three times with a saturated sodium chloride solution, dried over magnesium sulfate, treated with charcoal, filtered, and evaporated to give 7.0 g of a white solid consisting of a mixture of title compound and 2-(4-fluorophenyl)-3H-imidazo[4,5-b]pyridine-3acetic acid 2-hydroxyethyl ester. This was dissolved in methylene chloride and purified using a silica gel (100 g) column and 1:1 methylene chloride/ethyl acetate and also 15% absolute ethanol in ethyl acetate as eluting solvents. The fraction containing pure title compound was evaporated under reduced pressure to give 1.72 g (19%) of title compound, mp 126°–128° C.

Analysis: Calculated for $C_{16}H_{14}N_3O_2F$: C, 64.21; H, 4.71; N, 14.04. Found: C, 64.23; H, 4.67; N, 14.04.

EXAMPLE 218

(R)-2-(4-Chlorophenyl)-α-methyl-3H-imidazo[4,5-b]pyridine-3-acetic acid

A solution of (R)-N-[3-[(4-chlorobenzoyl)amino]-2-pyridinyl]alanine methyl ester (42.5 g, 0.127 mole) in ethylene glycol (250 ml) was refluxed under nitrogen atmosphere for one hour and then cooled. Water (40 ml) and solid potassium hydroxide pellets (10.13 g, 0.181 mole) were added and the solution was refluxed for an additional two hours, filtered into ice water (1 liter) and acidified with 3N hydrochloric acid solution to give a solid which was collected by filtration and rinsed with water to give 29 g of crude title compound (76%) yield). A 3.5-g portion of the solid was recrystallized twice from isopropyl alcohol/water and dried under high vacuum at 50° C. overnight to give 1.81 g of title compound, mp 225°–227° C.

Analysis: Calculated for $C_{15}H_{12}N_3O_2Cl$: C, 59.71; H, 4.01; N, 13.93. Found: C, 59.51; H, 4.07; N, 13.68.

EXAMPLE 219

2-(5-Methyl-2-thienyl)-N,N-dipropyl-3H-imidazo[4,5-b]pyridine-3-acetamide

A solution of 2-(5-methyl-2-thienyl)-3H-imidazo[4,5-b]pyridine-3-acetic acid (5.0 g, 0.0183 mole) and 1,1'-carbonyldiimidazole (2.97 g, 0.0183 mole) in tetrahydrofuran (100 ml) was stirred at room temperature for 3 hours with a stream of nitrogen bubbling through it. A solution of dipropylamine (5.56 g, 0.055 mole) in tetrahydrofuran (7 ml) was added and the reaction mixture was stirred overnight at room temperature. The solvents were evaporated and the residue was partitioned between water and ethyl acetate. The layers were separated and the aqueous layer was extracted again with ethyl acetate. The combined organic layer was washed twice with water, twice with a 5% potassium hydroxide solution, and twice again with water. The organic layer was dried over magnesium sulfate, treated with charcoal, filtered, and evaporated to give a solid which was dissolved in hot isopropyl alcohol and filtered while hot. Addition of water and cooling caused a solid to precipitate. The solid was dissolved again in hot isopropyl alcohol with charcoal, filtered while hot and brought to the cloud point by addition of water. Upon cooling, solid precipitated which was collected by filtration, rinsed with water, and dried under high vacuum at 50° C. overnight to give 2.28 g (35%) of title compound, mp 125°–127° C.

Analysis: Calculated for $C_{19}H_{24}N_4OS$: C, 64.02; H, 6.78; N, 15.72. Found: C, 63.90; H, 6.79; N, 15.69.

EXAMPLE 220

2-(5-Bromo-2-furanyl)-3H-imidazo[4,5-b]pyridine-3-acetic acid ethyl ester

A solution of N-[3-[(5-bromo-2-furanylcarbonyl)amino]-2-pyridinyl]glycine ethyl ester (110 g, 0.30 mole) was refluxed in ethylene glycol (510 ml) for 2 hours. A 20-ml aliquot (0.01 mole) was removed and water was added to the sample. The product was extracted twice into ethyl acetate and the combined organic layer was washed several times with water, dried over magnesium sulfate, charcoaled, filtered, and evaporated under reduced pressure to give 2.5 g of crude title compound (73% yield). The solid was dissolved in hot isopropyl alcohol, filtered while hot, brought to the cloud point by addition of water and cooled to give a solid which was purified on a column of 20 g of silica gel using 1:1 methylene chloride/ethyl acetate as the eluting solvent. Evaporation of the solvent from the pure fraction gave 1.2 g of product which was recrystallized from isopropyl alcohol/water and dried under high vacuum at room temperature overnight to give 0.88 g of title compound, mp 122.5°–125° C.

Analysis: Calculated for $C_{14}H_{12}N_3O_3Br$: C, 48.02; H, 3.45; N, 12.00. Found: C, 47.83; H, 3.40; N, 11.93.

EXAMPLE 221

2-(5-Methyl-2-thienyl)-3H-imidazo[4,5-b]pyridine-3-acetic acid ethyl ester

A solution of N-[3-[(5-methyl-2-thienylcarbonyl)amino]-2-pyridinyl]glycine ethyl ester (93.8 g, 0.293 mole) in ethylene glycol (500 ml) was refluxed for 45 minutes and cooled. A 10-ml aliquot was taken (0.005 mole) and added to water. The product was extracted into ethyl acetate twice and the combined organic layer was washed twice with water, dried over magnesium sulfate, treated with charcoal, filtered, and evaporated under reduced pressure to give 0.8 g (53% yield) of solid. The solid was recrystallized from isopropyl alcohol/water to give 0.31 g of solid which was purified on a silica gel column using 1:1 methylene chloride/ethyl acetate as the eluting solvent. Evaporation of the solvent from the pure fraction and recrystallization of the resulting solid from isopropyl alcohol/water give title compound, mp 123°–125° C.

Analysis: Calculated for $C_{15}H_{15}N_3O_2S$: C, 59.78; H, 5.02; N, 13.94. Found: C, 59.61; H, 5.05; N, 13.67.

EXAMPLE 222 a to k

The following compounds are reacted with sodium hydride and the product thereof is reacted with N,N-dimethyl-chloroacetamide:

(a) 2-(4-chlorophenyl)-7-chloro-3H-imidazo[4,5-b]pyridine, (b) 2-(4-chlorophenyl)-6-chloro-3H-imidazo[4,5-b]pyridine, (c) 2-(4-chlorophenyl)-5,7-dichloro-3H-imidazo[4,5-b]pyridine, (d) 2-(4-chlorophenyl)-6-nitro-3H-imidazo[4,5-b]pyridine, (e) 2-(4-chlorophenyl)-5-methoxy-3H-imidazo[4,5-b]pyridine, (f) 2-(4-chlorophenyl)-5,6-dichloro-3H-imidazo[4,5-b]pyridine, (g) 2-(4-chlorophenyl)-6-bromo-3H-imidazo[4,5-b]pyridine, (h) 2-(4-chlorophenyl)-5-chloro-3H-imidazo[4,5-b]pyridine, (i) 2-(4-chlorophenyl)-7-methyl-3H-imidazo[4,5-b]pyridine, (j) 2-(4-chlorophenyl)-6-methyl-3H-imidazo[4,5-b]pyridine, and (k) 2-(4-chlorophenyl)-5-methyl-3H-imidazo[4,5-b]pyridine to give mixtures of the following pairs of compounds which are separated by dissolving out the minor constituent with an appropriate solvent (see Example 188):

(a) 2-(4-chlorophenyl)-7-chloro-N,N-dimethyl-1H-imidazo[4,5-b]pyridine-1-acetamide and 2-(4-chlorophenyl)-7-chloro-N,N-dimethyl-3H-imidazo[4,5-b]pyridine-3-acetamide, (b) 2-(4-chlorophenyl)-6-chloro-N,N-dimethyl-1H-imidazo[4,5-b]pyridine-1-acetamide and 2-(4-chlorophenyl)-6-chloro-N,N-dimethyl-3H-imidazo[4,5-b]pyridine-3-acetamide, (c) 2-(4-chlorophenyl)-5,7-dichloro-N,N-dimethyl-1H-imidazo [4,5-b]pyridine-1-acetamide and 2-(4-chlorophenyl)-5,7-dichloro-N,N-dimethyl-3H-imidazo [4,5-b]pyridine-3-acetamide, (d) 2-(4-chlorophenyl)-N,N-dimethyl-6-nitro-1H-imidazo[4,5-b]pyridine-1-acetamide and 2-(4-chlorophenyl)-N,N-dimethyl-6-nitro-3H-imidazo[4,5-b]pyridine-3-acetamide, (e) 2-(4-chlorophenyl)-N,N-dimethyl-5-methoxy-1H-imidazo[4,5-b]pyridine-1-acetamide and 2-(4-chlorophenyl)-N,N-dimethyl-5-methoxy-3H-imidazo[4,5-b]pyridine-3acetamide, (f) 2-(4-chlorophenyl)-5,6-dichloro-N,N-dimethyl-1H-imidazo [4,5-b]pyridine-1-acetamide and 2-(4-chlorophenyl)-5,6-dichloro-N,N-dimethyl-3H-imidazo [4,5-b]pyridine-3-acetamide,
(g) 6-bromo-2-(4chlorophenyl)-N,N-dimethyl-1H-imidazo[4,5-b]pyridine-1-acetamide and 6-bromo-2-(4-chlorophenyl)-N,N-dimethyl-3H-imidazo[4,5-b]pyridine-3-acetamide,
(h) 2-(4-chlorophenyl)-5-chloro-N,N-dimethyl-1H-imidazo[4,5-b]pyridine-1-acetamide and 2-(4-chlorophenyl)-5-chloro-N,N-dimethyl-3H-imidazo[4,5-b]pyridine-3-acetamide,
(i) 2-(4-chlorophenyl)-N,N-dimethyl-7-methyl-1H-imidazo[4,5-b]pyridine-1-acetamide and 2-(4-chlorophenyl)-N,N-dimethyl-7-methyl-3H-imidazo[4,5-b]pyridine-3-acetamide,
(j) 2-(4-chlorophenyl)-N,N-dimethyl-6-methyl-1H-imidazo[4,5-b]pyridine-1acetamide and 2-(4-chlorophenyl)-N,N-dimethyl-6-methyl-3H-imidazo[4,5-b]pyridine-3-acetamide,
(k) 2-(4-chlorophenyl)-N,N-dimethyl-5-methyl-1H-imidazo[4,5-b]pyridine-1-acetamide and 2-(4-chlorophenyl)-N,N-dimethyl-5-methyl-3H-imidazo[4,5-b]pyridine-3-acetamide.

EXAMPLE 223 a to i

The following compounds are reacted with sodium hydride and the product thereof is reacted with chloroacetamide:
(a) 2-(4-chlorophenyl)-4methoxy-3H-imidazo[4,5-c]pyridine,
(b) 2-(4-chlorophenyl)-6-chloro-7-bromo-3H-imidazo[4,5-c]pyridine,
(c) 2-(4-chlorophenyl)-3H-imidazo[4,5-c]pyridine,
(d) 2-(4-chlorophenyl)-4-chloro-3H-imidazo[4,5-c]pyridine,
(e) 2-(4-chlorophenyl)-4,6-dichloro-3H-imidazo[4,5-c]pyridine,
(f) 2-(4-chlorophenyl)-7-nitro-3H-imidazo[4,5-c]pyridine,
(g) 2-(4-chlorophenyl)-4chloro-6-bromo-3H-imidazo[4,5-c]pyridine,
(h) 2-(4-chlorophenyl)-7-bromo-3H-imidazo[4,5-c]pyridine and
(i) 2-(4-chlorophenyl)-6chloro-1H-imidazo[4,5-c]pyridine
to give mixtures of the following pairs of compounds which are separated dissolving out the minor constituent with an appropriate solvent:
(a) 2-(4-chlorophenyl)-4-methoxy-1H-imidazo[4,5-c]pyridine-1-acetamide and 2-(4-chlorophenyl)-4-methoxy-3H-imidazo[4,5-c]pyridine-3-acetamide,
(b) 7-bromo-2-(4-chlorophenyl)-6-chloro-1H-imidazo[4,5-c]pyridine-1-acetamide and 7-bromo-2-(4-chlorophenyl)-6-chloro-3H-imidazo[4,5-c]pyridine-3-acetamide,
(c) 2-(4-chlorophenyl)-1H-imidazo[4,5-c]pyridine-1-acetamide and 2-(4-chlorophenyl)-3H-imidazo[4,5-c]pyridine-3-acetamide,
(d) 2-(4-chlorophenyl)-4-chloro-1H-imidazo[4,5-c]pyridine-1-acetamide and 2-(4-chlorophenyl)-4-chloro-3-imidazo[4,5-c]pyridine-3-acetamide,
(e) 2-(4-chlorophenyl)-4,6-dichloro-1H-imidazo[4,5-c]pyridine-1-acetamide and 2-(4-chlorophenyl)-4,6-dichloro-3H-imidazo[4,5-c]pyridine-3-acetamide,
(f) 2-(4-chlorophenyl)-7-nitro-1H-imidazo[4,5-c]pyridine-1-acetamide and 2-(4-chlorophenyl)-7-nitro-3H-imidazo[4,5-c]pyridine-3acetamide,
(g) 6-bromo-2-(4-chlorophenyl)-4-chloro-1H-imidazo[4,5-c]pyridine-1-acetamide and 6-bromo-2-(4-chlorophenyl)-4-chloro-3H-imidazo[4,5-c]pyridine-3-acetamide,
(h) 7-bromo-2-(4-chlorophenyl)-1H-imidazo[4,5-c]pyridine-1-acetamide and 7-bromo-2-(4-chlorophenyl)-3H-imidazo[4,5-c]pyridine-3-acetamide,
(i) 2-(4-chlorophenyl)-6-chloro-1H-imidazo[4,5-c]pyridine-1-acetamide and 2-(4-chlorophenyl)-6-chloro-3H-imidazo[4,5-c]pyridine-3-acetamide.

EXAMPLE 224

Following the procedure of Example 25, but substituting the following for N-[3-[(4-chlorobenzoyl)amino]-2-pyridinyl]glycine ethyl ester:
(a) N-[3-(4-chlorobenzoylamino)-4-methyl-2-pyridinyl]glycine ethyl ester,
(b) N-[3-(4-chlorobenzoylamino)-5-methyl-2-pyridinyl]glycine ethyl ester,
(c) N-[3-(4-chlorobenzoylamino)-6-methyl-2-pyridinyl]glycine ethyl ester,
(d) N-[3-(4-chlorobenzoylamino)-5,6-dimethyl-2-pyridinyl]glycine ethyl ester,
(e) N-[5-(4-chlorobenzoylamino)-6-diethylamino-2-methyl-4-pyridinyl]glycine ethyl ester,
(f) N-[3-(4-chlorobenzoylamino)-2-methyl-4-pyridinyl]glycine ethyl ester and
(g) N-[3-(4-chlorobenzoylamino)-6-methoxy-2-pyridinyl]glycine ethyl ester
there are obtained:
(a) 2-(4-chlorophenyl)-7-methyl-3H-imidazo[4,5-b]pyridine-3-acetic acid ethyl ester,
(b) 2-(4-chlorophenyl)-6-methyl-3H-imidazo[4,5-b]pyridine-3-acetic acid ethyl ester,
(c) 2-(4-chlorophenyl)-5-methyl-3H-imidazo[4,5-b]pyridine-3-acetic acid ethyl ester,
(d) 2-(4-chlorophenyl)-5,6-dimethyl-3H-imidazo[4,5-b]pyridine-3-acetic acid ethyl ester,
(e) 2-(4-chlorophenyl)-4-diethylamino-6-methyl-1H-imidazo[4,5-c]pyridine-1-acetic acid ethyl ester,
(f) 2-(4-chlorophenyl)-4-methyl-1H-imidazo[4,5-c]pyridine-1-acetic acid ethyl ester and
(g) 2-(4-chlorophenyl)-5-methoxy-3H-imidazo[4,5-b]pyridine-3-acetic acid ethyl ester.

EXAMPLE 225

(R)-2-(4-Chlorophenyl)-α-methyl-3H-imidazo[4,5-b]pyridine-3-acetic acid 2-hydroxyethyl ester A solution of (R)-N-[3-[(4-chlorobenzoyl)amino]-2-pyridinyl]alanine methyl ester (27.4 g, 0.0822 mole) in ethylene glycol (150 ml) was refluxed under nitrogen for 1.75 hours and then cooled. One-third of this solution was added to water (1 liter), extracted with ethyl acetate twice and the combined organic layers were washed three times with water and once with a saturated sodium chloride solution. The organic layer was dried over magnesium sulfate, treated with charcoal, filtered, and evaporated to give 8.3 g of a yellow solid (96% yield). The solid was dissolved in hot isopropyl ether (with a little isopropyl alcohol) and filtered hot. Upon cooling to room temperature, solid precipitated, which was collected by filtration, rinsed with isopropyl ether, and dried under high vacuum at room temperature to give 3.29 g of title compound, mp 110°-113° C.

Analysis: Calculated for $C_{17}H_{16}N_3O_3Cl$: C, 59.05; H, 4.66; N, 12.15. Found: C, 59.00; H, 4.67; N, 12.15.

EXAMPLE 226

(R)-2-(4-Chlorophenyl)-α-methyl-3H-imidazo[4,5-b]pyridine-3-acetic acid 2-hydroxyethyl ester A solution of (R)-2-(4-chlorophenyl)-α-methyl-3H-imidazo [4,5-b]pyridine-3-acetic acid (4.22 g, 0.014 mole) and concentrated sulfuric acid (4 drops) in ethylene glycol (50 ml) was refluxed under nitrogen for three hors, and then poured into a saturated sodium bicarbonate solution (200 ml). Water (50 ml) was added and the product was extracted into three portions of ethyl acetate. The combined organic layers were washed twice with water and once with a saturated sodium chloride solution, dried over magnesium sulfate, treated with charcoal, filtered, and evaporated under reduced pressure to give 2.6 g (54% yield) of an oily glass. The glass was dissolved in hot isopropyl ether (with a little isopropyl alcohol added), filtered while hot, and cooled to room temperature with stirring, causing a solid to precipitate. The mixture was cooled in the freezer, and the solid was collected by filtration, rinsed with isopropyl ether and dried under high vacuum at room temperature to give 1.60 g of title compound, mp. 110°–113° C.

Analysis: Calculated for $C_{17}H_{16}N_3O_3Cl$: C, 59.05; H, 4.66; N, 12.15. Found: C, 58.99; H, 4.66; N, 12.13.

EXAMPLE 227

2-(4-Chlorophenyl)-3H-imidazo[4,5-b]pyridine-3-propanamide

A mixture of 2-(4-chlorophenyl)-3H-imidazo[4,5-b]pyridine-3-propanoic acid (5.52 g, 0.0183 mole) and 1,1'-carbonyldiimidazole (2.97 g, 0.0183 mole) was stirred at room temperature in dry tetrahydrofuran (100 ml) for 2.5 hours with a stream of nitrogen bubbling through it. Liquid ammonia (50 ml) was added to the reaction mixture (cooled in dry ice/acetone bath) and the mixture was allowed to warm to room temperature and was stirred for 2 days under nitrogen atmosphere. The solvents were removed under reduced pressure and the resulting solid was triturated in water (100 ml), collected by filtration, rinsed twice with water, twice with a 5% potassium hydroxide solution, and twice again with water. The solid was recrystallized from hot methanol and dried under high vacuum at 40° C. to give 2.86 g (52%) of title compound, mp. 248°–250° C.

Analysis: Calculated for $C_{15}H_{13}N_4OCl$: C, 59.90; H, 4.36; N, 18.63. Found: C, 59.66, H, 4.31; N, 18.57.

EXAMPLE 228

2-(5-Bromo-2-furanyl)-3H-imidazo[4,5-b]pyridine-3-acetamide

A mixture of 2-(5-bromo-2-furanyl)-3H-imidazo[4,5-b]pyridine-3-acetic acid (5.90 g, 0.0183 mole) and 1,1'-carbonyldiimidazole (2.97 g, 0.0183 mole) was stirred at room temperature in dry tetrahydrofuran (100 ml) for 2.5 hours with a stream of nitrogen bubbling through it. The reaction mixture was cooled in a dry ice/acetone bath, and liquid ammonia (50 ml) was added. The mixture was allowed to warm to room temperature and was stirred for 2 days under nitrogen atmosphere. The solvents were removed under reduced pressure and the resulting solid was triturated in water (100 ml), collected by filtration, rinsed twice with water, twice with a 5% potassium hydroxide solution and twice again with water. The solid was recrystallized from hot methanol and dried under high vacuum at 40° C. to give 2.23 g (38%) of title compound, mp. >250° C.

Analysis: Calculated for $C_{12}H_9N_4O_2Br$: C, 44.88; H, 2.82; N, 17.45. Found: C, 44.79; H, 2.83; N, 17.39.

EXAMPLE 229

2-(5-Methyl-2-thienyl)-3H-imidazo[4,5-b]pyridine-3-acetamide

A mixture of 2-(5-methyl-2-thienyl)-3H-imidazo[4,5-b]pyridine-3-acetic acid (5.0 g, 0.0183 mole) and 1,1'-carbonyldiimidazole (2.97 g, 0.0183 mole) was stirred at room temperature in dry tetrahydrofuran (100 ml) for 2.5 hours with a stream of nitrogen bubbling through it. The reaction mixture was cooled in a dry ice/acetone bath, and liquid ammonia (50 ml) was added. The mixture was allowed to warm to room temperature and was stirred for 2 days under nitrogen atmosphere. The solvents were removed under reduced pressure and the resulting solid was triturated in water, collected by filtration, rinsed twice with water, twice with a 5% potassium hydroxide solution and twice again with water. The solid was recrystallized from hot methanol and dried under high vacuum at 40° C. to give 2.82 g (56%) of title compound, mp>250° C.

Analysis: Calculated for $C_{13}H_{12}N_4OS$: C, 57.34; H, 4.44; N, 20.57. Found: C, 57.10; H, 4.39; N, 20.41.

EXAMPLE 230

2-(4-Fluorophenyl)-N-methyl-3H-imidazo[4,5-b]pyridine-3-acetamide

A mixture of 2-(4-fluorophenyl)-3H-imidazo[4,5-b]pyridine-3-acetic acid (5.0 g, 0.01845 mole) and 1,1'-carbonyldiimidazole (2.99 g, 0.01845 mole) was stirred at room temperature in dry tetrahydrofuran (100 ml) for three hours with a stream of nitrogen bubbling through it. A solution of methylamine in tetrahydrofuran (37 ml of a 3.03M solution, 0.111 mole) was added and the reaction mixture was stirred at room temperature under nitrogen overnight. The solvents were removed under reduced pressure and the residue was triturated in water (100 ml). The solid was collected by filtration, rinsed twice with water, twice with a 5% potassium hydroxide solution and twice again with water. The solid was dissolved in hot isopropyl alcohol, filtered hot, cooled to room temperature and isopropyl ether was added to the cloud point. The resulting solid was collected by filtration, rinsed with isopropyl ether, and dried under high vacuum at 42° C. overnight to give 2.30 g (44%) of title compound, mp. 215°–217° C.

Analysis: Calculated for $C_{15}H_{13}N_4OF$: C, 63.37; H, 4.61; N, 19.71. Found: C, 63.28; H, 4.60; N, 19.68.

EXAMPLE 231

2-(4-Fluorophenyl)-N,N-dimethyl-3H-imidazo[4,5-b]pyridine-3-acetamide

A mixture of 2-(4-fluorophenyl)-3H-imidazo[4,5-b]pyridine-3-acetic acid (5.0 g, 0.01845 mole) and 1,1'-carbonyldiimidazole (2.99 g, 0.01845 mole) was stirred at room temperature in dry tetrahydrofuran (100 ml) for three hours with a stream of nitrogen bubbling through it. A solution of dimethylamine in tetrahydrofuran (48 ml of 2.29M solution, 0.111 mole) was added and the reaction mixture was stirred at 45° C. under nitrogen overnight. The solvents were removed under reduced pressure and the residue was triturated in water (100 ml), the solid was collected by filtration, rinsed twice with water, twice with a 5% potassium hydroxide solution and twice again with water. The solid was dissolved in hot isopropyl alcohol, filtered hot, cooled to room temperature and isopropyl ether was added to the cloud point. The resulting solid was collected by filtration, rinsed with isopropyl ether and dried under high vacuum at 42° C. overnight to give 2.15 g (39%) of title compound, mp. 180°–183° C.

Analysis: Calculated for $C_{16}H_{15}N_4OF$: C, 64.42; H, 5.07; N, 18.78. Found: C, 64.34; H, 5.14; N, 18.63.

EXAMPLE 232

2-(4-Fluorophenyl)-N,N-dipropyl-3H-imidazo[4,5-b]pyridine-3-acetamide

A mixture of 2-(4-fluorophenyl)-3H-imidazo[4,5-b]pyridine-3-acetic acid (5.0 g, 0.01845 mole) and 1,1'-carbonyldiimidazole (2.99 g, 0.01845 mole) was stirred at room temperature in dry tetrahydrofuran (100 ml) for three hours with a stream of nitrogen bubbling through it. A solution of dipropylamine (5.6 g, 0.0554 mole) in tetrahydrofuran (7 ml) was added and the reaction mixture was refluxed overnight under nitrogen. The solvents were removed under reduced pressure and the residue was triturated in 100 ml of water, the solid was collected by filtration, rinsed twice with water, twice with a 5% potassium hydroxide solution and twice again with water. The solid was dissolved in hot isopropyl alcohol, filtered hot, cooled to room temperature, and water was added to the cloud point. The resulting solid was collected by filtration, rinsed with water, and dried under high vacuum at 42° C. overnight to give 2.22 g (34%) of title compound, mp. 135°–136° C.

Analysis: Calculated for $C_{20}H_{23}N_4OF$: C, 67.78; H, 6.54; N, 15.81. Found: C, 67.76; H, 6.56; N, 15.72.

EXAMPLE 233

2-(4-Fluorophenyl)-3H-imidazo[4,5-b]pyridine-3-acetamide hydrate [1:1]

A mixture of 2-(4-fluorophenyl)-3H-imidazo[4,5-b]pyridine-3-acetic acid (4.49 g, 0.0166 mole) and 1,1'-carbonyldiimidazole (2.69 g, 0.0166 mole) was stirred at room temperature in dry tetrahydrofuran (100 ml) for 2.5 hours with a stream of nitrogen bubbling through it. The reaction mixture was cooled in a dry ice/acetone bath and liquid ammonia (50 ml) was added. The mixture was allowed to warm to room temperature and was stirred overnight under nitrogen. The solvents were removed under reduced pressure and the resulting solid was triturated in water (100 ml), collected by filtration, rinsed twice with water, twice with a 5% potassium hydroxide solution and twice with water. The solid was dissolved in hot methanol, filtered while hot and cooled to room temperature. Water was added to the cloud point. The resulting solid was collected by filtration, rinsed with water, and dried under high vacuum at room temperature to give 3.04 g (68%) of title compound, mp. 246°–248° C.

Analysis: Calculated for $C_{14}H_{13}N_4O_2F$: C, 58.33; H, 4.54; N, 19.43. Fond: C, 58.30; H, 4.50; N, 19.38.

EXAMPLE 234

(S)-2-(4-Chlorophenyl)-α-methyl-3H-imidazo[4,5-b]pyridine-3-acetamide

A mixture of (S)-2-(4-chlorophenyl)-α-methyl-3H-imidazo[4.5-b]pyridine-3-acetic acid (3.65 g, 0.012 mole) and 1,1'-carbonyldiimidazole (1.96 g, 0.0121 mole) was stirred at room temperature in dry tetrahydrofuran (100 ml) for 2.5 hours with a stream of nitrogen bubbling through it. The reaction mixture was cooled in a dry ice/acetone bath, liquid ammonia (50 ml) was added, the mixture was allowed to warm to room temperature and was stirred overnight under nitrogen. The solvents were removed under reduced pressure and the resulting solid was partitioned between water (100 ml) and ethyl acetate (100 ml). The insoluble solid was collected by filtration (1.38 g). The layers were separated, the aqueous layer was extracted once with ethyl acetate and the combined organic layers were washed twice with water, twice with a 5% potassium hydroxide solution and twice again with water, dried over magnesium sulfate, treated with charcoal, filtered, and evaporated under reduced pressure to give 1.9 g of solid. The 3.28 g (91% yield) of solids were combined and dissolved in hot methanol, filtered hot, cooled to room temperature and water was added to the cloud point. The resulting solid was collected by filtration, rinsed with water and dried under high vacuum at room temperature to give 2.50 g of title compound, mp. 202°–204° C.

Analysis: Calculated for $C_{15}H_{13}N_4OCl$: C, 59.90; H, 4.36; N, 18.63. Found: C, 59.85; H, 4.34; N, 18.44.

EXAMPLE 235

2-(4-Bromophenyl)-3H-imidazo[4,5-b]pyridine-3-acetamide

A mixture of 2-(4-bromophenyl)-3H-imidazo[4,5-b]pyridine-3-acetic acid (5.51 g, 0.0166 mole) and 1,1'-carbonyldiimidazole (2.69 g, 0.0166 mole) was stirred at room temperature in dry tetrahydrofuran (100 ml) for 2.5 hours with a stream of nitrogen bubbling through it. The reaction mixture was cooled in a dry ice/acetone bath, and liquid ammonia (50 ml) was added. The mixture was allowed to warm to room temperature and was stirred overnight under nitrogen. The solvents were removed under reduced pressure and the resulting solid was triturated in water (100 ml), collected by filtration, and rinsed twice with water, twice with a 5% potassium hydroxide solution and twice again with water. The solid was dissolved in hot methanol, filtered while hot, and cooled to room temperature. The resulting solid was collected by filtration and dried under high vacuum at room temperature to give 3.00 g (54%) of title compound, mp>250° C.

Analysis: Calculated for $C_{14}H_{11}N_4OBr$: C, 50.78; H, 3.35; N, 16.92. Found: C, 50.63; H, 3.32; N, 16.84.

EXAMPLE 236

2-[2-(4-Chlorophenyl)-1H-imidazo[4,5-b]pyridin-1-yl]-1-phenylethanone

Under nitrogen atmosphere, the 2-(4-chlorophenyl)-3H-imidazo[4,5-b]pyridine (5.0 g, 0.022 mole) was added to a suspension of sodium hydride (0.96 g of 60% in oil, 0.024 mole, washed once with hexanes) in dimethylformamide (100 ml). The mixture was heated at 70°–85° C. for 1.5 hr before adding the α-bromoacetophenone (4.38 g, 0.022 mole) at room temperature. The reaction mixture was stirred at room temperature overnight, then poured into water. The precipitate was collected by filtration, washed with water, and dried under high vacuum. A sample was dissolved in isopropyl alcohol, then concentrated to initiate crystallization. The crystals were collected by filtration, washed with isopropyl alcohol, and dried under high vacuum at 70° C. over a weekend to give 1.5 g (20%) of title compound, mp. 262°–263° C.

Analysis: Calculated for $C_{20}H_{14}N_3OCl$: C, 69.07; H, 4.06; N, 12.08. Found: C, 68.78; H, 4.03; N, 12.02.

EXAMPLE 237

2-(4-Chlorophenyl)-α-phenyl-3H-imidazo[4,5-b]pyridine-3-ethanol

4-Chloro-N-[2-[(2-hydroxy-2-phenylethyl)amino]-3-pyridinyl]benzamide (13.2 g, 0.036 mole) was heated at 180°–190° C. in a glass flask on a Wood's metal bath for 12 minutes. The residue was dissolved in ethyl acetate, treated with Florisil ®, and filtered. The filtrate was diluted with hexanes to initiate crystallization. The solid was collected by filtration, washed with ethyl acetate/hexanes mixture and then hexane. The solid still contained 10–15% uncyclized material, and therefore a portion of the solid (1.25 g) was heated at 180°–190° C. for an additional 17 minutes. The solid residue was recrystallized from methylene chloride/hexane and dried under high vacuum at 70° C. overnight to give 0.8 g of solid, mp. 166°–168° C.

Analysis: Calculated for $C_{20}H_{16}N_3OCl$: C, 68.67; H, 4.61; N, 12.01. Found: C, 68.46; H, 4.54; N, 12.02.

EXAMPLE 238

2-[2-(4-Chlorophenyl)-3H-imidazo[4,5-b]pyridin-3-yl]-1-phenyl ethanone

Under nitrogen atmosphere, a solution of 2-(4-chlorophenyl)-α-phenyl-3H-imidazo[4,5-b]pyridine-3-ethanol (9.44 g, 0.027 mole) in methylene chloride (50 ml) was added to a stirred suspension of pyridinium chlorochromate (8.75 g, 0.041 mole) in methylene chloride (100 ml) and allowed to stir at room temperature overnight. The reaction mixture was filtered. The residue was treated with boiling methylene chloride and filtered. The methylene chloride filtrate was treated with Florisil ® and filtered. The filtrate was evaporated to dryness and the residue was recrystallized from isopropyl alcohol. The crystals were collected by filtration, washed with isopropyl alcohol/water, and dried under high vacuum overnight at room temperature to give 5.0 g (54%) of title compound, mp. 211°–212.5° C.

Analysis: Calculated for $C_{20}H_{14}N_3OCl$: C, 69.07; H, 4.06; N, 12.08. Found: C, 68.92; H, 4.02; N, 12.09.

EXAMPLE 239

2-(4-Chlorophenyl)-N,N-dimethyl-1H-imidazo[4,5-c]pyridine-1-acetamide

Crude N-[3-[bis(4-chlorobenzoyl)amino]-4-pyridinyl]N,N-dimethyl-glycinamide (9.24 g) obtained by evaporating the final filtrate of preparation 50 was heated in a glass flask in a Wood's metal bath at 180°–190° C. for 10 minutes. The residue was dissolved in methylene chloride and extracted with dilute aqueous sodium hydroxide (3x). The aqueous basic layers were combined and extracted with methylene chloride. The methylene chloride layers were combined, dried, and evaporated. The residue was purified by flask chromatography (375 g) eluting first with ethyl acetate (5.5 liters) followed by 90% ethyl acetate/10% methyl alcohol, and finally 80% ethyl acetate/20% methyl alcohol. The desired product, which was contained in the latter fractions, were combined and evaporated. The solid was recrystallized from isopropyl alcohol/isopropyl ether to give 1.4 g (24%) of solid, mp. 236°–238° C.

Analysis: Calculated for $C_{16}H_{15}N_4OCl$: C, 61.05; H, 4.80; N, 17.80. Found: C, 60.61; H, 4.86; , 17.49.

EXAMPLE 240

5-Chloro-2-(4-chlorophenyl)-3H-imidazo[4,5-b]pyridine-3-acetic acid

A solution of N-[6-chloro-3-[(4-chlorobenzoyl)amino]-2-pyridinyl]glycine ethyl ester (1.7 g, 0.00462 mole) in ethylene glycol (25 ml) was refluxed under nitrogen for two hours. To one-half of the solution (0.0023 mole) was added water (2 ml) and solid potassium hydroxide (0.20 g, 0.003515 mole) and the mixture was refluxed for an additional 15 minutes, poured into ice water (100 ml) and acidified with 3N hydrochloric acid solution. The resulting solid was collected by filtration, rinsed with water, dissolved in hot methanol and filtered hot. Addition of water to the cloud point and cooling to room temperature gave a solid which was collected by filtration, washed with water, and dried at 60° C. under high vacuum to give 0.4 g (54% yield) of title compound, mp >250° C.

Analysis: Calculated for $C_{14}H_9N_3O_2Cl_2$: C, 52.20; H, 2.82; N, 13.04. Found: C, 52.22; H, 2.79; N, 13.00.

EXAMPLE 241

5-Chloro-2-(4-chlorophenyl)-N,N-dipropyl-3H-imidazo[4,5-b]pyridine-3-acetamide

A suspension of 5-chloro-2-(4-chlorophenyl)-3H-imidazo[4,5-b]pyridine-3-acetic acid (3.1 g, 0.00963 mole) and 1,1'-carbonyldiimidazole (1.56 g, 0.00963 mole) in tetrahydrofuran (100 ml) was refluxed for 3.25 hours under nitrogen, cooled to room temperature, a stream of nitrogen was bubbled through the solution for 0.75 hr then a solution of dipropylamine (2.92 g, 0.0289 mole) in tetrahydrofuran (4 ml) was added. The reaction mixture was refluxed overnight under nitrogen and evaporated under reduced pressure. The residue was partitioned between water and ethyl acetate, the layers were separated, sodium chloride was added to the aqueous layer and it was re-extracted with ethyl acetate. The combined organic layers were washed twice with a saturated sodium chloride solution, dried over magnesium sulfate, charcoaled, filtered and evaporated under reduced pressure to a solid (3.7 g, 95% yield). The solid was recrystallized from isopropyl alcohol/water and dried under high vacuum at 58° C. to give 2.11 g of title compound, mp 170°–173.5° C.

Analysis: Calculated for $C_{20}H_{22}N_4OCl_2$: C, 59.27; H, 5.47; N, 13.82. Found: C, 59.09; H, 5.43; N, 13.79.

EXAMPLE 242

5-Chloro-2-(4-chlorophenyl)-3H-imidazo[4,5-b]pyridine-3-acetamide hydrate [1:1]

A suspension of 5-chloro-2-(4-chlorophenyl)-3H-imidazo [4,5-b]pyridine-3-acetic acid (3.1 g, 0.00963 mole) and 1,1'-carbonyldiimidazole (1.56 g, 0.00963 mole) in tetrahydrofuran (100 ml) was refluxed under nitrogen for 1.5 hours, cooled to room temperature, and a stream of nitrogen, was bubbled through the solution for one hour. The solution was cooled in a dry ice/acetone bath and liquid ammonia (50 ml) was added. The reaction mixture was allowed to warm to room temperature and was stirred at room temperature for two days. The solvents were removed under reduced pressure and the solid was triturated in water (100 ml), collected by filtration, and rinsed twice with water, twice with a 5% potassium hydroxide solution, and twice again with water. The solid was recrystallized twice from isopropyl alcohol/water and dried under high vacuum at 70° C. to give 1.78 g (54%) of title compound, mp>250° C.

Analysis: Calculated for $C_{14}H_{12}N_4O_2Cl_2$: C, 49.58; H, 3.57; N, 16.52. Found: C, 49.86; H, 3.50; N, 16.55.

EXAMPLE 243

5-Chloro-2-(4-chlorophenyl)-N,N-dimethyl-3H-imidazo[4,5-b]pyridine-3-acetamide hydrate [1:0.5]

A suspension of 5-chloro-2-(4-chlorophenyl)-3H-imidazo [4,5-b]pyridine-3-acetic acid (3.1 g, 0.00963 mole) and 1,1'-carbonyldiimidazole (1.56 g, 0.00963 mole) in tetrahydrofuran (100 ml) was refluxed under nitrogen for 3.25 hours, cooled to room temperature and a stream of nitrogen was bubbled through the solution for 0.75 hours. A solution of dimethylamine in tetrahydrofuran (21.9 ml of a 2.65M solution, 0.0578 mole) was added and the solution was stirred at 50° C. under nitrogen overnight. The solvents were evaporated under reduced pressure, the residue was triturated in water (50 ml), collected by filtration, and rinsed twice with water, twice with a 5% potassium hydroxide solution and twice again with water. The resulting solid was recrystallized from isopropyl alcohol/water to give 1.70 g of solid (50% yield) which was dissolved in hot isopropyl alcohol, treated with charcoal, filtered while hot and brought to the cloud point by addition of water. Cooling to room temperature gave a solid which was collected by filtration and dried under high vacuum at 70° C. to give 1.05 g title compound, mp 203°–205° C.

Analysis: Calculated for $C_{16}H_{15}N_4O_{1.5}Cl_2$: C, 53.65; H, 4.22; N, 15.64. Found: C, 53.71; H, 3.95; N, 15.62.

EXAMPLE 244

2-(4-Bromophenyl)-N-[4-(dimethylamino)phenyl]-3H-imidazo[4,5-b]pyridine-3-acetamide Under a nitrogen atmosphere, oxalyl chloride (2.6 g, 0.020 mole) was added dropwise (slowly) to a stirred and chilled (5°–10° C.) suspension of 2-(4-bromophenyl)-3H-imidazo[4,5-b]pyridine-3-acetic acid (6.4 g, 0.019 mole) in anhydrous dimethylformamide (50 ml). The reaction mixture was heated at 55°–60° C. for 5 hours, cooled to room temperature, and added dropwise to a stirred and chilled (10°–15° C.) suspension of N,N-dimethyl-p-phenylenediamine dihydrochloride (4.04 g, 0.0193 mole), triethylamine (8.2 g, 0.081 mole), and anhydrous dimethylformamide (100 ml). The reaction mixture was stirred overnight at room temperature, filtered, and poured into ice water (500 ml). The mixture was allowed to precipitate, and filtered. The filter cake was triturated in potassium bicarbonate solution (100 ml), filtered, and rinsed with water (100 ml). The cake was twice recrystallized from tetrahydrofuran-/ethyl alcohol, giving 2.8 g (31%) of a white solid, mp 248°–250° C.

Analysis: Calculated for $C_{22}H_{20}N_5OBr$: C, 58.68; H, 4.48; N, 15.55. Found: C, 58.58; H, 4.41; N, 15.51.

EXAMPLE 245

2-(4-Chlorophenyl)-N-[4-(dimethylamino)phenyl]-3H-imidazo [4,5-b]-pyridine-3-propanamide Under a nitrogen atmosphere, oxalyl chloride (1.75 g, 0.0138 mole) was added dropwise, slowly, to a stirred and chilled (10° C.) suspension of 2-(4-chlorophenyl)-3H-imidazo[4,5-b]pyridine-3-propanoic acid (4.0 g, 0.0133 mole) in anhydrous dimethylformamide (20 ml). A yellow solid formed. The suspension was stirred at room temperature for a few minutes and then a solution of N,N-dimethylphenylenediamine (2.0 g, 0.0147 mole) in dimethylformamide (25 ml) was added. The resulting purple solution was stirred at room temperature overnight under a nitrogen atmosphere. The reaction mixture was poured into 150 ml of water and stirred at room temperature. Triethylamine (2.0 ml) was added to pH 8 and a solid precipitated. The solid was collected by filtration, dissolved in hot isopropyl alcohol, treated with charcoal, and filtered. Addition of water and cooling to room temperature caused a solid to form. The solid was collected by filtration and rinsed with water to give 1.1 g of solid (20% yield). Drying under high vacuum at room temperature and then at 80° C. gave a grayish solid, mp 216°–218° C.

Analysis: Calculated for $C_{23}H_{22}N_5OCl_1$: C, 65.79; H, 5.28; N, 16.68. Found: C, 65.60; H, 5.38N, 16.49.

EXAMPLE 246

5-Chloro-2-(4-chlorophenyl)-N-methyl-3H-imidazo[4,5-b]pyridine-3-acetamide

A solution of 5-chloro-2-(4-chlorophenyl)-3H-imidazo[4,5-b]pyridine-3-acetic acid 5.0 g, 0.0155 mole) and 1,1'-carbonyldiimidazole (2.52 g, 0.0155 mole) in dry tetrahydrofuran (100 ml) was refluxed under nitrogen for two hours. The solution was cooled to room temperature and a stream of nitrogen was bubbled through it for thirty minutes. A solution of methylamine in tetrahydrofuran (36 ml of a 2.59M solution, 0.0932 mole) was added and the suspension was stirred at room temperature under nitrogen for three days. The solvents were evaporated under reduced pressure and the resulting solid was triturated in water (100 ml), collected by filtration, and rinsed twice with water, twice with a 5% potassium hydroxide solution and twice again with water. The solid was dissolved in hot isopropyl alcohol, dried over magnesium sulfate, treated with charcoal and filtered while hot. The filtrate was reduced to one-half its original volume and isopropyl ether was added. Upon cooling to room temperature, solid precipitated, which was collected by filtration, rinsed with isopropyl ether and dried under high vacuum at 60° C. to give 3.45 g (66% yield) of title compound, mp>250° C.

Analysis: Calculated for $C_{15}H_{12}N_4OCl_2$: C, 53.75; H, 3.61; N, 16.71. Found: C, 53.83; H, 3.60; N, 16.76.

EXAMPLE 247

5-Chloro-2-(4-methylphenyl)-N-methyl-3H-imidazo[4,5-b]pyridine-3-acetamide

A slurry of 5-chloro-2-(4-methylphenyl)-3H-imidazo[4,5-b]pyridine-3-acetic acid (2.8 g, 0.0093 mole) in tetrahydrofuran (11.3 ml) and dimethylformamide (0.68 g, 0.0093 mole) was cooled in an ice bath under nitrogen. Thionyl chloride (1.22 g, 0.0102 mole) was added dropwise to the stirred suspension. After stirring at room temperature for twenty minutes, the solution was cooled again in an ice bath and a solution of methylamine in tetrahydrofuran (21.5 ml of a 2.59M solution, 0.056 mole) was added dropwise. The suspension wa stirred at room temperature under nitrogen for one hour and then the solvents were removed under reduced pressure. The residue was triturated in water (100 ml) and the resulting solid was collected by filtration and rinsed three times with water. The solid was dissolved in hot isopropyl alcohol, filtered while hot, and brought to the cloud point with isopropyl ether. Upon cooling, a solid precipitated which was collected by filtration, rinsed with isopropyl ether, and dried under high vacuum at 70° C. give 1.86 g (64% yield) of title compound, mp>250° C.

Analysis: Calculated for $C_{16}H_{15}N_4OCl$: C, 61.05; H, 4.80; N, 17.80. Found: C, 61.01; H, 4.74; N, 17.68.

EXAMPLE 248

5-Chloro-N,N-dimethyl-2-(4-methylphenyl)-3H-imidazo[4,5-b]pyridine-3-acetamide

A slurry of 5-chloro-2-(4-methylphenyl)-3H-imidazo[4,5-b]pyridine-3-acetic acid (2.8 g, 0.0093 mole) in tetrahydrofuran (11.3 ml) and dimethylformamide (0.68 g, 0.0093 mole) was cooled in an ice bath under nitrogen. Thionyl chloride (1.22 g, 0.0102 mole) was added dropwise to the stirred suspension. After stirring at room temperature for twenty minutes, the solution was cooled again in an ice bath and a solution of dimethylamine in tetrahydrofuran (18.9 ml of a 2.95M solution, 0.056 mole) was added dropwise. The suspension was stirred at room temperature under nitrogen for one hour and then the solvents were removed under reduced pressure. The residue was triturated in water (100 ml) and the resulting solid was collected by filtration and rinsed three times with water. The solid was dissolved in hot isopropyl alcohol, filtered while hot, and brought to the cloud point with water. Upon cooling, a solid precipitated which was collected by filtration, rinsed with water, and dried under high vacuum at 70° C. to give 2.17 g (71% yield) of title compound, mp 182°–185° C.

Analysis: Calculated for $C_{17}H_{17}N_4OCl$: C, 62.10; H, 5.21; N, 17.04. Found: C, 61.70; H, 5.12; N, 16.80.

TABLE 1

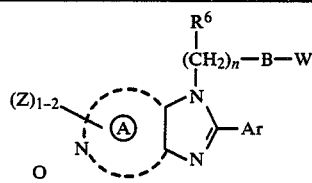

| Ex. No. | $(Z)_{1-2}$-A | Ar | $R^6$ $\|$ $-(CH)_n-$ | B | W | Opt.* Isomer | Salt |
|---|---|---|---|---|---|---|---|
| 1 | [4,5-b]pyridine-3H | 4-Cl-pyridin-2-yl | —CH$_2$— | —C(O)— | OH | — | — |
| 2 | [4,5-b]pyridine-3H | 4-Cl—C$_6$H$_4$— | —CH$_2$— | —C(O)— | OH | — | — |
| 3 | [4,5-b]pyridine-3H | 2-Cl—C$_6$H$_4$— | —CH$_2$— | —C(O)— | OH | — | — |
| 4 | [4,5-b]pyridine-3H | 3-Cl—C$_6$H$_4$— | —CH$_2$— | —C(O)— | OH | — | — |
| 5 | [4,5-b]pyridine-3H | 3-F—C$_6$H$_4$— | —CH$_2$— | —C(O)— | OH | — | — |
| 6 | [4,5-b]pyridine-3H | 4-Br—C$_6$H$_4$— | —CH$_2$— | —C(O)— | OH | — | — |
| 7 | [4,5-b]pyridine-3H | 4-F—C$_6$H$_4$— | —CH$_2$— | —C(O)— | OH | — | — |
| 8 | [4,5-b]pyridine-3H | 3-Br—C$_6$H$_4$— | —CH$_2$— | C(O)— | OH | — | — |
| 9 | [4,5-b]pyridine-3H | pyridin-2-yl | —CH$_2$— | —C(O)— | OH | — | — |
| 10 | [4,5-b]pyridine-3H | 3-CF$_3$—C$_6$H$_4$— | —CH$_2$— | —C(O)— | OH | — | — |
| 11 | [4,5-b]pyridine-3H | 4-CF$_3$—C$_6$H$_4$— | —CH$_2$— | —C(O)— | OH | — | — |
| 12 | [4,5-b]pyridine-3H | 3,4-Cl$_2$—C$_6$H$_3$— | —CH$_2$— | —C(O)— | OH | — | — |
| 13 | [4,5-b]pyridine-3H | 4-OCH$_3$—C$_6$H$_4$— | —CH$_2$— | —C(O)— | OH | — | — |
| 14 | [4,5-b]pyridine-3H | 4-Cl—C$_6$H$_4$— | —(CH$_2$)$_2$— | —C(O)— | OH | — | — |
| 15 | [4,5-b]pyridine-1H | 4-Cl—C$_6$H$_4$— | —CH$_2$— | —C(O)— | OH | — | H$_2$O |
| 16 | [4,5-b]pyridine-3H | 5-Br-furan-2-yl | —CH$_2$— | —C(O)— | OH | — | — |
| 17 | [4,5-b]pyridine-3H | 4-NO$_2$—C$_6$H$_4$— | —CH$_2$— | —C(O)— | OH | — | H$_2$O |
| 18 | [4,5-b]pyridine-3H | 4-Cl—C$_6$H$_4$— | —CH— $\|$ CH$_3$ | —C(O)— | OH | (S) | — |
| 19 | [4,5-b]pyridine-3H | C$_6$H$_5$— | —CH$_2$— | —C(O)— | —OC$_2$H$_5$ | — | — |
| 20 | [4,5-b]pyridine-3H | C$_6$H$_5$— | —CH$_2$— | —C(O)— | —NH$_2$ | — | — |
| 21 | [4,5-b]pyridine-3H | pyridin-2-yl | —CH$_2$— | —C(O)— | —NH$_2$ | — | — |
| 22 | [4,5-b]pyridine-3H | pyridin-2-yl | —CH$_2$— | —C(O)— | —OC$_2$H$_5$ | — | — |
| 23 | [4,5-b]pyridine-3H | 4-Cl-pyridin-2-yl | —CH$_2$— | —C(O)— | —OC$_2$H$_5$ | — | — |
| 24 | [4,5-b]pyridine-3H | 3-Cl—C$_6$H$_4$— | —CH$_2$— | —C(O)— | —OC$_2$H$_5$ | — | — |
| 25 | [4,5-b]pyridine-3H | 4-Cl—C$_6$H$_4$— | —CH$_2$— | —C(O)— | —OC$_2$H$_5$ | — | — |
| 26 | [4,5-b]pyridine-3H | 4-OCH$_3$—C$_6$H$_4$— | —CH$_2$— | —C(O)— | —OC$_2$H$_5$ | — | — |
| 27 | [4,5-b]pyridine-3H | 2-Cl—C$_6$H$_4$— | —CH$_2$— | —C(O)— | —OC$_2$H$_5$ | — | — |
| 28 | [4,5-b]pyridine-3H | 2-OCH$_3$—C$_6$H$_4$— | —CH$_2$— | —C(O)— | —OC$_2$H$_5$ | — | HCl |
| 29 | [4,5-b]pyridine-3H | 4-Cl-pyridin-2-yl | —CH$_2$— | —C(O)— | 4-CH$_3$-piperazin-1-yl | — | — |
| 30 | [4,5-b]pyridine-3H | 4-Cl—C$_6$H$_4$— | —CH$_2$— | —C(O)— | —NH$_2$ | — | — |
| 31 | [4,5-b]pyridine-3H | 2-Cl—C$_6$H$_4$— | —CH$_2$— | —C(O)— | —NH$_2$ | — | HCl |
| 32 | [4,5-b]pyridine-3H | 3-Cl—C$_6$H$_4$— | —CH$_2$— | —C(O)— | 4-CH$_3$-piperazin-1-yl | — | 1.5 fumarate |
| 33 | [4,5-b]pyridine-3H | 3-F—C$_6$H$_4$— | —CH$_2$— | —C(O)— | 4-CH$_3$-piperazin-1-yl | — | 1.5 fumarate |
| 34 | [4,5-b]pyridine-3H | 4-F—C$_6$H$_4$— | —CH$_2$— | —C(O)— | 4-CH$_3$-piperazin-1-yl | — | fumarate |
| 35 | [4,5-b]pyridine-3H | 4-Cl—C$_6$H$_4$— | —CH$_2$— | —C(O)— | 4-CH$_3$-piperazin-1-yl | — | fumarate |
| 36 | [4,5-b]pyridine-3H | 4-Br—C$_6$H$_4$— | —CH$_2$— | —C(O)— | 4-CH$_3$-piperazin-1-yl | — | fumarate |
| 37 | [4,5-b]pyridine-3H | 3-Cl—C$_6$H$_4$— | —CH$_2$— | —C(O)— | NH$_2$ | — | fumarate |

TABLE 1-continued

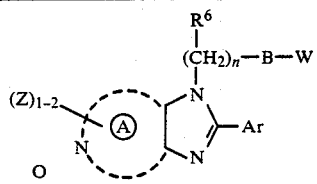

| Ex. No. | (Z)$_{1-2}$-A | Ar | R$^6$ —(CH)$_n$— | B | W | Opt.* Isomer | Salt |
|---|---|---|---|---|---|---|---|
| 38 | [4,5-b]pyridine-3H | 4-Cl—C$_6$H$_4$— | —(CH$_2$)$_2$ | —C(O)— | —OC$_2$H$_5$ | — | — |
| 39 | [4,5-b]pyridine-3H | 3-Br—C$_6$H$_4$— | —CH$_2$— | —C(O)— | —OC$_2$H$_5$ | — | — |
| 40 | [4,5-b]pyridine-3H | 4-Cl—C$_6$H$_4$— | —CH$_2$— | —C(O)— | morpholin-4-yl | — | — |
| 41 | [4,5-b]pyridine-3H | 4-Cl—C$_6$H$_4$— | —CH$_2$— | —C(O)— | —NH(CH$_2$)$_2$—N—(CH$_3$)$_2$ | — | — |
| 42 | [4,5-b]pyridine-3H | 4-Cl—C$_6$H$_4$— | —CH$_2$— | —C(O)— | —NH(CH$_2$)$_2$—N—(CH$_3$)$_2$ | — | 2HCl |
| 43 | [4,5-b]pyridine-3H | 4-Cl—C$_6$H$_4$— | —CH$_2$— | —C(O)— | —NH(-pyridin-3-yl | — | 0.5 H$_2$O |
| 44 | [4,5-b]pyridine-3H | 4-Cl—C$_6$H$_4$— | —CH$_2$— | —C(O)— | —NH(-pyridin-3-yl | — | 2 HCl 1.5 H$_2$O |
| 45 | [4,5-b]pyridine-3H | 3-Br—C$_6$H$_4$— | —CH$_2$— | —C(O)— | 4-CH$_3$-piperazin-1-yl | — | 1.5 fumarate |
| 46 | [4,5-b]pyridine-3H | 4-Cl—C$_6$H$_4$— | —CH$_2$— | —C(O)— | 4-(3-CF$_3$—C$_6$H$_4$—)-piperazin-1-yl | — | — |
| 47 | [4,5-b]pyridine-3H | 4-Cl—C$_6$H$_4$— | —CH$_2$— | —C(O)— | —NHCH$_3$ | — | — |
| 48 | [4,5-b]pyridine-3H | 4-Cl—C$_6$H$_4$— | —CH$_2$— | —C(O)— | —N(CH$_3$)$_2$ | — | — |
| 49 | [4,5-b]pyridine-3H | 4-Cl—C$_6$H$_4$— | —CH$_2$— | —C(O)— | —N(CH$_3$)$_2$ | — | HCl |
| 50 | [4,5-b]pyridine-3H | 3-Cl—C$_6$H$_4$— | —(CH$_2$)$_2$— | —C(O)— | —OC$_2$H$_5$ | — | HCl |
| 51 | [4,5-b]pyridine-3H | 2-Cl—C$_6$H$_4$— | —(CH$_2$)$_2$— | —C(O)— | —OC$_2$H$_5$ | — | HCl |
| 52 | [4,5-b]pyridine-3H | 4-Cl—C$_6$H$_4$— | —CH$_2$— | —C(O)— | —OC(CH$_3$)$_3$ | — | — |
| 53 | [4,5-b]pyridine-3H | 4-Cl—C$_6$H$_4$— | —CH$_2$— | —C(S)— | —NH$_2$ | — | 0.5 H$_2$O |
| 54 | [4,5-b]pyridine-3H | 4-Cl—C$_6$H$_4$— | —CH$_2$— | —C(O)— | —OCH$_3$ | — | — |
| 55 | [4,5-b]pyridine-3H | 4-Cl—C$_6$H$_4$— | —CH$_2$— | —C(O)— | —O—CH(CH$_3$)$_2$ | — | — |
| 56 | [4,5-b]pyridine-3H | 4-CF$_3$—C$_6$H$_4$— | —CH$_2$— | —C(O)— | —N(CH$_3$)$_2$ | — | — |
| 57 | [4,5-b]pyridine-3H | pyridin-2-yl | —CH$_2$— | —C(O)— | 4-CH$_3$-piperazin-1-yl | — | fumarate |
| 58 | [4,5-b]pyridine-3H | pyridin-2-yl | —CH$_2$— | —C(O)— | —OCH$_3$ | — | HCl |
| 59 | [4,5-b]pyridine-3H | 3-CF$_3$—C$_6$H$_4$— | —CH$_2$— | —C(O)— | —N(CH$_3$)$_2$ | — | — |
| 60 | [4,5-b]pyridine-3H | pyridin-2-yl | —CH$_2$— | —C(O)— | —NHCH$_3$ | — | — |
| 61 | [4,5-b]pyridine-3H | pyridin-2-yl | —CH$_2$— | —C(O)— | —OC(CH$_3$)$_3$ | — | — |
| 62 | [4,5-b]pyridine-3H | 4-Cl—C$_6$H$_4$— | —CH$_2$— | —C(O)— | —N(C$_3$H$_7$)$_2$ | — | — |
| 63 | [4,5-b]pyridine-3H | 3-Cl—C$_6$H$_4$— | —CH$_2$— | —C(O)— | —NHCH$_3$ | — | HCl |
| 64 | [4,5-b]pyridine-3H | 4-Cl—C$_6$H$_4$— | —CH$_2$— | —C(O)— | —N(C$_2$H$_5$)$_2$ | — | 0.5 H$_2$O |
| 65 | [4,5-b]pyridine-3H | 4-Cl—C$_6$H$_4$— | —CH$_2$— | —C(O)— | —NH[—CH(CH$_3$)$_2$] | — | — |
| 66 | [4,5-b]pyridine-3H | 4-Cl—C$_6$H$_4$— | —CH$_2$— | —C(O)— | —NH[1-C$_2$H$_5$-piperidin-2-yl] | — | 2 HCl H$_2$O |
| 67 | [4,5-b]pyridine-1H | 4-Cl—C$_6$H$_4$— | —CH$_2$— | —C(O)— | CH$_3$ | — | HCl |
| 68 | [4,5-b]pyridine-3H | 4-Cl—C$_6$H$_4$— | —CH$_2$— | —C(O)— | —NH[—CH$_2$C(O)OC$_2$H$_5$] | — | — |
| 69 | [4,5-b]pyridine-3H | 4-Cl—C$_6$H$_4$— | —CH$_2$— | —C(O)— | NHC$_3$H$_7$ | — | — |
| 70 | [4,5-b]pyridine-3H | 3-Cl—C$_6$H$_4$— | —CH$_2$— | —C(O)— | NH[—CH$_2$C(O)OC$_2$H$_5$] | — | — |
| 71 | [4,5-b]pyridine-3H | 4-Cl—C$_6$H$_4$— | —CH$_2$— | —C(O)— | —NH[—CH$_2$-[(1-C$_2$H$_5$)-pyrrolidin-2-yl]] | — | 2 HCl |
| 72 | [4,5-b]pyridine-3H | 4-Cl—C$_6$H$_4$— | —CH$_2$— | —C(O)— | —NHCH$_2$C(O)OK | — | **2 H$_2$O |
| 73 | [4,5-b]pyridine-3H | 4-Cl—C$_6$H$_4$— | —CH$_2$— | —C(O)— | —NHC$_6$H$_5$ | — | — |
| 74 | [4,5-b]pyridine-3H | 4-Cl—C$_6$H$_4$— | —CH$_2$— | —C(O)— | —NH[(1-C$_2$H$_5$)-pyrrolidin-3-yl] | — | 2 HCl H$_2$O |
| 75 | [4,5-b]pyridine-3H | 4-Cl—C$_6$H$_4$— | —CH$_2$— | —C(O)— | —NH[—(CH$_2$)$_3$-C(O)OC$_2$H$_5$] | — | — |
| 76 | [4,5-b]pyridine-3H | 3-Cl—C$_6$H$_4$— | —CH$_2$— | —C(O)— | —NH(pyridin-3-yl) | — | 2 HCl |
| 77 | [4,5-b]pyridine-3H | 3-Cl—C$_6$H$_4$— | —CH$_2$— | —C(O)— | —NH[—(CH$_2$)$_3$N(CH$_3$)$_2$] | — | 2 HCl |
| 78 | [4,5-b]pyridine-3H | 3-Cl—C$_6$H$_4$— | —CH$_2$— | —C(O)— | —NH[—CH$_2$-(1-C$_2$H$_5$)-pyrrolidin-2-yl] | — | 2 HCl |
| 79 | [4,5-b]pyridine-3H | 3-Cl—C$_6$H$_4$— | —CH$_2$— | —C(O)— | —NH[(1-ethyl)-piperidin-3-yl)] | — | HCl |
| 80 | [4,5-b]pyridine-3H | 3-Cl—C$_6$H$_4$— | —CH$_2$— | —C(O)— | —NH[4-N(CH$_3$)$_2$—C$_6$H$_4$—] | — | HCl |
| 81 | [4,5-b]pyridine-3H | 4-Cl—C$_6$H$_4$— | —CH$_2$— | —C(O)— | —NH(1-piperidinylethyl-) | — | HCl 0.5 H$_2$O |
| 82 | [4,5-b]pyridine-3H | 4-Cl—C$_6$H$_4$— | —CH$_2$— | —C(O)— | —NH[—(CH$_2$)$_3$—N(CH$_3$)$_2$] | — | 2 HCl H$_2$O |
| 83 | [4,5-b]pyridine-3H | 4-Cl—C$_6$H$_4$— | —CH$_2$— | —C(O)— | —NH[—(CH$_2$)$_2$—NHC(O)—CH$_3$] | — | 0.5 H$_2$O |
| 84 | [4,5-b]pyridine-3H | 3-Cl—C$_6$H$_4$— | —CH$_2$— | —C(O)— | —NH[—(CH$_2$)$_3$—C(O) | — | — |

TABLE 1-continued $$\begin{array}{c} R^6 \\ | \\ (CH_2)_n-B-W \end{array}$$

(with structure showing (Z)$_{1-2}$-A fused ring system with imidazole bearing Ar and the (CH$_2$)$_n$-B-W substituent)

| Ex. No. | (Z)$_{1-2}$-A | Ar | $R^6$<br>—(CH)$_n$— | B | W | Opt.*<br>Isomer | Salt |
|---|---|---|---|---|---|---|---|
| 85 | [4,5-b]pyridine-3H | 3-Cl—C$_6$H$_4$— | —CH$_2$— | —C(O)— | —NH[—(CH$_2$)$_2$N(CH$_3$)$_2$OC$_2$H$_5$] | — | — |
| 86 | [4,5-b]pyridine-3H | 3-Cl—C$_6$H$_4$— | —CH$_2$— | —C(O)— | -1-piperidinyl | — | — |
| 87 | [4,5-b]pyridine-3H | 4-Br—C$_6$H$_4$— | —CH$_2$— | —C(O)— | —N(CH$_3$)$_2$ | — | — |
| 88 | [4,5-b]pyridine-3H | 4-Cl—C$_6$H$_4$— | —CH$_2$— | —C(O)— | —NH(—CH$_2$CH=CH$_2$) | — | — |
| 89 | [4,5-b]pyridine-3H | 4-Br—C$_6$H$_4$— | —CH$_2$— | —C(O)— | —OC$_2$H$_5$ | — | — |
| 90 | [4,5-b]pyridine-3H | 4-Br—C$_6$H$_4$— | —CH$_2$— | —C(O)— | —NHCH$_3$ | — | — |
| 91 | [4,5-b]pyridine-3H | 4-Br—C$_6$H$_4$— | —CH$_2$— | —C(O)— | —NHCH$_3$ | — | HCl |
| 92 | [4,5-b]pyridine-3H | 4-Cl—C$_6$H$_4$— | —CH$_2$— | —C(O)— | —NH[—(CH$_2$)$_3$—C(O)OK] | — | **H$_2$O |
| 93 | [4,5-b]pyridine-3H | 4-Cl—C$_6$H$_4$— | —CH$_2$— | —C(O)— | -1-piperidinyl | — | — |
| 94 | [4,5-b]pyridine-3H | 4-Cl—C$_6$H$_4$— | —CH$_2$— | —C(O)— | —NHCH$_2$C$_6$H$_5$ | — | — |
| 95 | [4,5-b]pyridine-3H | 4-Cl—C$_6$H$_4$— | —CH$_2$— | —C(O)— | —NHC$_3$H$_5$ | — | — |
| 96 | [4,5-b]pyridine-3H | 4-Cl—C$_6$H$_4$— | —CH$_2$— | —C(O)— | 1-pyrrolidinyl | — | — |
| 97 | [4,5-b]pyridine-3H | 4-Br—C$_6$H$_4$— | —CH$_2$— | —C(O)— | —NH[(1-ethyl)-pyrrolidin-3-yl] | — | — |
| 98 | [4,5-b]pyridine-3H | 4-Br—C$_6$H$_4$— | —CH$_2$— | —C(O)— | —NH[(1-ethyl)-pyrrolidin-3-yl] | — | HCl H$_2$O |
| 99 | [4,5-b]pyridine-3H | 4-Br—C$_6$H$_4$— | —(CH$_2$)— | —C(O)— | —NH(1-piperidinylethyl-) | — | — |
| 100 | [4,5-b]pyridine-3H | 4-Br—C$_6$H$_4$— | —(CH$_2$)— | —C(O)— | —NH(1-piperidinylethyl-) | — | 2 HCl H$_2$O |
| 101 | [4,5-b]pyridine-3H | 4-Br—C$_6$H$_4$— | —CH$_2$— | —C(O)— | —NH[(1-ethyl-piperidin-3-yl] | — | — |
| 102 | [4,5-b]pyridine-3H | 4-Br—C$_6$H$_4$— | —CH$_2$— | —C(O)— | —NH[(1-ethyl-piperidin-3-yl] | — | 2 HCl H$_2$O |
| 103 | [4,5-b]pyridine-3H | 3-Cl—C$_6$H$_4$— | —CH$_2$— | —C(O)— | —NH[—CH$_2$C(O)OK] | — | **2 H$_2$O |
| 104 | [4,5-b]pyridine-3H | 4-Cl—C$_6$H$_4$— | —CH$_2$— | —C(O)— | —NH(pyridin-2-yl) | — | — |
| 105 | [4,5-b]pyridine-3H | 4-Cl—C$_6$H$_4$— | —CH$_2$— | —C(O)— | —NHC$_5$H$_9$ | — | — |
| 106 | [4,5-b]pyridine-3H | 4-Cl—C$_6$H$_4$— | —CH$_2$— | —C(O)— | —NH(—CH$_2$—C$_3$H$_5$) | — | — |
| 107 | [4,5-b]pyridine-3H | 4-Cl—C$_6$H$_4$— | —CH$_2$— | —C(O)— | —NHC$_6$H$_{11}$ | — | — |
| 108 | [4,5-b]pyridine-3H | 3-Cl—C$_6$H$_4$— | —CH$_2$— | —C(O)— | —NH[(1-ethyl)-pyrrolidin-3-yl] | — | 2 HCl 0.5 H$_2$O |
| 109 | [4,5-b]pyridine-3H | 4-Br—C$_6$H$_4$— | —CH$_2$— | —C(O)— | —NH[—(CH$_2$)$_2$N(CH$_3$)$_2$] | — | — |
| 110 | [4,5-b]pyridine-3H | 4-Br—C$_6$H$_4$— | —CH$_2$— | —C(O)— | —NH[—(CH$_2$)$_2$N(CH$_3$)$_2$] | — | 2 HCl 0.5 H$_2$O |
| 111 | [4,5-b]pyridine-3H | 3-Cl—C$_6$H$_4$— | —CH$_2$— | —C(O)— | —NHC$_6$H$_5$ | — | — |
| 112 | [4,5-b]pyridine-3H | 4-Cl—C$_6$H$_4$— | —CH$_2$— | —C(O)— | —NH(2-Cl—C$_6$H$_4$—) | — | — |
| 113 | [4,5-b]pyridine-3H | 3-Cl—C$_6$H$_4$— | —CH$_2$— | —C(O)— | —NH(1-piperidinylethyl-) | — | — |
| 114 | [4,5-b]pyridine-3H | 4-Br—C$_6$H$_4$— | —CH$_2$— | —C(O)— | -1-piperidinyl | — | — |
| 115 | [4,5-b]pyridine-3H | 4-Cl—C$_6$H$_4$— | —CH$_2$— | —C(O)— | —NCH$_3$(—CH$_2$—C$_6$H$_5$) | — | — |
| 116 | [4,5-b]pyridine-3H | 4-Br—C$_6$H$_4$— | —CH$_2$— | —C(O)— | —NH(2-Cl—C$_6$H$_4$—) | — | — |
| 117 | [4,5-b]pyridine-3H | 4-Br—C$_6$H$_4$— | —CH$_2$— | —C(O)— | —NH(pyridin-3-yl) | — | 2 HCl |
| 118 | [4,5-b]pyridine-3H | 4-Br—C$_6$H$_4$— | —CH$_2$— | —C(O)— | —NH(pyridin-3-yl) | — | 0.5 H$_2$O |
| 119 | [4,5-b]pyridine-3H | pyridin-2-yl | —CH$_2$— | —C(O)— | —N(CH$_3$)$_2$ | — | HCl 0.5 H$_2$O |
| 120 | [4,5-b]pyridine-3H-4-oxide | 4-Cl—C$_6$H$_4$— | —CH$_2$— | —C(O)— | —N(CH$_3$)$_2$ | — | — |
| 121 | [4,5-b]pyridine-3H-4-oxide | 4-Cl—C$_6$H$_4$— | —CH$_2$— | —C(O)— | —NH$_2$ | — | — |
| 122 | [4,5-b]pyridine-3H | 4-Cl—C$_6$H$_4$— | —CH$_2$— | —C(O)— | —N(C$_4$H$_9$)$_2$ | — | — |
| 123 | [4,5-b]pyridine-3H | 4-Br—C$_6$H$_4$— | —CH$_2$— | —C(O)— | —NH(pyridin-2-yl) | — | — |
| 124 | [4,5-b]pyridine-3H | 4-Cl—C$_6$H$_4$— | —CH$_2$— | —C(O)— | —N(—CH$_2$CH=CH$_2$)$_2$ | — | — |
| 125 | [4,5-b]pyridine-3H | 4-Br—C$_6$H$_4$— | —CH$_2$— | —C(O)— | —NHC$_6$H$_5$ | — | — |
| 126 | [4,5-b]pyridine-3H | 3-Br—C$_6$H$_4$— | —CH$_2$— | —C(O)— | —NHCH$_3$ | — | — |
| 127 | [4,5-b]pyridine-3H | 3-Br—C$_6$H$_4$— | —CH$_2$— | —C(O)— | —N(CH$_3$)$_2$ | — | — |
| 128 | [4,5-b]pyridine-3H | 4-CF$_3$—C$_6$H$_4$— | —CH$_2$— | —C(O)— | —N(C$_3$H$_7$)$_2$ | — | — |
| 129 | [4,5-b]pyridine-3H | 4-CF$_3$—C$_6$H$_4$— | —CH$_2$— | —C(O)— | —NH(—CH$_2$C$_6$H$_5$) | — | — |

TABLE 1-continued

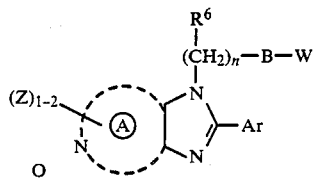

| Ex. No. | (Z)$_{1-2}$-A | Ar | R$^6$ —(CH)$_n$— | B | W | Opt.* Isomer | Salt |
|---|---|---|---|---|---|---|---|
| 130 | [4,5-b]pyridine-3H | 4-Br—C$_6$H$_4$— | —CH$_2$— | —C(O)— | —NH[4-N(CH$_3$)$_2$—C$_6$H$_4$—] | — | 2HCl 1.5 H$_2$O |
| 131 | [4,5-b]pyridine-3H | 4-CF$_3$—C$_6$H$_4$— | —CH$_2$— | —C(O)— | —N(CH$_3$)(C$_6$H$_5$) | — | — |
| 132 | [4,5-b]pyridine-3H | 4-CF$_3$—C$_6$H$_4$— | —CH$_2$— | —C(O)— | —N(C$_2$H$_5$)$_2$ | — | — |
| 133 | [4,5-b]pyridine-3H | 4-CF$_3$—C$_6$H$_4$— | —CH$_2$— | —C(O)— | —N(CH$_3$)(—CH$_2$C$_6$H$_5$) | — | 0.5 H$_2$O |
| 134 | [4,5-b]pyridine-3H | 4-Cl—C$_6$H$_4$— | —CH$_2$— | —C(O)— | —N[—CH(CH$_3$)$_2$]$_2$ | — | — |
| 135 | [4,5-b]pyridine-3H | 3-Cl—C$_6$H$_4$— | —CH$_2$— | —C(O)— | —N(CH$_3$)$_2$ | — | 0.5 H$_2$O |
| 136 | [4,5-b]pyridine-3H | 4-CF$_3$—C$_6$H$_4$— | —CH$_2$— | —C(O)— | —N(C$_4$H$_9$)$_2$ | — | — |
| 137 | [4,5-b]pyridine-3H | 3-Cl—C$_6$H$_4$— | —CH$_2$— | —C(O)— | —NH(pyridin-2-yl) | — | — |
| 138 | [4,5-b]pyridine-3H | 4-Cl—C$_6$H$_4$— | —CH$_2$— | —C(O)— | —N(CH$_3$)(C$_6$H$_5$) | — | — |
| 139 | [4,5-b]pyridine-3H | 4-Cl—C$_6$H$_4$— | —CH$_2$— | —C(O)— | —NH[4-N(CH$_3$)$_2$—C$_6$H$_4$—] | — | — |
| 140 | [4,5-b]pyridine-3H | 4-OCH$_3$—C$_6$H$_4$ | —CH$_2$— | —C(O)— | —N(CH$_3$)$_2$ | — | — |
| 141 | [4,5-b]pyridine-3H | 3,4-Cl$_2$—C$_6$H$_3$— | —CH$_2$— | —C(O)— | —OC$_2$H$_5$ | — | — |
| 142 | [4,5-b]pyridine-3H | 3-Cl—C$_6$H$_4$— | —CH$_2$— | —C(O)— | —NH[—(CH$_2$)$_3$COOH] | — | 0.5 H$_2$O |
| 143 | [4,5-b]pyridine-3H | 4-OCH$_3$—C$_6$H$_4$— | —CH$_2$— | —C(O)— | —N(C$_3$H$_7$)$_2$ | — | — |
| 144 | [4,5-b]pyridine-3H | 4-OCH$_3$—C$_6$H$_4$— | —CH$_2$— | —C(O)— | -1-piperidinyl | — | — |
| 145 | [4,5-b]pyridine-3H | 4-OCH$_3$—C$_6$H$_4$— | —CH$_2$— | —C(O)— | —N(C$_2$H$_5$)$_2$ | — | 0.5 H$_2$O |
| 146 | [4,5-b]pyridine-3H | 3,4-Cl$_2$—C$_6$H$_3$— | —CH$_2$— | —C(O)— | —N(C$_3$H$_7$)$_2$ | — | 0.5 H$_2$O |
| 147 | [4,5-b]pyridine-3H | 4-CF$_3$—C$_6$H$_4$— | —CH$_2$— | —C(O)— | —OC$_2$H$_5$ | — | — |
| 148 | [4,5-b]pyridine-3H | 3-Br—C$_6$H$_4$— | —CH$_2$— | —C(O)— | -1-piperidinyl | — | — |
| 149 | [4,5-b]pyridine-3H | 3-Br—C$_6$H$_4$— | —CH$_2$— | —C(O)— | —N(C$_3$H$_7$)$_2$ | — | — |
| 150 | [4,5-b]pyridine-3H | 3-Cl—C$_6$H$_4$— | —CH$_2$— | —C(O)— | —NCH$_3$[—CH$_2$CH$_2$CH$_2$-[(4-CH$_3$)-piperazin-1-yl]] | — | — |
| 151 | [4,5-b]pyridine-3H | 4-Cl—C$_6$H$_4$— | —CH$_2$— | —C(O)— | —NH[—(CH$_2$)$_2$OCH$_3$] | — | — |
| 152 | [4,5-b]pyridine-3H | 3,4-Cl$_2$—C$_6$H$_3$— | —CH$_2$— | —C(O)— | 1-piperidinyl | — | — |
| 153 | [4,5-b]pyridine-3H | 3,4-Cl$_2$—C$_6$H$_3$— | —CH$_2$— | —C(O)— | —NH[—(CH$_2$)$_2$N(CH$_3$)$_2$] | — | 2 HCl |
| 154 | [4,5-b]pyridine-3H | 4-Cl—C$_6$H$_4$— | —CH$_2$— | —C(O)— | —N(C$_6$H$_5$)$_2$ | — | — |
| 155 | [4,5-b]pyridine-3H | 4-CF$_3$—C$_6$H$_4$— | —CH$_2$— | —C(O)— | —NH[—(CH$_2$)$_2$N(CH$_3$)$_2$] | — | — |
| 156 | [4,5-b]pyridine-3H | 4-CF$_3$—C$_6$H$_4$— | —CH$_2$— | —C(O)— | —NH[—(CH$_2$)$_2$N(CH$_3$)$_2$] | — | 2 HCl |
| 157 | [4,5-b]pyridine-3H | 4-Cl—C$_6$H$_4$— | —(CH$_2$)$_2$— | —C(O)— | —N(C$_3$H$_7$)$_2$ | — | — |
| 158 | [4,5-b]pyridine-3H | 4-Cl—C$_6$H$_4$— | —(CH$_2$)$_2$— | —C(O)— | —NH[—(CH$_2$)$_2$N(CH$_3$)$_2$] | — | 2 HCl |
| 159 | [4,5-b]pyridine-3H | 4-Cl—C$_6$H$_4$— | —(CH$_2$)$_2$— | —C(O)— | —NH[—(CH$_2$)$_2$N(CH$_3$)$_2$] | — | — |
| 160 | [4,5-b]pyridine-3H | 4-Cl—C$_6$H$_4$— | —CH$_2$— | —C(O)— | 1-azetidinyl | — | — |
| 161 | [4,5-b]pyridine-3H | 4-Cl—C$_6$H$_4$— | —(CH$_2$)$_2$— | —C(O)— | —NH[4-N(CH$_3$)$_2$—C$_6$H$_4$—] | — | 2 HCl |
| 162 | [4,5-b]pyridine-3H | 4-Cl—C$_6$H$_4$— | —CH$_2$— | —C(O)— | —NH[—(CH$_2$)$_2$—N(C$_2$H$_5$)$_2$] | — | — |
| 163 | [4,5-b]pyridine-3H | 4-Cl—C$_6$H$_4$— | —CH$_2$— | —C(O)— | —NH[—(CH$_2$)$_2$N(C$_2$H$_5$)$_2$] | — | 2 HCl 0.5 H$_2$O |
| 164 | [4,5-b]pyridine-3H | 4-Cl—C$_6$H$_4$— | —CH$_2$— | —C(O)— | —NH[—(CH$_2$)$_3$N(C$_2$H$_5$)$_2$] | — | — |
| 165 | [4,5-b]pyridine-3H | 4-Cl—C$_6$H$_4$— | —CH$_2$— | —C(O)— | —NH[—(CH$_2$)$_3$N(C$_2$H$_5$)$_2$] | — | 2 HCl |
| 166 | [4,5-b]pyridine-3H | 4-Cl—C$_6$H$_4$— | —CH$_2$— | —C(O)— | 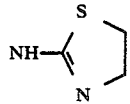 | — | — |
| 167 | [4,5-b]pyridine-3H | 4-Cl—C$_6$H$_4$— | —(CH$_2$)$_2$— | —C(O)— | —N(CH$_3$)$_2$ | — | HCl |
| 168 | [4,5-b]pyridine-3H | 4-Cl—C$_6$H$_4$— | —(CH$_2$)$_2$— | —C(O)— | —N(CH$_3$)(C$_6$H$_5$) | — | HCl |
| 169 | [4,5-b]pyridine-3H | 4-Cl—C$_6$H$_4$— | —CH$_2$— | —C(O)— | 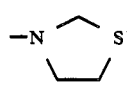 | — | — |

TABLE 1-continued

Structure:
$(Z)_{1-2}$—A ring fused with imidazole bearing $-(CH_2)_n-B-W$ with $R^6$ on the CH, and Ar at the 2-position; O on the A ring N.

| Ex. No. | $(Z)_{1-2}$-A | Ar | $\begin{array}{c}R^6\\-(CH)_n-\end{array}$ | B | W | Opt.* Isomer | Salt |
|---|---|---|---|---|---|---|---|
| 170 | [4,5-b]pyridine-3H | 4-Cl—C$_6$H$_4$— | —CH$_2$— | —C(O)— | —NH-(2-thiazolyl) | — | — |
| 171 | [4,5-b]pyridine-3H | 4-Cl—C$_6$H$_4$— | H, —C(CH$_3$)— | —C(O)— | —N(CH$_3$)$_2$ | (S) | — |
| 172 | [4,5-b]pyridine-3H | 4-Cl—C$_6$H$_4$— | H, —C(CH$_3$)— | —C(O)— | —N(C$_3$H$_7$)$_2$ | (S) | — |
| 173 | [4,5-b]pyridine-3H | 4-Cl—C$_6$H$_4$— | H, —C(CH$_3$)— | —C(O)— | —N(CH$_3$)(C$_6$H$_5$) | (S) | — |
| 174 | [4,5-b]pyridine-3H | 4-Cl—C$_6$H$_4$— | —CH$_2$— | —C(O)— | —NCH$_3$[—(CH$_2$)$_2$N(CH$_3$)$_2$] | — | — |
| 175 | [4,5-b]pyridine-3H | 4-Cl—C$_6$H$_4$— | —CH$_2$— | —C(O)— | —NCH$_3$[—(CH$_2$)$_2$N(CH$_3$)$_2$] | — | 2 HCl |
| 176 | [4,5-b]pyridine-3H | 4-Cl—C$_6$H$_4$— | H, —C(CH$_3$)— | —C(O)— | NH[—(CH$_2$)$_2$N(CH$_3$)$_2$] | (S) | — |
| 177 | [4,5-b]pyridine-3H | 4-Cl—C$_6$H$_4$— | H, —C(CH$_3$)— | —C(O)— | —NH[—(CH$_2$)$_2$N(CH$_3$)$_2$] | (S) | 2 HCl 0.5 H$_2$O |
| 178 | [4,5-b]pyridine-3H | 4-Cl—C$_6$H$_4$— | —CH$_2$— | —C(O)— | —NCH$_3$(CH$_2$CH=CH$_2$) | — | — |
| 179 | [4,5-b]pyridine-3H | 4-Cl—C$_6$H$_4$— | —CH$_2$— | —C(O)— | —NH-(1,2-diethyl-pyrazolidin-4-yl) | — | 2 HCl 0.5 H$_2$O |
| 180 | [4,5-b]pyridine-3H | 4-Cl—C$_6$H$_4$— | —CH$_2$— | —C(O)— | —NH-(quinuclidinyl) | — | 2 HCl H$_2$O |
| 181 | [4,5-b]pyridine-3H | 4-Cl—C$_6$H$_4$— | —CH$_2$— | —C(O)— | —NH(CH$_2$)$_2$-(1-methylpyrrolidin-2-yl) | — | 2 HCl H$_2$O |

TABLE 1-continued

| Ex. No. | $(Z)_{1-2}$-A | Ar | $R^6$ —(CH)$_n$— | B | W | Opt.* Isomer | Salt |
|---|---|---|---|---|---|---|---|
| 182 | [4,5-b]pyridine-3H | 4-Cl—C$_6$H$_4$— | —CH$_2$— | —C(O)— | —NH(CH$_2$)$_2$-(1-methylpyrrolidin-2-yl) | — | — |
| 183 | [4,5-b]pyridine-3H | 4-Cl—C$_6$H$_4$— | —CH$_2$— | —C(O)— | —N(CH$_3$)[4-N(CH$_3$)$_2$—C$_6$H$_4$—] | — | — |
| 184 | [4,5-b]pyridine-3H | 4-Cl—C$_6$H$_4$— | —CH$_2$— | —C(O)— | —N(CH$_3$)[4-N(CH$_3$)$_2$—C$_6$H$_4$—] | — | 2 HCl 2.5 H$_2$O |
| 185 | [4,5-b]pyridine-3H | 4-Cl—C$_6$H$_4$— | —CH$_2$— | —C(O)— | —N(piperazin-1-yl)—C(O)OC$_2$H$_5$ | — | — |
| 186 | [4,5-b]pyridine-1H | 4-Cl—C$_6$H$_4$— | —CH$_2$— | —C(O)— | —N(C$_3$H$_7$)$_2$ | — | 0.5 H$_2$O |
| 187 | [4,5-b]pyridine-1H | 4-Cl—C$_6$H$_4$— | —CH$_2$— | —C(O)— | —OC$_2$H$_5$ | — | HCl |
| 188 | [4,5-b]pyridine-1H | 4-Cl—C$_6$H$_4$— | —CH$_2$— | —C(O)— | —NH$_2$ | — | — |
| 189 | [4,5-b]pyridine-3H | 4-Br—C$_6$H$_4$— | —CH$_2$— | —C(O)— | —N(C$_3$H$_7$)$_2$ | — | — |
| 190 | [4,5-b]pyridine-3H | 4-Cl—C$_6$H$_4$— | —CH$_2$— | —C(O)— | —NH-(pyridin-4-yl) | — | 0.5 H$_2$O |
| 191 | [4,5-b]pyridine-3H | 4-NO$_2$—C$_6$H$_4$— | —CH$_2$— | —C(O)— | —OC$_2$H$_5$ | — | — |
| 192 | [4,5-b]pyridine-3H | 4-Cl—C$_6$H$_4$— | H —C(CH$_3$)— | —C(O)— | —OC$_2$H$_5$ | (S) | — |
| 193 | [4,5-b]pyridine-3H | 4-Cl—C$_6$H$_4$— | —CH$_2$— | —C(O)— | —N(4-acetylpiperazin-1-yl) | — | — |
| 194 | [4,5-b]pyridine-3H | 4-Cl—C$_6$H$_4$— | —CH$_2$— | —C(O)— | —NH(CH$_2$)$_2$-(1-methylpyrrol-2-yl) | — | — |
| 195 | [4,5-b]pyridine-3H | 4-Cl—C$_6$H$_4$— | —CH$_2$— | —C(O)— | —NH[4-[—N(CH$_3$)$_2$]C$_6$H$_4$—] | — | H$_2$O |
| 196 | [4,5-b]pyridine-3H | 4-Cl—C$_6$H$_4$— | —CH$_2$— | —C(O)— | —NH[3-[—N(CH$_3$)$_2$]C$_6$H$_4$—] | — | 2 HCl 0.5 H$_2$O |
| 197 | [4,5-b]pyridine-3H | 4-NO$_2$—C$_6$H$_4$— | —CH$_2$— | —C(O)— | —N(C$_3$H$_7$)$_2$ | — | — |
| 198 | [4,5-b]pyridine-3H | 4-NO$_2$—C$_6$H$_4$— | —CH$_2$— | —C(O)— | —NHCH$_3$ | — | — |
| 199 | [4,5-b]pyridine-3H | 5-Br-furan-2-yl | —CH$_2$— | —C(O)— | —N(CH$_3$)$_2$ | — | 0.5 H$_2$O |
| 200 | [4,5-b]pyridine-3H | 5-Br-furan-2-yl | —CH$_2$— | —C(O)— | —NHCH$_3$ | — | — |
| 201 | [4,5-b]pyridine-3H | 4-NO$_2$—C$_6$H$_4$— | —CH$_2$— | —C(O)— | —N(CH$_3$)$_2$ | — | — |
| 202 | [4,5-b]pyridine-3H | 4-Cl—C$_6$H$_4$— | —CH$_2$— | —C(O)— | —N(CH$_3$)(C$_3$H$_7$) | — | 2 H$_2$O |
| 203 | [4,5-b]pyridine-3H | 5-Br-furan-2-yl | —CH$_2$— | —C(O)— | —N(C$_3$H$_7$)$_2$ | — | — |
| 204 | [4,5-b]pyridine-3H | 4-Cl—C$_6$H$_4$— | CH$_3$ —CH— | —C(O)— | —NHCH$_3$ | (R) | — |

TABLE 1-continued $$\text{structure with } (Z)_{1-2}, A, N, O, Ar, R^6, (CH_2)_n-B-W$$

| Ex. No. | (Z)$_{1-2}$-A | Ar | $R^6$<br>—(CH)$_n$— | B | W | Opt.* Isomer | Salt |
|---|---|---|---|---|---|---|---|
| 205 | [4,5-b]pyridine-3H | 4-Cl—C$_6$H$_4$— | CH$_3$<br>\|<br>—CH— | —C(O)— | —NHCH$_3$ | (S) | — |
| 206 | [4,5-b]pyridine-3H | 4-Cl—C$_6$H$_4$— | CH$_3$<br>\|<br>—CH— | —C(O)— | —NH[4-N(CH$_3$)$_2$—C$_6$H$_4$—] | (S) | 2 HCl H$_2$O |
| 207 | [4,5-b]pyridine-3H | 4-Cl—C$_6$H$_4$— | CH$_3$<br>\|<br>—CH— | —C(O)— | —N(CH$_3$)$_2$ | (R) | — |
| 208 | [4,5-b]pyridine-3H | 4-Cl—C$_6$H$_4$— | CH$_3$<br>\|<br>—CH— | —C(O)— | —N(C$_3$H$_7$)$_2$ | (R) | — |
| 209 | [4,5-b]pyridine-3H | 4-Cl—C$_6$H$_4$— | —CH$_2$— | —C(O)— | —CH$_3$ | — | — |
| 210 | [4,5-b]pyridine-3H | 4-Cl—C$_6$H$_4$— | CH$_3$<br>\|<br>—CH— | —C(O)— | —O—(CH$_2$)$_2$OH | (R) | HCl |
| 211 | [4,5-b]pyridine-3H | 4-Cl—C$_6$H$_4$— | —CH$_2$— | —CH—<br>\|<br>OH | —CH$_3$ | Rac | HCl |
| 212 | [4,5-b]pyridine-3H | 5-CH$_3$-thiophen-2-yl | —CH$_2$— | —C(O)— | OH | — | — |
| 213 | [4,5-b]pyridine-3H | 4-Cl—C$_6$H$_4$— | CH$_3$<br>\|<br>—CH— | —C(O)— | —OC$_2$H$_4$OH | (S) | — |
| 214 | [4,5-b]pyridine-3H | 5-CH$_3$-thiophen-2-yl | —CH$_2$— | —C(O)— | —N(CH$_3$)$_2$ | — | — |
| 215 | [4,5-b]pyridine-3H | 5-CH$_3$-thiophen- | —CH$_2$— | —C(O)— | —NHCH$_3$ | — | — |
| 216 | [4,5-b]pyridine-3H | 4-F—C$_6$H$_4$— | —CH$_2$— | —C(O)— | —OC$_2$H$_4$OH | — | — |
| 217 | [4,5-b]pyridine-3H | 4-F—C$_6$H$_4$— | —CH$_2$— | —C(O)— | —OC$_2$H$_5$ | — | — |
| 218 | [4,5-b]pyridine-3H | 4-Cl—C$_6$H$_4$— | CH$_3$<br>\|<br>—CH— | —C(O)— | —OH | (R) | — |
| 219 | [4,5-b]pyridine-3H | 5-CH$_3$-thiophen-2-yl | —CH$_2$— | —C(O)— | —N(C$_3$H$_7$)$_2$ | — | — |
| 220 | [4,5-b]pyridine-3H | 5-Br-furan-2-yl | —CH$_2$— | —C(O)— | —OC$_2$H$_5$ | — | — |
| 221 | [4,5-b]pyridine-3H | 5-CH$_3$-thiophen-2-yl | —CH$_2$— | —C(O)— | —OC$_2$H$_5$ | — | — |
| 222(a) | 7-Cl[4,5-b]pyridine-1H | 4-Cl—C$_6$H$_4$— | —CH$_2$— | —C(O)— | —N(CH$_3$)$_2$ | — | — |
|  | 7-Cl[4,5-b]pyridine-3H | 4-Cl—C$_6$H$_4$— | —CH$_2$— | —C(O)— | —N(CH$_3$)$_2$ | — | — |
| (b) | 6-Cl[4,5-b]pyridine-1H | 4-Cl—C$_6$H$_4$— | —CH$_2$— | —C(O)— | —N(CH$_3$)$_2$ | — | — |
|  | 6-Cl[4,5-b]pyridine-3H | 4-Cl—C$_6$H$_4$— | —CH$_2$— | —C(O)— | —N(CH$_3$)$_2$ | — | — |
| 222(c) | 5,7-Cl$_2$[4,5-b]pyridine-1H | 4-Cl—C$_6$H$_4$— | —CH$_2$— | —C(O)— | —N(CH$_3$)$_2$ | — | — |
|  | 5,7-Cl$_2$[4,5-b]pyridine-3H | 4-Cl—C$_6$H$_4$— | —CH$_2$— | —C(O)— | —N(CH$_3$)$_2$ | — | — |
| (d) | 6-NO$_2$[4,5-b]pyridine-1H | 4-Cl—C$_6$H$_4$— | —CH$_2$— | —C(O)— | —N(CH$_3$)$_2$ | — | — |
|  | 6-NO$_2$[4,5-b]pyridine-3H | 4-Cl—C$_6$H$_4$— | —CH$_2$— | —C(O)— | —N(CH$_3$)$_2$ | — | — |
| (e) | 5-OCH$_3$[4,5-b]pyridine-1H | 4-Cl—C$_6$H$_4$— | —CH$_2$— | —C(O)— | —N(CH$_3$)$_2$ | — | — |
|  | 5-OCH$_3$-[4,5-b]pyridine-3H | 4-Cl—C$_6$H$_4$— | —CH$_2$— | —C(O)— | —N(CH$_3$)$_2$ | — | — |
| (f) | 5,6-Cl$_2$[4,5-b]pyridine-1H | 4-Cl—C$_6$H$_4$— | —CH$_2$— | —C(O)— | —N(CH$_3$)$_2$ | — | — |
|  | 5,6-Cl$_2$[4,5-b] | 4-Cl—C$_6$H$_4$— | —CH$_2$— | —C(O)— | —N(CH$_3$)$_2$ | — | — |

TABLE 1-continued

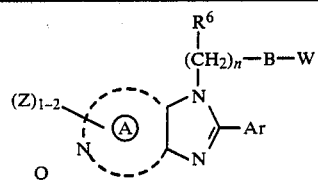

| Ex. No. | $(Z)_{1-2}$-A | Ar | $R^6$ $\|$ $-(CH)_n-$ | B | W | Opt.* Isomer | Salt |
|---|---|---|---|---|---|---|---|
| | pyridine-3H | | | | | | |
| (g) | 6-Br[4,5-b] pyridine-1H | 4-Cl—$C_6H_4$— | —$CH_2$— | —C(O)— | —N($CH_3$)$_2$ | — | — |
| | 6-Br[4,5-b] pyridine-3H | 4-Cl—$C_6H_4$— | —$CH_2$— | —C(O)— | —N($CH_3$)$_2$ | — | — |
| (h) | 5-Cl[4,5-b] pyridine-1H | 4-Cl—$C_6H_4$— | —$CH_2$— | —C(O)— | —N($CH_3$)$_2$ | — | — |
| | 5-Cl[4,5-b] pyridine-3H | 4-Cl—$C_6H_4$— | —$CH_2$— | —C(O)— | —N($CH_3$)$_2$ | — | — |
| (i) | 7-$CH_3$[4,5-b] pyridine-1H | 4-Cl—$C_6H_4$— | —$CH_2$— | —C(O)— | —N($CH_3$)$_2$ | — | — |
| | 7-$CH_3$[4,5-b] pyridine-3H | 4-Cl—$C_6H_4$— | —$CH_2$— | —C(O)— | —N($CH_3$)$_2$ | — | — |
| 222(j) | 6-$CH_3$[4,5-b] pyridine-1H | 4-Cl—$C_6H_4$— | —$CH_2$— | —C(O)— | —N($CH_3$)$_2$ | — | — |
| | 6-$CH_3$[4,5-b] pyridine-3H | 4-Cl—$C_6H_4$— | —$CH_2$— | —C(O)— | —N($CH_3$)$_2$ | — | — |
| (k) | 5-$CH_3$[4,5-b] pyridine-1H | 4-Cl—$C_6H_4$— | —$CH_2$— | —C(O)— | —N($CH_3$)$_2$ | — | — |
| | 5-$CH_3$[4,5-b] pyridine-3H | 4-Cl—$C_6H_4$— | —$CH_2$— | —C(O)— | —N($CH_3$)$_2$ | — | — |
| 223(a) | 4-$OCH_3$-[4,5-c] pyridine-1H | 4-Cl—$C_6H_4$— | —$CH_2$— | —C(O)— | —$NH_2$ | — | — |
| | 4-$OCH_3$-[4,5-c] pyridine-3H | 4-Cl—$C_6H_4$— | —$CH_2$— | —C(O)— | —$NH_2$ | — | — |
| (b) | 7-Br,6-Cl[4,5-c] pyridine-1H | 4-Cl—$C_6H_4$— | —$CH_2$— | —C(O)— | —$NH_2$ | — | — |
| | 7-Br,6-Cl[4,5-c] pyridine-3H | 4-Cl—$C_6H_4$— | —$CH_2$— | —C(O)— | —$NH_2$ | — | — |
| (c) | [4,5-c] pyridine-1H | 4-Cl—$C_6H_4$— | —$CH_2$— | —C(O)— | —$NH_2$ | — | — |
| | [4,5-c] pyridine-3H | 4-Cl—$C_6H_4$— | —$CH_2$— | —C(O)— | —$NH_2$ | — | — |
| (d) | 4-Cl-[4,5-c] pyridine-1H | 4-Cl—$C_6H_4$— | —$CH_2$— | —C(O)— | —$NH_2$ | — | — |
| | 4-Cl-[4,5-c] pyridine-3H | 4-Cl—$C_6H_4$— | —$CH_2$— | —C(O)— | —$NH_2$ | — | — |
| (e) | 4,6-($Cl_2$)-[4,5-c] pyridine-1H | 4-Cl—$C_6H_4$— | —$CH_2$— | —C(O)— | —$NH_2$ | — | — |
| | 4,6-($Cl_2$)-[4,5-c] pyridine-3H | 4-Cl—$C_6H_4$— | —$CH_2$— | —C(O)— | —$NH_2$ | — | — |
| 223(f) | 7-$NO_2$-[4,5-c] pyridine-1H | 4-Cl—$C_6H_4$— | —$CH_2$— | —C(O)— | —$NH_2$ | — | — |
| | 7-$NO_2$-[4,5-c] pyridine-3H | 4-Cl—$C_6H_4$— | —$CH_2$— | —C(O)— | —$NH_2$ | — | — |
| (g) | 6-Br,4-Cl[4,5-c] pyridine-1H | 4-Cl—$C_6H_4$— | —$CH_2$— | —C(O)— | —$NH_2$ | — | — |
| | 6-Br,4-Cl[4,5-c] pyridine-3H | 4-Cl—$C_6H_4$— | —$CH_2$— | —C(O)— | —$NH_2$ | — | — |
| (h) | 7-Br-[4,5-c] pyridine-1H | 4-Cl—$C_6H_4$— | —$CH_2$— | —C(O)— | —$NH_2$ | — | — |
| | 7-Br-[4,5-c] pyridine-3H | 4-Cl—$C_6H_4$— | —$CH_2$— | —C(O)— | —$NH_2$ | — | — |
| (i) | 6-Cl-[4,5-c] pyridine-1H | 4-Cl—$C_6H_4$— | —$CH_2$— | —C(O)— | —$NH_2$ | — | — |
| | 6-Cl-[4,5-c] pyridine-3H | 4-Cl—$C_6H_4$— | —$CH_2$— | —C(O)— | —$NH_2$ | — | — |
| 224(a) | 7-$CH_3$-[4,5-b] pyridine-3H | 4-Cl—$C_6H_4$— | —$CH_2$— | $\underset{\underset{-C-}{\|}}{O}$ | —$OC_2H_5$ | — | — |
| (b) | 6-$CH_3$[4,5-b] pyridine-3H | 4-Cl—$C_6H_4$— | —$CH_2$— | $\underset{\underset{-C-}{\|}}{O}$ | —$OC_2H_5$ | — | — |
| (c) | 5-$CH_3$-[4,5-b] pyridine-3H | 4-Cl—$C_6H_4$— | —$CH_2$— | $\underset{\underset{-C-}{\|}}{O}$ | —$OC_2H_5$ | — | — |

TABLE 1-continued

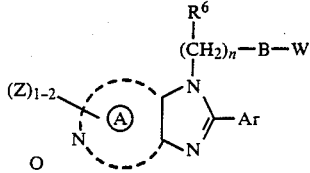

| Ex. No. | (Z)₁₋₂-A | Ar | R⁶ \| -(CH)ₙ- | B | W | Opt.* Isomer | Salt |
|---|---|---|---|---|---|---|---|
| (d) | 5,6-(CH₃)₂-[4,5-b]pyridine-3H | 4-Cl—C₆H₄— | —CH₂— | —C(O)— | —OC₂H₅ | — | — |
| 224(e) | 4-(C₂H₅)₂N—, 6-CH₃-[4,5-c]pyridine-1H | 4-Cl—C₆H₄— | —CH₂— | —C(O)— | —OC₂H₅ | — | — |
| (f) | 4-CH₃-[4,5-c]pyridine-1H | 4-Cl—C₆H₄— | —CH₂— | —C(O)— | —OC₂H₅ | — | — |
| (g) | 5-OCH₃-[4,5-b]pyridine-3H | 4-Cl—C₆H₄— | —CH₂— | —C(O)— | —OC₂H₅ | — | — |
| 225 | [4,5-b]pyridine-3H | 4-Cl—C₆H₄— | CH₃ \| —CH— | —C(O)— | —O(CH₂)₂OH | (R) | — |
| 226 | [4,5-b]pyridine-3H | 4-Cl—C₆H₄— | CH₃ \| —CH— | —C(O)— | —O(CH₂)₂ | (R) | — |
| 227 | [4,5-b]pyridine-3H | 4-Cl—C₆H₄— | —(CH₂)₂— | —C(O)— | —NH₂ | — | — |
| 228 | [4,5-b]pyridine-3H | 5-Br-furan-2-yl | —CH₂— | —C(O)— | —NH₂ | — | — |
| 229 | [4,5-b]pyridine-3H | 5-CH₃-thiophene-2-yl | —CH₂— | —C(O)— | —NH₂ | — | — |
| 230 | [4,5-b]pyridine-3H | 4-F—C₆H₄— | —CH₂— | —C(O)— | —NHCH₃ | — | — |
| 231 | [4,5-b]pyridine-3H | 4-F—C₆H₄— | —CH₂— | —C(O)— | —N(CH₃)₂ | — | — |
| 232 | [4,5-b]pyridine-3H | 4-F—C₆H₄— | —CH₂— | —C(O)— | —N(C₃H₇)₂ | — | — |
| 233 | [4,5-b]pyridine-3H | 4-F—C₆H₄— | —CH₂— | —C(O)— | —NH₂ | — | H₂O |
| 234 | [4,5-b]pyridine-3H | 4-Cl—C₆H₄— | CH₃ \| —CH— | —C(O)— | —NH₂— | (S) | — |
| 235 | [4,5-b]pyridine-3H | 4-Br—C₆H₄— | —CH₂— | —C(O)— | —NH₂ | — | — |
| 236 | [4,5-b]pyridine-1H | 4-Cl—C₆H₄— | —CH₂— | —C(O)— | —C₆H₅ | — | — |
| 237 | [4,5-b]pyridine-3H | 4-Cl—C₆H₄— | —CH₂— | OH \| —CH— | —C₆H₅ | Rac | — |
| 238 | [4,5-b]pyridine-3H | 4-Cl—C₆H₄— | —CH₂— | —C(O)— | —C₆H₅— | — | — |
| 239 | [4,5-c]pyridine-1H | 4-Cl—C₆H₄— | —CH₂— | —C(O)— | —N(CH₃)₂ | — | — |
| 240 | 5-Cl-[4,5-b]pyridine-3H | 4-Cl—C₆H₄— | —CH₂— | —C(O)— | OH | — | — |
| 241 | 5-Cl-[4,5-b]pyridine-3H | 4-Cl—C₆H₄— | —CH₂— | —C(O)— | —N(C₃H₇)₂ | — | — |
| 242 | 5-Cl-[4,5-b]pyridine-3H | 4-Cl—C₆H₄ | —CH₂— | —C(O)— | —NH₂ | — | H₂O |
| 243 | 5-Cl-[4,5-b]pyridine-3H | 4-Cl—C₆H₄— | —CH₂— | —C(O)— | —N(CH₃)₂ | — | 0.5 H₂O |
| 244 | [4,5-b]pyridine-3H | 4-Br—C₆H₄— | —CH₂— | —C(O)— | —NH[4-N(CH₃)₂—C₆H₄—] | — | — |
| 245 | [4,5-b]pyridine-3H | 4-Cl—C₆H₄— | —(CH₂)₂— | —C(O)— | —NH[4-N(CH₃)₂—C₆H₄—] | — | — |
| 246 | 5-Cl-[4,5-b]pyridine-3H | 4-Cl—C₆H₄— | —CH₂— | —C(O)— | —NH(CH₃) | — | — |
| 247 | 5-Cl-[4,5-b]pyridine-3H | 4-CH₃—C₆H₄— | —CH₂— | —C(O)— | —NH(CH₃) | — | — |
| 248 | 5-Cl-[4,5-b]pyridine-3H | 4-CH₃—C₆H₄— | —CH₂— | —C(O)— | —N(CH₃)₂ | — | — |

*Rac = racemic mixture.
**Metal salt as indicated in W definition.

PHARMACOLOGICAL TEST PROCEDURES
MUSCLE RELAXANT TEST

The test procedure relied on to indicate positive muscle relexant activity is the morphine-induced Straub Tail in Mice Test described by G. D. Novak in DRUG DEVELOPMENT RESEARCH (1982) 2: 383–386, except 8 animals per group were used per test rather than 10. The test is summarized as follows: The test drug, reference drug, and control articles to be administered are prepared in saline, 0.5% aqueous methylcellulose suspension or other, depending on solubility, in such concentration that the volume administered is 10 ml/kg. The initial screening dose of the test drug is usually 10 mg/kg. Groups of 8 mice are given an IP dose of a compound or vehicle prepared as described above. After 15 min, mice are administered morphine sulfate, 60 mg/kg, subcutaneously. Fifteen minutes after administration of morphine (i.e., 30 min after test compound administration), mice were scored for presence of Straub Tail defined as an elevation of the tail at least 90 degrees from the horizontal. An $ED_{50}$ value may be determined from at least three logarithmically spaced doses by the method of Litchfield and Wilcoxon (1949), J. PHARMACOL. EXP. THER. 96: 99–113. Illustratively, some of more active compounds such as those prepared in Examples 47, 48, 56, 90, 243 and 246 exhibited $ED_{50}$ values of about 1–10 mg/kg in the foregoing Straub Tail Test.

ANTIANXIETY TEST

The test screening procedure relied on to indicate positive antianxiety response is a modification of the Vogel Conflict Test which is based on shock-suppressed drinking behavior in rats outlined by J. R. Vogel, et al. in PSYCHOPHARMACOLOGY 21: 1–7 (1971). The procedure used is as follows: The test reference and control articles to be administered intraperitoneally in physiological saline, 0.5% aqueous methylcellulose or other, depending on a solubility in such concentration that the volume administered is 5 mg/kg. The initial screening dose of the test article is usually 100.0 mg/kg initially.

Prior to dosing, rats are housed 2 per cage and deprived of water for 48 hr and thereafter randomized into treatment groups of five. Feed is available ad libitum. Thirty minutes after dosing, each rat is placed individually in a plexiglass cage measuring 18 cm in width, 13 cm in height and 29.5 cm in length and equipped with a stainless steel grid floor. The cage is covered with a plastic lid containing holes to facilitate introduction of a water bottle (30 ml plastic centrifuge tube) with a rubber stopper and metal drinking tube. A Drinkometer circuit (Omniteck Electronics, Inc., 3000 Cortona Road, Columbus, Ohio 43204, is connected between the drinking tube and the grid floor of the apparatus so that the rat completes the circuit whenever it licks the tube. The procedure is to allow the rat to find the drinking tube and complete 20 licks (as displayed on the Drinkometer digital readout) prior to the start of the experimental session. Rats not reaching this criterion are discarded. A three minute experimental session is initiated by a 0.25 mA shock at the 20th lick. Rats that continue drinking will experience a shock at each successive 20th lick. The total number of shocks during the experimental session are recorded as follows:

$$\frac{\text{total licks}}{20} + 1 = \text{total shocks}$$

Statistical analysis is performed by the Dunn's Multiple Comparison Test described by O. J. Dunn (1964) TECHNOMETRICS 6(3):241–52. The mean number of shocks experienced by the control group is compared with those of each drug-treated group. Significance is considered at $P<0.1$. The higher the total shocks compared to control, the more active is the compound. Active compounds may then be similarly tested at reduced dosages. Five rats were tested at a given dosage level and 5 rats were used as controls. Illustratively, some of the more active compounds such as those of Examples 47, 65, 74, 82, 86, 88, 246, 247 and 248 have significant activity in the foregoing Vogel test at 10 mg/kg.

Anticonvulsant activity was determined for compounds of Formula I as evidenced by using chemical or electrical challenge as follows:

METRAZOLE CHEMICAL CHALLENGE (SWINYARD METHOD)

Groups of 8 adult female mice were randomly assigned to dosage groups according to the method of Steel, R. G. D., and Torrie, J. H. (1960) in "Principles and Procedures of Statistics", McGraw-Hill Book Company, Inc., pp 99–100, pp 428–31. Each mouse was identified with a color code on its tail. The test compounds were administered as solutions or suspensions in 10 ml/kg mouse body weight of 0.5% aqueous methyl cellulose within 15 minutes of preparation of the suspension. Metrazole ® (pentylenetetrazol) was prepared as a solution in physiological saline. The mice were not fasted prior to the test. Eight mice were tested at each dosage level.

Each mouse received one dose of the test drug (usually 100 mg/kg for screening) in the 0.5% aqueous methylcellulose or the control article (0.5% aqueous methylcellulose alone) intraperitoneally. Metrazole (80 mg/kg S. C.) was then given in a loose fold of skin on the back of the neck; i.e., ½ hr after the test compound or control article was given. Injections were given with a 1 ml glass tuberculin syringe with appropriate size hypodermic needle (27 gauge for solutions; 23 gauge for suspensions). All injections were given in a volume of 10 ml/kg mouse body weight. Each mouse was observed for 30 minutes following Metrazole injection. Failure of the animals to exhibit a threshold seizure (a single episode of clonic spasms at least 5 seconds in duration) was defined as protection. Anticonvulsant data were tabulated as the present protection, i.e., $$\frac{\text{No. Mice Protected}}{\text{No. Mice Tested}} \times 100.$$

The $ED_{50}$, 95% confidence limits and potency ratio may be ascertained by the computer-based probit analysis ascribed to Finney, D. J. (1964) *Statistical Method in Biological Assay*, 2nd Ed., New York. Hefner Publishing Co. Illustratively, some of the more active compounds such as those of Examples 30, 48, 56, 242, 243, 246, 247 and 248 exhibit $ED_{50}$ values of about 1–10 mg/kg in the foregoing metrazole test.

ELECTRICAL CHALLENGE

Adult female mice in groups of eight were administered the test drug intraperitoneally (usually 100 mg/kg initially for screening) in liquid carrier, usually physiological saline or water. Animals were challenged electrically by placing brass electrodes on the corneas and applying an electrical stimulus (60 Hz, 5 m sec. pulse width, 34 m A intensity) for 0.2 seconds by way of a Grass Stimulator ® and constant current unit and a Hunter Timer ®. The absence of tonic seizures upon cessation of the stimuli was scored as protection in that animal. The number of animals protected from tonic seizures at a given dose of test drug was determined. The $ED_{50}$, 95% confidence limits and potency ratio may be ascertained by the method of J. T. Litchfield and F. Wilcoxon (1949) J. PHARMACOL. EXP. THER. 96, 99–113. Illustratively, some of the more active compounds such as those of Example 47, 48, 56, 90 and 243 exhibit $ED_{50}$ values in the range of about 2–15 mg/kg.

PHARMACEUTICAL COMPOSITIONS

The methods of treating anxiety, muscle tension, and spasticity in mammals is best carried out by administering as active ingredients in a pharmaceutical composition at least one of the compounds of Formula I in association with a pharmaceutical carrier or excipient. The compounds are thus presented in a therapeutic composition suitable for oral, rectal, parenteral, subcutaneous, intramuscular, intraperitoneal, or intravenous administration. Thus, for example, the composition for oral administration can take the form of elixirs, capsules, tablets, or coated tablets containing carriers conveniently used in the pharmaceutical art. Suitable tableting excipients include lactose, potato and maize starches, talc, gelatin, stearic and silicic acids, magnesium stearate and polyvinyl pyrrolidone.

For parenteral administration the carrier can be comprised of a sterile parenterally acceptable liquid; e.g., water or arachis oil contained in ampoules.

In compositions for rectal administration, the carrier can be comprised of a suppository base; e.g., cocoa butter or glyceride.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount; i.e., such that a suitable effective dosage will be consistent with the dosage form employed. The exact individual dosages as well as daily dosages will, of course, be determined according to standard medical principles under the direction of a physician or veterinarian.

Animal testing suggests that the more active compounds of Formula I will be effective in humans for muscle relaxant effects at about 1 to 20 mg/kg body weight per day. Thus, an active compound such as that of Example 243 may be administered to effectively control muscle spasms in unit dosage form to an adult human at about 75–200 mg once or twice a day.

Animal testing suggests that the more active compounds of Formula I such as those cited above in the Vogel test will be effective in humans for the relief from anxiety at about 4 to 40 mg administered once or twice daily.

The compounds of Formula I have anticonvulsant property as exhibited by activity against seizures caused by electrical or chemical challenge. The animal data suggest the more active compounds of Formula I, such as those cited above under Electroshock Experiments, have anticonvulsant activity ranging from about 1.5 to 10 times that of phenobarbital. The animal data suggest the more active compounds of Formula I, such as those cited above under Metrazole Chemical Challenge, have anticonvulsant activity ranging from about 10 to 100 times that of valproic acid. The more active compounds of Formula I are projected to be effective in all types of epilepsy, both grand mal and petit mal, seizures. For example, oral daily doses of about 2–75 mg of the active agent 3 times a day are projected for treatment of epilepsy.

The active ingredients of the invention may be combined with other pharmacologically active agents as previously indicated, or with buffers, antacids or the like, for administration and the proportion of the active agent in the composition may be varies widely.

CAPSULES

Capsules of 5 mg, 25 mg, and 50 mg of active ingredient per capsule are prepared; with higher amounts of ingredient reduction may be made in the amount of lactose.

| Typical blend for encapsulation | Per Capsule, mg. |
|---|---|
| Active ingredient | 5.0 |
| Lactose | 296.7 |
| Starch | 129.0 |
| Magnesium stearate | 4.3 |
| Total | 435.0 mg. |

Uniformly blend the selected active ingredient with lactose, starch and magnesium stearate and encapsulate the blend.

Additional capsule formulations preferably contain higher dose of active ingredient and are as follows:

| Ingredients | 100 mg. per Capsule | 250 mg. per Capsule | 500 mg. per Capsule |
|---|---|---|---|
| Active ingredient | 100.0 | 250.0 | 500.0 |
| Lactose | 231.5 | 126.5 | 31.1 |
| Starch | 99.2 | 54.2 | 13.4 |
| Magnesium stearate | 4.3 | 4.3 | 5.5 |
| Total, mg. | 435.0 | 435.0 | 550.0 |

TABLETS

A typical formulation for a tablet containing 5.0 mg of active ingredient per tablet follows. The formulation may be used for other strengths of active ingredient by adjustment of weight of dicalcium phosphate.

| Ingredients | Per Tablet, mg. |
|---|---|
| (1) Active ingredient | 5.0 |
| (2) Corn Starch | 13.6 |
| (3) Corn Starch (paste) | 3.4 |
| (4) Lactose | 79.2 |
| (5) Dicalcium phosphate | 68.0 |
| (6) Calcium Stearate | 0.9 |
| Total | 170.1 mg. |

Uniformly blend 1, 2, 4 and 5. Prepare 3 as a 10 percent paste in water. Granulate the blend with the starch paste and pass the wet mass through a number eight mesh screen. The wet granulation is dried and passed through a number twelve mesh screen. The dried granules are blended with calcium stearate and compressed.

Additional tablet formulations preferably contain a higher dosage of the active ingredient and are as follows:

| 50 mg. Tablet | |
| --- | --- |
| Ingredients | Per Tablet, mg. |
| Active ingredient | 50.0 |
| Lactose | 90.0 |
| Corn Starch | 58.0 |
| Calcium stearate | 2.0 |
| Total | 200.0 |

Uniformly blend the active ingredient, lactose, and corn starch. The blend is granulated, using water as a granulating medium. The wet granules are passed through an eight mesh screen and dried at 140 to 160 degrees Fahrenheit overnight. The dried granules are passed through a number ten mesh screen and blended with the proper amount of calcium stearate and this blend is then converted into tablets on a suitable tablet press.

Various modifications and equivalents will be apparent to one skilled in the art and may be made in the compounds, methods, processes and pharmaceutical compositions of the present invention without departing from the spirit and scope thereof; and it is therefore to be understood that the invention is to be limited only by the scope of the appended claims.

What is claimed is:

1. A method for the treatment of a living animal body for muscle tension and spasticity and/or anxiety and/or convulsions which comprises administering a compound selected from the group having the formula:

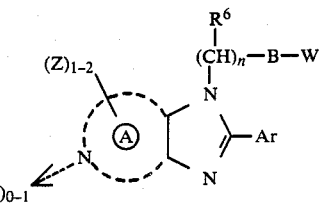

wherein
  A represents a heterocyclic ring having two of its carbon atoms held mutually with the imidazo moiety selected from the group consisting of pyridine in any of its four positions wherein nitrogen is unshared by the imidazo moiety and substituted by one or two Z radicals on a carbon not shared by the imidazo moiety selected from the group consisting of hydrogen, halogen, loweralkyl, hydroxy, loweralkoxy, diloweralkylamino or nitro;
  n is 1 to 3;
  $R^6$ is hydrogen or loweralkyl;
  Ar is selected from:

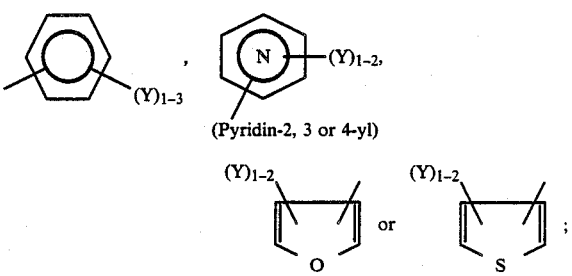

B is carbonyl;
  W is selected from:
    hydrogen,
    loweralkyl
    $(Y)_{1-3}$-phenyl,
    $(Y)_{1-3}$-phenyl-loweralkyl,
    $-OR^1$, $-OM$, $-O(CH_2)_p-OH$,
    $-NR^2(CH_2)_pCOOR^1$,
    $-NR^2(CH_2)_pCOOM$ or
    $-NR^2[(CH_2)_pNHC(O)R^1]$,
  wherein $R^1$ and $R^2$ are selected from hydrogen, loweralkyl, $(Y)_{1-3}$-phenyl, or $(Y)_{1-3}$-phenyl-loweralkyl;
    p is 0–3;
  wherein all of the above Y is hydrogen, halo, loweralkoxy, loweralkyl, trifluoromethyl, cyano, nitro or diloweralkylamino;
    M is a pharmaceutically acceptable metal, forming an acid salt;
    the optical isomers, the oxides represented by O and the pharmaceutically acceptable acid addition salts thereof.

* * * * *